(12) United States Patent
Hu et al.

(10) Patent No.: US 7,851,190 B2
(45) Date of Patent: Dec. 14, 2010

(54) BIOSYNTHETIC GENE CLUSTER FOR LEPTOMYCINS

(75) Inventors: Zhihao Hu, Castro Valley, CA (US); Ralph C. Reid, San Rafael, CA (US)

(73) Assignee: Kosan Biosciences, Inc., Princeton, NJ (US)

( * ) Notice: Subject to any disclaimer, the term of this patent is extended or adjusted under 35 U.S.C. 154(b) by 735 days.

(21) Appl. No.: 11/895,327

(22) Filed: Aug. 24, 2007

(65) Prior Publication Data

US 2008/0233618 A1  Sep. 25, 2008

Related U.S. Application Data

(62) Division of application No. 10/937,730, filed on Sep. 8, 2004, now Pat. No. 7,288,396.

(60) Provisional application No. 60/502,423, filed on Sep. 11, 2003, provisional application No. 60/553,384, filed on Mar. 15, 2004.

(51) Int. Cl.
 C12N 9/00  (2006.01)
 C12N 9/16  (2006.01)
 C12N 1/20  (2006.01)
 C07H 21/04 (2006.01)

(52) U.S. Cl. .................... 435/183; 435/196; 435/252.3; 435/252.35; 435/320.1; 536/23.2; 536/23.1

(58) Field of Classification Search ....................... None
See application file for complete search history.

(56) References Cited

U.S. PATENT DOCUMENTS

| 7,288,396 B2 | 10/2007 | Hu et al. |
| 2005/0112726 A1 | 5/2005 | Hu et al. |

*Primary Examiner*—Nashaat T Nashed
(74) *Attorney, Agent, or Firm*—Stephen C. D'Amico

(57) ABSTRACT

Polypeptides and domains of leptomycin polyketide synthase and the nucleic acids encoding them are provided. Methods to prepare leptomycin, leptomycin analogs, and leptomycin derivatives are described, as are methods to prepare other polyketides using the nucleic acids encoding leptomycin polyketide synthase domains or modifying enzymes.

11 Claims, 41 Drawing Sheets

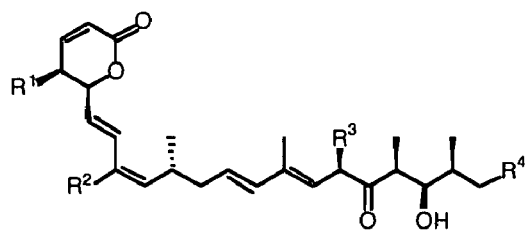

| Compound | Source | Reference | R¹ | R² | R³ | R⁴ |
|---|---|---|---|---|---|---|
| Leptomycin A | *Streptomyces* ATCC 39366 | US 4,792,522 20 Dec 1988 | Me | Me | Me | A |
| Leptomycin B | *Streptomyces* ATCC 39366 | US 4,792,522 20 Dec 1988 | Me | Et | Me | A |
| Anguinomycin A | *Streptomyces* R2827 | | H | Me | Me | A |
| Anguinomycin B | *Streptomyces* R2827 | | H | Et | Me | A |
| Anguinomycin C | *Streptomyces* KR2827-2 | | H | Me | Me | Me |
| Anguinomycin D | *Streptomyces* KR2827-2 | | H | Et | Me | Me |
| Callystatin A | *Callyspongia truncata* | | H | Et | Me | Et |
| Kazusamycin A | *Streptomyces* 81-484 | | Me | Et | $CH_2OH$ | A |
| Kazusamycin B | *Streptomyces* 81-484 | US 4,725,621 16 Feb 1988 | Me | Me | $CH_2OH$ | A |
| Leptolstatin | *Streptomyces* SAM1595 | | Me | Me | Me | A |
| Leptofuranin A | *Streptomyces tanashiensis* 3007-H1 | | Me | Me | Me | B |
| Leptofuranin B | *Streptomyces tanashiensis* 3007-H1 | | Me | Et | Me | B |
| Leptofuranin C | *Streptomyces tanashiensis* 3007-H1 | | Me | Me | Me | B |
| Leptofuranin D | *Streptomyces tanashiensis* 3007-H1 | | Me | Et | Me | B |

FIGURE 1

FIGURE 5. DNA Sequence of the Leptomycin Biosynthetic Gene Cluster (SEQ ID NO:3).

```
   1 CGGTGGGCTC GGGTGAGAAA AAATTAGTCC GAATCGATGC GCTCCCGTGC TGTTGCGCAT
  61 GTGACCGATA TGTAAGCGAC ATGTGAACGT TCGTCGCAAG CAGGTGCGTT CGCCCCCGCC
 121 GGCGGGTCGT CGGGACCGCG CGCGCGGGCG TGCGAGCCGG GTGCGCGGCC GGTCTGATCA
 181 AGGGTTCTCG CGCGTCGACG ACGCAGGTCG AAGGCGGGCG TGCGCGGGGC GTTCGCGCAC
 241 TACACCAGGT GACCCGAATG GTTCAACCGC GCCGTCGAAA GCGCCCGAAC GGGGCCTGAA
 301 TTCACCCCTT GCGGCCGATC GACCCGGTAC TCCAATGTGT TGATCTGTGT TCGTCCGTGT
 361 ACTCAACGTA TGCAGGTCAT GGAGCGCGGA ATGACGGAAT TCAACGCCGA TGCCCATCGC
 421 GCACACCCCG CGCCGGAAGA CGCGGTGGCC ATCGTCGGGT TGGCCTGCCG ACTCCCCGGC
 481 GCCGACGGCC CCGACGAGTT CTGGGACCTG CTGAGCAACG GACGCGACAC GATCACCGAA
 541 GTGCCCCGCC ATCGCCGGGA CGCGAGAGCG GCGGACGACA CGAATCGAAC GGCCGGCGGA
 601 TCCCCCCACC CAGCCGCGAA CCGACCGCGA AGAGGCGGAT TCCTGGACGC GGTGGACCGG
 661 TTCGACGCCG CCTTCTTCGG CATCACCCCG GGCGAGGCCG CCCTGATCGA CCCGCAACAG
 721 CGCCTGATGC TCGAACTGTG CTGGGAGGCC CTGGAACACG CGGGCATCCC GCCGACCCGG
 781 ATTCGGGGCA GCGCCACCGG GGTGTTCGCC GGCGCGATCT GGACGACTA CGCCACCCTG
 841 CTGCGCCGCG CCGGCGTCGA GCCGGCCCC CGACACGCCA CCGGCCTGCA CCGCAGCATG
 901 ATCGCCAACC GGGTCTCGTA CACCCTCGGC CTGCGCGCC CAGCATGAC GGTGGACGCG
 961 GCCCAGTCCT CGTCCCTGGT CGCGGTACAC CTGGCCGGCG AGAGCCTGCG CCGGGGCGAG
1021 TCGACACTGG CCCTGGTCGG CGGGGTCAAC CTGGACCTGG TTCCCGACCA CGACGGCGAC
1081 GCGGCCAAGT TCGGCGGGCT CTCCCCGCAG GCCGCTGCT TCACCTTCGA CGCCCGGGCC
1141 GACGGCTACG TGCGCGGCGA GGGCGGCGCG TGGTGGTGC TCAAGCCGCT GTCCCGGGCG
1201 CTGGCCGACG GCGACGTCGT GCACGGCGTG ATCCGCGGCA GCGCGATGAA CAACGACGGG
1261 GGCGGCGACG CGCTGACCGC GCCGGACCCC CGGGCCCAGG CGGAGGTGAT CCGGCTGGCC
1321 CGGCGGCGGG CCGGGGTCGC CGCGTCCGCC GTCCAATACG TCGAACTGCA CGGCACGGGC
1381 ACCCCCGTCG GCGACCCGAT CGAAGCCGCC GCACTCGGTG CGGCGCTCGG CACCGAGCGG
1441 GCGAACCGGC CGCCGCTGGC CGTCGGTTCG GTCAAGACCA ACGTCGGGCA CCTGGAGGGT
1501 GCGGCCGGCA TCGTCGGCCT GGTCAAGACG GTGTTGGCGA TCCGACACCG GCGGCTCCCG
1561 GCAAGCCTGA ACTTCGCCGA ACCCCATCCG CGAATCCCGT TGGGCGAACT GGGCCTGCGG
1621 GTGCAGACGG CGGAGGGTGA CTGGCCCTGC CCGGACGAAA CCCTGATCGC CGGGGTGAGT
1681 TCGTTCGGGA TGGGTGGGAC CAACTGCCAT GTGGTGCTCG CGGAGGCGGA GCCCGCGGAT
1741 GGGGTGGGGC CGTCGGTCGC GTCGGCGCCC TCGGGTGGGT CGGATCCGGG CATGGAGTCC
1801 GCCACCGGCC CGGTGCCTTC GGACGCGGTT GCCGTGCCGA TCTCCGGTGT CGACGCCGAC
1861 GGGCTTCGGG CCCAGGCCGG GCGGTGGCAC GGCCATGTAC GCGAACATCC CGACGTGGCG
1921 CCGGCCGACC TCGGCTACTC GGCCGCCACC ACCCGGACCG CGTTTGCCGC CCGCGCCGTC
1981 GTCCTCGCTC GCGACCACGC CGAACTCCTC GCCGGGCTCG ACGCGTTACG CGGAGCCGGC
2041 GCGGATCCAC ACCTGGTCCG AGCCGACGCG CAACCCGGCC GCACCGCCTT CCTGTTCACC
2101 GGACAGGGCA GCCAACGCCC GGCCATGGCG CAAGAGTCGT ACGCCCGCCA CGCCGTCTTC
2161 GCGGCGGCCT TCGACGCCGC CTGCGCCCAC CTGGACCCAC ACCTGCCGCG CCCGCTGCGC
2221 GAGGTGTTGT TCGCGTCGCC CGACAGCCCG GACGCGGCGC TCGTGCACCG CACCGAGTAC
2281 ACCCAACCCG CGCTGTTCGC CGTCGAGGTC GCGCTGTACC GGCTGTTCGA GCACTGGGGA
2341 GTGCACCCGA ACCTGCTGCT CGGCCACTCG ATCGGCGAGC TGTGCGCCGC GCATGTGGCC
2401 GGCGTCTGGT CCCTGCCCGA CGCGTGTGCG CTGGTCGCGG CCCGGGGTCG GCTGATGCAG
2461 GAACTGCCGG ACGGCGGGGC GATGGTGTCG CTGCGGGTCG CCGAGGACGA CGTGCTCGCC
2521 TCGCTCGAAC CGGTCCGCGA CCGGGTCTCG ATCGCGGCCG TCAACGGGCC GCTGGCCACG
2581 GTGATATCGG GCGACCGGGA CGCGGTCCTG GACGTCGCGG CCGGCTGGCG GGCACAGGGC
2641 CACAAGACCA CCCGACTGCG GGTCGCACAC GCCTTCCACT CACCGCGCAT GGACGCGATG
2701 ACGGACGCCT TCGCCGAGGT GGCCGCCGGG TTGACCGCTC GGGCACCCAC CCTGCCCGTC
2761 GTGTCGAACC TGACCGGCCT GCCGCTGACC GCCGAACAGG CCTGCTCCCC GGACTACTGG
2821 GTCCGCCATG TACGGCACAC CGTGCGCTTC CACGACGGAG TGCGCCGGCT GCGCGCGGAA
2881 GGCGCGACGA TACTGCTCGA ACTGGGCCCG GACGGCAGCC TGTCGGCGGC GGCCCGGACC
2941 TGCCTGCTCG ACGGCGAGCG GGACACCGTG GCCACGATCC CGACGCTGCG CCGCAACCGC
3001 CCCGAGACGG ACGCGTTGAC CACGGCGGTG GCCCGCCTGT ACGCCAACGG CGTGGACCCG
3061 GACTGGGAGC GGGTGTTCGC GGGGCGGGGG GCGCGCCGGG TCGCGTTGCC CACGTACGCC
3121 TTCCGACGCG CACGCCACTG GCCGGTGCC TCGGCGGAAG CCGCCGACAC CGCCGTGCCG
3181 GACGAATCGC TCGCCGTGGT ACCGACGTTG GCCGAGCGGT TGGCCGCCCT GTCCGCTGTC
3241 GAGCAGCATC GGATCCTGCT CGACCTGATC CGGGCACACG CGACCGCGGT CCTGGGCCCC
3301 GGCGCGACCA CGACCGTCGA ACCCGACCGC ACCTACCGCG AATCGGGCCT GGACTCGCTC
3361 GGCACCGTCG AACTGATCAC CAGGCTGGCC CGGGACACCG GCCTCGACCT GCCCCCGACC
3421 ACGGTCTTCG ACCACCCCAC ACCCACCGCG CTCGCCCACC ACCTGCGCAC CCGGGCGCTC
3481 GACCTGCCCG TGCCGACCCG CCCCGGCCG ACACCCGGGC CGGCCCGCGC CGACGAACCG
3541 ATCGCCATCG TGGCAATGGG CTGCCGGTTG CCCGGCGCGG TGCGCACCCC CGAGGACCTG
3601 TGGCGGCTGG TCGCGGACGG CGTGGACGCG ATCACGGCCT TCCCCACCGA CCGCGGCTGG
```

FIGURE 5 (Continued)

```
3661 GACCTGGACC GGCTCCACCA CGACGACCCG GACCGACCCG GCACCAGCTA TGTACGATCC
3721 GGCGGATTCC TGGACCGCGC GGGCGACTTC GACGCGGAGT TCTTCGGGAT CGGCCCGCGC
3781 GAGGCGCTGG CCATGGACCC GCAGCAACGG CTGCTCCTGG AGACCTCCTG GGAGGCGATC
3841 GAACGCGCCG GACTCGACCC GAGCACGCTG CGCGGCGAGC GGGTGGGGGT GTTCGTCGGC
3901 GCCACCGCGC AGGAATACGG CCCGCGCATG CACGAATCCA CCGACGCCCT CGCCGGGTTC
3961 CTGCTGACCG GCACCACGCC CAGCGTCGCG TCCGGGCGGA TCGCATACAC CCTCGGCCTG
4021 TCGGGCCCGG CGCTCACCGT CGACACCGCC TGCTCGTCCT CGCTGGTCGC GGTGCACCTG
4081 GCCGCCCGTT CGCTGGCGAG CGGGGAATGT GCGCTGGCCC TGGCGGGCGG CGCCACCGTG
4141 ATGGCCGGTC CCGGCATGTT CGTCGAGTTC GCCCGGCAGC GCGGCTTGGC CCCCGACGGT
4201 CGTTGCAAGC CGTTCTCGGC GGACGCCGAC GGCACGGCCT GGGCCGAGGG CGTCGGCGTG
4261 CTCCTGCTGG AACGCCTGTC CGACGCGCGC CGCAACGGCC ATCCCGTACT CGCCGTGCTG
4321 CGCGGCTCGG CGATCAACCA GGACGGGGCC AGCAACGGGC TCAGCGCGCC AACGGGACC
4381 GCCCAGCAGC GGGTGATCCG GGACGCGCTG GCCGCCGCCG GGCTCGATCC GCAAGACGTC
4441 GACCTGGTCG AGGCACACGG CACCGGGACA CCGCTGGGCG ACCCGATCGA GGCGCAGGCG
4501 CTGCTGGCGA CGTACGGGCG CGATCGGGCC GCCGATCGGC CGCTGCTGCT CGGCTCGGTG
4561 AAGTCCAACA TCGGCCACAC CCAGGCCGCG GCGGGTGTGG CCGGGCTGAT CAAGACCGTG
4621 CTGGCCCTGC GACACGGCGC GATACCGGGG ACGCTGCACC TGCGCGAACC GTCGCCCCAC
4681 GTGCGGTGGT CGGACGGGGC GGATCACGCTG CCGACGACGA CCACGGACTG GCCCGCGTAC
4741 GACCGTCCGC GCCGCGCGGC GGTGTCGTCG TTCGGGATCA GCGGGACGAA CGCGCACGTG
4801 ATCGTGGAGG AGGCGGGCGG GGGCGCGGAG ATACCGGGGC CTGCCCCTGC CCGCGGGCTT
4861 GCGTCCGCCG GTGTCGCCGA CCCCGTGCCG CTGGTGGTTT CCGCGCGGAG CGAGGCCGCG
4921 TTGCGGGGGC AGGCGGAGCA GCTTGCGGGA CTGCTGCGAG CGGCGGACGC TCCGGCCCTG
4981 GCCGATGTCG GATATTCGCT GCTGCGCGGC CGGGCCGGGT TCGAGTACAC CGCCGTGATA
5041 CCGGCGCGCA CCCACGCCGA GGCGCTGCAC GGGTTGACCG CGCTCGCCGC CGATCGACCC
5101 GCCGACCGGC TGATCCGGGG CGGCGCCGCG GCGGCCCGGG GCGGGACCGT GTTCGTCTTC
5161 CCCGGGCAGG GCACCCAGTG GTCCGGGATG GCGCTGGAAC TCCTTGACAC CAGCGAGCCG
5221 TTCGCCGCCT CCATGCGGGC CTGCACCGAC GCGCTCGACC CGTACGCCGT CGACTGGTCG
5281 CTGCTCGACG TGCTCCGCGA ACCCGGGACG CCGGGGTTGA CGCGCGTCGA TGTCGTGCAG
5341 CCGGCGCTGT TCGCGGTGAT GGTCTCGCTG GCCGCGCTGT GGCGCTCGAT CGGGATCGAA
5401 CCGCAGGCCG TGGTCGGCCA CTCGCAGGGC GAGATCGCCG CCGCGTACGT CGCGGGCGCA
5461 CTGTCCCTGG CCGACGCCGC CAAGGTGGTC GCCCTGCGCA GCGGGCACT GGTCGCGGCG
5521 GCGGGCAGCG GCGGGATGGC CCTCGTGTCG CTGCCCGCCG AACAGGTCGC CGCGCTGCTC
5581 GAACCCTGGG CCGGCCGACT CGGCGTGGCC GCCGTCAACG GGCCGAGCGC CACCGTGGTC
5641 AGCGGCGACA CCGCGGCACT GGACACGTTC CTGGACCGAT GCGCGGCGGA CGACCTGCGG
5701 GCCCGGCGGA TCCCCGTCGA CTACGCGTCG CACTCCGTGC ACATGGAGGA GATCCGCGAT
5761 CGACTCCTGA CCGACCTGGC CGACGTGACC CCGCGAGCCG CGTCGACAGC CTTCTACTCC
5821 ACCCTGACCG GCGGTCGCAT GGCCGACACG AGCGGCCTCG ACGCCGACTA CTGGTACCGC
5881 AACCTGCGTC GAACGGTGCG ATACGAGACG GCCGTTCGGG CATTGAGCGA GGACGGTCAC
5941 CGGCTGTTCG TCGAGGTCGG CCCGCACCCC GTGCTCACGC TCGGTACCCA GGAAACGTTG
6001 GACGCGTGCG GCAGCGGCGG CACCACGATC GGCACGCTGA GCCGCGACGA CGGCGGCCGG
6061 GCCCGCTTTC TGGTTGCGGT GGCGGAGGCC GTCGCGCACG GCGCCCGGCC CGACGCCGAA
6121 GCGCTGTTCG ACCCGCCCGG AACCGGAGTG CGGGCGGTTG CCCTGCCCAC CTACGCGTTC
6181 CAACACCGCC GCTACTGGCT GACCCCGCGT GAGGCGGCTC CGAGGGTAC GGCTGCCCTC
6241 GGTCTGACGC CGATCTCCCA TCCGCTGCTC GGCGCGCTTG GCGCGCTCGG CGTCGAGCCG
6301 GATGGCACGG TGATCGCGAC CGGTCGGATC TCGCTGCGGG AGTTGCCGTG GCTGGCGGAC
6361 CACGCGGTCG CGGACACCGT GGTGTTGCCG GGGACCGCGT TTCTCGAACT GGCCCTGTGC
6421 GTCGGGGAGT CCGTGGGTGC TCCGCAGGTC GAGGAACTGA CCCTGGAGAG CCCGCTGCTC
6481 TTGCCCGAGA CCGGTGACGT GTACCTGCGG GTTGCCGTGG CCCCGGCGGA CGAGGCGCGG
6541 CGACGGGCGG TCACCATCCA CTCCCGGCGT GCGGGTGGGG GCGGTGCCGA TGCGGAGCGG
6601 GAGTCGTGGG TTCGGCATGC GGGCGGGCTG CTCGTTGATT CGGTGCGGGA GGTGGACGAC
6661 GGCGGCAGTG GTGGGCTCAC CCAGTGGCCG CCGCCCGGTG CCGATGTGCT CGATCTCGCC
6721 GATGCCTACC CGGTGTTGGC GGGGCTCGGT TACGGCTACG GCCGGCCTT TCGGGGACTG
6781 CGTGCGGCTT GGCGCGGGGC CGGCGGCGAA CTCTTCGCCG AGGTGCGGCT GCCGGATGAA
6841 CTGCGGGAAT CGGAGTCGGG GGTGGTGGGG CCCGAGTTCG GGATTCACCC GGCGCTCTTG
6901 GACGCGGCAC TGCATCCGTT GCTTTCGTCG CTTTCGTTGA CTTCGTTGTC GTCGACGCGG
6961 GACGGACCGG CGGGTGCGCC GCCGCGTATT CCGTTCTCGC TGGCGGACGT GCGGCTGTAC
7021 GCCACCGGGG CCGACATGTT GCGGGTACGG CTGCGCCGGG CGGATGGCGG GGCCGCGGCG
7081 CTCACGGTTG CCGACGGCGT CGGTGCGCCG GTCCTGTCCA TCGGTGCGCT CACCCTGCGC
7141 GAACTGCCTG CGGACGGGCT GATCGGCGAG GAACCCGACC CGGGCGAGGC GATGTTCGAC
7201 CTGCGCTGGA TCGCCGGATC GATCCCGGCC GAGCCGACGG GTCTCGGGTA TGCGTTCATC
7261 GGGGACGACC TCGGCCTGGG CGACGGCGAG GTGTATCCGA GCCTCGCGGA TCTCGATGCG
7321 CGACTGCTCG CGACGGGGGA ACCCACGCCC GACGTGGTGT CGCCGCCGC ACCGGTGGGG
```

FIGURE 5 (Continued)

```
 7381 GTGGACGACG ACGTCCCGGG CGCCGCGCAC GACAGCGCGC GCTGGGCGTT GGACCTGGTC
 7441 GGGGGTTGGC TTGCCGGCGA GCGGTCGAGT GCGGCGCGGC TGGTCGTGGT CACCCGTGGT
 7501 GCGGTTGCTG CTCGGACCGG TGACGCGCTG TCCGGGCTGC CCGCAGCCCC CGTATGGGGG
 7561 CTGTTGCGGA CCGCGCAGTC CGAACACCCC GATCGTTTCG TGCTGATCGA CCTGGACGAT
 7621 GCGGTGCGAT CCCCTTCCGC GCTGCTTGGC GCGGCCGTTG CGGGTGAACC TCAACTCGCC
 7681 CTGCGTGACG GGGTGGTTCA TCTACCCCGC ATGGTGGCGG TGGATTCGGC GGACGCGCAG
 7741 GTGACTCGAC GCCGACCCGA TCCGAACGGG ACCGCGCTGA TCACCGGTGG CACCGGCACC
 7801 CTGGGTGCGC TGATCGCCCG CCGGCTGGCC GCCGAACACG GCATCCGGCA CCTGCTCCTG
 7861 CTCGGACGTG CGGGTCGGGA GGCCCCGGC GCCGAGGAGT TGATCGCCGA ACTCGGCGCG
 7921 CTCGGCGCCC GGGTGACCGT GGCCGCGTGC GACGTCGCCG ACCGGGCCGC GCTCCGCCGC
 7981 GTGATCGAGG ACATCCCCGC CGAGCACCCG CCCACGATCG TCGTACACGC CGCCGGTGTG
 8041 CTCGACGACG CGACGCTGTT GTCGTTGACC CCGGATCGGC TCGACGCGGT GCTGCGCCCC
 8101 AAGGTGGACG CGGCCTGGCA TCTGCACGAG CTGACCCGAG CGGCGAACCC GGCGGCGTTC
 8161 GTGCTGTTTT CGTCCATCAC CGCGATCACG GGCAACGCCG GCCAGGGCGC GTACACGGCG
 8221 GCCAACACCT TCCTGGACGC CCTCGCCGAA CACCGCCGCG CAGCCGGGCT GCCCGCCAAC
 8281 GCCCTGGCCT GGGGACTGTG GGCCGAGGGC AGCGGGATGA CCCGACACCT CGACCACACC
 8341 GACCGGGCCC GGATGTCCCG GGGCGGGATC GCGGCGCTGC CCACCGAGAC CGGACTCGCC
 8401 CTGTTCGACG CCGCGTTGCA CCGGGACCGC CCGTACACGA TCCCCGCCCG CCTGGACCGC
 8461 GGCGCGCTGC GGGCCCTGGC CGCGAGCGGT GTGCTGCCCG CCGTACTGCG CAGCCTCGTG
 8521 CGTGTCCCGC CGCCGCGTGC CGCCGCCTCC GGCGACGGCA CGGACGCGTC GTCGTGGCCC
 8581 CGGCGGATCC GGGAACTCCC GGGCGAGCAG CGGGAACGGG CGATCACCGA CCTGGTGCGC
 8641 GGGCAACTCG CCGCCGTCCT CGGACACGAC GCACCCGAAC GACTCGACCT CGACCGCGCC
 8701 TTCCGCGAAC TGGGAGTCGA CTCGCTGACC GCACTCGAAC TGCGCAACCG GATCAATGCG
 8761 TTCACCGGCC TGCGACTGCC CGCGACGGTG GTCTTCGACC ACCCCAGCGG TACGGCCCTG
 8821 GTCGCTCGGA TGATGCGCGA GCTGGTCGGT GCGGTGCCGA GCGAGCCGAC CACGCCCGTC
 8881 GTCGCACCGA CCGTGACGGT CGACGAGCCG ATCGCCGTCG TCGGCATCGG CTGTCGCTAT
 8941 CCGGGCGGTG TGGCCGGTCC CGAGGACCTG TGGCGACTGG TCGCGGCCGG CACGGACGCG
 9001 GTCGGCGACT TCCCCGAGGA TCGTGGCTGG GACCTGGCGA AGCTGTACGA CCCCGACCCG
 9061 GACAAGGTCG GCAAGGTCTA CACCCGTCGG GGCGGATTCC TCTACGAGTC GGGGGAGTTC
 9121 GACGCCGAGT TCTTCGGCAT CTCGCCGCGC GAGGCGGCGG CGATGGACCC GCAGCAGCGG
 9181 CTGCTCCTGG AGACCGCGTG GGAGGCGTTC GAGCACGCGG GCCTGGACCC CAGGACGCTG
 9241 CGCGGGAGCA ACACGGGTGT GTTCGCCGGG GTGATGTACA ACGACTACGC CTCGCGGCTG
 9301 CACCGCGCCC CCGACGGGTT CGAGGGCATG CTGTTGGCCG GCAACGTGGG CAGCGTCGTG
 9361 ACCGGCAGAG TGTCCTACGC GCTGGGCCTG GAGGGGCACG GGTCAGCGT GGACACCGCC
 9421 TGCTCGTCGT CGCTCGTGGC GCTGCACCTG GCGGCCAACG CGCTGCGGTC GGGGGAGTGC
 9481 GATCTGGCGC TCGCCGGTGG GGTGACGGTG ATGTCCACCC CGAACGTCTT CGTCGAGTTC
 9541 TCCCGACAGC GCGGCCTGTC GGCGGACGGC CGGTGCCGGT CGTTCGCGGC GGGCGCGGAC
 9601 GGGACGGGTT GGGGCGAGGG TGTCGGGCTG CTGGTGGTGG AACGACTGTC CGACGCGCGG
 9661 CGCAACGGGC ATCCCGTGCT GGCGCTGCTG CGTGGCTCGG CGGTCAACCA GGACGGCGCC
 9721 TCGAACGGGC TGACCGCGCC GAACGGACCG TCCCAGGAGC GGGTGATCCG GGCGGCGTTG
 9781 GCCGGTGCGG GGTTGTCGGC GACGGACGTG GACGCGGTGG AGGCGCACGG CACCGGGACG
 9841 ACGCTGGGCG ACCCGATCGA GGCGCAGGCG TTGTTGGCCA CGTACGGGCG GGACCGGCCG
 9901 GCGGATCGGC CGCTGTGGCT GGGCTCGATC AAATCGAACA TCGGGCACAC GCAGGCCGCG
 9961 GCGGGGGCGG CCGGCCTGAT CAAGATGATC ATGGCGATGC GGCACGGCGT ACTGCCCGAG
10021 ACACTGCACG TCGACGCGCC GTCGCCGCAC GTGGACTGGT CGACGGGACA CGTCGAGCTG
10081 CTGGCCGAAC GTCGACCGTG GCCCGAGGTC GACCGGGCGC GCCGGGCCGC CGTGTCGTCG
10141 TTCGGGATCA GCGGGACGAA CGCGCACGTG ATCGTCGAAC AGGCGCCGGC GGCCGAGGCG
10201 GTGGTGTCCC GGGACGAGCC GGTGGGTGTG GCGGGCCTGG TGCCGTGGGT GTTGTCGGCC
10261 AGGACCGCCG ACGGTCTGCG GGCGCAGGCG GCGCGGTTGC GGGAGTGGTC GGCGCGGCAT
10321 CCGGAGGCGG ATCCGGTCGA CGTGGGGTGG TCGTTGGTTC GGGAGCGGTC GGTTTTCGAT
10381 CGGCGGGCGG TGGTCGGTGG CCGCGATCCG GGTGAACTCG GGGCTGGGTT GGACAGGTTG
10441 GCCGCGGGTG GCGGTATTGC CGACGGTCGG CCGATGTTTT CGGGTCCCGG TCCGGTGTTC
10501 GTGTTTCCCG GCAGGGGTC GCAGTGGGTG GGGATGGCGG CCGGGCTGTT GGAGTGCTCG
10561 CCGGTATTTG CGGAGGCGGT GACGGAGTGC GCCGCCGTGA TGGATCCGTT GGTGGCGGAT
10621 TGGTCGTTGT TGGATGTGTT GCGGGGTGGG TCTGCCGGTG AGTTGGAGCG GGTGGATGTT
10681 GTTCAGCCGG TGCTGTTTGC GGTGATGGTG GGCTTGCGC GGTGGTGGGA GTCGTGTGGG
10741 GTCAAGCCGG GTGCGGTCAT CGGGCACTCG CAGGGGGAGA TCGCTGCCGC GCATGTGGCG
10801 GGTTATCTGT CGCTGGCGGA TGCGGTATGG GTGGTCGTGT TGCGGAGTCG GGCCCTGCTG
10861 GGGGTCGCGT CCGCCGGGGG CGGGATGGTG TCCGTCGGGG TGTCGGCGGA GCGTGCTCGC
10921 GAGCTGGTCG CCGGGGATGA CCGGCTGTCG TTGGCGGCGG TGAACGGGCC GACGAGTGTG
10981 GTGCTTTCGG GTGATGTCGA AGCGCTGTCG GTGGTTGTCG AGGCGTGCGA GCGGGATGGT
11041 GTGCGGGCTC GGTGGATTCC GGTGGATTAC GCGTCGCATT CGGCGCGGAT GGAGGCCGTG
```

FIGURE 5 (Continued)

```
11101 CGGGACGAGG TGGAGCGGCT GTTGGCGGAT GTGACGCCGC AGGTGGGCCG CGTGCCGATG
11161 TACTCGACCG TGAGCGGGGA GGTGGTCGTC GATCCCGCCG AGTTGGGCGG GGCGTACTGG
11221 TTCGAGAATC TGCGGCGCAC GGTCGAGCTT GAGCGGGCCG TGGGTGCGGC GGTCGCGGAT
11281 GGGCATGGTG CGTTTGTGGA GTGCAGCCCG CATCCGGGGC TGGTGGTGCC GATGGGGGAC
11341 ACCCTGGAGG CGGCCGGGGT GGACGGCGTC GTTCTGGAGA CGTTGCGGCG GGGTGAGGGT
11401 GGGCCCGATC GGCTGGTCGC CGCGCTCTCG GCGGCGTTCG TGGCGGGTGT CGCGGTGGAC
11461 TGGGCCGGAA TGTTGCCGGG GCGCCATGTC GAGCTGCCGA CGTATGCGTT CCAGCGGCGG
11521 CGCTACTGGT TGACGGGTGG GGAACGTGCG GGCGATCCGG CCGGGTTGGG GCTGGTCGCG
11581 GCCGATCATC CGCTGCTGGG GGCTGTCGTC GGTTCGGTGC GGGACGGGGA ACTCCTCTAC
11641 ACCGGGCGGT TGTCCGCCGC GACGCACGGC TGGCTTGCGG ACCACGCGGT GTTCGGCTCG
11701 GTGGTGGTAC CGGGGACGGC CTTCGTCGAG CTGGCGTCGT GGGTCGGTGT CGAGGCCGGT
11761 TGCCCGGTCG TCGACGAACT CACGCTGCAT GCGCCCCTGG TGCTGCCGGA CGGGGTCGGC
11821 ATCCGGCTTC GGGTGGCGGT GGGCGCGGCG GATTCGGCGG GGCGTCGGGT GGTGGAGTTC
11881 CATTCGCGGC CCGAGGATGC CCCCGACGAG CAGTCGTGGA CTCGGCATGC GACCGGCACG
11941 CTGGGTGCCG CGAGTGTGCC CGGATCCGCG TCGGCCGGGG CCGCGGCGTG GGCGGTCTGG
12001 CCGCCGGCGG ACGCCGAGGT GGTCGACCCG GAGGCCGTTT ACGAGCGACT TGCGGAGCAC
12061 GGGTACGAAT ACGGGCCGAT TTTCCGGGGG TTGCGGGCCG CATGGCGGCG GGGTGACGAC
12121 TTCTTCGCCG AGGTCGCGCT GCCGGAGGCG GCCGGTCGGG ACGCGCACGG CTACGACCTG
12181 CATCCGGCGG TGCTGGACGC CGCGCTGCAT GTGGCCGCGG CCGAGGCGGT GGCGGAGTCG
12241 GGGGCGACGT TGTTGCCGTT CGCCTGGACC GGGGTCGCAC TGCATGGGCC GGGGGCGTCG
12301 GTGCTTCGGG TGATGTTGCG GCGTACCGGG CGGGAGACGC TGGCGGTCGA CGTGGCCGAC
12361 GAGCGTGGTG TTCCGGTGGC GTCGGTCGCG TCGCTGACGC TGCCGCCGGT GGCTGCCGAC
12421 CAGTTGGTGG CGGCCGAGGA AGCGGGCCGC GAGTGGCTTT ACCGGATGGT CTGGGAGATC
12481 GCGGACGCGC CGGTGGCGGA GCACGTCGAG GGTGAACTTC TTGGTTCGGA TGAGGAGTCC
12541 GACGCGTCGG CGGAGCTTGT GGCGGGCGGG ATTCGGGTGG TGACCCCTGC GGGCGCCGAA
12601 CAGGTCTCCG AGGTGGGGCT GTTCGATTGC CGCCCCGTGG TCGGCGAAGC CCCCGAGGAG
12661 GTGGCCGGCG CCGTGCATGC GGTGCTGGCC GCGGTTCGGG CGTGGGTGGC GGACGAGCGG
12721 TTTGCCGGGG CGCGGCTGGT GGTTCGTACC CGTGGCGCGG TTGCCACGGA TGCGCAGGAC
12781 CGGGTCGGTT CTCCCGCGCA TGCGGCGATC TGGGGTCTCG TGCGGGTCGC GCAGAGCGAG
12841 CATCCGGGGC GCTTCGTCCT GGTCGATGGG GACGACGTCG ATTCGGGTGC GGCGCTGCGT
12901 GCGGCGGTGG CGTGCGGGCT GCCGCAGGTG GCGATTCGCG AAGGTGTGGT GCTGGCGCCG
12961 CGCCTGGTGG GGGCGGTGCA CGACACGGCG CTGGTGCCGC CGGCGCCGGG TGCGGATCAG
13021 GCGTGGCGGA TCGAGTCCGG GACGGCCGGG ACGCCGGACG ATCTGGTGGT GACGGCGCAT
13081 CCGGCCGCCT CGGCCGCCGTT GGCCGCCGGG CAGGTGCCGG TGGCGGTGCG GGCGGCCGGA
13141 GTGAACTTCC GCGATGTGCT GATCACGCTC GGCATGTACC CGGGGCGGGC GGTGGTCGGC
13201 GCCGAGGCGG CCGGGGTGGT CGTGGAGGTC GGCCCGGGCG TGTCGGAACC GGCCGTCGGC
13261 GACCGGGTGA TGGGCTTGTT CGAGGGGGCG TTCGGGCCGC TTGCGGTGGC CGATCGGCGG
13321 CTGTTGGCCC GGGTGCCGGC GGGTTGGTCG TTTGCTCAGG CGGCGTCGGT GCCGGTGGTC
13381 TTCCTCACCG CGCTCTACGG GCTGCACGAT CTGGCCGGGC TGCGGTCGGG TGAATCGGTG
13441 CTGGTGCATG CGGCCACGGG TGGGGTCGGC ATGGCCGCCA CCCAGCTGGC CCGGCATCGG
13501 GGCGCCGAGG TGTACGCGAC CGCGAGTGCG ACGAAGTGGG CCACCGTGCG CGGGCTGGGT
13561 GTTCCGGACG AACGGATCGC CTCGTCTCGG GACCTGTCCT TCGAACAGCG CTTCGCACGG
13621 GCCACGGACG GGCGCGGGAT CGACGTGGTG TTGAACTCGC TGGCGGGCGA GTTCACCGAC
13681 GCGTCGTTGC GACTCCTGGC CGAGGGTGGC CGGTTCGTGG AGATGGGCAA GACGGACGTC
13741 CGGACCGAGG GGCTGCCGGC CGGGGTGCGC TATCGGGCCT TCGACCTGAT CGAGGCCGGT
13801 CCGGATCGGA TCGCCGAGAT GTTCGTCGAC CTGCTCGAGC CGGTGTGCTG
13861 CAACCCCTGC CGATTCGGAC CTGGGACATC CGTCGGGCCC GCGAGGCGCT GCGTTTCCTG
13921 GGCCAGGCCC GGCATGTGGG CAAGGTGGTG CTGACCGTGC CGCAGCCGCT CGCGGCCGAC
13981 GGCACGGTCC TGATCACCGG CGGCACGGGC ACGCTGGGTC GCAGTCTGGC CCGACACCTG
14041 GTCACGCGGT GGGGTGTGCG CCGGCTGGTG CTGACCGGCC GGGCCGGGCC CGCCGCTCCC
14101 GGCGCCGCCG AACTGGTCGC GGAATTGGCC GAGTCGGGTG CCGACACCAC GATCGTGGCC
14161 TGCGATGCGG CGGACCGGGC GGCGATGCCC GAGGTGTTGG CCGCGATCCC GGCCGAACAC
14221 CCGTTGACCG CCGTGGTGCA TGCCGCCGGA ACACTCGACG ACGCGCCGAT CGAGGCGCTG
14281 ACCCCGGAGC GGGTCGACCA CGTGTTGCGG CCCAAGGTGG ACGCCGCCCT CGTACTGGAC
14341 GAACTCACCC GGGACGCGGA CCTGGCCGCG TTCGTGCTGT TCTCGTCGGT GGCCGGCGTA
14401 CTCGGTGTGG CCGGCCAGGG CGGCTATGCA GCGGGGAACG CGTTCCTGGA CGGTCTCGCC
14461 GGTCGGCGCC GCGAGCGGGG GCTGCCGCG ACCGCTCTGG CCTGGGGCCT GTGGGCGGAA
14521 CGCAGCGCAA TGACCGCGCA GTTGGGCGTC GGCACCTGA AGCGCCTGGC GCGCGGCGGC
14581 CTGGTGCCGA TCTCGACCGC CCAGGGGCTC GCCCTGTTCG ACGCCGCCTG ACAGGCCGAC
14641 GAGGCGGCGC TGATCCCGGC CCGCCTGGAC CTTGCCGCAC TGCGCGCACA GGCGGCGACC
14701 CAGCCGGTAC ATCCGCTGCT GCGCGGTCTG GTCGGCACCA CCCCGACCCG CCGGAACGGC
14761 ACACCTTCGG AGGCGCCGTG GGCCCGACGG CTCGCCTCGG CCGCGCCCGC CGAGCGGGTG
```

FIGURE 5 (Continued)

```
14821 GACGTGGCAT TGCGGCTGGT CCGGGCCGAG GCGGCGGTGG TCCTGGGGCA CGAGTCGATC
14881 GACGGGGTGC GGCCCGAAGT CACCTTCCGC GACCTCGGGT TCGACTCACT GACGGGTGTG
14941 GAACTGCGCA ACCGGCTGAG CGGCGCCACC GGATTGCGGC TGCCGTCCAC GCTGGTCTTC
15001 GACTTCCCGA CCCCGCTCGG CCTGGCCGGT TTCCTGGTCG CCGAGTCGGT CGGCGAGATG
15061 GACACGGCGC CGACCGGGCC GGTTGCCGGG GGTGCGGTGG TCGCGGCCGA TCCGGTGGTG
15121 ATCGTCGGGA TGGGCTGCCG ATTCCCGGGC GGGGTGGACT CGGCGGCGGG TCTGTGGGAC
15181 CTGGTGGCCG CGGGCGGCGA TGCGATCGGG CCGTTCCCGA CCGACCGTGG CTGGGACGTC
15241 GACGCGCTGT TCGATCCCGA TCCGGAGCGG GTCGGCAAGA GCTACGTCCG TACCGGCGGA
15301 TTCCTCTCCG GGGCGGCCGA GTTCGACGCC GAGTTCTTCG GTGTGTCGCC GCGCGAGGCG
15361 TTGGCGATGG ACCCGCAGCA GCGGCTGCTG CTGGAAACCG CGTGGGAGAC CTTCGAGCAG
15421 GCGGGCATCG ATCCCACCTC GCTCCGGGGC AGCCGGACCG GCGTCTTCGC CGGGATGGCC
15481 GGCCACGACT ACGCGACCGG GGGCGCCCGT TCGCAGGCCG GGCTGGAGGG CCACCTGCTG
15541 ACCGGGAACG CGGCCAGCGT GGCCTCGGGA CGGGTGGCCT ACACGTTCGG CCTGGAGGGG
15601 CCGGCGGTGA CCGTGGACAC GGCGTGCTCG TCGTCGCTGG TGGCGCTGCA CCTGGCGGCC
15661 AACGCGCTGC GGGCGGGGGA ATGCGACCTG GCGCTCGCCG GCGGGGTGAC CGCGATGTCC
15721 ACGCCGGACT TCTTCCTGGA GTTCTCCCGG CAGCGCGGAC TGTCCGTGGA CGGCCGTTGC
15781 AAGGCGTTCG CGGCCACGGC GGACGGGATG GGCGCGGCCG AGGGCGTGGG CCTGCTCCTG
15841 GTCGAGCGGC TGTCGGATGC GCGGCGCAAC GGGCATTCGG TACTGGCGGT GGTGCGTGGG
15901 TCGGCGGTGA ACCAGGACGG CGCGTCGAAT GGGTTGACCG CGCCGAACGG GCCGTCGCAG
15961 CAGCGGGTGA TCCGGGCCGG CCTGGCCGAC GCCGGGCTGT CCGCGGCCGA TGTGGATGCG
16021 GTGGAGGCGC ACGGGACCGG CACGACGCTC GGCGATCCGA TCGAGGCGCA GGCGTTGCTC
16081 GCGACCTACG GCGGGATCG GCGCCGGAT CGGCCGCTGT GGTTGGGGTC GGTGAAGTCC
16141 AACATCGGGC ACACCCAGGC GGCGGCGGGT GTGGCCGGGG TGATCAAGAT GGTCTCGGCG
16201 CTGCGGCATG GGATGTTGCC GCGCACGCTG CACGTGGACG AGCCGACGCC GCATGTGGAC
16261 TGGTCGGCGG GTGGGGTCGA ACTGCTCACG AGCGCGCGGG CGTGGCCGGA GGCCGGGCGG
16321 GTGCGTCGGG CGGGGGTGTC GTCGTTCGGG ATCAGCGGGA CGAACGCGCA TGTGATCCTG
16381 GAGCAGGCGG AGGAGAGCCC GGCGGGTTCG GTGCCTTCGG CGACTCCTCC GGTGGCCGGG
16441 ACTCCGGTGT GGGGCGGTCG GGTGCCCTGG GTGTTGTCGG CCCGGTCCGA ACCCGCTTTG
16501 CGGGCACAGG CCGCGCGGTT GCGGGACTGG CTGGCCGTAC ATCCCGACGC CGATCCGCTC
16561 GATGTGGGGC GGTCGTTGGC GACCGGGCGG GCGGCGCTCG ATCACCGGGC GGTGGTGCAT
16621 GGGCGGGACC TCGCGGAATT GCGCCTGGCG GTCGCGAAGT TGGCCGACAG CGGGCCGGGT
16681 GACGAGGCGT CGATCGTCGG CTCGGTCTCC GCCGCCGGTC CGGTTTTCGT GTTTCCGGGG
16741 CAGGGGTCGC AGTGGGTGGG GATGGCGGCC GGGTTGTTGG AGTGTTCGCC GGTGTTTGCG
16801 GGTGTGGTTG CCGAGTGTGC TGCGGTGATG GATCCGTTGG TGGCGGATTG GTCGTTGTTG
16861 GATGTGTTGC GGGGTGGGTC TGCCGGTGGT GAGGCGTTGG CGGAGCGGGT GGATGTGGTT
16921 CAGCCGGCGT TGTTCGTGGT GATGGTGGGG CTTGCGCGGT GGTGGGAGTC GTGTGGGGTC
16981 AAGCCGGGTG CGGTGATCGG ACACTCACAG GGGGAGATCG CGGCTGCGCA TGTGGCGGGA
17041 TATCTGTCGC TGGCGGATGC GGTGCGGGTG GTTGTGCTGC GGAGTCGGGC GTTGCTCGGG
17101 GTTGCGTCTT CCGGTGGCGG GATGGTGTCG GTGGGTGTGT CCGCCGATCG GGCCCGGGAG
17161 CTGGTCGCCG AGGACGACCG GTTGTCGCTG GCGGCCGTGA ACGGGCCGAC GAGTGTGGTG
17221 CTTTCGGGTG ATGTCGAAGC GCTGGCCGTG GTTGTCGACG GCTGTGAGCG GGACGGGGTC
17281 CGGGCTCGGT GGATTCCGGT GGATTACGCG TCGCATTCGG CGCGGATGGA GGCCGTGCGG
17341 GACGAGGTGG AGCGGCTGTT GGCGGATGTG ACGCCGCAGG CGGGCCGCGT GCCGATGTAC
17401 TCCACGGTGA GTGGGGGGCA CGTTACCGAC CCGAGTGTGC TCGGTGGTTC GTACTGGTTC
17461 GACAATCTGC GGCGTACGGT CGAGTTGGAG CGGGCCGTCG GAGCGGCGGT TGTCGACGGG
17521 CATTCGGTCT TCGTCGAGTG CAGTCCGCAT CCGGGGCTGG TGGTGCCACT GGGGGACACC
17581 CTGGAGGCGG CCGGGGTGGA TGGCGTCGTT CTGGAGACGC TGCGGCGGGG CGAGGGCGGT
17641 CCCGATCGGC TGGTCGGCGC GCTTTCGGCG GCGTTCCGGA GCGGTCTGGC CGTGGACTGG
17701 GCCGGGTCCG GGATGGTGCC GGGGCGGCGG GTCGAGCTGC CGACCTATGC CTTCCAGCGG
17761 CGGCGGTACT GGGTCGAGCC CGGCGAGAGG GCCGGCGGGG TCGGGTGGGG GCAGTTCACG
17821 GTCGAACATC CGGTGCTGGG CGCCGGGGTC GATCTGGCCG ACGGAGCCGG GACGGTCTTC
17881 ACCGGGCGGC TGTCCGCGGC CTCGCACGGG TGGCTCGCGG AGCATGTGGT GCTCGGCACG
17941 GTGATCGCGC CCGGCACGGC GTTCGTCGAC CTGGCGCTGC GTGCGGGGGC GACGGTCGGC
18001 CGGGCGACGG TCGAGGAACT GACCCTGCAC GCGCCGCTGA TCCTGCCCGA CGCGGGCGGT
18061 GTACGGATTC AGGTCGGGGT CGGCGCACCC GACGCCGCCG GGGTCGGATC GGTGGAGATC
18121 CATTCCCGAC CGGAGGACGC GGCCGGCGAC GAGCCATGGA CCCGGCACGC CTCCGGGACC
18181 CTGACCGCGA CCGACCTCGA CCCGGCGGAC GTGGCCACGG AGGCGGCGAT CTGGCCGCCC
18241 GCGGGCAGTA CGCCGGTCGA TCTGGACGGA GCCTACGAGC GACTGGCCAC GGCCGGATTC
18301 GAGTACGGTC CCGCCTTCCA GGGGCTGCGA GCCCTGTGGC GGCGCGGCGC CGAGTCGTTC
18361 GCCGAGATCG AACTCGCGGA CGACGCACGG CAGGAGGCCG AACGCTACGA GGTGCATCCC
18421 GCGCTGTTGG ATGCGGCCGT GCATGCGCTG GGGATGGAGC CGACGGCGGA GGTTGCGCCG
18481 GATGAGGCGC GGATTGCCTT CTCCTGGCGA GGGGTTCGGC TGGTTGCCGC CGGAGCGGGG
```

FIGURE 5 (Continued)

```
18541 CGGTTGCGGG TGCGGCTGGC ACCGGTGGGC TCGGACGCGG TGTCGTTGTG GCTGAGCGAC
18601 ATGGACGGTG AGCCGGTCGG GTCGGTCCGG GCCCTGACCG TGCGGCCGGT CGCGGCCGAG
18661 CGGCTGCGTC CGGCTGGGGC GCCGCCGCGC GACTCGATGT TCCGGGTGGA GTGGCGGCCG
18721 GTGTCGGGCG ACGAGTCGGG CGTGGCGGTT CGCTGGGCGG TGGTGGGCGC GGCGGACTCC
18781 GGGCCGCTTG CCCGGCTGGT GGCGGCGTAT CCGGATGTGC CGGTGTACCG CAGTGTGGTC
18841 GAGGCGGCCG GGGATGTGGC GGCGGGACCG CCCGATGTCG TGGTGGTGGG CGTGGGCGAG
18901 GCCGACTGTT CGGAGGGGTC GGTCGAGCGC ACTCGGCGGG TGCTTGCGGA CGTGCTGGCG
18961 TGGATGCAGG ACTGGCTGGC CGACTCCGC TTCGCGGCGA CGCGCCTGGT CGTGGTGACC
19021 TCCGGGGCCG TCGCCGCCGA CGTGGACGCC GACCCCGACG AGCGGGTGGC GGACCTGGCC
19081 GGCGCGGCGG TGTGGGGGTT GTTGCGCTCG GCCCAGTCCG AACACCCCGA CCGATGCACG
19141 CTGGTCGACC TCGACGAGGA CGCGGCGTCG ATTGACGCCT GGCCGGCGAT TCTTGCCTCC
19201 GCCGAGCCGC AACTCGCCGT CCGGATGGGC CGATTCCGGG TGCCTCGGCT GGCCAGGGTG
19261 ACTGCCGGGG GCGGCGAGCC GGTCGCCTTC GCGCCCGACG GCACGGTGTT GGTCACCGGT
19321 GCCACCGGCG GCCTGGGCGC CCTGGTGGCC CGGCACCTGG TGACCGCGCA CGGCGTGCGC
19381 CGACTTCTGC TGCTGTCCCG CCGGGGCGCG GCCGCACCCG GCGCGGCCGA ACTGGTCGAG
19441 GACCTGACCG CGCAGGGGGC GGAGGTCACC CTCGCCGCCT GCGATCTGGC CGATCGTGCC
19501 GCGCTGGCCG CCGAGTTGGC GCGTATCCCG GCCGAGCACG CGCTGACCGG CGTGATCCAC
19561 ACCGCCGGAG TGGTGGACGA CGCCACCATC GCGAACCTGA CCGATGCGCA CATGGAACAC
19621 GCGCTGCGCC CCAAGGCGGA CGCCGCGTTC CATCTGGACG AGTTGACCCG GGACGTGAAC
19681 CCGGCCGCAT TCGTCCTGTT CTCCTCCGGG GCCACCACCT TCGGTGGCCC GGGACAGGGC
19741 AACTACGCGG CGGCCAACGC CTTCCTGGAC GGCCTGGCCC GGCAGCGCCG CGACCGCGGC
19801 CTGCCCGGGA TCTCGCTGGC CTGGGGCCTG TGGGCGGGCG CGCAGGGGAT GGGCGGGCGG
19861 CTGAGCGAGG CCGACCTGGC CCGCTGGGCC CGGACCGGCG CGGTGGCGAT GCCGGCGGCC
19921 GAGGCACTGC GGTTGTTCGA TATCGCGCTG GGCCGGCCCG AGGCGGCCCT GGTGCCGGCA
19981 CACCTGGACC TCCCGGCGAT GCGGGCGGAT GCCGGTGCTC GACCCGCGCT GTTCCGCGAG
20041 TTGCTCGGGA TCGGTACGCG ACGGGCGGCA GTGGGCGCGG GCGGGTCGGC GCTGACCCGG
20101 CGGCTGGCGG GGATGTCTCC GGCCGAGCGG GAGCAGGCGG TCCTGGACGT GGTGCGGACC
20161 GAGGCCGCGA ACACGCTGGG ACACGAGTCG GCCGGGGCGG TGTCGGCCGG GCGAGCGTTC
20221 AAGGAGCTGG GGTTCGACTC GCTGACCGGG GTGAACTGC GCAACCGGTT GAACACCGCG
20281 ACCGGGCTGC GGTTGCCGTC CACGCTGGTC TTCGACTACC CGACGCCGGC GGGGCTGGCG
20341 GCGTTCCTGG TCGCCGAGTT GGTCGGTCGT TCGGTACAGG CGGTGCCGGT GCCGCCGGTC
20401 GGTGGGCGGC ACGGGGACGC CGACGATGCG ATCGTGATCG TCGGCATGGG CTGCCGGTTC
20461 CCGGGCGGGG TGGCCTCGCC GGAGGACCTG TGGAATCTGC TGGCCTCGGG TGGGGACGCG
20521 ATCGGACCGT TCCCGACGGA CCGGGGATGG GACCTGGCCG GGCTGTTCGA CCCCGATCCC
20581 GAGCGGGCCG GGAAGAGCTA CGTGGAATCG GCGGATTCC TGTATGGGAT CGGCGAGTTC
20641 GACGCGGAGT TCTTCGGGAT CTCGCCGCGT GAGGCGTTGG CGATGGATCC GCAGCAGCGG
20701 TTGCTCCTGG AGACGGCGTG GGAGACGTTC GAGCGGGCGG GCATCGATCC GACCTCGCTG
20761 CGCGGCAGCC GGACCGGGGT TTTCGCCGGG GTGATCGACA ACGACTACGG CGCCCGGGTG
20821 AACCAGGTGC CGGACGAGGT CGAGGGCTAT CTGGGCTACG GCAGTTCGGC CAGCATCGCG
20881 TCCGGGCGGG TCTCGTACGT CCTGGGCCTG GAGGGCCCGG CGGTCAGTAT CGACACCGCG
20941 TGCTCGTCGT CCCTGGTCGC GCTGCACCTG GCGGTGAACG CGGTGCGGTC GGGCGAATGC
21001 GAACTGGCCC TGGCCGGTGG TGTGACGGCG ATGGCCACCA CCGAGTTCTT CGTGGAGTTC
21061 TCCCGACAGC GGGGCCTGTC GCCGGACGGC CGCTGCAAGG CGTTCGCGGC GGCGGCGGAC
21121 GGGATGGGCG CGGCCGAGGG CATCGGGCTG GTGCTGGTGG AGCGGTTGTC GGATGCGCGG
21181 CGCCATGGGC ATTCGGTACT GGCGGTGGTG CGTGGGTCGG CGGTGAACCA GGACGGCGCG
21241 TCGAATGGGT TGACCGCGCC GAACGGGCCG TCGCAGCAGC GGGTGATCCG GCAGGCGTTG
21301 GGTGCTGCGG GCTTGTCTGC GGCGGATGTG GATGCGGTGG AGGCGCACGG GACCGGGACG
21361 ACGTTGGGTG ATCCGATCGA GGCGCAGGCG TTGTTGGCGA CCTATGGGCA GGATCGGCCG
21421 GGGGATCGGC CGCTGTGGTT GGGGTCGGTG AAGTCGAATA TCGGGCACAC GCAGGCGGCT
21481 GCGGGTGTGG CCGGGGTGAT CAAGATGGTG TTGGCGCTGC GGCATGGGGT GTTGCCTCGG
21541 ACGTTGCATG TGGACGAGCC GACGCCGCAT GTGGATTGGT CGGCCGGGCG GGTCGAGGTG
21601 TTGGCGGACG AGGTGCGTG GCCGGCAGGG GAGCGGGTGG GCCGGGCGGG TGTGTCGTCC
21661 TTCGGAATCA GCGGGACGAA CGTGCACGTG GTCCTGGAGG AGGCGCCGGC GGACGCCGCC
21721 GAGCCTGCGC CCGCCGCGCC GGAGGTCCCG GGCGTCGGCG GCGTGCTGCC CTGGGTGGTG
21781 TCGGCGCGCA CCGAGGCCGG GCTGCGGGCG CAGGCGGCGC GGTTGCGGGA TTGGGTGAGC
21841 GAACATCCGG ACGCCGAACC GACGGATGTC GCACGGTCGT TGGTGGTCGG GCGAGCGGTG
21901 TTGGACGTGC GCGCGGTGGT GCGCGGGCGG GAATCCGGCG AACTTGTCGC CGGCCTGGAC
21961 GAGTTGGCGC GGGCCGGGGT GGGAGACCCC GGCTCGCTGG TGAGCGGCTC GGATCCGGTG
22021 TTCGTGTTTC CGGGGCAGGG GTCGCAGTGG GTGGGATGG CGGCCGGGTT GTTGGAGTGT
22081 TCGCCGGTGT TTGCGGGTGT GGTTGCCGAG TGTGCTGCGG TGATGGATCC GTTGGTGGCG
22141 GATTGGTCGT TGTTGGATGT GTTGCGGGGT GGGTCTGCCG GTGAGTTGGA GCGGGTGGAT
22201 GTTGTTCAGC CGGTGCTGTT TGCGGTGATG GTGGGGCTTG CGCGGTGGTG GGAGTCGTGT
```

FIGURE 5 (Continued)

```
22261 GGGGTCAAGC CGGGTGCGGT GATCGGGCAC TCGCAGGGGG AGATTGCGGC TGCGCACATC
22321 GCGGGTTATC TGTCGCTGGC GGATGCGGTG CGGGTGGTTG TGCTGCGGAG TCGGGCTCTG
22381 CTGGGGGTTG CGTCTTCCGG TGGCGGGATG GTTTCGGTCG GGGTGTCTGC GGAGCGGGCG
22441 CGGGAGTTGG TTGCCGGAGC TGACGGGTTG TCGTTGGCGG CGGTGAACGG GCCGACGAGT
22501 GTGGTGCTTT CGGGTGATGT CGAAGCGCTG TCGGTGGTTG TCGAGGCGTG CGAGCGGGAT
22561 GGTGTGCGGG CTCGGTGGAT TCCGGTGGAT TACGCGTCGC ATTCGGCGCG GATGGAGGCC
22621 GTGCGGGACG AGGTGGAGCG GCTGTTGGCG GATGTGACGC CGCAGGTGGG CTGCGTGCCG
22681 ATGTACTCGA CCCTGACCGG TGCGCCGATC GCCGATCCCG CCGAGTTGGG CGGGGCGTAC
22741 TGGTTCGAAA ACCTGCGGCG CACGGTCGAG TTGGAGCGGG CGGTCGGTGC GGCAGTGGCG
22801 GATGGGCGCA CCGTGTTCGT CGAGTGCAGT CCGCATCCGG GGCTGGTGGT GCCGCTGGGG
22861 GACACCCTGG AGGCGGCCGG GGTGGATGGC GCGGTTCTGG AGACGTTGCG GCGGGGTGAA
22921 GGTGGGCCCG ATCGGCTGGT CGCCGCGCTC TCGGCGGCGT TCGTGCGTGG TCTGGCGGTG
22981 GATTGGGCCG GGTTGATCGT CGGTGCTCGG GTGGAGTTGC CGACCTACGC CTTCCAACGA
23041 CGGCGCTATT GGTTGGACGA CGGGGCGCGG TCGGGGGATC CGGGCGGGTT GGGACTGGCC
23101 GCGGTCGCAC ATCCCCTGCT GGGTGCGGCG GTACGGCCGG CGCAGGGCGC GGGGTTGTTG
23161 TTCACCGGAC GGTTGTCGAC GGCGACCCAC CCGTGGCTCG CGGATCATGT GGTGCTCGGC
23221 TCGACGATCG TGCCCGGCAC GGTGTTCGTG GACCTGGCGC TGTGGGCCGG GGCCGAGGCG
23281 GAGTGCCCGG TGGTGGACGA ACTGACCCTG CACACCCCGC TGGTGCTGCC GGAACACGGC
23341 GGCGTGCATG TACAGGTGAC CGTCGACGGG CCGGACGCCG CCGGGGCCCG GGCGGTCGCG
23401 GTGTACTCCC GGCCGGAGGA CGCTCCCGGC GAGGAGCCGT GGACCCGGCA CGCCGTCGGT
23461 GCCCTCGTTG CCGACGCCGA TACGGGTGCC GCTCCCGACG CGGCTGCGGA GGCGTGGCCG
23521 CCGGTCGGCG CGAAGCCGAT CGAGGTGGCG GACTTCTATG CGCGGCTGGT GGAGTCCGGG
23581 GTCGACTACG GGCCGGCGTT TCGCGGGATG CGGGCCGCCT GGCGGCGCGG GGACGAGCTG
23641 TTCGCCGATG TGGCGCTGCC GGCCGAGGAG GAGCGCGACG CACACCGCTT CGGGGTACAT
23701 CCGGCGCTGC TCGACGCGGG CGTGCAGACC CTGCGGGTGG ATCCGGGGCA GGTCGACGAG
23761 GACGACATCC GGGTGGCCTT CTCCTGGCAC GGGGTGCGGC TCTTCGCGGC CGGCGTGACC
23821 CGGCTGCGGG TGTCGTGCGT GCCGTCGGGC GAGGGTGCGG TGTCGTTGCG GATCACGGAC
23881 GAGACCGGAC GGGCGGTCGC CGCGATCGAG GCGTTGACGG TGCGGCGAT CTCGGCCGAC
23941 CAGCTACGGC GGGCCGGCGG CGGGCGGGAC GTGCTGTACC GGCTCGCGTG GCGGGCATCG
24001 GCGGTTCCCG TACCGGTGGC GACGCCTCGT GTGGCGGTGG TCGGCGGGTG GGATCTGCCC
24061 GGTCTGGGCG GGTTGGTGGA CCGGTATCCG GGCTTTGCCG AACTTGCTTC GTGTGACCCG
24121 CCGTTGCCCG ATCTGGTACT GCTCCCGGTT GGTGATCCGG ATGCGGATGT GCCGTTCTCC
24181 GAGCGGCGTA TGCGGGAGGT GACGGCGGAA CTGATCGGGC GGCTGGAGGC GTTTCTCGGC
24241 GACGAACGGT TCGCGGCGGC CCGGGTGGTC GTGGTGACTC GTTCGGCGGT GCTCGTGGAC
24301 GGGGACGCGG GGCTCGGGGA CCCGGCGTCG CGTCGGTCT GGGGAGTGGT CCGGGCGGCG
24361 CAGGCCGGGC ATCCGGGGCG GATCGTGCTG GTCGACCTGG ACGACGAGCC GGCTTCGGCG
24421 GCGGCTTTGG CGGCGGTGGC CTCGGCCGGT GGTGAGCCGC AGTTCGCGGT GCGCGGTGGT
24481 CGGGTGTCGG TACCGAGACT GGAGCGGATT CCGGCCTCCG GCGGAGCACG GTCGGCGGTG
24541 GGGACCGGCA CGGTGTTGAT CGCCGGTGCG GACCGGGCGG TCGGCGCGGG GGTGGCCGAG
24601 CATCTGGCCG GGGCGTACGG GGTGGGCCGG TTCGTGTTGT TGTCCGTGGA TCCTTCGGGT
24661 GCGGGGCCGA CCGAACTGGC CGCCCGGCTG GGTGAGGCCG GTGCCGAGGT CGTCTCGGCG
24721 GCCTGGGACG GGCACGATCC GGGCGTGCTT GCCGCGCTTG TGACCGAACA CCGGCCGGCG
24781 GGCGTGGTGG ACGCGTCGGG CGAGTCGGAT GCAGCCTGGG CCCTGCACGA GCTGACCGCC
24841 GACGTGGACC CGGCGTTCTT CGTGCTGTTC TCGTCGGCGG CGAGCCTGCT CGGTTCGTCG
24901 GCGCATGCGG CCACGGCCGG GGTGGATGCC TTCCACGATG CGCTGGCCGC ACATCGGCGG
24961 GCGAGTGGGC TGCCCGGGGT GTCGCTTGCG TGCGGGACGG ATCCGCTGCC GGGGCTGCCC
25021 GACCTGTTCG ACGAGGCGAT ACGCCGGGAG GACGCCGTGT TGGTTTCGGC GTCGACGGAT
25081 CTCACCGGGC CGCGTCGAC GTCACCATTG TTGCCCTCCC GGAACGGTCG TGGCGCGACC
25141 AACTCCGCCG AGACCTCGAT CGAGGCGGAC GGCGAGGCCC TGGCCCGGCG CCTGGCGGCG
25201 TTGTCCGAGG AGGAGCGCGA GCGCGAACTG GTCGGCCTGG TACGGGCCCA GGCCGCGGCG
25261 GTGCTCGGGC ATGCCGGCAT CGGCGAGATC GGACCCGAAC GGGCGTTCAA GGAGGTCGGG
25321 TTCGACTCGC TCACCGCGGT GGAACTGCGC AACCGGCTGA TCCGGGGCAC CGGGGTCGGC
25381 CTGCGCTCCA CCCTCGTCTT CGACTTCCCC ACGCCGCGAA TACTGGCCCG CCACCTGAGC
25441 GGCCGGCTGG TCGAGGCGGC ATCCCCGATC GGTGCGCTGC TGGCCGATCT GGACCGATTC
25501 GAGGGCGAGT TGCACGCGGT GCTCGGCGAG GCGGAGGCCC GCGACCGGCT GGCCGAGCGG
25561 CTGCGTCGGC TGTTGGCCGA CTGTACCGCG CCGGACGAGA GCGCCCCGC CGCCGACGAT
25621 GTCTCGGACG TGCAGTCGGC CACCGACGAC GAGTTGTTCT CGCTCGTCGA CCAGGGCTTC
25681 GAATGACCCG GCCCATCCAC GCATACGACC GTGTCGGCAA GGAGTAGAGG CAACGTGGCT
25741 GAGTCGGAAG AGAAACTGCG CTCGTACCTG CGGAAGGCCA TCACCGATGC GCGCGACGCG
25801 CATCGCCGGG TACGCGAGTT GGAGGACCGG CAGCGCGAGC CGATCGCGAT CGTGGGCATG
25861 GCCTGCCGCT TCCCCGGCGG TTTGGGTACG CCGGAGGACC TGTGGCGGTT CGTCGTCGAA
25921 GGCGGCGATG CGATCGGCGA GTTCCCCGACC GACCGGGGCT GGGACCTCGA CGGCCTGTAC
```

FIGURE 5 (Continued)

```
25981 GACCCGGATC CCGACCGGCC GGGCACGTCG TACGTCCGCG AGGGCGGATT CCTGTACGAC
26041 GTCGCCGACT TCGACGCCGA GTTCTTCGGC ATCTCGCCCC GCGAGGCGGC GGCGATGGAC
26101 CCGCAGCAGC GACTGCTTCT GGAGACCTCT TGGGAGGCCG TGGAACGCGC GGGCATCGAC
26161 CCGACGTCGC TGCGGCACAG CCGGACCGGG ATCTACACCG GGATCAACGG CCTCGACTAC
26221 ACGACCGTGT TGGCCCGCAC CGCCAAGGGC CGGGACGGCA CGCTCGGCAT GGCCAACGGG
26281 GCCAGCCTGC TGGCGGGTCG GGTGGCGTAC ATCCTCGGCC TGGAGGGGCC GGCGGTGACC
26341 GTGGACACGG CGTGTTCGTC GTCCCTGGTG GCACTGCACC TGGCGAGCAA CGCACTGCGG
26401 TCGGGGGAAT GCGACCTGGC CCTGGCCGGC GGTGCGACGG TGATGTGCAC GCCGGAGATC
26461 TTCGTCAACT TCAGCCGGCA GCGCGGACTG GCCCGCGACG GCCGATGCAA GCCGTTCTCG
26521 GCGGCGGCCG ACGGGTTCAT CCTCTCCGAC GGCGCGGGCC TGTTCCTGAT CGAACGGCTC
26581 TCCGACGCGC GGCGCAACGG ACATCCGGTA CTGGCCGTGC TGCGCGGTTC GGCGATCAAC
26641 CAGGACGGCG CGTCGAACGG GCTGACCGCG CCGAACGGCC CGGCCCAGGA GCGGGTGATC
26701 CGGCAGGCCC TGCAGAGCGC CGGGTTGGTG ACCGGTGACG TGGACGCCGT GGAGGCACAC
26761 GGCACCGGGA CCACGCTCGG CGACCCCATC GAGGCGCACG CGCTGTTGGC GACCTACGGG
26821 CAGGATCGGC CCGCGGATCG GCCGCTGAGG CTCGGGTCGA TCAAGTCCAA CATCGGACAC
26881 ACCCAGGCCG CCGCGGGGGT GGCCGGGATG ATCAAGATGG TGTTGGCCCT GCGGCACGGC
26941 GTGCTGCCCA GGACGCTGCA CGTCGACGCG CCCTCGCCGC ACATCGACTG GTCGGCCGGG
27001 CGGGTGGAAC TGCTCACGGA GCCCGTGCCG TGGCCGAGGT CGGACCGGCC GCGCCGGGCC
27061 GGTGTCTCGT CGTTCGGGGC GAGCGGGACG AACGCGCACG TGGTGGTGGA GGAGGCGCCG
27121 TCGGACGGCG ACGACGGTGT CGTGGAGGTG CCCGCGCCCA CGGGCATCGG CAGTGTCCTG
27181 CCGTGGGTGT TGTCGGCCCG ATCCGAGCCG GCGTTGCCGC GCAGGCGGG GCGATTGCGG
27241 GACTGGCTGG CCGAGCACCC CGAGGCGGAT CCGGTCGACG TGGGCCGGTC GTTGGCGGTG
27301 GGGCGTGCGG TGCTGGAACG TCGCGCCGTG GTGCGCGGGC GGGATGTCGC CGAACTCGCC
27361 GTCGGGATCG GCGAGGTGGC CGACCGCGGA GAACTCGCCG GTGGGCGGCC GATGTTCGCC
27421 GGACCCGGTC CGGTGTTCGT GTTTCCGGGG CAGGGGTCGC AGTGGGTGGG GATGGCGGCC
27481 GGGTTGTTGG AGTGTTCGCC GGTGTTTGCG GGTGTGGTTG CCGAGTGTGC TGCGGTGATG
27541 GATCCGTTGG TGGCGGATTG GTCGTTGTTG GATGTGTTGC GGGGTGGGTC TGCCGGTGGT
27601 GAGGCGTTGG CGGAGCGGGT GGATGTGGTT CAGCCGGCGT TGTTCGCGGT GATGGTGGGG
27661 CTTGCGCGGT GGTGGGAGTC GTGTGGGGTC AAGCCGGGTG CGGTGATCGG ACACTCACAG
27721 GGGGAGATCG CGGCTGCGCA TGTGGCGGGA TATCTGTCGC TGGCGGATGC GGTACGGATC
27781 GTGGTGTTCC GCAGTCGGGC GCTGCGCGGG ATCGCGGCGG CCGGTGGCGG CATGGTCTCC
27841 GTGGGCGTGT CCGTCGAGCG TGCCGAGGAA CTGGTGGCCG GCTCTGCCGG GTTGTCGCTC
27901 GCGGCCGTCA ACGGGCCGCA GAGCGTGGTG CTTTCCGGCG ACCGTGAGGC ACTGGCCGCC
27961 GTCGTCGACG CGTGCGAGCG CGAGGGTGCG CGAGCCCGGT GGATCCCCGT GGACTACGCG
28021 TCGCATTCCG CGCACATGGA GGTGGTCCGG GACGAGGTCG AGCGTTTGTC GGCCGAGGTG
28081 ACGCCGCGGG CGGGTCGGGT GCCGATGTAC TCGACGCTGA CCGGGGAAGT CGTCACGGAC
28141 CCGGCCGAGT TGGGCGCCGG CTACTGGTTC GAGAACCTGC GCGGGACGGT ACGGCTGACC
28201 ACCGCAGTGG GGGCAGCCGT TGCCGACGGA CACGTCGCCT TCGTCGAGTG CAGCCCGCAT
28261 CCGGGCCTGG TCGTGCCGCT CGCGGACACC CTCGATGAGC TGGGCGTCGA CGACGGCACG
28321 GTCCTGGAGA CGTTACGGCG GGACGACGGC GGCCCCGATC GGCTGGTCGC CGCGCTCTCG
28381 GCGGCGTTCG TGGCGGGTGT GCCGGTGGAC TGGGCCGCAC TGTTTCCGGG CGAGGGGCGG
28441 GCCGACCTGC CCACGTACGC CTTCCAACAT CGGCGCTATT GGGCCGAGGC CGAATCGCCC
28501 GCAGGCGGCG GCGTGGCCTG GGGGCAGCGC GCGGTGACGC ATCCGGTACT CGGCGCCGCC
28561 GTCGACCTGG CCGGCGACGC GGGCACCGTG TTCACCGGGC GGCTGTCGAC GACCGCCCAA
28621 CCGTGGCTGG CCGACCACGC CGTGCTCGGC ACGGTGATCG TGCCCGGGAC GGCGTTCCTG
28681 GACCTGGTCC TGCGGGCCGG AGCCGAGGTC GGCTACCCGG CGATCGAGGA ACTGACCCTG
28741 CACACGCCGC TCGTGCTGCC GGACGCCTCG GCGTCCTGG TACAGGTCGT GGTCGGTGCC
28801 GCGGACGGCG ACGGCGGCGA CGGCGGCGAC GGGGCCCGGA CGGTCGATGT GCACTCGCGG
28861 GCCGAGGACG CGCCGCCGGA CCACCCGTGG ACCCGGCACG CCTCGGGGGT GCTGGTCGCG
28921 GCGGGCGAGG AGCGGGCCGA GGACGCGCCG GCCGGGCGGT GGCCGCCGAC CGGTGCCGAG
28981 GTGGTGGGGG TCGACGACGC CTACGAGCGG CTGGCGGTGG CGGGCTTCGA CTACGGCCCC
29041 GTGTTCCAGG GGCTGCGGTC GGTCCGGGCG CGAGGCGACG AGTTGTTCGC CGAGGTGGAG
29101 TTGCCGGAGG AGGGGCACGC GGACGCGGAC CGGTTCGCGG TGCACCCGGC GCTGCTCGAT
29161 GCCGCGTTGC ACCCGCTGGT GGTCGCGGCC GGTGCCGACG CGCCGGTCGT GGCCGGGCTG
29221 CCGTTCGTGT GGCACGGCAT TCGGGCGGGT GTTCCCGGGG CGCGACGGTT GCGGGTTCGG
29281 CTGGTGCGCT CGGCGTCGGG GTCGGCGTCG GGGTCGGCTG CGGGCTCGGA CTCGGCTTCC
29341 GGCGAGGTGT CGGTCCGGGC GTGGGACGAG GGCGGCCGGG AGGTGGTGGC GATCGAGTCG
29401 CTGACCATTC GCCCGGTCTC GGCGGACGGG TTGCGGACGC CCGATGCTTT GGTCCGCGAC
29461 TCCCTGTTCA CGCTCGCGTG GACCGCGTTG GAGCTACCGG ACGTCGATGA CGACGTGCCG
29521 AACGCGACCC TGCTGGGCGG CGACGGTGCG GCCGATCTCG CCGCGCTGGT GGCTGCCATG
29581 GACACCGGAA CGGACGTACC GGCTCTGGTG GCTCTGCCCG TATCGGTCGA CGACGCGGAC
29641 CCCGTGGCGG CGGCGCACAC GGCCGGCCGG CAGGTGCTGG CGGTACTCCG GGACTGGCTG
```

FIGURE 5 (Continued)

```
29701 GCGGACGAGC GGTTCGCCGA CTCTCGGCTG GTGTTCGTCA CCTCCGGCGC GGTCGCGGTC
29761 GCCGACGAGC AGGTACGTCC GGCCTCGGCG GCTGTCTGGG GCCTGGTCCG CTCCGCCCAG
29821 TCCGAACACC CGGGGCGCTT CGTCCTGGTG GACGCGGACT CCGTCGCCGA CCCCGGCCCG
29881 GAGTTCGACC GGGCCCTGCG GACCGGTGCG GACCAGCTGA TCCTGCGAGA TGGAACGGCC
29941 CTGATACCGA GGCTGGTTCG AGCCCCGGCG GACGGCGGAT CGGGCGGATT CGTGCCCGCT
30001 GCCGACGGCA CGGTCCTGAT CACCGGCGGC ACCGGCACCC TGGGCACGCT GCTTGCCCGG
30061 CACCTGGTCA CCGAACACGG CGTGCGCCGG CTCCTGTTGC TCAGTCGGCG CGGCGGTACG
30121 GCCGCCGGCG CGACGGACCT GGTCGCGGAA CTCGCCGCGT TCGGTGCCGA GGTGACCTGC
30181 GTGGCCGGGG ACGCCGCAGA CCGCGCCACG CTGGAGCGGG TGTTGGCGGA CATCCCCGCC
30241 GAACACCCGC TGACGGCGGT GATCCACGCG GCGGGTGTGG TGGACGACGG CGTCGTACAG
30301 TCCCTCACCG CCGACCGGCT GGACGCGGTG TTGCGCCCTA AGGTGGACGC CGCGTGGAAC
30361 CTGCACGAGG CGACCCGGCA CCTGGACCTG ACCGCGTTTG TGCTGTTCTC CTCTGCGGCG
30421 GGTGTGCTCG GAAACCCCGG CCAGGGCAAC TACGCGGCGG CCAACGCCTT TCTCGACGCG
30481 CTCGCACGCC GCCGGCCGCG TGAGGGCCTG CCCGGCAGCT CGTTGGCGTG GGGCTGGTGG
30541 GCGCCGACCA GCGAGATGAC CGCGGGGCTC GGCGACGCCG ACCGGCAGCG GATGGCGCGT
30601 TTGGGTGTAC TGCCCCTGGC GCCGGAACAG GGGTTGGCCC TGTTCGACGC GGCGACGAAC
30661 CATGCCGAAC CGACACCGAC CGTGGTCCGG ATGGACCTCG CGGTGCTACG CACCGCCGGA
30721 TCGGTGGTGC CCACGCTGCT GCGCGGTCTG GCCCGGGTGC CCAACCGGCG GGCTGCGACG
30781 GCGGGTTCGG TGGCCGAGCT GCGCCGTCGT CCGGCCGGCG TATCGGCCTT CGACTGGGAG
30841 CAGACGCTGA TCCGGGCGGT GTGCGTGCAT GCCGCCGCCG TCATCGGCCA CGCCGACGCG
30901 ACCGAGATCG ATGAGACACG GCGTTCCGC GACCTGGGCT TCGATTCGCT CACAGGTCTG
30961 GAGCTGCGCA ATCGACTGAA CACGGCAACC GGACTGCGGC TGCCCGCCAC GCTGGTCTTC
31021 GACTACCCCA GCCCGGTGGT CCTGGGCCGG TGGTTGCGTG ATCGGCTCGC CGAGGAGGAC
31081 GCCGGGGGCC CGGTCGGCTC GACCCTCGGA GCGCAGGTGG TGTCGCCGGT CGGTTCCGAC
31141 GCCGGCGAGG ACTCGATCGT GATCGTCGGC ATGGGCTGCC GGTTCCCCGG CGGGATCACC
31201 GCGCCCGAAC ACCTGTGGGA CGTGGTGGCC GGTGGGGTGG ACACCCTCAC CGACTTCCCC
31261 ACCGATCGTG GCTGGGATGT CGAGCGCATC TTCGACCCGG ACCCGGACCG ACCCGGCAGC
31321 ACCTACGTGC GCACCGGCGG ATTCGTGGAC TCGGCCGCCG ACTTCGACCC GGACCTCTTC
31381 GGGATCTCGC CGCGTGAGGC GTTGGCGATG GATCCGCAGC AGCGATTGCT CCTGGAGACG
31441 GCGTGGGAGA CGTTCGAGCG GCGGGCATC GATCCGACCT CGCTGCGCGG CAGCCGGACC
31501 GGGGTTTTCG CCGGCGCCAT CTACTACGAC TACGCGGGTG GCCGGCTGCG GAAGGTGCCG
31561 GACGAACTGG AAGGCTACAT CGGCAACGGC AATGTGGGCA GCGTCGCCTC GGGCCGGGTG
31621 GCCTACACGT TCGGTCTGGA GGGGCCGGCG GTCACCGTGG ACACGGCGTG CTCGTCGTCC
31681 CTGGTGGCGC TGCACCTGGC GGTGAACGCG GTGCGGTCGG GCGAGTGTGA ACTGGCCCTG
31741 GCGGGTGGCG TCACCGTGAT GTCGACGCCC AGCGTCTTCC TCGACTTCTC CCGGCAGCGC
31801 GGCCTGTCGT CCGACGGCCG GTGCCGGTCG TTCGCGGCGG CGGCGGACGG CACCGGGTGG
31861 GGTGAGGGTG TCGGGTTGGT GCTGGTGGAG CGGTTGTCGG ATGCGCGGCG CAATGGGCAT
31921 CCGGTTCTGG CGGTGGTGCG TGGGTCGGCG GTGAACCAGG ACGGCGCGTC GAATGGTTTG
31981 ACCGCGCCGA ACGGGCCGTC GCAGCAGCGG GTGATCCGGC AGGCGTTGGG CAGCGCCGGG
32041 TTGTCGCCCG CCGATGTGGA CGCCGTGGAG GCGCACGGAA CCGGGACGAC GTTGGGTGAT
32101 CCGATCGAGG CGCAGGCGTT GTTGGCGACC TATGGGCAGG ATCGGCCGGG GGATCGGCCG
32161 CTGTGGCTCG GGTCGGTCAA GTCCAACCTC GGGCACACGC AGGCGGCTGC GGGTGTGGCC
32221 GGGGTGATCA AGATGGTGTT GGCGCTGCGG CATGGGGTGT TGCCTCGGAC GTTGCATGTG
32281 GACGAGCCGA CGCCGCATGT GGATTGGTCG GCCGGGCGGG TCGAGGTGTT GGCGGACGAG
32341 GTGGCGTGGC CGGCGGGGGA GCGGGTGCGC CGGGCGGGTG TGTCGTCCTT CGGAATCAGC
32401 GGGACGAATG CACACGTGGT GCTGGAAGAG CCGCCGCCGG TGACCGAAGT GCCGGATGTG
32461 GCCGTCGAGT CCGGGCTGGG CGGGCGGCAC ACCTGGGTGG TGTCGGCGCG GTCCGAGGCA
32521 GCGGTACGGG AACAGGCGGC CCGGCTGCGC GACTGGGTCA CGGCCCGTCC GGATCTCGAT
32581 CCGGCGCACG TGGCCCGGTC GTTGGTGTGC GAACGGGCGC TGTTCGGCCA TCGGGCGGTG
32641 GTCTCCGGCG CCGATCTCGC CGAGCTGGCC GATGGGTTGT CCGCCGTGGC GGCGGGCGCC
32701 GAGGGCGCGG TGGTCGGTGC GGTGGGGTCG GGGCCGGGGA AGACGGCCGT GCTGTGCACG
32761 GGTCAGGGGG TGCGGGCGCT CGGTATAGGC CGCGAACTTC ACGCGGCGTT CCCGGTGTTC
32821 GCCGGCGCCC TGGACGAGGT GTGTGCGGCC TTCGACGATG TGGTGCCGTT CTCGGTGCGG
32881 GACGTCGTGC TCGGTGCCGA AGGGGTGTCG GATGCCGACG CGCAGGACAC CGGGGTGGCC
32941 CAGCCGGCGC TGTTCGCGTT CGAGGTGGCG CTGTACCGGC TGTGGGCCTC GTGGGGGCAG
33001 GCGCCCGACT TCGTGGTGGG GCATTCGCTC GGCGAGATCG TTGCGGCGCA TGTGGCGGGA
33061 GTGTTCTCGC TCGCGGATGC GGTGGTCTTC GTCGCGGCGC GGGCTCGGTT GATGAGTGCG
33121 CTGCCGAGTG GAGGGGCGAT GCTCGCCGTC GGTGCGAGCG AGGCCGAGGT GGCGGCGTCG
33181 TGCCCGGCCG AGGTGACGAT CGCAGCGGTG AACGGCCCGG CGAGTGTGGT GGTTTCCGGA
33241 CCCGCCGAGG CGGTGGCCGC GCTCGAACCG GACTGCGTGA TGCGCGGGTG GCGGATCTCG
33301 CGCCTGTCGG TGTCGCACGC CTTCCACTCG GCGCTGATGC AACCGATGTT GGCCGAACTC
33361 CGCGAGGTGC TGACCGGGTT GACCTACGGC ACGCCCGAGA TCGCGGTGGT GTCGGACACC
```

FIGURE 5 (Continued)

```
33421 ACCGGGCGGG TTGCGGGCGC CGAAGAGTTG GCTGATCCCG AGTACTGGGT GCGGCACGTA
33481 CGCCGCGCGG TGCGCTTCGG GGATGCGATC GCCACGCTGC GCGCCGAAGG GGTACGGACC
33541 TTCGTGGAGA TCGGGCCGGA GGCGGCGTTG ACCGCGATGG TGGTCGAGGG CACGGCCGGC
33601 GCGGAGGACG TGGCCGCCGT AGCGACCCGG CGTCGGGGTC GAGCGGCCGT GTCGAGTGTG
33661 GTGGAGGCGC TCGCCCGGGT GTTCGTGCAC GGCGCGACGG TGGATTGGGC CGCGTTGTCC
33721 ACCGGTTCCG GGCCCGGGGG ACGGGTGGAT CTGCCGACCT ACGCCTTCGA GCGGCGGCGC
33781 TTCTGGTTGC ACGCCGGTGT GGACGCGGGC GACGCGGTCG GCTGGGGCA GGGTGTGGTG
33841 GACCATCCGC TGCTCGGTGC GGTCGTGGGC CTGGCGGACG ACCAGGGCGT CCTGTTCACC
33901 GGCCGGTTGG CCCTGGACAC CCATCCGTGG TTGGCCGAAC ACACCGTCTT GGGCACGGTA
33961 TTGCTGCCGG GCACGGCATT CCTGGAGCTG GCCCTGCACG TCGGCCGCCT CCTGGACTGC
34021 GCGCGGGTCG ACGAGCTGAC CCTGTCGCCG CCGCTGGCGC TGCCGTCGAC GGGCGGTGTG
34081 CAGGTCCAGG TCCGAGTCGG TGTACCGGAG GAGAGCGGGA CACGGACGAT CACGGTGCAT
34141 GCCCGCCCGG ATTCGGCGGA GGAGGCGCCT TGGACGCTGC ACGCCGCCGG GGCCCTGGGT
34201 CCATCAGCCG AGGTGGATGC ACCCTCGGAT GCCGCGAGTT GGCCGCCTGC CGATGCGACC
34261 GCGATGGACT CGGCGGGGCT GTATCCCTGG TTCGCCGAGA CCGGCGTCGA CTACGGACCC
34321 TCGTTCCGGG GCGTACAAGC GACCTGGCGC CGTGATGACG AGGTGTTCGC GGAGATCGTG
34381 CTCGCGGCCG ACGACCCGGC CGCCGACGGC CGGTTCGAGC TGCACCCCGC GCTGTTCGAC
34441 GCCGCGTTGC ACCCGCTGGG CCTGACCCTG CTCGACGCGG CGGAGCCGCG CCTGCGGCTG
34501 CCGTTCTCCT GGCGCGGAGT GGCGCTGCAC ACGTCCGGGG CTCGCACGTT GCGGGTTCGG
34561 CTGCGTCCCA CCGGGCCCGA CACCATCGCG GTGACGGCCA CCGACGAGAC GGGTCGACCG
34621 GTGGTCGCGG TCGAGGCCCT GGCGGTGCGC GAACCCTCGC GGGACCGACT GCCACGACCC
34681 GACGCGAACG CGGGCGAGTT GTTCGAGCCG CAGTGGACGC CGCTGTCACC GGCGGACACG
34741 GCGGACATGG CGGACACGCT CGGGGCGGTG GTGGGCGGCC CCGAACTCGC CTCGACAGCC
34801 ACCCGATTCG GTGCCACACA TCACCCTGAC CTGGCCGCCC TGGCCGAATC GGCAATCCCC
34861 GAGACGGTCC TGTACGACCT GGTCACCGCC GTTCCCGGCG TATCCGCCGA AGCCGTACAC
34921 CAAGCCGCCG CCCAAGCGCT GGACCTGGCC CGATCCTGGC TCGCCGACGA GCGCTTCGAG
34981 TCGGCCCGCC TGATCGTGCG CACCCGACAC GCGGTCGCCG CCGCCGAAGG CGACGCGCCG
35041 GACCCGGCCG CCGCCGCGAC CCATGGCCTG TTTCGTACCG CCTGCTCCGA ACACCCCGAG
35101 CGGTTCGCGC TCGTCGACGC CGACGACCTC GACGAGGTCT CGCCCGAGGC CATCGCCGCC
35161 GTCGTGGTCG AGCCCGAGGC GGCCGTGCGG GCCGGTCGCG TCCTGGTTCC GCGCCTGCGC
35221 CGAGCGGCCG TGGCGCCCAA GGCCGACTTC GGCTTCGCCG CCGAAGGCAC CGTTCTGATC
35281 ACCGGTGGCA CCGGAGCACT GGGCCGGCAG GTCGCCCGGC ACCTGGTGCG CGTACACGGG
35341 GTGCGCCGCC TCCTCCTGCT CTCCCGTCGC GGCGACGAAG CCCCCGAGGC CGCCGAGTTG
35401 CGGGCCGAAC TGATCGAGGC CGGCGCGCAC GTCACCTTCG CCGCCGGAGA CGCTGCCGAA
35461 CGTGGCGTGC TGGCCGACGT GTTGGCCGCG ATCCCGGCCG CCCACCCGCT GACCGGCGTG
35521 GTGCACCTGG CCGGGGTGAC CGACGACGGG CTGGTCGGGA CGCTGACCCC CGAGCGGCTG
35581 GCGGCGGTGT TGCGCCCCAA GATCGACGCG CGCCTGCACC TGGACGAACT CACCGCCGAC
35641 GCCGACCTGT CGGCCGTTCGT CCTGTTCTCC TCGGCCGCCG GTCCGGTCGG CAACCCCGGC
35701 CAGGCCAACT ACGCGGCCGC CAATGTCCGC CTCGACGCGC TGGCCCGCCG GCGCCGAGCG
35761 CGCGGCCGAC CGGCCGTGTC GTTGCAGTGG GGGTTGTGGG CCGAACGCAG TGCGCTGACC
35821 GCGACGATGA GCGCGACCGA TCGGCGCCGG GCGGCCGGCG CGGGTGTGCG GGCGTTGTCC
35881 GTGGAGCAGG GCCTCGCACT GCTGGACGCG GCGGCCGGGC GGCCCGAGGC GGTGCTGACG
35941 CCGCTGCGCC TCGATCCGGC GATCCTGCGC GGTCCGGAGG AGCGGGTGGC GCCCGTGTTG
36001 CGCGGGCTGG TGCCGACCCG GGCCCGGCGT GCGCCGGCCC GTACCTCGGA CACCGCCCGC
36061 TCACTGGTGC GCCGATTGGC CGCGTTGCCC GAGGCCGAGC AGGACCGGCT GTTGGTCGAC
36121 CTGGTCCGTA CCCACGCGGC CGGTGTGCTC GGCCACGCCG ACGCGCGCAC GATCGACCCG
36181 GACCGCGCGT TCGGCGAACT GGGCCTGGAC TCGCTGGCGG CGTTGGAACT GCGCACCCGG
36241 TTGAGCACGG CGGTCGGGCT GCGCCTGCCC GCCACGATGT TGTTCGACCA TCCGTGCGCG
36301 CGTGCCGTGG GCGTACACCT GCGCGCGCAA CTGCTCGACG CGCCGACACC CGGGCGGGCG
36361 GCGGGTGTCG CCCGGCCGGT GTCGGACGAG CCGGTCGCGG TGGTGGCGAT CAGCTGCCGC
36421 TTCCCCGGCG GCGTCGCGAG CCCCGAGGAC CTGTGGCGGC TGGTGTCGGA ACACACCGAC
36481 GCCATCTCGG AGTTCCCGCA GGATCGGGAC TGGGACCTGG CCGAGCTGTT CCACCCGGAC
36541 CCCGAACATG CCGGTACCTC GTATGTAAGC GAGGGCGGAT TCCTTTACGA GGCAACCGAG
36601 TTCGACCCGG AGTTCTTCGG CATCTCGCCG CGCGAGGCGC TGGCCATGGA CCCGCAGCAG
36661 CGGTTGCTCC TGGAGGCGTC CTGGGAGGCG ATCGAGCGCG CCGGCGTGGA TCCCAGGTCG
36721 CTGCGCGGCA GTCGTACCGG GGTGTACGCG GGCCTGATGT ACGCCGACTA CGCGTCGCGG
36781 CTGGGCAGCG CGCCGGAGGG CGTGGACGGC TATCTCGGCA ACGGCAGCGC GGGCAGTATC
36841 GCGTCCGGGC GGGTGGCCTA CACGCTGGGT CTGGAGGGGC CCGGCGGTGAC CGTGGACACC
36901 GCCTGCTCGT CGTCCTTGGT CGCACTGCAC CTGGCGGCCA ACGCACTGCG CCAGGGTGAG
36961 TGTGATCTGG CGCTGGCGGG CGGGGTGACG GTGATGTCCA GCCCGGCCAC GTTCGTCGAG
37021 TTCTCCCGGC AGCGCGGCCT GGCCCCGGAT GCGCGGTGCA AGTCGTTCGC GGCCGGCGCC
37081 GACGGTACCT CGTGGTCCGA GGGCATCGGT CTGCTCCTGG TGGAACGCCT GTCGGACGCG
```

FIGURE 5 (Continued)

```
37141 CGCCGGTTGG GCCATCCGGT GCTGGCCGTG GTGCGCGGCA GTGCGATCAA CCAGGACGGC
37201 GCCAGCAACG GCCTGGCCGC GCCCAACGGG CTCGCCCAGG AGCGGGTGAT CCGGGATGCG
37261 CTCGCGCACG CCGAGTTGCG TCCGTCCGAC GTGGACGCGG TGGAGGCGCA CGGCACCGGC
37321 ACGCCGCTGG GCGACCCGAT CGAGGCGCGC GCCCTGCTCG CCACCTACGG GCAGGACCGG
37381 CCGGCGGATC GGCCGTTGTG GCTGGGGTCG GTCAAGTCCA ACCTCGGGCA CACCCAGGCG
37441 GCGGCGGGCG TGGCCGGCGT GATCAAGATG ATCATGGCGA TGCGGCATGC CGAACTGCCC
37501 GGGACGCTGC ACGTGGACGC CCCCTCACCG CACGTGGACT GGTCGGCGGG GGCGGTGTCG
37561 CTGCTCACCG CCGCGACCCC GTGGCCGCAG ACCGGGCGTC CGCGCCGTGC GGGGGTGTCG
37621 TCGTTCGGGA TCAGCGGGAC CAACGCGCAC GTGATCCTGG AACAGGGCGA CCCCGCCCCG
37681 ACCGCGCCCG CCGAACCGGC ACCGGCGTCG GCGCCTTTGG CCGCGCTGGC GTGGCCACTG
37741 TCCGGGGCGA GCGCGGTGGC ACTGCGCGGG CAGGCCGAGC GGCTGCGCGC ACATCTGGAC
37801 GCGCACCCCG AGTACGGGCC GGTCGACATC GCGCACGCGC TCGTCGGCGG CCGATCCCGG
37861 TTCGAACACC GCGCCGTGGT GGTCGCCGAG GACGCGGCGG GCCTGCGGGC CGGGCTGGAC
37921 GCGCTGAGCG CCGACCGGCC CGACGCGGCG GTGCCGGTGG GCGTGGCCGG CGAACCCGGC
37981 CGGATCGCCT TCGTGTTCGG CGGACAGGGT TCGCAGTGGC CCGGCATGGG CGCCCGACTG
38041 CTCACCGAGT CGCCGGTCTT CGCCGCCCGG ATCCGCGACT GCGACGCGGC ACTCGCGCCG
38101 CACACCGACT GGTCGCTGCT CGCCGTGCTG CGCGGCGAGC CCGACGCGCC GCCGCTCGAC
38161 CGGGTCGACG TGGTGCAACC GGTCGTTGTTC GCGGTGATGG TCGCGCTCGC CGAACTGTGG
38221 CGCTCGCTGG GCGTACGGCC GGCTTCGGTG GTCGGCCACT CGCAGGGCGA GATCGCCGCC
38281 GCCCACATCG CGGGCGCGCT CACCCTCGAC GACGCGGCCC GGATCGTCGC ACTGCGCAGC
38341 CGCGCCCTGC GCGGGTTGTC CGGCGACGGC GGGATGATGT CCGTCGCGGC CGGCCCGGAG
38401 CAGATCGCCC GATTGCTCGA CGGATTCGCG GACCGGCTCG GCATCGCCGC CGTCAACGGC
38461 CCCGCCGCCG TGGTGATTTC CGGCGCGGCC GACGCGCTCG CCGAACTGCA CGCCCACTGC
38521 GAGGCGGACG GGATCCGCGC CCGGGTGCTC CCGGTCGACT ACGCCTCGCA CTCCGCCCAG
38581 GTCGAGCAGG TCCGCGAGGA ACTGCTCGCC GCCCTGGGCG AGATCGTGCC CACGCCGACC
38641 ACCGACGCGG TCTTCTACTC CTCGGTCACC GGCGAACCCG TCGAGGGCAC CGCGCTCGAC
38701 GCCGAGTACT GGTACCGCAA CCTGCGCGCC ACCGTCGCCT TCGACCGGGC CACCGATGCC
38761 CTGCTGCGGG ACGGCCACAC GGTGTTCGTC GAGACCAGCC CGCATCCGGT CCTTGCGCCC
38821 GCCGTCGAGG ATAGTGCCCA GCGCGCCGGT ACGGACGTGA CGGTCGTGGG CAGCCTCCAG
38881 CGCGACACCG ACACCCTCGC CCGTTTCCTC ACCGCCGCGG CCGGCCTGCA CGTGCACGGC
38941 GTCCCGGTGG ACTGGTCCGC GACCCACGCC GGACACCGGC CCGGCCGGT CGACCTGCCC
39001 ACCTACGCAT TCCAACGCGA GGCTACTGG CTGGAGGCGG GCAAGACGCC CACCGACGCG
39061 GCCGGCCTCG GCCTGCACCC GGCGGCACAC CCCCTGTTGG GCGCGGCCGT GGTACCCGCC
39121 GAGGGCGACC GGCACATCCT CACCGGCCGC ATCTCGCTGC GCACCCACCC CTGGCTCGCC
39181 GACCACACGA TCCTGGACAC GGTGCTGCTC CCGGGCACCG CGTTCGTCGA ACTCGCCCTC
39241 CAGGCGGGCG ATCGGGCCGA CTGTGACCTG ATCGAGGAGC TGACCGTCGA GGCCCCGCTG
39301 CGGCTCACCG ACACCGGCGC CGTACACCTG CAGGTGTTGC TGGACGAGCC GGACGAGCAG
39361 GGCCGCCGAG CGCTGACCAT CCACTCCCGA GCCGACGACG CGCCCGCGGA GCAGACGTGG
39421 ACGCGGCACG CGAGCGGGGT ACTGGCGCCG GTCGCGGACG GCCTCGACGC CGTGCCGGCG
39481 ACCGACGCCG CGTGGCCGCC CGCCGGGGCC GTCGCGCTGG ACGTGGACGG GCTGTACGAG
39541 CGGTTGGCCG GGCAGGGCTA CCGGTACGGA CCGGCCTTCC GGGCGGTGCG GGCCGCGTGG
39601 CGCCTGGGCG ATACGGTCCT GGCCGAGGTC GCGCCGGGCG ACGAGGCGCA CGGCGCACGG
39661 GACTTCGCGC TGCACCCGGC CCTGCTGGAC GCCGCGCTGC ACGCCGCCGG CGCCGCCGAC
39721 AGCGGAACAT CCGGCGGGGA CGGTGCCATC GGCCTACCCT TCGCCTGGAC CGACGTACGC
39781 CTGCACGCCG TCGGCGCCGC CGCGCTCCGG GTCCGCCTGG AACGCGCCGG CCCGGACACC
39841 GTCGGCCTCG AACTCACCGA TCACACCGGC GCCTTGGTCG CCACCGTCGG TGCCCTGGTC
39901 GGCCGCCCCG CGACCGCCGA CCGGCTCGCG CCCGCCGCCG ACCGGCCCA CCGCGACCTC
39961 CACCACGTCG ACTGGTCCCC GCTGCCCACT CCCACCGAAC CCAGCACCGC CCGCTGGTCG
40021 TTGCTCGGCC CGGACGAACT GGAGGCGGTG GCCGGGCTGC GCGCCGCCGG CGCCGAGGTG
40081 CACGCGGACG GCGACCCCGA CCCCGCCGAC GTACTGCTGA TCACCTGCGC CGGCCGGACC
40141 GGGGACGACG TCCCCGAAGC CGCCCGGGCC GCCACACACC GCGTACTCGA CCTGCTCCAG
40201 CGCGCACTGA CCGACCCACG CCTCACCGCA TGCACCCTGG TCGTGCTGAC CGGGGCGCA
40261 GTACCCGGGC ACCACGGCGA GGACGTGTGC GACCTGGTCG CCGCGCCGAT CGTGGGCCTG
40321 GTCCGCTCCG CGCAGACCGA ACACCCGGGC CGGATCGTGC TGGTCGACCT GGACGACCAC
40381 GCCGACTCCT TCGCCGCGCT GCGCGCCGCC GTCGTCACCG ACGTCGGCGA ACCGCAACTG
40441 GCCATCCGCA CGGGCACCGT GTCCGCACCC CGACTGATCC GCACCGGCAC CGAACCGCGC
40501 CTGAGCCCGC CCGCCGGCGC CCCGGCCTGG CGGCTCGACC TGCTCGGCGG TGGCACCCTG
40561 GACCGGCTCG CGCTGCTCCC GAACGCCGAC GCGGCGGTCC CGCTCGCGCC CGGACAGGTC
40621 CGGATCGCCG TCCGCGCCGC CGGGCTGAAC TTCCGCGACG TCGTGGTCGC CCTCGGCATG
40681 GTCACCGACA CCCGCCCGCC CGGCGGCGAG GGGGCCGGAA TCGTAGTGGA GGTCGGCCCC
40741 GATGTGCCCG AACTCGTCCC GGGCGACCGG GTGATGGGCC TGTTCGGCGG CGGCACCGGA
40801 CCGATTACCG TGGCCGACCA CCGGCTGCTC GCGCCGATCC CCACCGGCTG GACCTACGCC
```

FIGURE 5 (Continued)

```
40861 CAGGCCGCGG CCGTCCCGGT GGTGTTCCTG ACCGCCTACT ACGGCCTGGC CGACCTCGGC
40921 GGGCTGCGCG CCGGCGAATC GCTGCTCGTC CACGCCGCCA CCGGCGGAGT GGGCATGGCG
40981 GCCGTGCAAC TGGCCCGGCA CTGGAACGTG GAGGTGTTCG GCACCGCCTC GCCCGGCAAA
41041 TGGGCCACCC TGCGCGGCCA GGGCGTGGAC GACGCGCATC TGGCGTCCTC GCGCGATCTC
41101 GACTTCGCGC ACCGGTTCGG CGAGGTCGAC GTGGTGCTCA ACTCGCTCGC GCACGAATTC
41161 GTCGACGCCT CACTGCGGTT GCTCGCGCCC GGCGGCCGAT TCCTGGAGAT GGGCAAGACC
41221 GACATCGCCG ACCGGGACGA GGTGCTTGCC GCCCATCCGG GCCGCGACTA CCGGGCGTTC
41281 GACCTGATGG ACGCGGGGCC GGAGCGGATC CGGGAGATGC TGGCCGACCT GTACCGGCTC
41341 TTCGAGACCG GCGTGCTGCA CCCGCTGCCC GTGACCCCGT GGGATGTGCG CGGTGCGGTC
41401 GGCGCGTTCC GGCACCTGAG CCAGGCCCGG CACACCGGCA AGATCGTGCT GACCCTGCCG
41461 CCCACCCTCG GCGCCGCTCC CGACCCGGAG GGCACGGTCC TGATCACCGG CGGCACCGGC
41521 ACCCTCGGCG GCCTGCTCGC CCGCCACCTC GTACGCACCG CCGGGGTACG ACACCTGCTC
41581 CTGATCGGCC GGCGCGGCCC GGCCGCCGAC GGGCGCGGCC AGTTGTCCGC CGAACTGACC
41641 GCGCTCGGCG CCCGGGTGAC CATCGCGGCC TGCGACGCCG CCGACCGTGC GGCGCTGGCC
41701 GCGCTGCTCG CCGACATCCC GGCCGAACAC GCGCTCACCT CGGTGATCCA CGCCGCCGGC
41761 GTGATCGACG ACGCGGCGCT GACCGCGCTC ACCCCCGAGC GGCTGGACCG GGTGCTGCGC
41821 CCGAAACTGC ACGCCGCCTG GAACCTGCAC GAGCTGACCC GCGACCTCGA CCTGGCCGAG
41881 TTCGTGCTGT TCTCCTCGAT GGCCGGCACC TTCGGCGGCG CCGGACAGGC CAACTACGCC
41941 GCCGCGAACG CCTTCCTGGA CGCGCTCGCC CAGCACCGCC GAGCCCGCGG CCTGGCCGCG
42001 ACCGCGGCCG CCTGGGGTCT GTGGGCGCAG GCCAGCGGGA TGACCGGACA CCTGGGCGCC
42061 GAGGACTGG ACCGCATTGC CCGCACCGGC GTCGCCGCGC TGGAGACCGC CCACGCACTC
42121 ACCCTGTACG ACGCGCTCCG CGCGGCCGAC CGCCCCACGA TCGTGCCCGC CCGCCTGGAC
42181 CCGGACGCGC TGCGCGCCGC CGCCCCGACC GTACCCGCAC TGCTGCGCGA CCTGGTGCGC
42241 GACCTGGTGC GCCCGCGCGG ACGCCGCGCC GCCGCCGACA CCGCGCCGGA CGCCGCGTCC
42301 CTGGCCGAGC GGCTGGCCCG ACTGCCCGAG GAGCGGCGCC GGCAGACGCT GCTGACCCTC
42361 GTCCGCACCG AGACCGCCGC CGTCCTGGGC CACGCCACCC CGGACGCGGT CGCCCCGCTG
42421 CGCCCGTTCA AGGCCCTCGG CTTCGACTCG CTCACGTCGG TCGAACTGCG CAACCGCATC
42481 GGTGCGGCGA CCGGCCTGCG CCTGCCCGTC ACCCTGGTCT TCGACCACCC GACCCCGCAG
42541 GCCCTCGCCG ACCACGTCGG CGCCGAACTC CTGGGCGTAG CGCCCGTGGT CGTCGAACCC
42601 GAGCGACCCG CCGCACACAC CGACGACGAC CCGATCGTGA TCGTGAGCGT CGGCTGCCGC
42661 TACCCGGGCG GGGTGGCCGG ACAGGACGAG ATGTGGCGGA TGCTCGCCGA GGGCACCGAC
42721 ACCATCGGGC CCTTCCCCCA AGACCGGGGT TGGGAGTTGG ACACACTCTT CGACCCGGAC
42781 CCCGACCGGG TGGGCAAGTC GTACGTCCGT GAAGGCGGAT TCGTCGCCGA CGCGGTGCAC
42841 TTCGACGCCG AGTTCTTCGG GATCTCGCCC CGCGAGGCGA CCTCGATGAA CCCGCAGCAG
42901 CGGCTCCTGT TGGAGACCGC GTGGGAAACG TTCGAGCAGG CCGGCATCGA CCCCACCACG
42961 CTGCGCGGCA GCGGCACGGG CGTGTTCGTC GGGGCCATGG CGCAGGACTA CCACGGCACT
43021 TCGCAGGCGA TGGCCGAGGG CCAGGAGGGC TACCTGCTGA CCGGGACCGC CACCAGCGTG
43081 ATCTCCGGCC GGGTCTCCTA CGTCCTGGGC CTGGAGGGGC CGGCGGTGAC CGTGGACACC
43141 GCGTGCTCGT CATCCCTGGT CGCCCTGCAC CTTGCGGCGA ACGCACTGCG TGCGGGTGAG
43201 TGCGATCTCG CGCTTGCGGG CGGGGTGGCG GTGTTGACGT CGCCGCAGGC GTTCATCGAG
43261 TTCAGCCGGC AGCGCGGACT GGCCGCGGAC GGGCGCTGCA AGCCCTTCGC GGCGGCGGCC
43321 AACGGCACCG GCTGGGGCGA GGGTGTCGGC CTGGTACTCG TCGAGCGGCT GTCCGACGCG
43381 CGCCGGCCGG GGCATCCGGT GCTGGCCGTG GTGCGCGGCT CGGCGGTCAA CCAGGACGGC
43441 GCCTCGAACG GGCTGACCGC ACCCAACGGC CCCTCGCAAC AGCGGGTGAT CCGACAGGCG
43501 TTGCGCAACG CGGGCCTGCT CGCGACGGAC GTCGACGCGG TCGAGGCGCA CGGCACCGGG
43561 ACCACGCTCG GCGACCCGAT CGAGGCGCAG GCGCTGCTGG CGACCTACGG GCAGGACCGG
43621 CCGGCGCAAC GGCCGCTGTG GCTGGGGTCG GTCAAGTCCA ACATCGGGCA CACTCAGGCC
43681 GCGGCGGGGG TCGCCGGGGT GATCAAGATG GTGCTCGCGC TGCGGCACGG GACGTTGCCG
43741 CCGACGTTGC ACGTGGACGC GCCCACGCCG CATGTGGACT GGGCGTCGGG ACAGGTGCGG
43801 CTGCTCACCG AGCCGGTGGC GTGGCCGGCG GGGGAACGGG TGCGTCGGGC CGGGATCTCC
43861 TCGTTCGGGG TGAGCGGGAC CAACGCGCAC GTGATCATCG AGCAGGCGCC GGCGGAGGGC
43921 GCGGTCGATG CCGCGCCGGT CGATGCCGCG CCGGCCGCCG CGCTCGGGGG GATCGTGCCG
43981 TGGGTGGTGT CCGCGCGATC CCAGGCCGGG TTGCGGGCGC AGGCGGCGCG GCTGCGGGAC
44041 TGGGCCGCCG TGCATCCGGA GTTTGCCCCG GCCGACGTGG CCGCCTCGCT GGTGCGCGGG
44101 CGGGCGGTGT TCGAGCGGCG CGCAGTGGTC GGGGTCGGG ATACCGACGA ACTGGTCGCC
44161 GCACTCGCTG AGTTGGTCGA CTCGTCGGCA ACGGGCGAGG CGCCGACGGC GATCGGGCCC
44221 GGGCCGGTGT TCGTCTTCCC CGGCCAGGGA TCGCAATGGG TGGGCATGGC GGCGGAGTTG
44281 CTGACGTGCT GCCCGGTCTT CGCGGAGACC GTCACGCAGT GCGCCGAGGT GATGGACCCG
44341 CTGCTGCCGG GCTGGGCGCT GCTCGACGTG CTGCGCGGCA CCGACGACGA GACGGCCGAA
44401 CTGCTGCGCC GGGTCGAGGT GGTGCAACCC GTGCTGTTCG CGGTGATGGT GGGTCTGGCC
44461 CGCTGGTGGG AGTCGTGCGG GGTGCGACCG GCCGCGGTGA TCGGGCACTC CCAGGGCGAG
44521 ATCGCCGCCG CGTACATAGC CGGCCACCTG ACCCTGCCGG ACGCCGCCCG GATCGCCGCG
```

FIGURE 5 (Continued)

```
44581 CTGCGGATCC GCGCGGTGCA GGCCGCCGAC ATGATCCGCG GCGCGATGGT GGCTGTCGCG
44641 GTATCCGCCC TGCGGGCCGA GGAGTTGATC ACCCGCACCG GCACCGGGGA CCTGGTCAAC
44701 GTGGGCGGGA TCAACAGCCG GACCAACACC GTGTTGTCCG GCGACACCGA CGCCTTGGCC
44761 CTGATCGTGG CCGACTGCGA GCGCGAGGGT GTACGGGCGC GCTGGATCCC GGCCGCGTAC
44821 TCCTCGCACT CGCCGCAGAT GGACGCTGTA CGCGGCGACC TGGAACGCCT GCTCGCGGGC
44881 ATCCAACCCA CCCCCGGGCG GGTGCCGATG TACTCCACGG TCACCGGCGG CCGACTCGCC
44941 GACGACGCGC TGCTCGACAT CGACTACTGG TTCGAGAACA TGCGGCGCAC CGTGCGGTTC
45001 GAGGAGGCGA TCGGCGCGGC GGCGGCCGAC GGACACACCG TGTTCCTCGA ATGCAGCTCG
45061 CACCCCGGCC TGGTGGTGCC GCTCGGCGAC ACCCTGGACT CGCTCGGCGT GCACGGCGCC
45121 ACCCTGGAGA CGCTGCGCCG CGCGGACGGC GGCGCCGATC GGCTGCTCGC CGCGCTCTCC
45181 GCGATGTTCG TGCACGGCGG CGCGGTGGAC TGGGCCGGGC TGCTACCGGG TCGCCGGGTC
45241 GCGCTGCCCA CGTACGCCTT CCAGCGTCGG CGGCACTGGG TGGAGCCCGT CGGACCGGCC
45301 CGAGGGGGCG TCGGCTGGGG GCAGTTCGCG GTGGAGCACC CGATCCTGGG CGCCGGGGTC
45361 GACCTGGCCG ACGGCTCGGC GACCGTGTTC ACCGGGCGCC TGGACACCAC CACACACGGT
45421 TGGCTCGCCG ACCACCTCGT GCTCGGCGAA GTCCTGGTCC CGGGCACGGT GTTCGTGGAC
45481 CTGGCGCTGC GCGCGGGCGG CGCCCTCGGC TGTGCGGTGG TCGAGGAGTT GGCCCTGCAC
45541 GAGCCGCTGG TGTTGCCGGA CGCGGACGGG GTGCGGATCC AGGTCACCGT CGAGGCACCG
45601 GACGACGCGG GTACGCGGGC GCTGACCATA CACTCCCGGC CCGAGGACGC GCCCGCCGCC
45661 GAGCCGTGGA CCCGACACGC CTCGGGCACG GTGGCCCCCG GCGCGCACCG GCCGCAGCAG
45721 GAGTCCGGCC CATGCCGCGC CGATCGGGCG ACGCCGCTGG ACGTGGCGGA CGTATATCTG
45781 CGGTTGACCG AACTGGCCT GGGCTACGGC CCGACGCTCG CCGGACTGCG GGCCGCGTGG
45841 CGGCGCGGCG ACGACCTGTT CGCCGAGGTC GCGCGCACCG CCGACGGCGA ACGTGGCACC
45901 GCCCGCTTCG GCCTGCACCC GGCCCTGCTC GATGCGGCCC TGCACGGGCT TGCCCCCGGC
45961 TCGGCACCCG GCGGCGCACC TACCGAGGTG CGGCTGGCCG GCGCCTGGCG CGGGGTGACG
46021 CTGGGCGGCG ATGCCGGTAC CGCCGGCCGG ATTCGGCTGC GGGGCGTCGA CGGGGACGGC
46081 GTCGAGGTCG AACTGGCCGA CGAGGCAGGT CGATCCATGG CCCGGATCGA GTCGGTGGCG
46141 CTGCGGCCAT GGAGCGCGGG GCAGGTGCGG GCGGCCGGGC GGGCCCGACC GTGGTTGACC
46201 CGCTGGGAGT GGGCCCGGGT CGAGCCGACC GACCGGCGG CGGCAGGAGG TCGCTGGGCC
46261 GTGCTCGGTG CGCGGGCTTG GACGGGGTG CCGGCCTATG CGACCGCCGC CGAACTGATC
46321 GCGGCCGTCG AGGTCGGCGT CCCGGTTCCG GATCTGGTCG CGCTGCCCGT GCGGATCGAC
46381 CCGGCCGGCG GGCTCGATCC GGAGGCGATC CGGGCCACGA TCCGGGCGGT GCGCGAGACC
46441 CTGCGGCAGT GGCGGGCCGA GCCGCGGCTG GCGGCCTCCC GCCTGGTCGT GGTGACCCAC
46501 GACGCGGTCT CGGCGCGGCC CGAGGACCGG GTCACCGATC CGGGCGCGGC GGCGGTGTGG
46561 GGCGTGGTCC GGGCGGCCCG GGCGGCGGAC CCCGAGCGGT TCGTGCTCGC CGACGTGGAC
46621 GGGGAGGACG GGTCCTGGCC GGTGCTGCTG GCCGAAGCGT CCGCCGGTCG CGCCGAGTTC
46681 GCGATCCGCG CGGGCACGGT ACTGCTGCCG GGCCTGGCCC GGGTACCGGC GGGCGAGACC
46741 GGCACGGCGG GCTTCCCGAC CGACGGCACG GTATTGGTCA CTGTCGCGAC CGACCCGACC
46801 GACCCGACCG ACGGCACCGA CCCGGTCGGC ACACTGCTGG CTCGGACACCT GGTGACCGCC
46861 CACGGAGTGC GCCGGCTGAT CCTGCCCGGC GGGCCCGCCG CCGGGATGCC GCTTGCCCGG
46921 GAACTGGCCG CGCAGGGCGC GGAGATCCAC GTGGTCGTCT GCGACGTGAC CGACCGCACC
46981 GAACTGGCGA AGCTGCTGGC CACGATCCCC GAGCACAGCC CGCTGACCGC CGTGGTGCAC
47041 ACCGCCGGGC TCGGCCGGTC GCACACCGAG GCCATGCTGC GGGCCCGGGT GGACGCGGCC
47101 GTACACCTGC ACGAACTCAC CCGCGACGCC GACCTGTCCG CCTTCGTGCT CTGCACCGCC
47161 CTGGACGGCG TACTCGCCGA CCCCGGGCGC GGCGAACACG CGGCCGGCGA CGCCTTCCTG
47221 GACGCCCTGG CCCGGCACCG GCACGCCGCC GGGCTGCCCG CGCTCGCGCT GGCCTGGGCA
47281 CCGGGGGCCG AACCGGTCGC CGGGCTGCTG CCGTTGCCCG GCGAGCAGGC CACGGTCCTG
47341 TTCGACCGGG CCCTCGGGCT GCCCGAACCG GCCCTGATCC CGCTCGCGCC GGACACCTCG
47401 GCGCTGCGCC GGGCCGAACC GGGCGCACTG CCGGCGCTGT TGACCACGCT GGTGGCCGAC
47461 CCGAACCACC GCGTCGGCGC CGCCGCCGAG GCGGCGCCCG CACTGATCGG CCGACTGCTC
47521 GACCTGCCGG ACGACGAGCG GGAAAGCGTC CTGGTCGACC TGGTTCGCGG CTGCGCCGCC
47581 GCGATCCTCG GTCATGCCGA TCCGACCGCG ATCGAGACGG GAGCGGCGTT CAAGGATCTC
47641 GGCTTCGACT CGCTGACCGC CCTGGAGATG CGCAACCGAC TGCGCGCCGC GCTGGGCCTG
47701 ACCCTGCCGG CCACGCTGAT CTTCAGCCAC CCCAACGCGG CGGCCCTGGG CCGGCACCTG
47761 CACGGCCTGC TGCGCCGCGA GCACGGGGTC TCGTGGGACT CGGTGCTCGG CGAGATCGAC
47821 CGGGTCGAGG CGATGCTCGC ACAACTCGAC GACGCGGCCG GCGCAGGGC GACGGAGCGG
47881 CTGCGGGACC TGATCCGGCA CCCGGAAGCC CCGCTCGCCG GCCGCGAGTC GGGCGCGAAC
47941 GGCGACGCGG CCGGCGGCCG AGGGTTCGAC GCGGCCACGG ACGAGGAGCT GTTCGACTTC
48001 ATCGACGGCG GGATCGAGCA CTGATTCGAC AACGGCGGGA TCGAGGACCG ACGACAGATC
48061 GCGGGGCTGG GACTCTCCCG TCCTCCTGAA CAGGCAAGGA GAAGCACCGA TGGCGAACGA
48121 AGACAAGCTC CGCGACTATC TGCGCCGGGC CACCACCGAA CTGCAGGAGA CCCGACTGCG
48181 GTTGCGCGAG ACAGAGGACA AGTGGCACGA ACCGCTCGCC ATCGTCGGCA TGCACTGCCG
48241 CTACCCGGGC GGGGTGGCCT CGCCGGACGA CCTGTGGGAC CTGGTCGACG CGGGCACCGA
```

FIGURE 5 (Continued)

```
48301 CGCGATCACC GGACTGCCCC CGGGCCGGGG CTGGGAGGTG GACGAGGCCG CGAACGGCAC
48361 GTCGTACCGG GGCGGTTTCC TGACCGACGC GGCCGACTTC GACGCCGACT TCTTCGGCAT
48421 CTCGCCGCGC GAGGCGCTGG CCATGGATCC GCAGCAGCGG GTGCTCCTGG AGGCGTCCTG
48481 GACGGTCTTC GAGCACGCCG GGATCGATCC GACCACGCTG CGCGGCAGCC GTACCGGGGT
48541 GTTCGTCGGG GTGATCGCCA GTGACTACCT GTCGCGCCTG GCCCGGGTGC CCAAGGAGGT
48601 CGAGGGCCAT CTGCTGACCG GCAGCCTGGT CAGCGTGGCG TCCGGTCGTC TCGCCTACCA
48661 CTTCGGGCTG GAGGGCGCGG CGGTCACCGT GGACACCGCC TGCTCGTCCT CGCTGGTGGC
48721 GGTACACCTG GCCGGCCAGG CGCTGCGCGC GGGCGAGTGC GACCTGGCCC TGGTCGGCGG
48781 GGCCACCGTC CTGGCCACCC CAGGCGCGTT CGACGAGTTC TCCCGGCAGC AGGGCCTGGC
48841 CGGCGACGGT CGTTGCAAGT CCTTCGCGGC CGGTGCAGAC GGCACCGGCT GGAGCGAGGG
48901 TGTGGGCCTG CTGTTGATGG AGCGGTTGTC CGACGCGCGC CGCAACGGAC ACCGGGTGCT
48961 CGCGGTGGTG CGCGGCTCGG CGGTCAACCA GGACGGCGCC TCGAACGGAC TGACCGCGCC
49021 GAACGACCTG GCCCAGGAGC GGGTGATCCG GCAGGCGCTG GCCAATGCCC GACTGGCCGC
49081 GAGCGACGTG GACGCGGTGG AGGCACACGG CACCGGCACC CGACTCGGCG ACCCGATCGA
49141 GGCCCAGGCG CTGCTGGCGA CCTACGGGCA GAACCGGCCG GCCGCACCGC CGTTGCGGCT
49201 GGGCTCGATC AAGTCGAACA TCGGCCACGC CCAGGCGGCG GCCGGGGTGG CGGGCGTGAT
49261 CAAGATGGTG CAGGCGCTGC GGCACGGTGT GCTGCCGCGC ACGTTGCACG TGGACGAGCC
49321 GACGCCGCAC GTGGACTGGT CCGCCGGGCG GGTGGCGCTG CTCACCGAGC CGATGGCGTG
49381 GCCGGCGGGT GAACGGGTGC GCCGCGCGGG GGTGTCCTCG TTCGGGGTGA GCGGGACCAA
49441 CGCGCACGTG ATCGTGGAGG AGGCGCCGCC GGTCGAGGAA CCGGTCGGGG CGGCCGATCC
49501 GGCGCGGCCC CTCGGCGTAG TGACGCCGTG GGTGGTGTCG GCGCGCACCG AGGACGGCCT
49561 GCGGGCCCAG GTGGAGAGGT TGCGGGAGTG GGCGATCGAG CATCCGGAGG CCGATCCGGC
49621 CGACGTGGGC CGGTCGTTGG CCTCGGGGCG GGCACTGTCC GGCCACCGGG CCGTGGTACT
49681 CGGCCGGGAC GCGGCGGAGT TGGTCGAGGG GTTGTCCGTC GTGGTGGACG GCGAGCCCGA
49741 GGCGATCGTG GGCGAGGCCC GGCGCGGATC GGGCCGTACC GCCGTGTTGT TCACCGGGCA
49801 GGGGGTGCGC TCGCGCGGGA TGGCGCGCGA ACTGCACGCG GCGTTCCCGG TGTTCGCGGC
49861 GGCGCTGGAC GAGGTGTGTG CCGCGTTCGA CGCGGTGTTG CCGTTCTCGG TACGGGACGT
49921 GCTGCTGGCA GAGGGCGAGG GCGGCGGCGC GGACGGTGAC GGCGGCGAGG ACACCGGTGT
49981 GGCGCAACCG GCGTTGTTCG CCTACGAGGT GGCGCTGTAC CGGTTGTGGA CCTCGTGGGC
50041 GGCGGCGCCC GACGCGGTGG CCGGGCACTC GCTCGGCGAG GTGGTCGCGG CCTATGTGGC
50101 AGGGGTGTTC TCGCTCGCCG ACGCAACCAC GTTCGTCGCG GCCCGCCGCA CGCTGATGAG
50161 CGCGCTGCCG CCCGGTGGCG CGATGGTCGC GGTGGGCACG TCGGAGAGCG CGGCGGCCCG
50221 GTTGCTCGCC GACCATCCGG GAGTGGGCAT CGCGGCGGTG AACGGGCCGA CCGGCGTGGT
50281 GCTTTCCGGC GAGGCGGCGG CCGTGGCGGA GGTTGCCCGG GTGTGTGCCG AGCGCGGGCT
50341 CCGCATCTCC CGGCTGCGGG TGTCGCATGC GTTCCACTCG GCGCTGATGG AACCGATGCT
50401 GGACGAACTG GCCGAGGTCG TCTCGGGATT GACGCTGCGT CCGGCGCGCA TGGCGATCGG
50461 GTCGAACGTG ACCGGCCGGA TCGGGTCGGC GGAGCAGCTG TGCGATCCGC GCTATTGGGT
50521 GGACCACGTG CGGCGCGCGG TGCGCTTCGG CGATGTGCTG GACGCGCTGC GCGCCGACGG
50581 GGTGCGTACG TTCGTCGAGA TCGGGCCGGA CGCCGCGTTG ACCCCGATGG TTGCCGATGT
50641 CACGGCCGAC GCCGACGATG TGGTGGCGGT CGCCACCCGG CGGCGTGACC GCGACCCGGT
50701 GACGGGTGTG GTCGAGGCGC TGGCCCGGGT GTTCGTGCGC GGCGCGGTGG TGGACTGGGC
50761 GGCGTTGGTG CCCGGACGGT GGGTCGAGCT GCCCACGTAC GCCTTCACCC GGCGGCGCTT
50821 TTGGCTGGAC GCCGGTACCG GCGCGGGCGA CCCGACCGGC CTGGGGCAGG GGACGGTGGA
50881 TCACCCGCTG CTCGGTGCGG TGGTCGGCCT GGCCGATGGA CACGGTTCGT TGTTCACCGG
50941 GCGGTTGTCC CTGGACACCC ATCCGTGGCT GGCCGATCAC GTCGTCCTGG ACACCGTCCT
51001 GCTGCCCGGG ACCGCGTTCG TGGAACTGGC CCTGCACACC GGGCGCCGGG TGGGCTGCGA
51061 TCGGGTCGAG GAACTGTCCC TGGAGACCCC GTTGGCGTTC GGCGAGCGCG GTGGTTGCCA
51121 GGTGCAGGTA TGGATCGAGG CGGCCGGCCC CGACGAGCGG CGGCGGGCGA TCACCATCCA
51181 CTCCCGGCCG GACGACGGAG ACGGCGACGA GGGGTGGATC CGCAACGCGG TGGGCACGGT
51241 CGCGCCGGTC GAGGACAAGG CGCCCGCCGA CGCCGTGGCC GACCCGACCC CCTGGCCGCC
51301 GACGGGCGCG ACACCCGTGC CGATCGACGA CTTCTACCCC TGGCTGGCCG ACAACGGCGT
51361 GGCCTACGGA CCGTGCTTCC GGGCGGTGCG CGCGGTCTGG CGTCGCGGGG AGGAGATCTT
51421 CGGCGAGATT GCGCTACCCG AGCAGGTCGG GTACGAGGCC GACCGGTTCG GCGTGCACCC
51481 CGCGCTGATG GACGCCACCC AACACCTTCT CGGGGTGGCC GCGTTCGCGG ACCCGGCGGA
51541 GAGCGAGGGC GGCGGTTTGG CGCTGCCGTT CTCGTGGCGT GAGGTACGGC TGCACACTCC
51601 CGGCGCGGCC TCGGTACGGG CGCGGGTGGT GCGGACCGGG CCGGAGTCGG TGACGCTGAG
51661 CCTGGCCGAC GAGGACGGCC GACCCGTCGC CGAGGTCGAG TCGTTGGCCG TGCGGCCGAT
51721 CTCGGCCGAA CAACTGCGCA CCTCCACGGC GGGTCGCCGC GACCCGCTGT ACACGCTGCG
51781 CTGGACGCCA CTGCCCCGGC CGTCGGCCGC GCCGGGCATC GGATCCCCGG CGATCATCGC
51841 CGATTCGGGC TCGGGGGACC CGTTCGCGGG CCGGCTCGGC GGCACCGTAC ATCCCGATCT
51901 GACCGCGCTC GCCGACGCGG TGGACGCCGG GCTGCCGACG CCCGAGGTCG TCGTCCTCGC
51961 GTGGCCCACG ATCCCGGCCG GACCGCTCGG CGACGTGCCG GACCCGGACG ACGTACACGC
```

FIGURE 5 (Continued)

```
52021 CGCCGTACAC CGGGCGTTGG CCACCGTGCA GACCTGGCTC GGGGACGAAC GCTTCACCGG
52081 CGCCCGCCTC GTCGTGGTCA CCCGGGGCGC GGTCGCCGTC GCGGACGAGG AGGTGCGGGA
52141 TCCGGCCGCC GCCGCCGTCG GCGGCCTGGT GCGGTCGGCC CAGTCCGAGC ACCCGGACCG
52201 GCTCGTCCTC GTCGACCTGG ACGAGGACGC GGCCTCGCCC GGGGCGCTGC CGGCCGCGAT
52261 CGGCGCGGGC GAGCCGCAAC TCGCGGTACG GGCCGGGGTG GCGTACCTGC CCAGGCTCAC
52321 CCGGACACCC GCGATCGAGC CGAGCACGCC ACTGTTCGCG CCCGACGGTA CGACCCTGGT
52381 CACCGGCGGC ACCGGTGCGC TCGGCGCCCT GGTCGCCCGG CACCTGGTGG TCGCGCACGG
52441 GGTGCGCCGG CTGCTCCTGG TCAGCCGGCG CGGGATCGCC GCACCGGGCG CCGGGTCGCT
52501 CGCCGCCGAA CTCACCGGCC TGGGCGCGAC GGTCGACGTG GTGGCCTGCG ACGTGTCGGA
52561 CCGGGCCGAC CTGGCCAAGA AGCTGGCCGC GATCCCGTCC GCACACCCAC TGTCCGCCGT
52621 CGTGCACGTC GCGGGAGTGG TCGACGACGG GGTGATCGGC GCACTGACGC CCGAGCGGGT
52681 CGACCGGGTG TTGCGGCCCA AGGTCGACGC GGCGCTGCAC CTGCACGAGT TGACCCGGGA
52741 CGCGGACCTG ACCGCGTTCG TGCTGTTCTC CTCGGTGGCC GGGGTGATCG CAGCCTCGG
52801 ACAGGCGAAC TACGCAGCCG GCAACGCCTT CCTGGACGCC TTCGCACAGC GGCGACGTGC
52861 CCTCGGGCTG CCCGCGGTGT CCATGGCCTG GGGATTGTGG GCCGAGGAAA GCGGGCTGAT
52921 GCGTGAGGAG TTCGCCGAGA CCGACCGGCA ACGCATCAAC CGCAGCGGTG TATTGCCGCT
52981 GTCCGACGAA CAGGGCCTGG CACTGTTCGA CGCGGCGCTC GCGCACGGCG AGCCGATCCT
53041 GGCCCCGGTC CGCCTGGACC TGAGCGCGCT GCGCCGCCTG GAGGACGAAC TTCCCGCCAT
53101 CCTGGGCGGA TTGGTGCCCA CCTCGCCGCC CGACGGCGCC CGCCCCGGCG CGGCGGACAC
53161 CCGCCGACTG GCCCAGCGGC TCGCCGGCCG CTCCGAGCCG GAGCAGCTGC GCCTGCTCAC
53221 CGAACTGACC CGCGCCCAGG CCGCCGTGGT GCTCGGGCAC GCGGGCGCCG ACGCGGTCGC
53281 CGCCGACCGC GCGTTCACCG AACTGGGCTT CGACTCGCTC ACCGCGCTGG AGATGCGCAA
53341 CCGGCTCAAC ACGGTCACCG GCCTGCGGCT GCCCGCCACG GTGCTGTTCG ACTATCCCAA
53401 CGCCGCCGCG CTGGCCCGCT TCCTGCGCGC CGAGACGCTG CGCGTACCGC AGTACACCCA
53461 GGCGGCGGCG AACACTGCCG CCAAGGCCCG GACTTCGGAC GAACCGATCG CGATCGTGGC
53521 GATGAGCTGT CGCTACCCGG GCGGCATCGA CACCCCCGAG GAGTTGTGGC GCTGCGTCGC
53581 CGGCGGAGTG GACCTGACCT CGCCGTTCCC GACCGACCGC GGCTGGGACC TGGGCGCGCT
53641 GTACGACCCG GACCCGGACC GCTCCGGGCG CTGCTACACC CGCGAGGGCT CGTTCATGCG
53701 CGACATCGAC CGCTTCGACG CCGAACTGTT CGGGATCTCC CCGCGCGAGG CGCTGGCCAT
53761 GGACCCGCAA CAGCGGCTGC TCCTGGAGAC CTCCTGGGAG GCGTTCGAAC GCGCGGGCAT
53821 CGACCCGTCC TCGCTGCGCG GGAGCAATAC GGCGGTCTTC GCGGGCCTGA TGTACGCGGA
53881 CTACGCCGCG GGTCGAGTGG GTGACGTCGG CGACGAGTTG GAGGCGTACA TCGGCAACGG
53941 CAACTCGTTC GGCGTCGCCT CCGGTCGGGT CGCCTACACG CTGGGACTGG AGGGCCCGGC
54001 GGTGACCGTG GACTCGGCCT GCTCGTCCTC GCTGGTCGCG CTGCACTGGG CGGCGCACGC
54061 GCTGCGCAGC GGGGAATGTG ATCTCGCGCT GGCGGGCGGG GCGACGGTGA TGTCCACGCC
54121 CAGTGTCTTC GTGGAGTTCG CCCGGCAGCG CGGCCTGGCA CCCGACGGCC GGTGCAAGTC
54181 GTTCGCCGCG GCGGCCGACG GCACGGCGTG GGGCGAGGGC ATCGGCATGT TGCTGGTGGA
54241 GCGGCTGGCC GATGCGCGCC GCAACGGGCA TCCGGTCCTC GCGGTGCTGC GGGGTTCGGC
54301 GATCAACCAG GACGGCGCCT CCAACGGCCT CACCGCGCCC AACGGCCCGT CGCAACAGCG
54361 GGTGATCCGG CAGGCGCTGG CGAACGCCGG GCTGGCCACG GCCGATGTGG ACGCGGTCGA
54421 GGCGCACGGC ACCGGGACGG TACTCGGCGA CCCGATCGAG GCCCAGGCGC TGCTGGCCAC
54481 CTACGGTCGG GACCGGCCGG CGGAACGGCC GCTGTGGTTG GGATCGATCA AGTCGAACTT
54541 CGGCCACACC CAGGCGGCGG CCGGGGTGGC CGGGGTGATC AAGATGGTGA TGGCGATGCG
54601 GCACGGGATG TTGCCGCCGA CGCTGCACGT GGACGAACCC TCGCCGCATG TGGACTGGTC
54661 GACCGGGCGG GTCGAACTGC TCGCCGAGGG GCGGCCGTGG CCCGAGGTGG GCGGGCCCG
54721 TCGGGTGGCG GTGTCCTCGT TCGGGATCAG CGGGACCAAC GCGCACGTCA TCCTCGAACA
54781 GGCCGACGAG GAGCCGGAAC CGCCGCCCG AACCACGTCC GGCACCGGCA TCGGCGGGGT
54841 GCTGCCGTGG GTGCTCTCGG CCCGGACCGA GGCGGGCGTG CGGGCCCAGG CGGCCCGGCT
54901 GAGGGACTGG GCCGGGGCCC GGCCCGAGGT CGATCCGGCC GACGTGGGCT GGTCGTTGGC
54961 GTCGGGACGG TCCGTATTCG AGCGGCGCGC GGTGGTGTGG GGCCGGGACG GCGCGGAGTT
55021 GACGGCGGGC CTGGACGCGC TGGCGGCCGG CGGGGATGCG GGAGCACGTG CCGTGCTTGC
55081 CGGCGGCACC GGCGTGTCGG GCGAGGCGGC CGTCGGGCCG GTGTTCGTGT TCCCGGTCA
55141 GGGCTCGCAG TGGGTCGGGA TGGCGGCGGA ACTGCTGACC TGCTGCCCGG TGTTCGCCGA
55201 GTCGGTGGCG GAGTGCGCGG CGGCGATGGA TCCGCTGCTG GCCGACTGGG CACTGCTCGA
55261 CGTGCTCCGG GACGCGTCCG CCGCGCTGTT GGAGCGGGTG GATGTGATCC AGCCCGTGCT
55321 GTTCGCCGTG ATGGTCGGCC TGGCCCGGTG GTGGGAGTCG TGCGGGGTGC GACCGAGCGC
55381 GGTGATCGGG CATTCCCAGG GGGAGATCGC CGCCGCGCAT GTGGCGGGCT TCCTGTCCCT
55441 GGAGGACGCG GTCCGGATCG TGGTGCTGCG CAGCCGGGCA CTGCGGGGCG TCGCGGCCGA
55501 CGGTGACGGG ATGTTGTCGG TGGGCGTGTC CGCCGAGCGT GGCCGCGAAC TCGTGGCACG
55561 CGTGCAGGGA TTGTCCCTGG CGGCGGTCAA CGGGCCCGAC AGCGTGGTGC TTTCCGGGCC
55621 GGTCGAGGGT CTGACGCCAA TCGCCGCCGC GTGCGAGCGC GACGGGGTTC GGGCGCGATG
55681 GATCCCGGTG GACTACGCCT CGCACTCGGC GCGGATGGAC GACGTACGCG AGGTGCTGGC
```

FIGURE 5 (Continued)

```
55741 CGAGTCGCTG GCCGGGGTCG AGCCGGGGAT CGGGCGGGTG CCGATGTACT CGACCGTGAG
55801 CGGGCTGAAG GTCACCGATG CGGCGGATCT GGGCGGGGAG TACTGGTTCG AGAACTTGCG
55861 TCGCACCGTG CAGTTGGCCA CGGCGGTCGG GGCGGCGGCG GCCGACGGGC ACAGCGTGTT
55921 CGTCGAATGC AGCCCGCACC CCGGTCTGGT GGTGCCGCTC GGCGACACCC TCGACGCCCT
55981 CGGGAGCACG TCCGGCACGG TCCTGGAGAC GCTGCGCCGG GGCGAGGGCG GCCCCGAACG
56041 CCTGGTCGCG GCACTGGCAG CGGCCTTCGT GAGCGGCCTG CCGGTCGACT GGGCCGGGCT
56101 GCTGCACCAC GACGGGGTCC GGCGAGTACA GCTGCCGACA TACGCCTTCC AGGGCCGCCG
56161 CTTCTGGCTC GAACCGGACA TGGGCACGGC GCTGCCCGGC CGGACGACAC CGACGCCGGT
56221 GGTGGGCGAC ACCGAGGACA GCAGGTTGTG GGAGGCGCTG GAGGCGGCGG GCGCCGAGGA
56281 CTTGGCCGCC GAACTGGAGG TGGCGGCGGA CGCGCCGCTG AGCGACGTGT TGCCGGCGCT
56341 GACGTCCTGG CGGGCGCGGC GGCGGGCGGA CGCGACGGTG CGGTCCTGGC GGTACGGAGT
56401 GCGGTGGGAG CCGTGGGCGG CGCCGGCCGC CTCCGCCGAC AGGATGGGGC GTCTGCTGCT
56461 CGTCGCTCCG GACGGGAGA TCGGGACGT GCTCGCGGGC GCGCTGGCCG AGTGTGGTGC
56521 CGAGGTGGTG GTGCTGTCCG GGAGGGGGA ACGGACCGCG TTGGCGCGGC GGCTCGCGGC
56581 AATCGGCGAG GAGGGTGTGC CGGCCGGGGT GGTGTCGTTG TCGGCGGTGG GTTGCGCCGC
56641 CGACGCGGAT CCCGTGCCCG CGCTCGCGCC GGTGCTCACG CTGGTGCAGG CGCTGGGCGA
56701 CGCCGGGATG GAGGCACCGT TGTGGGTGCT GACGCGCGGC GCGGTGTCGG TGCTGGGCGA
56761 GGAGCCGACC GGCCCGGCGG GTGCGGCCGT GCAGGGGCTC GGGCGGGTGG TCGGGCTGGA
56821 ACATCCCGGG CGGTGGGGTG GGCTGATCGA TCTGCCGCAG GTGGTGGACG GCCGGGTGGC
56881 GGAGACGCTG GCGGGGATCC TGGCCGCCGG CGCGGGCGGC ACCGGCTCGG GTGAGGACGA
56941 GATCGCGATC CGGCCGCTGG GAGTGTTCGT CCGGCGGTTG GCGCGGATGG CCGGGCCGGA
57001 GGGCAGCGGG ACGAGCCGGT GGCGCCCCGG TGGTACGCGC TTGGTCACCG GCGGTACCGG
57061 TGCGCTGGGC GGGCGGGTCG CGCGGTGGCT GGTCCGGGAG GGCGTCGAGC GGGTGGTGTT
57121 GGCCGGGCGG CGTGGGCCCG ACGCGCCGGG CGCGGACCGA CTGCGCGAGG AACTGGCGGC
57181 GGCCGGGGCC GAGGTGGCGG TGCTCGCCTG TGACCTGGGC GATCGCGACG CGGTGGCCGC
57241 GCTGTTGGCG GAGGTGCGGG CCGGCGGCCG GCGGATCGAC ACCGTCGTAC ACGCGGCCGG
57301 CGCGGTGGTG GTCGGCCCGC TGGCGGACAG CACCGTCGCG GATCTCGCCG ACGCCTCGGC
57361 GGCCAAGGTC GGCGGCGCGC TGCTCCTGGA CGAGTTGTTG CGGGCCGACG AGCCCGACAC
57421 CGTGGTGCTG TTCTCCTCCG CCGCCGGGGT GTGGGGCGGC GCGGGGCAGG GGGCGTACGC
57481 GGCGGCCAAT GCCTGCCTCG ACACGATCGC CGAGCGGCGC CGGGCGCGCG GGCTGCGTAC
57541 CGTCTCGATC GCTTGGGGGC AGTGGGCCGG TGGCGGGATG GCCGACGGCG CGGCCGGCGC
57601 GCACCTCGAC CGGATCGGGG TCCCGGCGAT GGACCCGGAT CGGGCCCTGG AGGCACTGCG
57661 GCAGGCCCTG GACGAGGACC TGACCTGCGT CACCGTGGCC GACGTGGACT GGCCGAGGTT
57721 CGCCGCCGGG TACACGGCGG CCCGGCCGCG ACCGCTGATC GCGGACCTGG TGGCGGCGGA
57781 GGTCGCGGCG GCGCCGGTCA CCGAAGCGCG CGGGGCGGGC GAGCCGGACG GTCCGAGTGT
57841 GTGGCGGGCC CGACTGGCCG AACTGGGCGC GGCGGATCGG GAGGCGGAAC TGCTCGCGCT
57901 GGTCCGCACC GAGGTCGCCG CGCAGTTGGG CCACGCCGAC CCGGCCGCGA TCGAACCCGA
57961 ACGGCCGTTC CGCGATCTCG GGTTCGACTC GCTCGCGGCG GTGGGCCTGC GCAACCGACT
58021 GACCGAGACC ATCGGTCTGC GGCTGCCCAG CACGCTGGTC TTCGACCACC CGACGGCCGT
58081 CGCACTGGCC GCGCACATCG ACGGCGAACT CTTCGCCGAG ACCGTCGGGA CGGTCTCCGT
58141 CTTCGCCGAA CTGGACCGCC TGGAAGCGGC GCTCGGCGAA CTGGGCGGCG ACTTCGCCGA
58201 ACGGGGCAGG GTCGGTGCCC GGTTGGCCGA ACTGCCGGG AAATGGCGGG AGATCGAGGC
58261 CGCGAGCCAA AAGGCCGAGC CCGAGGGAGC CGACTTCGCG GCAGCGGAGG ACGAGGAGAT
58321 GTTCGACATG CTCGGAAAGG AGTTCGGCAT CTCCTGAGCG GGGCCGGCGA CGACCGCCGG
58381 TCACGGGTCC CGACGGCACA CGGCTCGATC AGGTTCGACC AGGCAGAGGA CGGACGTACG
58441 GACATGTCGA ACGAAGAACG GCTGCGGCAC TTCCTCCGGG AGACCGCCAC GGATCTGCGC
58501 CGCACCAAGC AGCGGCTGCA CGAGGTGGAG TCGGCCGCCC GCGAGCCGGT GGCGATCGTG
58561 GCGATCGGGT GCCGACTGCC GGGCGGCGTG CGCTCCGCCG AGGACCTGTG GGAGCTGGTG
58621 CGGACCGGGA CGGACGCGAT CGCCGGCTTC CGTCCGACC GGGGTTGGGA TCCGGCGAAC
58681 GTCTACGCGG ACCTGCCGGG CGGCGAGGGC GTCTCGGGCG GTTCGGCCGG ATCCGGCGGG
58741 TCGACCACCC GGCAGGGCGG ATTGCTCTAC GACGCGGCTG CGTTCGACGC CGAGTTCTTC
58801 GGCGTCTCGC CGCACGAGGC GTTGGCGATG GACCCGCAGC AGCGGCTGCT CCTGGAGACC
58861 GCGTGGGAGA CCTTCGAGCG GGCCGGCATC GATCCGCTGT CGATGCGGCG CAGCCGGACC
58921 GGCGTGTTCG TCGGCGCCGG TGCGCTCGGC TACGGCGGCG GGATGCGGGC GGACAACGCC
58981 GAGATCCAGG CCCATCGGGT CACCGGCGGC TCGATGTCCG TGGTGTCGGG GCGGATCGCC
59041 TACACGCTCG GTCTGGAGGG CCCGGCGGTC ACCCTCGACA CGGCGTGTTC GTCGTCGCTG
59101 GTGGCGCTGC ACCTGGCGGC CAACGCGCTG CGCTCGGGGG AGTGCGACCT GGCCCTGGCC
59161 GGGGGCGTCA CGGTGATGGC CCGGCCGACC GCCTTCGTGG AGTTCTCCCG GCAGGGCGGA
59221 TTGGCCCTCG ACGGCCGCTG CCGGTCGTTC GCGGCGGCGG CGGACGGCAC CGGGTGGGT
59281 GAGGGTGTCG GGCTGCTGCT GGTGGAGCGG TTGTCGGATG CGCGGCGCAA CGGCCATCCC
59341 GTACTGGCGG TGCTGCGCGG CTCGGCGGTG AACCAGGACG GCGCGTCGAA CGGGTTGACC
59401 GCGCCGAACG GGCCGTCGCA ACAGCGGGTG ATTGACAGG CGTTGGCGGC GGCGGGCTTG
```

FIGURE 5 (Continued)

```
59461 TCGGCCGCCG ATGTGGACGC GGTGGAGGCG CATGGGACCG GGACGGTGCT CGGCGACCCG
59521 ATCGAGGCGC ACGCGCTGTT GGCCACCTAC GGGCGGGATC GGCCCGCGGA TCGGCCGTTG
59581 TGGCTGGGGT CGGTCAAGTC CAACATCGGG CACACCCAGT CCGCGGCCGG GGTCGCCGGG
59641 GTGATCAAGA TGGTGATGGC CCTGCGGCAC GGGCTGCTGC CGCGCACCCT GCATGTGGAC
59701 CGGCCGTCGC CGCACGTGGA CTGGGCCTCG GGACGGGTCG AGCTGCTGAC CGACGAGGTG
59761 CCGTGGCCCG CGGGCGGTCG GGTGCGTCGG GCGGGTGTGT CGTCGTTCGG GATCAGCGGG
59821 ACGAACGCGC ACGTGGTCCT GGAGGAGGCG CCGGCCGTCG AGGGGGCCTC GGGGGAGGGG
59881 GCCGAACCCG CGCCGGGTGT CGGTGGGTTG ATTCCGTGGG TGGTATCGGC GCGCTCCCCG
59941 GAGGCGTTGC GCGCGCAGGC GGCGCGGTTG CGGGAGCCGG CGGTCGCGGA TCCGGCGGAT
60001 GTCGGTCGGT CCTTGGTGAC GGGACGGGCG TTGCTCGACC ATCGGGCGGT GGTGCTGGGT
60061 CGGGACGCCG CCGAGTTGGG CCGTGGACTG GCCGCGTTGG CGGCCGGGTC TCCGGGTGCG
60121 GTCGAGCCGT CGGAGGGGGG AACTCCGGTC GTGGTGACCG GGAATGTGCC CCGAGCGGGT
60181 GGTGCGGGTG GTCGGGTCGC CGGGCGGGGC GCGGTGGTGT TCACCGGGCA GGGGGGTCGG
60241 TTGCCCGGGA TCGGGCGGGA ACTGTACGCG GGTTTCCCGG TGTTCGCTCG CGCGCTGGAC
60301 GAGGTGGGTG CGGCGTTCGA CGCGGTGGTG CCGTTCTCGG TCCGGGACGT GTTGCTCGGC
60361 GTGGAGGGCA CGGTCGGCGT CGATGCCGAC GACACCGGCG TGGCTCAGCC GGTGTTGTTC
60421 GCGTTCGAGG TGGCGCTGTA CCGGCTGTGG AGTTCGCTGG GGTCGGTCCC GGATTTCGTG
60481 GTCGGACACT CGTTGGGTGG GATCGTCGCG GCGCATGTGG CGGGGGTGTT CTCGCTCGCG
60541 GACGCGGTGG CGTTCGTCGC GGCGCGCGCC CGGTTGATGA GCGCGTTGCC GGGCGGGGGC
60601 GCGATGCTCG CGGTGGGGGC GAGCGAGGCG CAGGTCACCG CGCTGTCGGA TGGGCTGCCG
60661 GTGTCGATCG CGGCGGTCAA CGGACCGGCG AGTGTGGTGG TTTCGGGCGC GGTGGCGGCG
60721 GTGGACGAGG TGGCGGCGCG GTGTGCGGCG CGCAGTTGGC GCAGTTCGCG GTTGCGGGTC
60781 TCGCACGCCT TCCATTCGGT GCTGATGGAG CCGATGTTGG CCGAACTACG GGACGTGCTG
60841 CGCCGGTTGT CGTTCGGGGC GCCGGAGATC GGGTTGGTGT CGGATACCAC CGGGCGGGTC
60901 GTTACGGCCG AGGAGGTGGG TGATCCCGAG TACTGGGTGC GGCATGTGCG CGACGCGGTG
60961 CGGTTCGCGG ATGCGGTCGG CACGTTGCGT GAGCGGGGTG TGGCCACCTT CGTGGAACTG
61021 GGTCCGGACG CGGCGTTGAC CGCGATGGTG GCCGAGTGCA CGGCGGGTGT GGGCGAGGTG
61081 CTGGGGGTGC CGGCCCAGCG GCGTGGCCGA CCGGCCGTGG CGACGCTGGC CGGCGCGCTG
61141 GCCACGGCGT TCGTGCGGGG GCTGCCGGTG GACTGGGTCG GGGCTCTCGG CGGCCCGGGC
61201 GGGCGGCGGG TGGAGCTGCC GACCTACGCG TTCCAGGGGC GGCGCTATTG GCTGGAGCCG
61261 GGGAAGGCTT CGGTGACGCC GGCCGGGCCG GATTCGGTGG ACGGTCCGCT GTGGGACGCG
61321 GTCGAGCGGG CCGGGGCGGG CGAACTGGCG GCGATCCTGG CGGTGTCCGA GGACGCGACG
61381 CTGCGCGAGG TGGTGCCGGC GCTGTCGTCC TGGCGAGCCC GACGACGGGT GGACGCGACG
61441 GCCGCGTCGT GGCGCTACGC GGTGCGGTGG GAGCCGTGGG CGGGTGGTTC GTCCGACGCG
61501 GCCGCGTTGT CCGGGCGTTG GCTGCTCGTG CACCCGGCGG CGAGCGAGCT GGCGGATGCG
61561 GTGGCCCGGG AGCTGACCGA GCGTGGCCGG GAGGTGGTGC GGGTCGGGGG CGAGGGCATC
61621 GGGTCGCACG TCGGTGCCGA ACCCGTCGCC GGGGTGGTGT CGTTGATCGG CTCCGGTTCG
61681 GGCTCCGGCT CCACTTCGGG TTCGGGCTCG GCTCCGGTT CCGCTTCGGG CTCGGGCTCC
61741 GGGTCCGGTT CGGGCTCCGG CTCCGGCTCT GGTTCGAGTT GCGGCTCCGG TTCGGTGCCG
61801 GGCTTGGGTT CGTGCGCGGG CGACGACTGC GCCGACCTCG TGGCCGCCGT GGTGGCGATG
61861 GGCGAACTGC TCGCGGAGCT GCGCCGGTTC GAGGTCGCCG CCCCGCTCTG TGTGTGACC
61921 CGGGCGGCGG TGTCGGTTCT GGGCGAGGAC CTGGCCAATC CCGTGGGCGC CGGCCTGTGG
61981 GGCAGGGGCC TGGTGGCGAG CCTGGAGCAA CCCGGGTGCT GGGGCGGCCT GGTCGACCTG
62041 CCGGCCGTCG CGGATACCCG CGCGCTGGGG GTGCTGGCCA CGATCCTGGC CGGGACTTCG
62101 GACGAGGACC AGTTCGCCAT CCGCCCGCTG GGCGTGTTCA CCCGGCGGCT GACCCCGCTG
62161 CCGGCCGAGG GATCGGGCCG GGTGGTGCGT ACCCGCGAAG CGGCGCTGAT CACCGGCGGC
62221 ACCGGCGTGT TGGGCGCGCA CGCCGCCCGC TGGCTGGTCG CGCACGGCAC CGAGCGGGTG
62281 ATCCTGCTGG GCCGACGCGG CGCTCGGGCG CCCGGATTCG ATGCGCTGCG GGCCGACCTC
62341 GAGGCGGCCG CGCCGAGGT GGTGGCGATC GCCTGCGACC TGACCGCGCC CGACGCGGCG
62401 GAGCGGCTGC GGGCCGCGTT GCCCGCGACG GGTGCGCCGA TCCGTACCGT CGTGCACGCG
62461 GCGGGCGTGC CCGGATCGCC CACCGCGACC GGCGCCGACG CCGTCGCGGA CACCGTCACC
62521 GCCAAGGTCG CCGGCGCGCT GGCCCTGGAC ACGCTTTTTG GGGCGGACCG GGCCCTGGAC
62581 GCGTTCGTGC TCTACTCCTC CGGCGCGGGG GTGTGGGGCG GCGCCGGACA GGGCGCCTAC
62641 GCGGCGGCCA ACGCCTTCCT GGACGCGCTC GCCGTACGCC GTCGGCAACG CGGCCTGCCC
62701 GCCACGGCGA TCGCGTGGGG GCCGTGGGCG GCCGGCGGGA TGGCGGACGG CGAGGGGGAA
62761 CGGCTGCTGG CCCGGGTCGG TGTACGGGCG ATGGACCCGG CCGCGGCGCT GGCCGCACTG
62821 GGCCGGGCCC TGGTCGAGGA CCTCACCTGC GTGACGGTGG CCGACCTGGA CCGGCCCCGA
62881 TTCGCGGCGG GCTACACCTC CGCCCGTCCC CGGCCGCTGA TCGCCGACCT GATCGACGCG
62941 GAGCCGCCGA CCGCGACCGC CCCGCCGACC CGGCCCGGCG GGTGTGGGA CCCGGCGGTG
63001 ACCCGCTCGC CGGCCCGGCT CGCGGCCGAA CTGCTCGACC TGGTCCGCGC CGAGGTCGCC
63061 GCGCAACTCG GCCACGCGGG CGTCGAGGCG ATCGAACCCG ACCGGCCGTT CCGCGACCTC
63121 GGCTTCGACT CGCTGGCCGC CGTCGGACTG CGCAACCGGA TCGCCGAGGC CACCGGGGTA
```

FIGURE 5 (Continued)

```
63181 CACCTGGCCG GCACCCTGAT CTACGACCAC GAGACACCCG CGGCCCTGGC CGCACACCTG
63241 GCCGACGCCC TGCGCGAGGG TGTGCCCGAG ACCCGCCCGG CGCCGACGGC ACCCGGCGGC
63301 GCCGAGGACT CGAACGACAT GCTCGGCACG GTCTACCGCA AACTGGCCCT GCTCGGCCGG
63361 ATGGACGACG CGGAATCGCT CCTGGTCGGC GCTGCCGGCC TGCGGCAGAC CTTCGAGGAC
63421 CCGAACCGGC TCCCGAAGAC ACCCGGCTTC ACCCGGCTCG CGCGCGGACC GGCCCGGCCC
63481 CGGGTGATCT GCTTCCCGCC GTTCGCGCCG GTCGAGGGCG CCATCCAGTT CGGCCGGCTG
63541 GCGGGCACGT TCGAGGGCCG GCACGACACG GCGGTGGTGA CCGTACCGGG CTTTCGGCCC
63601 GGCGAGCCGC TGGCCGCCTC GCTGGACGTG CTGCTCGACC TGCTGGCCGA CGCGACGCTG
63661 CGGTGCGCCG GAGACGACCC GTTCGCCGTG CTCGGCTACT CCTCCAGCGG CTGGCTCGCC
63721 CAGGGGGTGG CCGGCCGCCT GGAGGCGACC GGCCGTACGC CCGCCGGGGT CGTACTGCTC
63781 GACACCTACC TGCCCGCCAC GATGTCGCGG CGCATGCGCA AGGCGATGAA CTACGAGGTG
63841 ATCGTGCGCC GGCAGGCGTT CACCGCGCTC GACTACATCG GGCTGACCGC GATCGGCACC
63901 TACCGCCGGA TGTTCCGGGG CTGGGAGCCC AAGCCCGGCT CCGCGCCGAC GCTCGTGGTG
63961 CGGCCCTCGC GCTGCGTCCC GGGCTCGCCG GAGGAGCCGA TGACCGGCGA GGACTGGCGT
64021 TCCACCTGGC CGTACGAGCA CACCGCCGCC GAGGTGGAGG GCGACCACTG CACGATGATC
64081 GGCGAACACG CGGAGCAGAC CGGTGCGGTG GTGCGCGCGT GGCTGGCCGG TGACAGGACG
64141 GTTTCGATCG ACACGAGGGA AGGCACGGCA TGACCGACCC GCGCTATCCG CGATACCCGC
64201 AACCCGGCTC CGTCGACCAT CTCGACGCGG AGTTCCTGGT CCACCGGGCC GCGATCCAGG
64261 ATCTCGTCGC CGCGTACAGC CTGCTCTACG ACGCGGGCGA CTACGACGGG CTCGGCGACC
64321 TGTTCACCGA GGACGCGACG TACGCGTTCA CTCCCGCCCC CGAGGGATTT CCGCCCTCGG
64381 TGTCCGGCCG GGACAAGATC GTCGCGGCGA TGGCCGCGCT GCGCGAGCAC AACCTGCGCA
64441 CCCGGGCCGC CCACCAGCGG CACTTCGTGA CCAACACGGT GATCACCCGC CTCGACGGCG
64501 ACACCGCCGA GGCGCGGTCG CTGATGGCGG TGGCGTTCGC CCATCCGGGG GACGGCCGCC
64561 AAGAGTTCAC CCGCAGTGGG GTGTACGCCG ACGTGCTGGC CGACAGGGA AGCCGGTGGC
64621 GCATCGCCGA CCGGCACCTG TGGTTGCCGG AGTTGCCGGC GCCGCGTCCG GGCGACACAT
64681 CCGCTCCCGA GGAGAGTCGG CCATGATTCC CGTGCTCGAA CTGGTCCAGA TCTCCACACT
64741 CCCCGACGCC GAACGGGAAC TGGAGCAACT GGCCCGGCGA TACCCGATCA TCCGCACCCG
64801 ACAGGTCGGC GGCATCGAGG CGTGGACCGT GCTCGGCGCC GGGCTGACCC GGCAACTCCT
64861 CGGCGACCCA AGGCTGTCCA ACGACCTGCA CACGCACGCG CCGCACGCGG CCCAGTCCGC
64921 CGACGGTCCG ACCGTGCTGT TCGAGCAGGA CAATCCGGAC CACGCCCGCT ACCGCCGCCT
64981 GGTCAGCGCC GCGTTCGCGT CGCGGGCCGT GCGCAACCTC GAACCGCGGA TCGTCGACAT
65041 CGCGCGCGCA CTGCTCGACC GGCTGCCGGC CGAAGGCGGC ACGGTGGACA TCGTCGAGGC
65101 GTTCGCCAAC CCCTTCCCGC TGGAGGTGAT CTGCGAACTG CTCGGGGTAC CGATGGCGGA
65161 CCGCGAGGTG TTCCGCACCC GGGTGGAGAA CATGGACTCG CCCTCGACGG CGGTACGCCG
65221 GGCGGCGATG GACGCGTTCG TCGCCTACTG CGCCAACCTC GTCGACGCCA AGCGCACCGA
65281 ACCGACCGAG GACCTGCTGA GCGAGCTGGT ACAGGCCGAA CTCGACGACG GATCACGGCT
65341 GTCGGCCAAT GAACTGATCG GCTTCGGCTC CGTGCTGCTG TTCGCGGGGC ACGTCACCAC
65401 GGCCTACCTG ATCGCCGCCG CGCTGTACGA ACTCATCACC CACAACGACC AGTTGGCCGC
65461 ACTCCGGGCC GATCCCACGC TCGTCGAGGG CACCGTCGAG GAGGCGCTGC GCTTTCGCGG
65521 CTCGTTGTTG TCCACCACGA ACCGGGTGGC GCTGACCGAC CTGGAGATCG GCGGCGTGCT
65581 CGTGCGCCGT GGCGACCTGG TGCGCTTCCT GCTCTCCGCC GCCAACCGCG ACCCGGCGAT
65641 CCGCGAGGAC CCGCACACCT TCGACATCAC CCGGTCCACC ACCGCCCACC TGGGCTTCGG
65701 CCACGGCCCC CACTTCTGCC TCGGCCAACG CCTGGCCCGC CAGGAGATCA AGGTCGCCCT
65761 CACCGAGATC GTCACCCGCT TCCCGACCCT CGAACTGGCG GTCCCGGCGG AAAAGCTGCG
65821 CTGGCGCGCC TCGGACTTCC TGCGCGGCCT TGCCGAACTA CCCCTGACGT ACGCCCCGTG
65881 ACCACCGACG AGGACAGGCG GCCCGGACCC GGGCCGCCCG GCTCCGCGG CGGTCCGCGC
65941 CGGTGTCCGG CGAGTGTGAC GCGCCGTCGA ACAGTCGATG TCGGCTGCGC GGCGTCCGTC
66001 GCGGATCCCG GACCCGTCGT GGTTGCGTAG CATCTCCGGG GGTCGGCGGG CGACGCCGGG
66061 CCACGAACGG CAGGGGCGCG GCGCCATGGA CGGACCGGCG GGGAGCCGAA GGCACCCACG
66121 GGCCTGCGCG AGCGCAAGAA GGCCCGCACC CGGCAGGTGA TCTCCACGGT CGCGTTCGAC
66181 CTGTTCGAGG AACAGGGCTT CGAACAGACC ACCGTCGACA TGATCTGCCG CCGCCACGCG
66241 ATGACGGTCA GCCACGGCAA CCTCGAAGAC CACGCCGAAC AAACCGCCCG CCGACACGCG
66301 CTGCGCCGCC GCTTCCTGGG CGTGCGCTCG GTCCACGACC ACGGCGTGGC CCTGATCGAC
66361 ACGGTCGCCC ACCGCATCGT CACCACCGCC GCGCCCGCC TCGGGGTCGA CCCGGCCGTG
66421 GACCTGCGCC CCCACGCCCT CGGCGCCCTG GTCGCGGCGA TGACCCGCCG CGTGGTGATC
66481 GACGACATCG CCCCGGGCCC GATCAACGAG TGGGCGGAGG CCTTCCGCAC CCTGCTCCCG
66541 ACGCCGGCCG CACACACCGA CTGACACACC GCCCGGGCGC CGACCCGGAA ACCGCCGGGT
66601 TCCTTCGCAC CGCAGGGTGA TCACCGGTCT TCGTCCGTGC GGACACATCT TCGGCCCGCC
66661 GCTCGTGTAC GGATCCGAGG CTCCCGGCCC GGCCGCGGGC GATACTCGGG AAACGTCGGG
66721 GCCCGGGGAG GCGGCGGGTT CCCCATACCC GAGAGGTTCC ACATGCAGCC CGACCCGCGG
66781 TTCGACCCGC AACCCGACAC GGCCGTCGAA ACACCCGTGG ACGAGCACGC CGCCGGCGCG
66841 CCCGCCGATC GGCTCGTCGA CCTCGTCGTC CGGGCCGGTT CCCTCGTCGA CGGCAGCGGA
```

FIGURE 5 (Continued)

```
66901 TCCCCCGCGT ACGACGGCGA CCTCGCGATC GACGGCGGGC GGATCGTCGC GCTCGGCGAC
66961 ATCGGCGCCA TCACGGGGCG TGACGAGATC GACGCACAGG GCTGCGTGGT GTGTCCGGGC
67021 TTCGTCAACG TGCTGAGCCA CGCCTACTTC ACCCTCCAGC AGGACCCCCG TGGCCTGTCC
67081 GACCTGTACC AGGGCGTGAC CACCCAGATC TTCGGCGAGG GCGTCTCGCT CGGCCCGGTG
67141 ACCGGGGCGA TGACCGAGTC CATGATC
```

**Figure 6. Amino acid sequence of the *lepA* gene.**

```
FEATURES            Location/Qualifiers
    source          1..67167
    misc_feature    <1..23206
                    /note="pKOS279-128.PF27 (partial insert)"
    misc_feature    8184..47817
                    /note="pKOS279-128.2L78 (insert)"
    misc_feature    32653..67167
                    /note="pKOS279-130.PFA42 (insert)"
    CDS             370..25686
                    /note="LepA"
                    /note="PKS (modules 0-4)"
```

/note="sequence=MQVMERGMTEFNADAHRAHPAPEDAVAIVGLACRLPGADGPDE

FWDLLSNGRDTITEVPRHRRDARAADDTNRTAGGSPHPAANRPRRGGFLDAVDRFDAAF

FGITPGEAALIDPQQRLMLELCWEALEHAGIPPTRIRGSATGVFAGAIWDDYATLLRRA

GVEPGPRHATGLHRSMIANRVSYTLGLRGPSMTVDAAQSSSLVAVHLAGESLRRGESTL

ALVGGVNLDLVPDHDGDAAKFGGLSPQGRCFTFDARADGYVRGEGGAVVVLKPLSRALA

DGDVVHGVIRGSAMNNDGGGDALTAPDPRAQAEVIRLARRRAGVAASAVQYVELHGTGT

PVGDPIEAAALGAALGTERANRPPLAVGSVKTNVGHLEGAAGIVGLVKTVLAIRHRRLP

ASLNFAEPHPRIPLGELGLRVQTAEGDWPCPDETLIAGVSSFGMGGTNCHVVLAEAEPA

DGVGPSVASAPSGGSDPGMESATGPVPSDAVAVPISGVDADGLRAQAGRWHGHVREHPD

VAPADLGYSAATTRTAFAARAVVLARDHAELLAGLDALRGAGADPHLVRADAQPGRTAF

LFTGQGSQRPAMAQESYARHAVFAAAFDAACAHLDPHLPRPLREVLFASPDSPDAALVH

RTEYTQPALFAVEVALYRLFEHWGVTPDLLLGHSIGELCAAHVAGVWSLPDACALVAAR

GRLMQELPDGGAMVSLRVAEDDVLASLEPVRDRVSIAAVNGPLATVISGDRDAVLDVAA

GWRAQGHKTTRLRVAHAFHSPRMDAMTDAFAEVAAGLTARAPTLPVVSNLTGLPLTAEQ

ACSPDYWVRHVRHTVRFHDGVRRLRAEGATILLELGPDGSLSAAARTCLLDGERDTVAT

IPTLRRNRPETDALTTAVARLYANGVDPDWERVFAGRGARRVALPTYAFRRARHWPGAS

AEAADTAVPDESLAVVPTLAERLAALSAVEQHRILLDLIRAHATAVLGPGATTTVEPDR

TYRESGLDSLGTVELITRLARDTGLDLPPTTVFDHPTPTALAHHLRTRALDLPVPTRPR

PTPGPARADEPIAIVAMGCRLPGAVRTPEDLWRLVADGVDAITAFPTDRGWDLDRLHHD

DPDRPGTSYVRSGGFLDRAGDFDAEFFGIGPREALAMDPQQRLLLETSWEAIERAGLDP

STLRGERVGVFVGATAQEYGPRMHESTDALAGFLLTGTTPSVASGRIAYTLGLSGPALT

VDTACSSSLVAVHLAARSLASGECALALAGGATVMAGPGMFVEFARQRGLAPDGRCKPF

SADADGTAWAEGVGVLLLERLSDARRNGHPVLAVLRGSAINQDGASNGLSAPNGTAQQR

VIRDALAAAGLDPQDVDLVEAHGTGTPLGDPIEAQALLATYGRDRAADRPLLLGSVKSN

IGHTQAAAGVAGLIKTVLALRHGAIPGTLHLREPSPHVRWSDGAITLPTTTTDWPAYDR

FIGURE 6 (Continued)

PRRAAVSSFGISGTNAHVIVEEAGGGAEIPGPAPARGLASAGVADPVPLVVSARSEAAL

RGQAEQLAGLLRAADAPALADVGYSLLRGRAGFEYTAVIPARTHAEALHGLTALAADRP

ADRLIRGGAAAARGGTVFVFPGQGTQWSGMALELLDTSEPFAASMRACTDALDPYAVDW

SLLDVLREPGTPGLTRVDVVQPALFAVMVSLAALWRSIGIEPQAVVGHSQGEIAAAYVA

GALSLADAAKVVALRSRALVAAAGSGGMASVSLPAEQVAALLEPWAGRLGVAAVNGPSA

TVVSGDTAALDTFLDRCAADDLRARRIPVDYASHSVHMEEIRDRLLTDLADVTPRAAST

AFYSTLTGGRMADTSGLDADYWYRNLRRTVRYETAVRALSEDGHRLFVEVGPHPVLTLG

TQETLDACGSGGTTIGTLSRDDGGRARFLVAVAEAVAHGARPDAEALFDPPGTGVRAVA

LPTYAFQHRRYWLTPREAAPEGTAALGLTPISHPLLGALGALGVEPDGTVIATGRISLR

ELPWLADHAVADTVVLPGTAFLELALCVGESVGAPQVEELTLESPLLLPETGDVYLRVA

VAPADEARRRAVTIHSRRAGGGGADAERESWVRHAGGLLVDSVREVDDGGSGGLTQWPP

PGADVLDLADAYPVLAGLGYGYGPAFRGLRAAWRGAGGELFAEVRLPDELRESESGVVG

PEFGIHPALLDAALHPLLSSLSLTSLSSTRDGPAGAPPRIPFSLADVRLYATGADMLRV

RLRRADGGAAALTVADGVGAPVLSIGALTLRELPADGLIAAEPGPGEAMFDLRWIAGSI

PAEPTGLGYAFIGDDLGLGDGEVYPSLADLDARLLATGEPTPDVVFAAAPVGVDDDVPG

AAHDSARWALDLVGGWLAGERSSAARLVVVTRGAVAARTGDALSGLPAAPVWGLLRTAQ

SEHPDRFVLIDLDDAVRSPSALLGAAVAGEPQLALRDGVVHLPRMVAVDSADAQVTRRR

PDPNGTALITGGTGTLGALIARRLAAEHGIRHLLLLGRAGREAPGAEELIAELGALGAR

VTVAACDVADRAALRRVIEDIPAEHPPTIVVHAAGVLDDATLLSLTPDRLDAVLRPKVD

AAWHLHELTRAANPAAFVLFSSITAITGNAGQGAYTAANTFLDALAEHRRAAGLPANAL

AWGLWAEGSGMTRHLDHTDRARMSRGGIAALPTETGLALFDAALHRDRPYTIPARLDRG

ALRALAASGVLPAVLRSLVRVPPPRAAASGDGTDASSWPRRIRELPGEQRERAITDLVR

GQLAAVLGHDAPERLDLDRAFRELGVDSLTALELRNRINAFTGLRLPATVVFDHPSGTA

LVARMMRELVGAVPSEPTTPVVAPTVTVDEPIAVVGIGCRYPGGVAGPEDLWRLVAAGT

DAVGDFPEDRGWDLAKLYDPDPDKVGKVYTRRGGFLYESGEFDAEFFGISPREAAAMDP

QQRLLLETAWEAFEHAGLDPRTLRGSNTGVFAGVMYNDYASRLHRAPDGFEGMLLAGNV

GSVVTGRVSYALGLEGPAVSVDTACSSSLVALHLAANALRSGECDLALAGGVTVMSTPN

VFVEFSRQRGLSADGRCRSFAAGADGTGWGEGVGLLVVERLSDARRNGHPVLALLRGSA

VNQDGASNGLTAPNGPSQERVIRAALAGAGLSATDVDAVEAHGTGTTLGDPIEAQALLA

TYGRDRPADRPLWLGSIKSNIGHTQAAAGAAGLIKMIMAMRHGVLPETLHVDAPSPHVD

WSTGHVELLAERRPWPEVDRARRAAVSSFGISGTNAHVIVEQAPAAEAVVSRDEPVGVA

FIGURE 6 (Continued)

```
GLVPWVLSARTADGLRAQAARLREWSARHPEADPVDVGWSLVRERSVFDRRAVVGGRDP
GELGAGLDRLAAGGGIADGRPMFSGPGPVFVFPGQGSQWVGMAAGLLECSPVFAEAVTE
CAAVMDPLVADWSLLDVLRGGSAGELERVDVVQPVLFAVMVGLARWWESCGVKPGAVIG
HSQGEIAAAHVAGYLSLADAVWVVVLRSRALLGVASAGGGMVSVGVSAERARELVAGDD
RLSLAAVNGPTSVVLSGDVEALSVVVEACERDGVRARWIPVDYASHSARMEAVRDEVER
LLADVTPQVGRVPMYSTVSGEVVVDPAELGGAYWFENLRRTVELERAVGAAVADGHGAF
VECSPHPGLVVPMGDTLEAAGVDGVVLETLRRGEGGPDRLVAALSAAFVAGVAVDWAGM
LPGRHVELPTYAFQRRRYWLTGGERAGDPAGLGLVAADHPLLGAVVGSVRDGELLYTGR
LSAATHGWLADHAVFGSVVVPGTAFVELASWVGVEAGCPVVDELTLHAPLVLPDGVGIR
LRVAVGAADSAGRRVVEFHSRPEDAPDEQSWTRHATGTLGAASVPGSASAGAAAWAVWP
PADAEVVDPEAVYERLAEHGYEYGPIFRGLRAAWRRGDDFFAEVALPEAAGRDAHGYDL
HPAVLDAALHVAAAEAVAESGATLLPFAWTGVALHGPGASVLRVMLRRTGRETLAVDVA
DERGVPVASVASLTLRPVAAEQLVAAEEAGREWLYRMVWEIADAPVAEHVEGELLGSDE
ESDASAELVAGGIRVVTPAGAEQVSEVGLFDCPPVVGEAPEEVAGAVHAVLAAVRAWVA
DERFAGARLVVRTRGAVATDAQDRVGSPAHAAIWGLVRVAQSEHPGRFVLVDGDDVDSG
AALRAAVACGLPQVAIREGVVLAPRLVGAVHDTALVPPAPGADQAWRIESGTAGTPDDL
VVTAHPAASAPLAAGQVRVAVRAAGVNFRDVLITLGMYPGRAVVGAEAAGVVVEVGPGV
SEPAVGDRVMGLFEGAFGPLAVADRRLLARVPAGWSFAQAASVPVVFLTALYGLHDLAG
LRSGESVLVHAATGGVGMAATQLARHRGAEVYATASATKWATVRGLGVPDERIASSRDL
SFEQRFARATDGRGIDVVLNSLAGEFTDASLRLLAEGGRFVEMGKTDVRTEGLPAGVRY
RAFDLIEAGPDRIAEMFAELVDLFERGVLQPLPIRTWDIRRAREALRFLGQARHVGKVV
LTVPQPLAADGTVLITGGTGTLGRSLARHLVTRWGVRRLVLTGRAGPAAPGAAELVAEL
AESGADTTIVACDAADRAAMAEVLAAIPAEHPLTAVVHAAGTLDDAPIEALTPERVDHV
LRPKVDAALVLDELTRDADLAAFVLFSSVAGVLGVAGQGGYAAGNAFLDGLAGRRRERG
LPATALAWGLWAERSAMTAQLGVGDLKRLARGGLVPISTAQGLALFDAAWQADEAALIP
ARLDLAALRAQAATQPVHPLLRGLVGTTPTRRNGTPSEAPWARRLASAAPAERVDVALR
LVRAEAAVVLGHESIDGVRPEVTFRDLGFDSLTGVELRNRLSGATGLRLPSTLVFDFPT
PLGLAGFLVAESVGEMDTAPTGPVAGGAVVAADPVVIVGMGCRFPGGVDSAAGLWDLVA
AGGDAIGPFPTDRGWDVDALFDPDPERVGKSYVRTGGFLSGAAEFDAEFFGVSPREALA
MDPQQRLLLETAWETFEQAGIDPTSLRGSRTGVFAGMAGHDYATGGARSQAGLEGHLLT
GNAASVASGRVAYTFGLEGPAVTVDTACSSSLVALHLAANALRAGECDLALAGGVTAMS
```

FIGURE 6 (Continued)

```
TPDFFLEFSRQRGLSVDGRCKAFAATADGMGAAEGVGLLLVERLSDARRNGHSVLAVVR
GSAVNQDGASNGLTAPNGPSQQRVIRAALADAGLSAADVDAVEAHGTGTTLGDPIEAQA
LLATYGRDRAPDRPLWLGSVKSNIGHTQAAAGVAGVIKMVSALRHGMLPRTLHVDEPTP
HVDWSAGGVELLTSARAWPEAGRVRRAGVSSFGISGTNAHVILEQAEESPAGSVPSATP
PVAGTPVWGGRVPWVLSARSEPALRAQAARLRDWLAVHPDADPLDVGRSLATGRAALDH
RAVVHGRDLAELRLAVAKLADSGPGDEASIVGSVSAAGPVFVFPGQGSQWVGMAAGLLE
CSPVFAGVVAECAAVMDPLVADWSLLDVLRGGSAGGEALAERVDVVQPALFVVMVGLAR
WWESCGVKPGAVIGHSQGEIAAAHVAGYLSLADAVRVVVLRSRALLGVASSGGGMVSVG
VSADRARELVAEDDRLSLAAVNGPTSVVLSGDVEALAVVVDGCERDGVRARWIPVDYAS
HSARMEAVRDEVERLLADVTPQAGRVPMYSTVSGGHVTDPSVLGGSYWFDNLRRTVELE
RAVGAAVVDGHSVFVECSPHPGLVVPLGDTLEAAGVDGVVLETLRRGEGGPDRLVGALS
AAFRSGLAVDWAGSGMVPGRRVELPTYAFQRRRYWVEPGERAGGVGWGQFTVEHPVLGA
GVDLADGAGTVFTGRLSAASHGWLAEHVVLGTVIAPGTAFVDLALRAGATVGRATVEEL
TLHAPLILPDAGGVRIQVRVGAPDAAGVGSVEIHSRPEDAAGDEPWTRHASGTLTATDL
DPADVATEAAIWPPAGSTPVDLDGAYERLATAGFEYGPAFQGLRALWRRGAESFAEIEL
ADDARQEAERYEVHPALLDAAVHALGMEPTAEVAPDEARIAFSWRGVRLVAAGAGRLRV
RLAPVGSDAVSLWLSDMDGEPVGSVRALTVRPVAAERLRPAGAPPRDSMFRVEWRPVSG
DESGVAVRWAVVGAADSGPLARLVAAYPDVPVYRSVVEAAGDVAAGPPDVVVVGVGEAD
CSEGSVERTRRVLADVLAWMQDWLADSRFAATRLVVVTSGAVAADVDADPDERVADLAG
AAVWGLLRSAQSEHPDRCTLVDLDEDAASIDAWPAILASAEPQLAVRMGRFRVPRLARV
TAGGGEPVAFAPDGTVLVTGATGGLGALVARHLVTAHGVRRLLLLSRRGAAAPGAAELV
EDLTAQGAEVTLAACDLADRAALAAELARIPAEHALTGVIHTAGVVDDATIANLTDAHM
EHALRPKADAAFHLDELTRDVNPAAFVLFSSGATTFGGPGQGNYAAANAFLDGLARQRR
DRGLPGISLAWGLWAGAQGMGGRLSEADLARWARTGAVAMPAAEALRLFDIALGRPEAA
LVPAHLDLPAMRADAGARPALFRELLGIGTRRAAVGAGGSALTRRLAGMSPAEREQAVL
DVVRTEAANTLGHESAGAVSAGRAFKELGFDSLTGVELRNRLNTATGLRLPSTLVFDYP
TPAGLAAFLVAELVGRSVQAVPVPPVGGRHGDADDAIVIVGMGCRFPGGVASPEDLWNL
LASGGDAIGPFPTDRGWDLAGLFDPDPERAGKSYVESGGFLYGIGEFDAEFFGISPREA
LAMDPQQRLLLETAWETFERAGIDPTSLRGSRTGVFAGVIDNDYGARVNQVPDEVEGYL
GYGSSASIASGRVSYVLGLEGPAVSIDTACSSSLVALHLAVNAVRSGECELALAGGVTA
MATTEFFVEFSRQRGLSPDGRCKAFAAAADGMGAAEGIGLVLVERLSDARRHGHSVLAV
```

FIGURE 6 (Continued)

```
VRGSAVNQDGASNGLTAPNGPSQQRVIRQALGAAGLSAADVDAVEAHGTGTTLGDPIEA
QALLATYGQDRPGDRPLWLGSVKSNIGHTQAAAGVAGVIKMVLALRHGVLPRTLHVDEP
TPHVDWSAGRVEVLADEVAWPAGERVRRAGVSSFGISGTNVHVVLEEAPADAAEPAPAA
PEVPGVGGVLPWVVSARTEAGLRAQAARLRDWVSEHPDAEPTDVARSLVVGRAVLDVRA
VVRGRESGELVAGLDELARAGVGDPGSLVSGSDPVFVFPGQGSQWVGMAAGLLECSPVF
AGVVAECAAVMDPLVADWSLLDVLRGGSAGELERVDVVQPVLFAVMVGLARWWESCGVK
PGAVIGHSQGEIAAAHIAGYLSLADAVRVVVLRSRALLGVASSGGGMVSVGVSAERARE
LVAGADGLSLAAVNGPTSVVLSGDVEALSVVVEACERDGVRARWIPVDYASHSARMEAV
RDEVERLLADVTPQVGCVPMYSTLTGAPIADPAELGGAYWFENLRRTVELERAVGAAVA
DGRTVFVECSPHPGLVVPLGDTLEAAGVDGAVLETLRRGEGGPDRLVAALSAAFVRGLA
VDWAGLIVGARVELPTYAFQRRRYWLDDGARSGDPGGLGLAAVAHPLLGAAVRPAQGAG
LLFTGRLSTATHPWLADHVVLGSTIVPGTVFVDLALWAGAEAECPVVDELTLHTPLVLP
EHGGVHVQVTVDGPDAAGARAVAVYSRPEDAPGEEPWTRHAVGALVADADTGAAPDAAA
EAWPPVGAKPIEVADFYARLVESGVDYGPAFRGMRAAWRRGDELFADVALPAEEERDAH
RFGVHPALLDAGVQTLRVDPGQVDEDDIRVAFSWHGVRLFAAGVTRLRVSCVPSGEGAV
SLRITDETGRAVAAIEALTVRAISADQLRRAGGGRDVLYRLAWRASAVPVPVATPRVAV
VGGWDLPGLGGLVDRYPGFAELASCDPPLPDLVLLPVGDPDADVPFSERRMREVTAELI
GRLEAFLGDERFAAARVVVVTRSAVLVDGDAGLGDPASASVWGVVRAAQAGHPGRIVLV
DLDDEPASAAALAAVASAGGEPQFAVRGGRVSVPRLERIPASGGARSAVGTGTVLIAGA
DRAVGAGVAEHLAGAYGVGRFVLLSVDPSGAGPTELAARLGEAGAEVVSAAWDGHDPGV
LAALVTEHRPAGVVDASGESDAAWALHELTADVDPAFFVLFSSAASLLGSSAHAATAGV
DAFHDALAAHRRASGLPGVSLACGTDPLPGLPDLFDEAIRREDAVLVSASTDLTGPAST
SPLLPSRNGRGATNSAETSIEADGEALARRLAALSEEERERELVGLVRAQAAVLGHAG
IGEIGPERAFKEVGFDSLTAVELRNRLIRGTGVGLRSTLVFDFPTPRILARHLSGRLVE
AASPIGALLADLDRFEGELHAVLGEAEARDRLAERLRRLLADCTAPDESAPAADDVSDV
QSATDDELFSLVDQGFE*
```

Figure 7. Amino acid sequence of the *lepB* gene.

```
CDS             25735..48024
                    /note="LepB"
                    /note="PKS (modules 5-8)"
```

/note="sequence=MAESEEKLRSYLRKAITDARDAHRRVRELEDRQREPIAIVGMA

CRFPGGLGTPEDLWRFVVEGGDAIGEFPTDRGWDLDGLYDPDPDRPGTSYVREGGFLYD

VADFDAEFFGISPREAAAMDPQQRLLLETSWEAVERAGIDPTSLRHSRTGIYTGINGLD

YTTVLARTAKGRDGTLGMANGASLLAGRVAYILGLEGPAVTVDTACSSSLVALHLASNA

LRSGECDLALAGGATVMCTPEIFVNFSRQRGLARDGRCKPFSAAADGFILSDGAGLFLI

ERLSDARRNGHPVLAVLRGSAINQDGASNGLTAPNGPAQERVIRQALQSAGLVTGDVDA

VEAHGTGTTLGDPIEAHALLATYGQDRPADRPLRLGSIKSNIGHTQAAAGVAGMIKMVL

ALRHGVLPRTLHVDAPSPHIDWSAGRVELLTEPVPWPRSDRPRRAGVSSFGASGTNAHV

VVEEAPSDGDDGVVEVPAPTGIGSVLPWVLSARSEAALRAQAGRLRDWLAEHPEADPVD

VGRSLAVGRAVLERRAVVRGRDVAELAVGIGEVADRGELAGGRPMFAGPGPVFVFPGQG

SQWVGMAAGLLECSPVFAGVVAECAAVMDPLVADWSLLDVLRGGSAGGEALAERVDVVQ

PALFAVMVGLARWWESCGVKPGAVIGHSQGEIAAAHVAGYLSLADAVRIVVFRSRALRG

IAAAGGGMVSVGVSVERAEELVAGSAGLSLAAVNGPQSVVLSGDREALAAVVDACEREG

ARARWIPVDYASHSAHMEVVRDEVERLSAEVTPRAGRVPMYSTLTGEVVTDPAELGAGY

WFENLRGTVRLTTAVGAAVADGHVAFVECSPHPGLVVPLADTLDELGVDDGTVLETLRR

DDGGPDRLVAALSAAFVAGVPVDWAALFPGEGRADLPTYAFQHRRYWAEAESPAGGGVA

WGQRAVTHPVLGAAVDLAGDAGTVFTGRLSTTAQPWLADHAVLGTVIVPGTAFLDLVLR

AGAEVGYPAIEELTLHTPLVLPDASGVLVQVVVGAADGDGGDGGDGARTVDVHSRAEDA

PPDHPWTRHASGVLVAAGEERAEDAPAGRWPPTGAEVVGVDDAYERLAVAGFDYGPVFQ

GLRSVRARGDELFAEVELPEEGHADADRFAVHPALLDAALHPLVVAAGADAPVVAGLPF

VWHGIRAGVPGARRLRVRLVRSASGSASGSAAGSDSASGEVSVRAWDEGGREVVAIESL

TIRPVSADGLRTPDALVRDSLFTLAWTALELPDVDDDVPNATLLGGDGAADLAALVAAM

DTGTDVPALVALPVSVDDADPVAAAHTAGRQVLAVLRDWLADERFADSRLVFVTSGAVA

VADEQVRPASAAVWGLVRSAQSEHPGRFVLVDADSVADPGPEFDRALRTGADQLILRDG

TALIPRLVRAPADGGSGGFVPAADGTVLITGGTGTLGTLLARHLVTEHGVRRLLLLSRR

GGTAAGATDLVAELAAFGAEVTCVAGDAADRATLERVLADIPAEHPLTAVIHAAGVVDD

GVVQSLTADRLDAVLRPKVDAAWNLHEATRHLDLTAFVLFSSAAGVLGNPGQGNYAAAN

AFLDALARRRREGLPGSSLAWGWWAPTSEMTAGLGDADRQRMARLGVLPLAPEQGLAL

FIGURE 7 (Continued)

```
FDAATNHAEPTPTVVRMDLAVLRTAGSVVPTLLRGLARVPNRRAATAGSVAELRRRPAG
VSAFDWEQTLIRAVCVHAAAVIGHADATEIDETRAFRDLGFDSLTGLELRNRLNTATGL
RLPATLVFDYPSPVVLGRWLRDRLAEEDAGGPVGSTLGAQVVSPVGSDAGEDSIVIVGM
GCRFPGGITAPEHLWDVVAGGVDTLTDFPTDRGWDVERIFDPDPDRPGSTYVRTGGFVD
SAADFDPDLFGISPREALAMDPQQRLLLETAWETFERAGIDPTSLRGSRTGVFAGAIYY
DYAGGRLRKVPDELEGYIGNGNVGSVASGRVAYTFGLEGPAVTVDTACSSSLVALHLAV
NAVRSGECELALAGGVTVMSTPSVFLDFSRQRGLSSDGRCRSFAAAADGTGWGEGVGLV
LVERLSDARRNGHPVLAVVRGSAVNQDGASNGLTAPNGPSQQRVIRQALGSAGLSPADV
DAVEAHGTGTTLGDPIEAQALLATYGQDRPGDRPLWLGSVKSNLGHTQAAAGVAGVIKM
VLALRHGVLPRTLHVDEPTPHVDWSAGRVEVLADEVAWPAGERVRRAGVSSFGISGTNA
HVVLEEPPPVTEVPDVAVESGLGGRHTWVVSARSEAAVREQAARLRDWVTARPDLDPAH
VARSLVCERALFGHRAVVSGADLAELADGLSAVAAGAEGAVVGAVGRGPGKTAVLCTGQ
GVRALGIGRELHAAFPVFAGALDEVCAAFDDVVPFSVRDVVLGAEGVSDADAQDTGVAQ
PALFAFEVALYRLWASWGQAPDFVVGHSLGEIVAAHVAGVFSLADAVVFVAARARLMSA
LPSGGAMLAVGASEAEVAASCPAEVTIAAVNGPASVVVSGPAEAVAALEPDCVMRGWRI
SRLSVSHAFHSALMQPMLAELREVLTGLTYGTPEIAVVSDTTGRVAGAEELADPEYWVR
HVRRAVRFGDAIATLRAEGVRTFVEIGPEAALTAMVVEGTAGAEDVAAVATRRRGRAAV
SSVVEALARVFVHGATVDWAALSTGSGPGGRVDLPTYAFERRRFWLHAGVDAGDAVGLG
QGVVDHPLLGAVVGLADDQGVLFTGRLALDTHPWLAEHTVLGTVLLPGTAFLELALHVG
RLLDCARVDELTLSAPLALPSTGGVQVQVRVGVPEESGTRTITVHARPDSAEEAPWTLH
AAGALGPSAEVDAPSDAASWPPADATAMDSAGLYPWFAETGVDYGPSFRGVQATWRRDD
EVFAEIVLAADDPAADGRFELHPALFDAALHPLGLTLLDAAEPRLRLPFSWRGVALHTS
GARTLRVRLRPTGPDTIAVTATDETGRPVVAVEALAVREPSRDRLPRPDANAGELFEPQ
WTPLSPADTADMADTLGAVVGGPELASTATRFGATHHPDLAALAESAIPETVLYDLVTA
VPGVSAEAVHQAAAQALDLARSWLADERFESARLIVRTRHAVAAAEGDAPDPAAAATHG
LFRTACSEHPERFALVDADDLDEVSPEAIAAVVVEPEAAVRAGRVLVPRLRRAAVAPKA
DFGFAAEGTVLITGGTGALGRQVARHLVRVHGVRRLLLLSRRGDEAPEAAELRAELIEA
GAHVTFAAGDAAERGVLADVLAAIPAAHPLTGVVHLAGVTDDGLVGTLTPERLAAVLRP
KIDAALHLDELTADADLSAFVLFSSAAGPVGNPGQANYAAANVALDALARRRRARGRPA
VSLQWGLWAERSALTATMSATDRRRAAGAGVRALSVEQGLALLDAAAGRPEAVLTPLRL
DPAILRGPEERVAPVLRGLVPTRARRAPARTSDTARSLVRRLAALPEAEQDRLLVDLVR
```

FIGURE 7 (Continued)

```
THAAGVLGHADARTIDPDRAFGELGLDSLAALELRTRLSTAVGLRLPATMLFDHPCARA
VGVHLRAQLLDAPTPGRAAGVARPVSDEPVAVVAISCRFPGGVASPEDLWRLVSEHTDA
ISEFPQDRGWDLAELFHPDPEHAGTSYVSEGGFLYEATEFDPEFFGISPREALAMDPQQ
RLLLEASWEAIERAGVDPRSLRGSRTGVYAGLMYADYASRLGSAPEGVDGYLGNGSAGS
IASGRVAYTLGLEGPAVTVDTACSSSLVALHLAANALRQGECDLALAGGVTVMSSPATF
VEFSRQRGLAPDARCKSFAAGADGTSWSEGIGLLLVERLSDARRLGHPVLAVVRGSAIN
QDGASNGLAAPNGLAQERVIRDALAHAELRPSDVDAVEAHGTGTPLGDPIEARALLATY
GQDRPADRPLWLGSVKSNLGHTQAAAGVAGVIKMIMAMRHAELPGTLHVDAPSPHVDWS
AGAVSLLTAATPWPQTGRPRRAGVSSFGISGTNAHVILEQGDPAPTAPAEPAPASAPLA
ALAWPLSGASAVALRGQAERLRAHLDAHPEYGPVDIAHALVGGRSRFEHRAVVVAEDAA
GLRAGLDALSADRPDAAVPVGVAGEPGRIAFVFGGQGSQWPGMGARLLTESPVFAARIR
DCDAALAPHTDWSLLAVLRGEPDAPPLDRVDVVQPVLFAVMVALAELWRSLGVRPASVV
GHSQGEIAAAHIAGALTLDDAARIVALRSRALRGLSGDGGMMSVAAGPEQIARLLDGFA
DRLGIAAVNGPAAVVISGAADALAELHAHCEADGIRARVLPVDYASHSAQVEQVREELL
AALGEIVPTPTTDAVFYSSVTGEPVEGTALDAEYWYRNLRATVAFDRATDALLRDGHTV
FVETSPHPVLAPAVEDSAQRAGTDVTVVGSLQRDTDTLARFLTAAAGLHVHGVPVDWSA
THAGHRPRPVDLPTYAFQRERYWLEAGKTPTDAAGLGLHPAAHPLLGAAVVPAEGDRHI
LTGRISLRTHPWLADHTILDTVLLPGTAFVELALQAGDRADCDLIEELTVEAPLRLTDT
GAVHLQVLLDEPDEQGRRALTIHSRADDAPAEQTWTRHASGVLAPVADGLDAVPATDAA
WPPAGAVALDVDGLYERLAGQGYRYGPAFRAVRAAWRLGDTVLAEVAPGDEAHGARDFA
LHPALLDAALHAAGAADSGTSGGDGAIGLPFAWTDVRLHAVGAAALRVRLERRGPDTVG
LELTDHTGALVATVGALVGRPATADRLAPAADPAHRDLHHVDWSPLPTPTEPSTARWSL
LGPDELEAVAGLRAAGAEVHADGDPDPADVLLITCAGRTGDDVPEAARAATHRVLDLLQ
RALTDPRLTACTLVVLTRGAVPGHHGEDVCDLVAAPIVGLVRSAQTEHPGRIVLVDLDD
HADSFAALRAAVVTDVGEPQLAIRTGTVSAPRLIRTGTEPRLSPPAGAPAWRLDLLGGG
TLDRLALLPNADAAVPLAPGQVRIAVRAAGLNFRDVVVALGMVTDTRPPGGEGAGIVVE
VGPDVPELVPGDRVMGLFGGGTGPITVADHRLLAPIPTGWTYAQAAAVPVVFLTAYYGL
ADLGGLRAGESLLVHAATGGVGMAAVQLARHWNVEVFGTASPGKWATLRGQGVDDAHLA
SSRDLDFAHRFGEVDVVLNSLAHEFVDASLRLLAPGGRFLEMGKTDIRDRDEVLAAHPG
RDYRAFDLMDAGPERIREMLADLYRLFETGVLHPLPVTPWDVRGAVGAFRHLSQARHTG
KIVLTLPPTLGAAPDPEGTVLITGGTGTLGGLLARHLVRTAGVRHLLLIGRRGPAADGA
```

FIGURE 7 (Continued)

```
AELSAELTALGARVTIAACDAADRAALAALLADIPAEHALTSVIHAAGVIDDAALTALT
PERLDRVLRPKLHAAWNLHELTRDLDLAEFVLFSSMAGTFGGAGQANYAAANAFLDALA
QHRRARGLAATAAAWGLWAQASGMTGHLGAEDLDRIARTGVAALETAHALTLYDALRAA
DRPTIVPARLDPDALRAAAPTVPALLRDLVRDLVRPRGRRAAADTAPDAASLAERLARL
PEERRRQTLLTLVRTETAAVLGHATPDAVAPLRPFKALGFDSLTSVELRNRIGAATGLR
LPVTLVFDHPTPQALADHVGAELLGVAPVVVEPERPAAHTDDDPIVIVSVGCRYPGGVA
GQDEMWRMLAEGTDTIGPFPQDRGWELDTLFDPDPDRVGKSYVREGGFVADAVHFDAEF
FGISPREATSMDPQQRLLLETAWETFEQAGIDPTTLRGSGTGVFVGAMAQDYHGTSQAM
AEGQEGYLLTGTATSVISGRVSYVLGLEGPAVTVDTACSSSLVALHLAANALRAGECDL
ALAGGVAVLTSPQAFIEFSRQRGLAADGRCKPFAAAANGTGWGEGVGLVLVERLSDARR
RGHPVLAVVRGSAVNQDGASNGLTAPNGPSQQRVIRQALRNAGLLATDVDAVEAHGTGT
TLGDPIEAQALLATYGQDRPAQRPLWLGSVKSNIGHTQAAAGVAGVIKMVLALRHGTLP
PTLHVDAPTPHVDWASGQVRLLTEPVAWPAGERVRRAGISSFGVSGTNAHVIIEQAPAE
GAVDAAPVDAAPAAALGGIVPWVVSARSQAGLRAQAARLRDWAAVHPEFAPADVAASLV
RGRAVFERRAVVRGRDTDELVAALAELVDSSATGEAPTAIGPGPVFVFPGQGSQWVGMA
AELLTCCPVFAETVTQCAEVMDPLLPGWALLDVLRGTDDETAELLRRVEVVQPVLFAVM
VGLARWWESCGVRPAAVIGHSQGEIAAAYIAGHLTLPDAARIAALRIRAVQAADMIRGA
MVAVAVSALRAEELITRTGTGDLVNVGGINSPTNTVLSGDTDALALIVADCEREGVRAR
WIPAAYSSHSPQMDAVRGDLERLLAGIQPTPGRVPMYSTVTGGRLADDALLDIDYWFEN
MRRTVRFEEAIGAAAADGHTVFLECSSHPGLVVPLGDTLDSLGVHGATLETLRRADGGA
DRLLAALSAMFVHGGAVDWAGLLPGRRVALPTYAFQRRRHWVEPVGPARGGVGWGQFAV
EHPILGAGVDLADGSATVFTGRLDTTTHGWLADHLVLGEVLVPGTVFVDLALRAGGALG
CAVVEELALHEPLVLPDADGVRIQVTVEAPDDAGTRALTIHSRPEDAPAAEPWTRHASG
TVAPGAHRPQQESGPWPPIGATPLDVADVYLRLTELGLGYGPTLAGLRAAWRRGDDLFA
EVARTADGERGTARFGLHPALLDAALHGLAPGSAPGGAPTEVRLAGAWRGVTLGGDAGT
AGRIRLRGVDGDGVEVELADEAGRSMARIESVALRPWSAGQVRAAGRARPWLTRWEWAR
VEPTDPAAAGGRWAVLGARAWDGVPAYATAAELIAAVEVGVPVPDLVALPVRIDPAGGL
DPEAIRATIRAVRETLRQWRAEPRLAASRLVVVTHDAVSARPEDRVTDPGAAAVWGVVR
AARAADPERFVLADVDGEDGSWPVLLAEASAGRAEFAIRAGTVLLPGLARVPAGETGTA
GFPTDGTVLVTVATDPTDPTDGTDPVGTLLARHLVTAHGVRRLILAGGPAAGMPLAREL
AAQGAEIHVVVCDVTDRTELAKLLATIPEHSPLTAVVHTAGLGRSHTEAMLRARVDAAV
```

FIGURE 7 (Continued)

HLHELTRDADLSAFVLCTALDGVLADPGRGEHAAGDAFLDALARHRHAAGLPALALAWA

PGAEPVAGLLPLPGEQATVLFDRALGLPEPALIPLAPDTSALRRAEPGALPALLTTLVA

DPNHRVGAAAEAAPALIGRLLDLPDDERESVLVDLVRGCAAAILGHADPTAIETGAAFK

DLGFDSLTALEMRNRLRAALGLTLPATLIFSHPNAAALGRHLHGLLRREHGVSWDSVLG

EIDRVEAMLAQLDDADRARATERLRDLIGGPEAPLAGRESGANGDAAGGRGFDAATDEE

LFDFIDGGIEH*

Figure 8. Amino acid sequence of the *lepC* gene.

CDS             48110..58357
                    /note="LepC"
                    /note="PKS (modules 9-10)"

MANEDKLRDYLRRATTELQETRLRLRETEDKWHEPLAIVGMHC

RYPGGVASPDDLWDLVDAGTDAITGLPPGRGWEVDEAANGTSYRGGFLTDAADFDADFF

GISPREALAMDPQQRVLLEASWTVFEHAGIDPTTLRGSRTGVFVGVIASDYLSRLARVP

KEVEGHLLTGSLVSVASGRLAYHFGLEGAAVTVDTACSSSLVAVHLAGQALRAGECDLA

LVGGATVLATPGAFDEFSRQQGLAGDGRCKSFAAGADGTGWSEGVGLLLMERLSDARRN

GHRVLAVVRGSAVNQDGASNGLTAPNDLAQERVIRQALANARLAASDVDAVEAHGTGTR

LGDPIEAQALLATYGQNRPAARPLRLGSIKSNIGHAQAAAGVAGVIKMVQALRHGVLPR

TLHVDEPTPHVDWSAGRVALLTEPMAWPAGERVRRAGVSSFGVSGTNAHVIVEEAPPVE

EPVGAADPARPLGVVTPWVVSARTEDGLRAQVERLREWAIEHPEADPADVGRSLASGRA

LSGHRAVVLGRDAAELVEGLSVVVDGEPEAIVGEARRGSGRTAVLFTGQGVRSRGMARE

LHAAFPVFAAALDEVCAAFDAVLPFSVRDVLLAEGEGGGADGDGGEDTGVAQPALFAYE

VALYRLWTSWAAAPDAVAGHSLGEVVAAYVAGVFSLADATTFVAARATLMSALPPGGAM

VAVGTSESAAARLLADHPGVGIAAVNGPTGVVLSGEAAAVAEVARVCAERGLRISRLRV

SHAFHSALMEPMLDELAEVVSGLTLRPARMAIGSNVTGRIGSAEQLCDPRYWVDHVRRA

VRFGDVLDALRADGVRTFVEIGPDAALTPMVADVTADADDVVAVATRRRDRDPVTGVVE

ALARVFVRGAVVDWAALVPGRWVELPTYAFTRRRFWLDAGTGAGDPTGLGQGTVDHPLL

GAVVGLADGHGSLFTGRLSLDTHPWLADHVVLDTVLLPGTAFLELALHTGRRVGCDRVE

ELSLETPLAFGERGGCQVQVWIEAAGPDERRRAITIHSRPDDGDGDEGWIRNAVGTVAP

VEDKAPADAVADPTPWPPTGATPVPIDDFYPWLADNGVAYGPCFRAVRAVWRRGEEIFG

EIALPEQVGYEADRFGVHPALMDATQHLLGVAAFADPAESEGGGLALPFSWREVRLHTP

GAASVRARVVRTGPESVTLSLADEDGRPVAEVESLAVRPISAEQLRTSTAGRRDPLYTL

RWTPLPRPSAAPGIGSPAIIADSGSGDPFAGRLGGTVHPDLTALADAVDAGLPTPEVVV

LAWPTIPAGPLGDVPDPDDVHAAVHRALATVQTWLGDERFTGARLVVVTRGAVAVADEE

VRDPAAAAVGGLVRSAQSEHPDRLVLVDLDEDAASPGALPAAIGAGEPQLAVRAGVAYL

PRLTRTPAIEPSTPLFAPDGTTLVTGGTGALGALVARHLVVAHGVRRLLLVSRRGIAAP

GAGSLAAELTGLGATVDVVACDVSDRADLAKKLAAIPSAHPLSAVVHVAGVVDDGVIGA

LTPERVDRVLRPKVDAALHLHELTRDADLTAFVLFSSVAGVIGSLGQANYAAGNAFLDA

FAQRRRALGLPAVSMAWGLWAEESGLMREEFAETDRQRINRSGVLPLSDEQGLALFDAA

FIGURE 8 (Continued)

LAHGEPILAPVRLDLSALRRLEDELPAILGGLVPTSRRDGARPGAADTRRLAQRLAGRS

EPEQLRLLTELTRAQAAVVLGHAGADAVAADRAFTELGFDSLTALEMRNRLNTVTGLRL

PATVLFDYPNAAALARFLRAETLRVPQYTQAAANTAAKARTSDEPIAIVAMSCRYPGGI

DTPEELWRCVAGGVDLTSPFPTDRGWDLGALYDPDPDRSGRCYTREGSFMRDIDRFDAE

LFGISPREALAMDPQQRLLLETSWEAFERAGIDPSSLRGSNTAVFAGLMYADYAAGRVG

DVGDELEAYIGNGNSFGVASGRVAYTLGLEGPAVTVDSACSSSLVALHWAAHALRSGEC

DLALAGGATVMSTPSVFVEFARQRGLAPDGRCKSFAAAADGTAWGEGIGMLLVERLADA

RRNGHPVLAVLRGSAINQDGASNGLTAPNGPSQQRVIRQALANAGLATADVDAVEAHGT

GTVLGDPIEAQALLATYGRDRPAERPLWLGSIKSNFGHTQAAAGVAGVIKMVMAMRHGM

LPPTLHVDEPSPHVDWSTGRVELLAEGRPWPEVGRARRVAVSSFGISGTNAHVILEQAD

EEPEPAARTTSGTGIGGVLPWVLSARTEAGVRAQAARLRDWAGARPEVDPADVGWSLAS

GRSVFERRAVVWGRDGAELTAGLDALAAGRDAGARAVLAGGTGVSGEAAVGPVFVFPGQ

GSQWVGMAAELLTCCPVFAESVAECAAAMDPLLADWALLDVLRDASAALLERVDVIQPV

LFAVMVGLARWWESCGVRPSAVIGHSQGEIAAAHVAGFLSLEDAVRIVVLRSRALRGLA

ADGDGMLSVGVSAERGRELVARVQGLSLAAVNGPDSVVLSGPVEGLTPIAAACERDGVR

ARWIPVDYASHSARMDDVREVLAESLAGVEPGIGRVPMYSTVSGLKVTDAADLGGEYWF

ENLRRTVQLATAVGAAAADGHSVFVECSPHPGLVVPLGDTLDALGSTSGTVLETLRRGE

GGPERLVAALAAAFVSGLPVDWAGLLHHDGVRRVQLPTYAFQGRRFWLEPDMGTALPGR

TTPTPVVGDTEDSRLWEALEAAGAEDLAAELEVAADAPLSDVLPALTSWRARRRADATV

RSWRYGVRWEPWAAPAASADRMGRLLLVAPDGEIGDVLAGALAECGAEVVVLSAEGERT

ALARRLAAIGEEGVPAGVVSLSAVGCAADADPVPALAPVLTLVQALGDAGMEAPLWVLT

RGAVSVLGEEPTGPAGAAVQGLGRVVGLEHPGRWGGLIDLPQVVDGRVAETLAGILAAG

AGGTGSGEDEIAIRPLGVFVRRLARMAGPEGSGTSRWRPGGTALVTGGTGALGGRVARW

LVREGVERVVLAGRRGPDAPGADRLREELAAAGAEVAVLACDLGDRDAVAALLAEVRAG

GRRIDTVVHAAGAVVVGPLADSTVADLADASAAKVGGALLLDELLRADEPDTVVLFSSA

AGVWGGAGQGAYAAANACLDTIAERRRARGLRTVSIAWGQWAGGGMADGAAGAHLDRIG

VPAMDPDRALEALRQALDEDLTCVTVADVDWPRFAAGYTAARPRPLIADLVAAEVAAAP

VTEARGAGEPDGPSVWRARLAELGAADREAELLALVRTEVAAQLGHADPAAIEPERPFR

DLGFDSLAAVGLRNRLTETIGLRLPSTLVFDHPTAVALAAHIDGELFAETVGTVSVFAE

LDRLEAALGELGGDFAERGRVGARLAELAGKWREIEAASQKAEPEGADFAAAEDEEMFD

MLGKEFGIS*

Figure 9. Amino acid sequence of the *lepD* gene.

CDS             58243..64173
                      /note="LepD"
                      /note="PKS (11 & TE)"

MAGDRGREPKGRARGSRLRGSGGRGDVRHARKGVRHLLSGAGD

DRRSRVPTAHGSIRFDQAEDGRTDMSNEERLRHFLRETATDLRRTKQRLHEVESAAREP

VAIVAIGCRLPGGVRSAEDLWELVRTGTDAIAGFPSDRGWDPANVYADLPGGEGVSGGS

AGSGGSTTRQGGFVYDAAAFDAEFFGVSPHEALAMDPQQRLLLETAWETFERAGIDPLS

MRRSRTGVFVGAGALGYGGGMRADNAEIQAHRVTGGSMSVVSGRIAYTLGLEGPAVTLD

TACSSSLVALHLAANALRSGECDLALAGGVTVMARPTAFVEFSRQGGLASDGRCRSFAA

AADGTGWGEGVGLLLVERLSDARRNGHPVLAVLRGSAVNQDGASNGLTAPNGPSQQRVI

RQALAAAGLSAADVDAVEAHGTGTVLGDPIEAHALLATYGRDRPADRPLWLGSVKSNIG

HTQSAAGVAGVIKMVMALRHGLLPRTLHVDRPSPHVDWASGRVELLTDEVPWPAGGRVR

RAGVSSFGISGTNAHVVLEEAPAVEGASGEGAEPAPGVGGLIPWVVSARSPEALRAQAA

RLREPAVADPADVGRSLVTGRALLDHRAVVLGRDAAELGRLAALAAGSPGAVEPSEGG

TPVVVTGNVPRAGGAGGRVAGRGAVVFTGQGGRLPGIGRELYAGFPVFARALDEVGAAF

DAVVPFSVRDVLLGVEGTVGVDADDTGVAQPVLFAFEVALYRLWSSLGSVPDFVVGHSL

GGIVAAHVAGVFSLADAVAFVAARARLMSALPGGGAMLAVGASEAQVTALSDGLPVSIA

AVNGPASVVVSGAVAAVDEVAARCAARSWRSSRLRVSHAFHSVLMEPMLAELRDVLRRL

SFGAPEIGLVSDTTGRVVTAEEVGDPEYWVRHVRDAVRFADAVGTLRERGVATFVELGP

DAALTAMVAECTAGVGEVLGVPAQRRGRPAVATLAGALATAFVRGLPVDWVGALGGPGG

RRVELPTYAFQGRRYWLEPGKASVTPAGPDSVDGPLWDAVERAGAGELAAILAVSEDAT

LREVVPALSSWRARRRVDATAASWRYAVRWEPWAGGSSDAAALSGRWLLVHPAASELAD

AVARELTERGAEVVRVGGEGIGSHVGAEPVAGVVSLIGSGSGSGSTSGSGSGSGSASGS

GSGSGSGSGSGSGSSCGSGSVPGLGSCAGDDCADLVAAVVAMGELLAELRRFEVAAPLW

CVTRAAVSVLGEDLANPVGAGLWGRGLVASLEQPGCWGGLVDLPAVADTRALGVLATIL

AGTSDEDQFAIRPLGVFTRRLTPLPAEGSGRVVRTREAALITGGTGVLGAHAARWLVAH

GTERVILLGRRGARAPGFDALRADLEAAGAEVVAIACDLTAPDAAERLRAALPATGAPI

RTVVHAAGVPGSPTATGADAVADTVTAKVAGALALDTLFGADRALDAFVLYSSGAGVWG

GAGQGAYAAANAFLDALAVRRRQRGLPATAIAWGPWAAGGMADGEGERLLARVGVRAMD

PAAALAALGRALVEDLTCVTVADLDRPRFAAGYTSARPRPLIADLIDAEPPTATAPPTR

PGGVWDPAVTRSPARLAAELLDLVRAEVAAQLGHAGVEAIEPDRPFRDLGFDSLAAVGL

FIGURE 9 (Continued)

RNRIAEATGVHLAGTLIYDHETPAALAAHLADALREGVPETRPAPTAPGGAEDSNDMLG

TVYRKLALLGRMDDAESLLVGAAGLRQTFEDPNRLPKTPGFTRLARGPARPRVICFPPF

APVEGAIQFGRLAGTFEGRHDTAVVTVPGFRPGEPLAASLDVLLDLLADATLRCAGDDP

FAVLGYSSSGWLAQGVAGRLEATGRTPAGVVLLDTYLPATMSRRMRKAMNYEVIVRRQA

FTALDYIGLTAIGTYRRMFRGWEPKPGSAPTLVVRPSRCVPGSPEEPMTGEDWRSTWPY

EHTAAEVEGDHCTMIGEHAEQTGAVVRAWLAGDRTVSIDTREGTA*

**Figure 10. Amino acid sequence of the *lepE* gene.**

```
CDS             64703..65881
                /note="LepE"
                /note="P450"
```

MIPVLELVQISTLPDAERELEQLARRYPIIRTRQVGGIEAWTV

LGAGLTRQLLGDPRLSNDLHTHAPHAAQSADGPTVLFEQDNPDHARYRRLVSAAFASRA

VRNLEPRIVDIARALLDRLPAEGGTVDIVEAFANPFPLEVICELLGVPMADREVFRTRV

ENMDSPSTAVRRAAMDAFVAYCANLVDAKRTEPTEDLLSELVQAELDDGSRLSANELIG

FGSVLLFAGHVTTAYLIAAALYELITHNDQLAALRADPTLVEGTVEEALRFGSLLSTT

NRVALTDLEIGGVLVRRGDLVRFLLSAANRDPAIREDPHTFDITRSTTAHLGFGHGPHF

CLGQRLARQEIKVALTEIVTRFPTLELAVPAEKLRWRASDFLRGLAELPLTYAP*

Figure 11. Amino acid sequence of the *lepF* gene.

```
CDS             66124..66564
                /note="LepF"
                /note="putative tetR-family transcriptional regulator"
```

MRERKKARTRQVISTVAFDLFEEQGFEQTTVDMICRRHAMTVS

HGNLEDHAEQTARRHALRRRFLGVRSVHDHGVALIDTVAHRIVTTAAARLGVDPAVDLR

PHALGALVAAMTRRVVIDDIAPGPINEWAEAFRTLLPTPAAHTD*

US 7,851,190 B2

BIOSYNTHETIC GENE CLUSTER FOR LEPTOMYCINS

CROSS REFERENCE TO RELATED APPLICATIONS

This application is a divisional of allowed application Ser. No. 10/937,730, filed 8 Sep. 2004 now U.S. Pat. No. 7,288,396, which claims benefit under 35 U.S.C. §119 to U.S. provisional applications No. 60/502,423 (filed 11 Sep. 2003) and No. 60/553,384 (filed 15 Mar. 2004), the entire contents of each prior application being incorporated herein by reference.

STATEMENT OF GOVERNMENT INTEREST

This invention was made with Government support under Grant No. 1 R43 CA108372-01 awarded by the National Institutes of Health. The Government has certain rights in this invention.

FIELD OF THE INVENTION

This invention relates to materials and methods for biosynthesis of leptomycins, leptomycin derivatives and analogs, and other useful polyketides. The invention finds application in the fields of molecular biology, recombinant DNA technology, chemistry, human and veterinary medicine, and agriculture.

BACKGROUND OF THE INVENTION

Polyketides are complex natural products that are produced by microorganisms such as fungi and mycelial bacteria. There are about 10,000 known polyketides, from which numerous pharmaceutical products in many therapeutic areas have been derived, including: adriamycin, epothilone, erythromycin, mevacor, rapamycin, tacrolimus, tetracycline, rapamycin, and many others. However, polyketides are made in very small amounts in microorganisms and are difficult to make or modify chemically. For this and other reasons, biosynthetic methods are preferred for production of therapeutically active polyketides. See PCT publication Nos. WO 93/13663; WO 95/08548; WO 96/40968; WO 97/02358; and WO 98/27203; U.S. Pat. Nos. 4,874,748; 5,063,155; 5,098,837; 5,149,639; 5,672,491; 5,712,146 and 6,410,301; Fu et al., 1994, *Biochemistry* 33: 9321-26; McDaniel et al., 1993, *Science* 262: 1546-1550; Kao et al., 1994, *Science,* 265:509-12, and Rohr, 1995, *Angew. Chem. Int. Ed. Engl.* 34: 881-88, each of which is incorporated herein by reference.

The biosynthesis of polyketides may be accomplished by heterologous expression of Type I or modular polyketide synthase enzymes (PKSs). Type I PKSs are large multifunctional protein complexes, the protein components of which are encoded by multiple open reading frames (ORF) of PKS gene clusters. Each ORF of a Type I PKS gene cluster can encode one, two, or more modules of ketosynthase activity. Each module activates and incorporates a two-carbon (ketide) unit into the polyketide backbone. Each module also contains multiple ketide-modifying enzymatic activities, or domains. The number and order of modules, and the types of ketide-modifying domains within each module, determine the structure of the resulting product. Polyketide synthesis may also involve the activity of nonribosomal peptide synthetases (NRPSs) to catalyze incorporation of an amino acid-derived building block into the polyketide, as well as post-synthesis modification, or tailoring enzymes. The modification enzymes modify the polyketide by oxidation or reduction, addition of carbohydrate groups or methyl groups, or other modifications.

In PKS polypeptides, the regions that encode enzymatic activities (domains) are separated by linker regions. These regions collectively can be considered to define boundaries of the various domains. Generally, this organization permits PKS domains of different or identical substrate specificities to be substituted (usually at the level of encoding DNA) from other PKSs by various available methodologies. Using this method, new polyketide synthases (which produce novel polyketides) can be produced. It will be recognized from the foregoing that genetic manipulation of PKS genes and heterologous expression of PKSs can be used for the efficient production of known polyketides, and for production of novel polyketides structurally related to, but distinct from, known polyketides (see references above, and Hutchinson, 1998, *Curr. Opin. Microbiol.* 1:319-29; Carreras and Santi, 1998, *Curr. Opin. Biotech.* 9:403-11; and U.S. Pat. Nos. 5,712,146 and 5,672,491, each of which is incorporated herein by reference).

One valuable class of polyketides includes the leptomycins and their analogs (FIG. 1). These compounds are selective inhibitors of protein export from the cell nucleus and thus affect the cellular location of proteins. The function of many key proteins and transcription factors involved in cell growth can be regulated by their cellular location. For instance, the tumor suppressor p53 normally resides in the cell nucleus where its activation promotes cell-cycle arrest and apoptotic cell death. Mislocation of p53 into the cytoplasm, especially its dominant negative mutant forms, is associated with development of many types of cancer. Nuclear factor κB (NFκB) is a transcriptional activator that targets genes involved in cell proliferation and apoptosis. It is constitutively activated in certain cancer cells, aiding tumor resistance to radiation and cancer chemotherapy drugs. NFκB resides in the cytoplasm in an inactive form complexed with the inhibitor of nuclear factor IκB; upon stimulation by factors such as TNF-α or CD-40 ligand, events are set in place that remove IκB and allow importation of NFκB into the cell nucleus.

Leptomycin B (LMB; also known as CI-940 or elactocin) and the ratjadones (FIG. 2) are the only known low molecular weight inhibitor of nuclear transport. Because of the structural similarities, the kazusamycins, leptofuranins and callystatins are also implicated. Callystatins come from a marine sponge whereas all the other compounds are bacterial metabolites. All of these molecules are exceptionally potent, typically displaying $IC_{50}$ values in the 100 picomolar to 10 nanomolar range.

Protein export from the cell nucleus requires a nuclear export signal (NES) as a domain in the exported protein, CRMI (exportin-1) to recognize the NES and Ran, a Ras-like GTPase. In the nucleus CRMI forms a complex with the NES-protein and Ran/GTP, then the complex is translocated through the nuclear pore complex into the cytoplasm. There, the Ran GTPase activating protein (RanGAP), found only in the cytoplasm, promotes hydrolysis of Ran/GTP to Ran/GDP, causing release of the NES-protein.

The high potency and novel mechanism of action prompted an investigation of the antitumor activity of LMB in mouse murine and xenograph cancer models. Activity was observed at low doses against adriamycin, amsacrine and mitoxantrone resistant P388 leukemia, other leukemias, B16 melanoma, Ridgway osteogenic and M5076 sarcomas and mammary adenocarinoma. Acute toxicity appeared to be gastrointestinal and was exacerbated upon more frequent or oral administration of the drug. The maximum tolerated dose (MTD) in mice ranged from 0.12 to 1 mg/kg, as a function of dosing schedule.

LMB has also attracted considerable interest as a biochemical tool to study the role and regulation of nucleocytoplasmic shuttling proteins and for its potential therapeutic use in combination with other drugs. Vigneri and Wang, "Induction of apoptosis in chronic myelogenous leukemia cells through nuclear entrapment of BCR-ABL tyrosine kinase," *Nature Medicine* (2001) 7:228-234, describes combined treatment of cultured CML cells with STI-571 and LMB. STI-571 effectively masks the ability of Bcr-Abl to be retained preferentially in the cytoplasm; upon nuclear importation of the drug-inactivated protein, LMB inhibits nuclear export of Bcr-Abl and withdrawal of STI-571 releases the ability of the constitutively activated Abl component to induce apoptosis. While the effect of either drug alone is fully reversible (STI-571 does not permanently inhibit Bcr-Abl and nuclear export is restored by synthesis of fresh CRM1), their combined use caused irreversible and complete killing of the Bcr-Abl transformed cells. Such treatment also preferentially eliminated mouse bone marrow cells that express Bcr-Abl. This strategy can overcome the main limitation of acute CML treatment with STI-571, which is acquired drug resistance due to mutation or overexpression of Bcr-Abl.

LMB has other types of potential therapeutic uses. Because it can promote nuclear retention of the p53 tumor suppressor protein, treatment with LMB can lead to p53 activation in the nucleus, which results in cell-cycle arrest and apoptosis. Combined use LMB and actinomycin D can reactivate p53 and prevent its degradation by HPV E6 protein in cervical carcinoma cells infected with human papillomavirus. LMB can also potentiate the effect of rapamycin, an emerging cancer drug, by blocking nuclear export of mTOR, the protein kinase target of rapamycin that controls the activity of two transcription factors. The antiviral activity of LMB has been elucidated as resulting from inhibition of the nuclear export of the HIV-1 Rev protein and Rev-dependent unspliced and partially spliced mRNA, which is an early step in viral replication. LMB interferes with cyclinB1/Cdc2, cyclinD1/CDK4 and TGF-beta dependent signaling also, suggesting possible uses against cancers with aberrant signaling involving these actors. A synthetic HIV-1 Rev inhibitor, PKF050-638 (FIG. 2), has been developed that mimics the activity of LMB.

Two limitations have to be overcome to increase the potential for development of LMB into an effective anticancer or antiviral drug. One, a reliable source of pure drug must be developed, because "The use of LMB . . . has been hampered by the variability of the quality of LMB production lots" (D. Daelemans et al. 2002, "A synthetic HIV-1 Rev inhibitor interfering with the CRM1-mediated nuclear export" *Proc. Natl. Acad Sci. USA* 99: 14440-5). This is not surprising given the close structural similarity of leptomycin-like compounds isolated from their natural sources (FIG. 1). In fact, at least 5 different forms of leptomycins have been detected in the culture extracts of the ATCC 39366 strain and 6 forms in another LMB producer. Two, a less toxic form of LMB would be more appealing for drug development studies. Even though the drug's effects have been reported to be fully reversible, toxicity is likely to be mechanism-related and exhibited in different bodily tissues given the widespread role of CRM1-mediated protein export. The available SAR data (FIG. 2) are insufficient for designing a less toxic analog. Analog production and evaluation will require both chemical and microbiological approaches, because little effort towards the total synthesis of LMB has been reported.

The following data suggest that analogs with an acceptable therapeutic index could be found. LMB displayed an approx. 250-fold difference in activity between a Rev-dependent assay and cytotoxicity to the same cells in vitro and PKF050-638 had a 75-fold difference in the same two assays (FIG. 2). These data show that LMB itself can have a good therapeutic window in certain instances. It is thus likely that less toxic LMB analogs can be discovered as a consequence of differential binding to CRMI or pharmacokinetic behavior that modulates their distribution, half-life or metabolism.

Given the promise of leptomycin B in the treatment of conditions and diseases characterized by undesired cellular hyperproliferation, there thus exists an unmet need for a production system that can provide large quantities of leptomycin B in a form substantially free of minor congeners and other impurities. The present invention meets this need by providing the biosynthetic genes responsible for the production of leptomycins and providing for their expression in heterologous hosts. Further, there is an unmet need for analogs of leptomycins potentially useful in the treatment of viral diseases. The present invention meets this need by providing the means for biological generation of leptomycin analogs through genetic engineering of the biosynthetic genes.

SUMMARY OF THE INVENTION

The present invention provides recombinant nucleic acids encoding polyketide synthases and polyketide modification enzymes. The recombinant nucleic acids of the invention are useful in the production of polyketides, including but not limited to leptomycin and leptomycin analogs and derivatives in recombinant host cells.

In one aspect, the invention provides the nucleic acids involved in leptomycin biosynthesis in isolated, purified, recombinant, or synthetic form, including but not limited to sequences incorporated into a vector or into the chromosome of a host cell. The biosynthesis of leptomycin is performed by a modular PKS and polyketide modification enzymes. The leptomycin polyketide synthase (herein also "leptomycin PKS" or "leptomycin synthase") is made up of several proteins, each having one or more modules. The modules have domains with specific synthetic functions.

In another aspect, the present invention provides domains and modules of the leptomycin PKS and corresponding nucleic acid sequences encoding them and/or parts thereof. Such compounds are useful in the production of hybrid PKS enzymes and the recombinant genes that encode them.

In another aspect, the present invention provides modifying genes of leptomycin biosynthetic gene cluster in recombinant form, including but not limited to isolated form and incorporated into a vector or the chromosomal DNA of a host cell. Such compounds are useful in the production of leptomycins, leptomycin analogs, and leptomycin derivatives according to the methods of the invention.

In another aspect the invention provides a recombinant PKS wherein at least 10, 15, 20, or more consecutive amino acids in one or more domains of one or more modules thereof are derived from one or more domains of one or more modules of leptomycin polyketide synthase. Preferably at least an entire domain of a module of leptomycin synthase is included. Representative leptomycin PKS domains useful in this aspect of the invention include, for example, KR, DH, ER, AT, ACP and KS domains. In one embodiment of the invention, the PKS is assembled from polypeptides encoded by DNA molecules that comprise coding sequences for PKS domains, wherein at least one encoded domain corresponds to a domain of leptomycin PKS. In such DNA molecules, the coding sequences are operably linked to control sequences so that expression therefrom in host cells is effective. In this manner, leptomycin PKS coding sequences or modules and/or domains can be made to encode PKS to biosynthesize compounds having antibiotic or other useful bioactivity other than leptomycin.

In one embodiment, the invention provides a recombinant DNA molecule that comprises a sequence encoding a chimeric polyketide synthase composed of at least a portion of the leptomycin PKS and at least a portion of a second PKS for a polyketide other than leptomycin. Such chimeric genes are useful in the production of leptomycin analogs, leptomycin derivatives, and other polyketides.

In another aspect, the present invention provides recombinant host cells that contain the nucleic acids of the invention. In one embodiment, the host cell provided by the invention is a *Streptomyces* host cell that produces a leptomycin modification enzyme and/or a domain, module, or protein of the leptomycin PKS. Methods for the genetic manipulation of *Streptomyces* are described in Kieser et al, "Practical *Streptomyces* Genetics," The John Innes Foundation, Norwich (2000), which is incorporated herein by reference in its entirety. In other embodiments, the host cells provided by the invention are eubacterial cells such as *Escherichia coli*, yeast cells such as *Saccharomyces cerevisiae*, or myxobacterial cells such as *Myxococcus xanthus*.

In another embodiment, the invention provides a recombinant *Streptomyces* host cell that produces leptomycin in its native state, wherein at least one domain-encoding region of the endogenous leptomycin PKS gene is deleted, inactivated, or replaced. Also provided is a recombinant *Streptomyces* host cell that produces leptomycin in its native state, wherein at least one polypeptide-encoding open reading frame of the leptomycin PKS gene cluster is deleted or otherwise inactivated.

In another aspect, the invention also provides methods for producing leptomycins, leptomycin analogs and derivatives, and other polyketides using the nucleic acids, proteins, vectors, and host cells of the invention.

These and other aspects of the present invention are described in more detail in the Detailed Description of the Invention, below.

BRIEF DESCRIPTION OF THE DRAWINGS

FIG. 1 shows various members of the leptomycin family of natural polyketides.

FIG. 4 shows the organization of the leptomycin biosynthetic gene cluster as deduced from SEQ ID NO:1.

FIG. 5 shows the DNA sequence of the leptomycin biosynthetic gene cluster.

FIG. 6 shows SEQ ID NO: 4, the polypeptide product of lepA, a gene in the leptomycin PKS cluster.

FIG. 7 shows SEQ ID NO: 5, the polypeptide product of lepB, a gene in the leptomycin PKS cluster.

FIG. 8 shows SEQ ID NO: 6, the polypeptide product of lepC, a gene in the leptomycin PKS cluster.

FIG. 9 shows SEQ ID NO: 7, the polypeptide product of lepD, a gene in the leptomycin PKS cluster.

FIG. 10 shows SEQ ID NO: 8, the polypeptide product of lepE, a gene encoding a cytochrome P450-type oxidase.

FIG. 11 shows SEQ ID NO: 9, the polypeptide product of lepF, a gene encoding a tetR-like transcriptional regulator.

Figure 2:
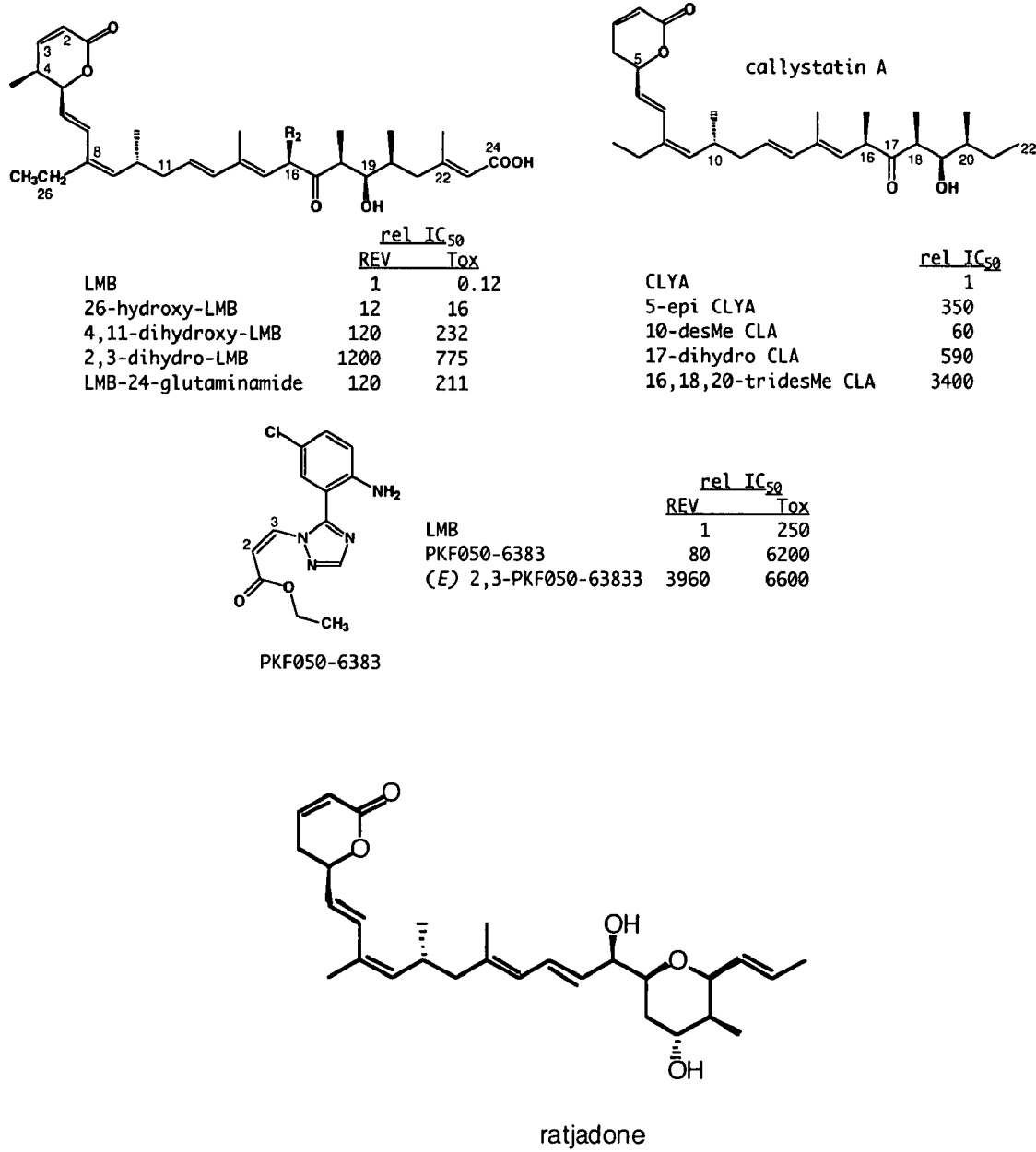
FIG. 2 shows biological activity results for several members of the leptomycin family, and the structure of ratjadone.

The following references provide background on the leptomycins and are hereby incorporated by reference:

1) Wolff B, Sanglier J J, Wang Y. Leptomycin B is an inhibitor of nuclear export: inhibition of nucleo-cytoplasmic translocation of the human immunodeficiency virus type 1 (HIV-1) Rev protein and Rev-dependent mRNA. Chem Biol. (1997) 4:139-147.

2) Lain S, Midgley C, Sparks A, Lane E B, Lane D P. An inhibitor of nuclear export activates the p53 response and induces the localization of HDM2 and p53 to U1A-positive nuclear bodies associated with the PODs. Exp Cell Res. (1999) 248:457-72

3) Hietanen S, Lain S, Krausz E, Blattner C, Lane D P. Activation of p53 in cervical carcinoma cells by small molecules. Proc Natl Acad Sci USA. (2000) 97:8501-8506.

4) Kim J E, Chen J. Cytoplasmic-nuclear shuttling of FKBP12-rapamycin-associated protein is involved in rapamycin-sensitive signaling and translation initiation. Proc Natl Acad Sci USA. (2000) 97:14340-14345.

5) Park I H, Bachmann R, Shirazi H, Chen J. Regulation of ribosomal S6 kinase 2 by mammalian target of rapamycin. J Biol Chem. (2002) 277:31423-31429.

6) Daelemans D, Afonina E, Nilsson J, Werner G, Kjems J, De Clercq E, Pavlakis G N, Vandamme A M. A synthetic HIV-1 Rev inhibitor interfering with the CRM1-mediated nuclear export. Proc Natl Acad Sci USA. (2002) 99:14440-14445.

7) Wang, Y, Ponelle M et al., Novel leptomycins for a *Streptomyces* strain A92-308902. Inhibitors of the nucelo-cytoplasmic translocation of the HIV-1 regulatory protein Rev. Helv Chim Acta (1997) 80:2157-2167.

8) Kalesse M, M. Christmann. The chemistry and biology of the leptomycin family. Synthesis (2002) 8:981-1003.

DETAILED DESCRIPTION OF THE INVENTION

The present invention provides recombinant materials for the production of polyketides. In one aspect, the invention provides recombinant nucleic acids encoding at least one domain of a polyketide synthase required for leptomycin biosynthesis. Methods and host cells for using these genes to produce a polyketide in recombinant host cells are also provided.

The nucleotide sequences encoding leptomycin PKS domains, modules and polypeptides of the present invention were isolated from *Streptomyces* sp. ATCC 39366 as described in Example 1. Alternatively, the DNA sequences provided herein may be obtained through gene synthesis as described in U.S. Patent Application 20040166567, which is incorporated herein by reference. Given the valuable properties of leptomycin and its derivatives and analogs, means to produce useful quantities of these molecules in a highly pure form is of great potential value. The compounds produced may be used as antitumor agents or for other therapeutic uses, and/or a intermediates for further enzymatic or chemical modification, and/or as agents for in vitro inhibition of protein phosphatase. The nucleotide sequences of the leptomycin biosynthetic gene cluster encoding domains, modules and polypeptides of leptomycin synthase, and modifying enzymes, and other polypeptides can be used, for example, to make both known and novel polyketides.

In one aspect of the invention, purified and isolated DNA molecules are provided that comprise one or more coding sequences for one or more domains or modules of leptomycin synthase. Examples of such encoded domains include leptomycin synthase KR, DH, ER, AT, ACP, and KS domains. In one aspect, the invention provides DNA molecules in which sequences encoding one or more polypeptides of leptomycin synthase are operably linked to expression control sequences that are effective in suitable host cells to produce leptomycin, its analogs or derivatives, or novel polyketides.

The sequence of the leptomycin gene cluster was assembled from sequences deduced from the cosmids pKOS279-128.PF27, pKOS279-128.2L78, and pKOS279-130.PFA42. The gene cluster is found to comprise six open reading frames (ORFs), named lepA, lepB, lepC, lepD, lepE, and lepF. The polyketide synthase is encoded by lepABCD, and is comprised of eleven modules terminating in a thioesterase domain. The lepA gene encodes modules 0-4, where module 0 is the loading module; the lepB gene encodes modules 5-8; lepC encodes modules 9-10; and lepD encodes module 11 and the terminating thioesterase domain. The lepE gene encodes a cytochrome P450-type oxidase, presumably responsible for oxidation of the C24 methyl group. The lepF gene appears to be a regulatory gene.

Tables 1 and 2 provide a description of genes in the leptomycin PKS gene cluster including sequences encoding encoding modules, domains and ORFs, as deduced from two contigs assembled from sequences of pKOS279-125.2L78. The nucleotide sequences of the two contigs are provided in the attached Sequence Listing, and have been assigned SEQ ID NOS: 1 and 2, respectively.

As indicated in Table 1, the nucleic acid having SEQ ID NO:1 was found to encode portions of two ORFs. ORF1, SEQ ID NO:6, comprises nucleotides <1 to 17260 of the SEQ ID NO:1. The start of ORF1 (LepA) lies upstream of the beginning of SEQ ID NO:1. The nucleic acid encodes a polypeptide comprising a portion of module 1 (a portion of KR1 and all of ACP1), and the complete modules 2, 3, and 4 of leptomycin synthase. The sequence of ORF2 comprises nucleotides 17546 to >29467 of the SEQ ID NO:1. The end of ORF2 (LepB) lies downstream of the end of SEQ ID NO:1. The nucleic acid sequence encodes a polypeptide comprising the complete modules 5 and 6 and a portion of module 7 (the beginning of KS7) of leptomycin synthase. The modules encoded by the nucleic acid of SEQ ID NO:1 are indicated in Table 1.

Table 2 provides the ORF, module, and domain descriptions for the second contig, the nucleic acid of SEQ ID NO:2. One partial ORF has been identified, encoding a polypeptide comprising a portion of module 7 (part of AT7, and all of DH7, ER7, KR7, and ACP7) and all of module 8 of leptomycin synthase. The modules encoded by the nucleic acid of SEQ ID NO:2 and domains within each module are indicated in Table 2.

Subsequent sequencing provided the complete sequence of the leptomycin biosynthetic gene cluster, given below as SEQ ID NO:3. The PKS modules encoded by the nucleic acid of SEQ ID NO:3 and domains within each module are indicated in Table 3. The ORFs encoding the PKS have been designated LepA, LepB, LepC, and LepD. LepA comprises a loading module, referred to as "module 0," which comprises a ketosynthase domain wherein there is a glutamine in place of the expected active-site cysteine ("KSq"), and thus likely functions as a decarboxylase. LepD comprises module 11 together with a thioesterase (TE) domain.

The LepE gene, corresponding to nucleotides 64703-65881 of SEQ ID NO:3 encodes a cytochrome-P450 type oxidase. The LepF gene, corresponding to nucleotides 66124-66564 of SEQ ID NO:3 encodes a putative tetR-family transcriptional regulator.

In another aspect of the invention, the polypeptides encoded by the above-described leptomycin PKS genes are provided as LepA (FIG. 6; SEQ ID NO:4), LepB (FIG. 7; SEQ ID NO:5), LepC (FIG. 8; SEQ ID NO:6), LepD (FIG. 9; SEQ ID NO:7), LepE (FIG. 10; SEQ ID NO:8), and LepF (FIG. 11; SEQ ID NO:9). These polypeptides may be in isolated, purified, or recombinant form, either singly or present in any combination comprising each other or other polyketide synthase polypeptides.

TABLE 1

ORFs, modules, and domains of the leptomycin PKS determined from the nucleotide sequence determined from the T3-side of the insert from cosmid pKOS279-125.2L78 (SEQ ID NO: 1).

| | feature | | Nucleotide sequence location |
|---|---|---|---|
| | Contig 1 | | 1-29467 |
| ORF 1 | | | <1-17260 |
| | module 1 | | <1-661 |
| | | KR1 | <1-358 |
| | | ACP1 | 404-661 |
| | module 2 | | 722-6868 |
| | | KS2 | 722-1999 |
| | | AT2 | 2306-3352 |
| | | DH2 | 3386-3991 |
| | | ER2 | 4910-5770 |
| | | KR2 | 5753-6571 |
| | | ACP2 | 6611-6868 |
| | module 3 | | 6929-12172 |
| | | KS3 | 6929-8206 |
| | | AT3 | 8537-9595 |
| | | DH3 | 9629-10204 |
| | | KR3 | 11057-11881 |
| | | ACP3 | 11915-12172 |
| | module 4 | | 12236-17260 |
| | | KS4 | 12236-13513 |
| | | AT4 | 13823-14869 |
| | | DH4 | 14903-15493 |
| | | KR4 | 16298-16807 |
| | | ACP4 | 17003-17260 |
| ORF2 (start) | | | 17546->29467 |
| | module 5 | | 17546-22879 |
| | | KS5 | 17648-18925 |
| | | AT5 | 19328-20299 |
| | | DH5 | 20333-20932 |
| | | KR5 | 21758-22603 |
| | | ACP5 | 22622-22879 |
| | module 6 | | 22961-28144 |
| | | KS6 | 22961-24241 |
| | | AT6 | 24551-25603 |
| | | DH6 | 25652-26206 |
| | | KR6 | 27014-27868 |
| | | ACP6 | 27887-28144 |
| | module 7 | | 28199->29467 |
| | | KS7 | 28199->29467 |

TABLE 2

ORFs, modules, and domains of the leptomycin PKS determined from the nucleotide sequence determined from the T7-side of the insert from cosmid pKOS279-125.2L78 (SEQ ID NO: 2).

| | feature | sequence location |
|---|---|---|
| | contig 2 | 1-9724 |
| ORF 2 (end) | | <1->9724 |

TABLE 2-continued ORFs, modules, and domains of the leptomycin PKS determined from the nucleotide sequence determined from the T7-side of the insert from cosmid pKOS279-125.2L78 (SEQ ID NO: 2).

| feature | | sequence location |
|---|---|---|
| module 7 | | <1-4501 |
| | AT7 | <1-967 |
| | DH7 | 1001-1585 |
| | ER7 | 2528-3382 |
| | KR7 | 3380-4225 |
| | ACP7 | 4244-4501 |
| module 8 | | 4559-9703 |
| | KS8 | 4559-5836 |
| | AT8 | 6152-7213 |
| | DH8 | 7250-7822 |
| | KR8 | 8639-9409 |
| | ACP8 | 9446-9703 |

TABLE 3

Complete list of ORFs, modules, and domains of the leptomycin PKS determined from SEQ ID NO: 3.

| feature | | | Nucleotide sequence location |
|---|---|---|---|
| LepA | | | 370-25686 |
| | module 0 | KSq(0) | 439-1725 |
| | | AT(0) | 2080-3147 |
| | | ACP(0) | 3220-3481 |
| | module 1 | | 3535-8844 |
| | | KS(1) | 3535-4812 |
| | | AT(1) | 5143-6204 |
| | | DH(1) | 6241-6831 |
| | | KR(1) | 7759-8547 |
| | | ACP(1) | 8587-8844 |
| | module 2 | | 8905-15048 |
| | | KS2 | 8905-10182 |
| | | AT2 | 10489-11535 |
| | | DH2 | 11569-12147 |
| | | ER2 | 13093-13953 |
| | | KR2 | 13936-14751 |
| | | ACP2 | 14791-15048 |
| | module 3 | | 15109-20361 |
| | | KS3 | 15109-16386 |
| | | AT3 | 16717-17775 |
| | | DH3 | 17809-16384 |
| | | KR3 | 19237-20070 |
| | | ACP3 | 20104-20361 |
| | module 4 | | 20425-25449 |
| | | KS4 | 20425-21702 |
| | | AT4 | 22012-23058 |
| | | DH4 | 23092-23682 |
| | | KR4 | 24487-24996 |
| | | ACP4 | 25192-25449 |
| LepB | | | 25735-48024 |
| | module 5 | | 25837-31068 |
| | | KS5 | 25837-27114 |
| | | AT5 | 27427-28488 |
| | | DH5 | 28522-29121 |
| | | KR5 | 29947-30792 |
| | | ACP5 | 30811-31068 |
| | module 6 | | 31150-36333 |
| | | KS6 | 31150-32430 |
| | | AT6 | 32740-33792 |
| | | DH6 | 33841-34395 |
| | | KR6 | 35203-36057 |
| | | ACP6 | 36076-36333 |
| | module 7 | | 36388-42570 |
| | | KS7 | 36388-37665 |
| | | AT7 | 37981-39036 |
| | | DH7 | 39070-39654 |
| | | ER7 | 40597-41451 |
| | | KR7 | 41449-42294 |
| | | ACP7 | 42313-42570 |

TABLE 3-continued

Complete list of ORFs, modules, and domains of the leptomycin PKS determined from SEQ ID NO: 3.

| feature | | | Nucleotide sequence location |
|---|---|---|---|
| | module 8 | | 42628-47772 |
| | | KS8 | 42628-43905 |
| | | AT8 | 44221-45282 |
| | | DH8 | 45319-45891 |
| | | KR8 | 46708-47478 |
| | | ACP8 | 47515-47772 |
| LepC | | | 48110-58357 |
| | module 9 | | 48209-53437 |
| | | KS9 | 48209-49417 |
| | | AT9 | 49775-50824 |
| | | DH9 | 50864-51454 |
| | | KR9 | 52325-53140 |
| | | ACP9 | 53180-53437 |
| | module 10 | | 53501-58111 |
| | | KS10 | 53501-54781 |
| | | AT10 | 55115-56173 |
| | | KR10 | 56975-57637 |
| | | ACP10 | 57854-58111 |
| LepD | | | 58243-64173 |
| | module 11 | | 58543-59847 |
| | | KS11 | 58543-59847 |
| | | AT11 | 60250-61257 |
| | | KR11 | 62143-62931 |
| | | ACP11 | 62995-63252 |
| | TE | | 63253-64170 |

In one aspect, the invention provides an isolated or recombinant DNA molecule comprising a nucleotide sequence that encodes at least one domain, alternatively at least one module, alternatively at least one polypeptide, involved in the biosynthesis of a leptomycin.

In one aspect, the invention provides an isolated or recombinant DNA molecule comprising a sequence identical or substantially similar to at least one of SEQ ID NOS: 1, 2, and 3 or their complement. [Hereinafter, each reference to a nucleic acid sequence is also intended to refer to and include the complementary sequence, unless otherwise stated or apparent from context.] In an embodiment the subsequence comprises a sequence encoding a complete leptomycin PKS domain, module or polypeptide.

In one aspect, the present invention provides an isolated or recombinant DNA molecule comprising a nucleotide sequence that encodes an open reading frame, module or domain having an amino acid sequence identical or substantially similar to an ORF, module or domain encoded by SEQ ID NOS: 1, 2 or 3. Generally, a polypeptide, module or domain having a sequence substantially similar to a reference sequence has substantially the same activity as the reference protein, module or domain (e.g., when integrated into an appropriate PKS framework using methods known in the art). In certain embodiments, one or more activities of a substantially similar polypeptide, module or domain are modified or inactivated as described below.

In one aspect, the invention provides an isolated or recombinant DNA molecule comprising a nucleotide sequence that encodes at least one polypeptide, module or domain encoded by SEQ ID NOs:1, 2 or 3, e.g., a polypeptide, module or domain involved in the biosynthesis of a leptomycin, wherein said nucleotide sequence comprises at least 10, 20, 25, 30, 35, 40, 45, or 50 contiguous base pairs identical to a sequence of SEQ ID NOS: 1, 2 or 3. In one aspect, the invention provides an isolated or recombinant DNA molecule comprising a nucleotide sequence that encodes at least one polypeptide, module or domain encoded by SEQ ID NOS: 1, 2 or 3, e.g., a polypeptide, module or domain involved in the biosynthesis of a leptomycin, wherein said polypeptide, module or domain comprises at least 10, 15, 20, 30, or 40 contiguous residues of a corresponding polypeptide, module or domain.

It will be understood that SEQ ID NOS: 1, 2 and 3 were determined using the insert of various cosmids. Accordingly, the invention provides an isolated or recombinant DNA molecule comprising a sequence identical or substantially similar to a ORF encoding sequence of the insert of one or more of these cosmids.

Those of skill will recognize that, due to the degeneracy of the genetic code, a large number of DNA sequences encode the amino acid sequences of the domains, modules, and proteins of the leptomycin PKS, the enzymes involved in leptomycin modification and other polypeptides encoded by the genes of the leptomycin biosynthetic gene cluster. The present invention contemplates all such DNAs. For example, it may be advantageous to optimize sequence to account for the codon preference of a host organism. The invention also contemplates naturally occurring genes encoding the leptomycin PKS that are polymorphic or other variants.

As used herein, the terms “substantial identity,” “substantial sequence identity,” or “substantial similarity” in the context of nucleic acids, refers to a measure of sequence similarity between two polynucleotides. Substantial sequence identity can be determined by hybridization under stringent conditions, by direct comparison, or other means. For example, two polynucleotides can be identified as having substantial sequence identity if they are capable of specifically hybridizing to each other under stringent hybridization conditions. Other degrees of sequence identity (e.g., less than “substantial”) can be characterized by hybridization under different conditions of stringency. “Stringent hybridization conditions” refers to conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, e.g., Berger and Kimmel, 1987, Methods In Enzymology, Vol. 152: Guide To Molecular Cloning Techniques, San Diego: Academic Press, Inc. and Sambrook et al., 1989, Molecular Cloning: A Laboratory Manual, 2nd Ed., Vols. 1-3, Cold Spring Harbor Laboratory). Typically, stringent hybridization conditions for probes greater than 50 nucleotides are salt concentrations less than about 1.0 M sodium ion, typically about 0.01 to 1.0 M sodium ion at pH 7.0 to 8.3, and temperatures at least about 50° C., preferably at least about 60° C. As noted, stringent conditions may also be achieved with the addition of destabilizing agents such as formamide, in which case lower temperatures may be employed. Exemplary conditions include hybridization at 7% sodium dodecyl sulfate (SDS), 0.5 M $NaPO_4$ pH 7.0, 1 mM EDTA at 65° C.; wash with 2×SSC, 1% SDS, at 50° C.

Alternatively, substantial sequence identity can be described as a percentage identity between two nucleotide or amino acid sequences. Two nucleic acid sequences are considered substantially identical when they are at least about 70% identical, or at least about 80% identical, or at least about 90% identical, or at least about 95% or 98% identical. Two amino acid sequences are considered substantially identical when they are at least about 60%, sequence identical, more often at least about 70%, at least about 80%, or at least about 90% sequence identity to the reference sequence. Percentage sequence (nucleotide or amino acid) identity is typically calculated using art known means to determine the optimal alignment between two sequences and comparing the two sequences. Optimal alignment of sequences may be conducted using the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. U.S.A.* 85: 2444, by the BLAST algorithm of Altschul (1990) *d. Mol. Biol.* 215: 403-410; and Shpaer (1996) *Genomics* 38:179-191, or by the Needleham et al. (1970) *J. Mol. Biol.* 48: 443-453; and Sankoff et al., 1983*, Time Warps, String Edits, and Macromolecules, The Theory and Practice of Sequence Comparison*, Chapter One, Addison-Wesley, Reading, Mass.; generally by computerized implementations of these algorithms (GAP, BESTFIT, FASTA, and TFASTA in the Wisconsin Genetics Software Package, Genetics Computer Group, 575 Science Dr., Madison, Wis.; BLAST from the National Center for Biotechnology Information at the World Wide Web (ncbi.nlm.nih.gov). In each case default parameters are used (for example the BLAST program uses as defaults a wordlength (W) of 11, the BLOSUM62 scoring matrix (see Henikoff (1992) *Proc. Natl. Acad. Sci. USA* 89: 10915-10919) alignments (B) of 50, expectation (E) of 10, M=5, N=−4, and a comparison of both strands).

The invention methods may be directed to the preparation of an individual polyketide. The polyketide may or may not be novel, but the method of preparation permits a more convenient or alternative method of preparing it. The resulting polyketides may be further modified to convert them to other useful compounds. Examples of chemical structures of that can be made using the materials and methods of the present invention include known analogs, such as those described in Kalesse & Christmann, 2002, “The Chemistry and Biology of the Leptomycin Family” *Synthesis* (8):981-1003 (incorporated herein by reference) and the references cited therein, and novel molecules produced by modified or chimeric PKSs comprising a portion of the leptomycin PKS sequence, molecules produced by the action of polyketide modifying enzymes from the leptomycin PKS cluster on products of other PKSs, molecules produced by the action on products of the leptomycin PKS of polyketide modifying enzymes from other PKSs, and the like.

As noted, in one aspect the invention provides recombinant PKS wherein at least 10, 15, 20, or more consecutive amino acids in one or more domains of one or more modules thereof are derived from one or more domains of one or more modules of leptomycin polyketide synthase. A polyketide synthase “derived from” a naturally occurring PKS contains the scaffolding encoded by all the portion employed of the naturally occurring synthase gene, contains at least two modules that are functional, and contains mutations, deletions, or replacements of one or more of the activities of these functional modules so that the nature of the resulting polyketide is altered. This definition applies both at the protein and genetic levels. Particular embodiments include those wherein a KS, AT, KR, DH, or ER has been deleted or replaced by a version of the activity from a different PKS or from another location within the same PKS, and derivatives where at least one noncondensation cycle enzymatic activity (KR, DH, or ER) has been deleted or wherein any of these activities has been added or mutated so as to change the ultimate polyketide synthesized. There are at least five degrees of freedom for constructing a polyketide synthase in terms of the polyketide that will be produced. See, U.S. Pat. No. 6,509,455 for a discussion.

As can be appreciated by those skilled in the art, polyketide biosynthesis can be manipulated to make a product other than the product of a naturally occurring PKS biosynthetic cluster. For example, AT domains can be altered or replaced to change specificity. The variable domains within a module can be deleted and or inactivated or replaced with other variable domains found in other modules of the same PKS or from another PKS. See e.g., Katz & McDaniel, *Med Res Rev* 19: 543-558 (1999) and WO 98/49315. Similarly, entire modules can be deleted and/or replaced with other modules from the same PKS or another PKS. See e.g., Gokhale et al., Science 284: 482 (1999) and WO 00/47724 each of which are incorporated herein by reference. Protein subunits of different PKSs also can be mixed and matched to make compounds having the desired backbone and modifications. For example, subunits of 1 and 2 (encoding modules 1-4) of the pikromycin PKS were combined with the DEBS3 subunit to make a hybrid PKS product (see Tang et al., Science, 287: 640 (2001), WO 00/26349 and WO 99/6159).

Mutations can be introduced into PKS genes such that polypeptides with altered activity are encoded. Polypeptides with "altered activity" include those in which one or more domains are inactivated or deleted, or in which a mutation changes the substrate specificity of a domain, as well as other alterations in activity. Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. (See, e.g., Kunkel, T. A. *Proc Natl Acad Sci USA* (1985) 82 448; Geisselsoder et al. *BioTechniques* (1987) 5:786.) Alternatively, the mutations can be effected using a mismatched primer (generally 10-20 nucleotides in length) that hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. (See Zoller and Smith, *Methods in Enzymology* (1983) 100: 468). Primer extension is effected using DNA polymerase. The product of the extension reaction is cloned, and those clones containing the mutated DNA are selected. Selection can be accomplished using the mutant primer as a hybridization probe. The technique is also applicable for generating multiple point mutations. (See, e.g., Dalbie-McFarland et al. *Proc Natl Acad Sci USA* (1982) 79:6409). PCR mutagenesis can also be used for effecting the desired mutations. Random mutagenesis of selected portions of the nucleotide sequences encoding enzymatic activities can be accomplished by several different techniques known in the art, e.g., by inserting an oligonucleotide linker randomly into a plasmid, In addition to providing mutated forms of regions encoding enzymatic activity, regions encoding corresponding activities from different PKS synthases or from different locations in the same PKS synthase can be recovered, for example, using PCR techniques with appropriate primers. By "corresponding" activity encoding regions is meant those regions encoding the same general type of activity—e.g., a ketoreductase activity in one location of a gene cluster would "correspond" to a ketoreductase-encoding activity in another location in the gene cluster or in a different gene cluster; similarly, a complete reductase cycle could be considered corresponding—e.g., KR/DH/ER could correspond to KR alone.

If replacement of a particular target region in a host polyketide synthase is to be made, this replacement can be conducted in vitro using suitable restriction enzymes or can be effected in vivo using recombinant techniques involving homologous sequences framing the replacement gene. One such system involving plasmids of differing temperature sensitivities is described in PCT application WO 96/40968. Another useful method for modifying a PKS gene (e.g., making domain substitutions or "swaps") is a RED/ET cloning procedure developed for constructing domain swaps or modifications in an expression plasmid without first introducing restriction sites. The method is related to ET cloning methods (see, Datansko & Wanner, 2000, Proc. Natl. Acad. Sci. U.S.A. 97, 6640-45; Muyrers et al, 2000, Genetic Engineering 22:77-98). The RED/ET cloning procedure is used to introduce a unique restriction site in the recipient plasmid at the location of the targeted domain. This restriction site is used to subsequently linearize the recipient plasmid in a subsequent ET cloning step to introduce the modification. This linearization step is necessary in the absence of a selectable marker, which cannot be used for domain substitutions. An advantage of using this method for PKS engineering is that restriction sites do not have to be introduced in the recipient plasmid in order to construct the swap, which makes it faster and more powerful because boundary junctions can be altered more easily.

In a further aspect, the invention provides methods for expressing chimeric or hybrid PKSs and products of such PKSs. For example, the invention provides (1) encoding DNA for a chimeric PKS that is substantially patterned on a non-leptomycin producing enzyme, but which includes one or more functional domains, modules or polypeptides of leptomycin PKS; and (2) encoding DNA for a chimeric PKS that is substantially patterned on the leptomycin PKS, but which includes one or more functional domains, modules, or polypeptides of another PKS or NRPS.

With respect to item (1) above, in one embodiment, the invention provides chimeric PKS enzymes in which the genes for a non-leptomycin PKS function as accepting genes, and one or more of the above-identified coding sequences for leptomycin domains or modules are inserted as replacements for one or more domains or modules of comparable function. Construction of chimeric molecules is most effectively achieved by construction of appropriate encoding polynucleotides. In making a chimeric molecule, it is not necessary to replace an entire domain or module accepting of the PKS with an entire domain or module of leptomycin PKS: subsequences of a PKS domain or module that correspond to a peptide subsequence in an accepting domain or module, or which otherwise provide useful function, may be used as replacements. Accordingly, appropriate encoding DNAs for construction of such chimeric PKS include those that encode at least 10, 15, 20 or more amino acids of a selected leptomycin domain or module.

Recombinant methods for manipulating modular PKS genes to make chimeric PKS enzymes are described in U.S. Pat. Nos. 5,672,491; 5,843,718; 5,830,750; and 5,712,146; and in PCT publication Nos. 98/49315 and 97/02358. A number of genetic engineering strategies have been used with DEBS to demonstrate that the structures of polyketides can be manipulated to produce novel natural products, primarily analogs of the erythromycins (see the patent publications referenced supra and Hutchinson, 1998, *Curr Opin Microbiol.* 1:319-329, and Baltz, 1998, *Trends Microbiol.* 6:76-83). In one embodiment, the components of the chimeric PKS are arranged onto polypeptides having interpolypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication WO 00/47724.

A partial list of sources of PKS sequences for use in making chimeric molecules, for illustration and not limitation, includes Avermectin (U.S. Pat. No. 5,252,474; MacNeil et al., 1993, Industrial Microorganisms: Basic and Applied Molecular Genetics, Baltz, Hegeman, & Skatrud, eds. (ASM), pp. 245-256; MacNeil et al., 1992, Gene 115: 119-25); Candicidin (FRO008) (Hu et al., 1994, *Mol. Microbiol.* 14: 163-72); Epothilone (U.S. Pat. No. 6,303,342); Erythromycin (WO 93/13663; U.S. Pat. No. 5,824,513; Donadio et al., 1991, *Science* 252: 675-79; Cortes et al., 1990, *Nature* 348: 176-8); FK-506 (Motamedi et al., 1998, *Eur. J. Biochem.* 256: 528-34; Motamedi et al., 1997, *Eur. J. Biochem.* 244:74-80); FK-520 (U.S. Pat. No. 6,503,737; see also Nielsen et al., 1991, *Biochem.* 30:5789-96); Lovastatin (U.S. Pat. No. 5,744,350); Nemadectin (MacNeil et al., 1993, supra); Niddamycin (Kakavas et al., 1997, *J. Bacteriol.* 179:7515-22); Oleandomycin (Swan et al., 1994, *Mol. Gen. Genet.* 242:358-62; U.S. Pat. No. 6,388,099; Olano et al., 1998, *Mol. Gen. Genet.* 259:299-308); Platenolide (EP Pat. App. 791,656); Rapamycin (Schwecke et al., 1995, *Proc. Natl. Acad. Sci. USA* 92:7839-43); Aparicio et al., 1996, *Gene* 169:9-16); Rifamycin (August et al., 1998, *Chemistry & Biology,* 5:69-79); Soraphen (U.S. Pat. No. 5,716,849; Schupp et al., 1995, *J. Bacteriology* 177: 3673-79); Spiramycin (U.S. Pat. No. 5,098,837); Tylosin (EP 0 791,655; Kuhstoss et al., 1996, Gene 183:231-36; U.S. Pat. No. 5,876,991). Additional suitable PKS coding sequences remain to be discovered and characterized, but will be available to those of skill (e.g., by reference to GenBank).

The leptomycin PKS-encoding polynucleotides of the invention may also be used in the production of libraries of PKSs (i.e., modified and chimeric PKSs comprising at least a portion of the leptomycin PKS sequence. The invention provides libraries of polyketides by generating modifications in, or using a portion of, the leptomycin PKS so that the protein complexes produced by the cluster have altered activities in one or more respects, and thus produce polyketides other than the natural leptomycin product of the PKS. Novel polyketides may thus be prepared, or polyketides in general prepared more readily, using this method. By providing a large number of different genes or gene clusters derived from a naturally occurring PKS gene cluster, each of which has been modified in a different way from the native PKS cluster, an effectively combinatorial library of polyketides can be produced as a result of the multiple variations in these activities. Expression vectors containing nucleotide sequences encoding a variety of PKS systems for the production of different polyketides can be transformed into the appropriate host cells to construct a polyketide library. In one approach, a mixture of such vectors is transformed into the selected host cells and the resulting cells plated into individual colonies and selected for successful transformants. Each individual colony has the ability to produce a particular PKS synthase and ultimately a particular polyketide. A variety of strategies can be devised to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, more preferably at least 50, reflecting similar numbers of different altered PKS gene clusters and PKS gene products.

The number of members in the library is arbitrarily chosen; however, the degrees of freedom outlined above with respect to the variation of starter, extender units, stereochemistry, oxidation state, and chain length is quite large. The polyketide producing colonies can be identified and isolated using known techniques and the produced polyketides further characterized. The polyketides produced by these colonies can be used collectively in a panel to represent a library or may be assessed individually for activity. See, for example, Colonies in the library are induced to produce the relevant synthases and thus to produce the relevant polyketides to obtain a library of candidate polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can be included.

As noted above, the DNA compounds of the invention can be expressed in host cells for production of proteins and of known and novel compounds. Preferred hosts include fungal systems such as yeast and procaryotic hosts, but single cell cultures of, for example, mammalian cells could also be used. A variety of methods for heterologous expression of PKS genes and host cells suitable for expression of these genes and production of polyketides are described, for example, in U.S. Pat. Nos. 5,843,718 and 5,830,750; WO 01/31035, WO 01/27306, and WO 02/068613; and U.S. patent application Ser. Nos. 10/087,451 (published as US2002000087451); 60/355,211; and 60/396,513 (corresponding to published application 20020045220).

Appropriate host cells for the expression of the hybrid PKS genes include those organisms capable of producing the needed precursors, such as malonyl-CoA, methylmalonyl-CoA, ethylmalonyl-CoA, and methoxymalonyl-ACP, and having phosphopantotheinylation systems capable of activating the ACP domains of modular PKSs. See, for example, U.S. Pat. No. 6,579,695. However, as disclosed in U.S. Pat. No. 6,033,883, a wide variety of hosts can be used, even though some hosts natively do not contain the appropriate post-translational mechanisms to activate the acyl carrier proteins of the synthases. Also see WO 97/13845 and WO 98/27203. The host cell may natively produce none, some, or all of the required polyketide precursors, and may be genetically engineered so as to produce the required polyketide precursors. Such hosts can be modified with the appropriate recombinant enzymes to effect these modifications. Suitable host cells include *Streptomyces, E. coli*, yeast, and other procaryotic hosts that use control sequences compatible with *Streptomyces* spp. Examples of suitable hosts that either natively produce modular polyketides or have been engineered so as to produce modular polyketides include but are not limited to actinomyctes such as *Streptomyces coelicolor, Streptomyces venezuelae, Streptomyces fradiae, Streptomyces ambofaciens*, and *Saccharopolyspora erythraea*, eubacteria such as *Escherichia coli*, myxobacteria such as *Myxococcus xanthus*, and yeasts such as *Saccharomyces cerevisiae*.

In one embodiment, any native modular PKS genes in the host cell have been deleted to produce a "clean host," as described in U.S. Pat. No. 5,672,491, incorporated herein by reference. In a variant of this embodiment, a host cell that produces leptomycin, a leptomycin analog, or a leptomycin derivative in its native state (e.g., *Streptomyces* sp. ATCC 39366) is engineered so as to delete or inactivate at least one domain in the leptomycin PKS gene cluster so as to produce a host cell that no longer produces leptomycin, a leptomycin analog, or a leptomycin derivative. Such a host cell can subsequently be transformed with a gene comprising an active variant of the deleted or inactivated domain, thus restoring polyketide production by complementation. When the active variant of the deleted or inactivated domain is derived from a second PKS gene cluster that produces a polyketide other than leptomycin, such complementation results in the production of a leptomycin analog or derivative. In one embodiment, one or more complete genes (ORFs) of the native leptomycin synthase are deleted from or inactivated in the host cell, which is subsequently complemented by transformation with engineered forms of the deleted or inactivated genes (ORFs). Methods for performing such complementation experiments are known in the art, for example as described in U.S. Pat. No. 6,505,737 which is incorporated herein by reference.

Figure 3:
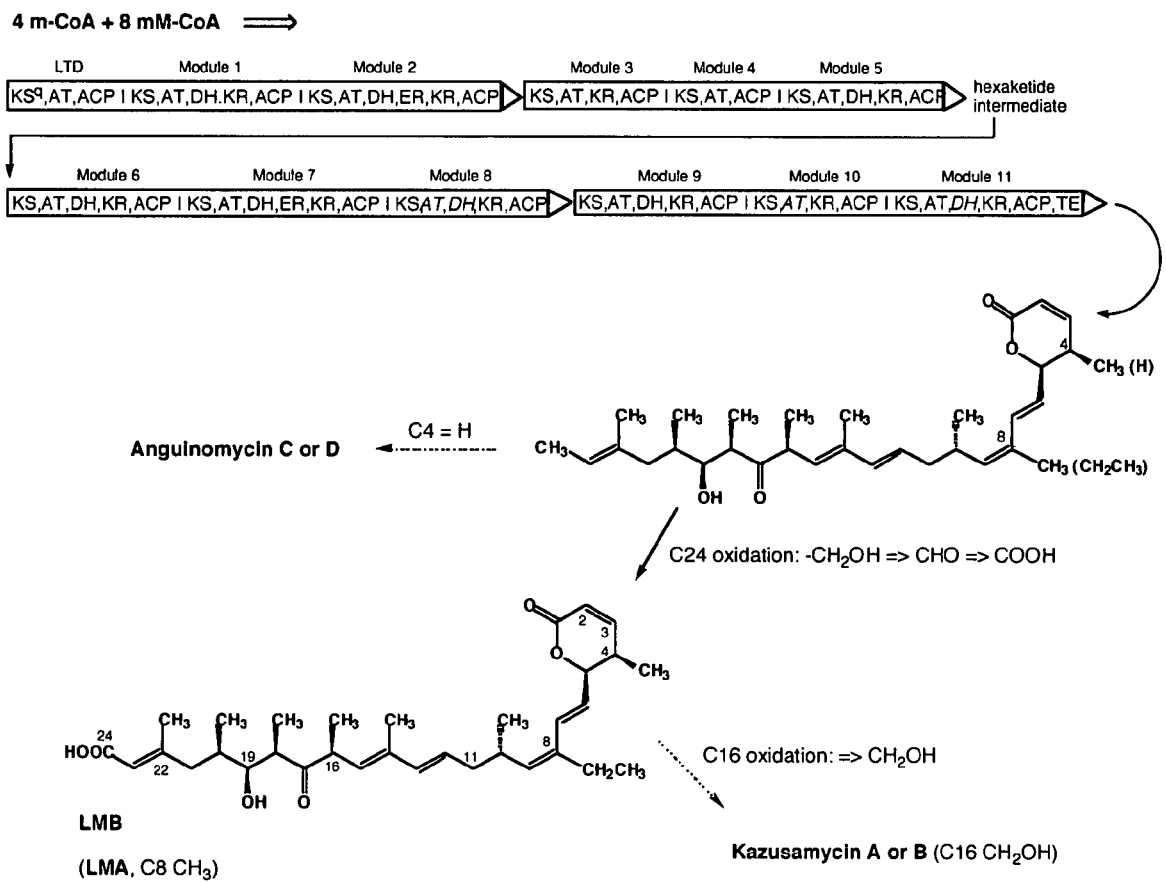
FIG. 3 shows the expected organization of the leptomycin PKS and a possible pathway for biosynthesis. Biosynthetic relationships of members of the leptomycin family are also indicated.

In some embodiments, the host cell expresses, or is engineered to express, a polyketide "tailoring" or "modifying" enzyme. Once a PKS product is released, it is subject to post-PKS tailoring reactions. These reactions are important for biological activity and for the diversity seen among polyketides. Tailoring enzymes normally associated with polyketide biosynthesis include oxygenases, glycosyl- and methyl-transferases, acyltransferases, halogenases, cyclases, aminotransferases, and hydroxylases. In addition to biosynthetic accessory activities, secondary metabolite clusters often code for activities such as transport. In the case of leptomycin biosynthesis (FIG. 3), tailoring enzymes are expected to include at least one P450 hydroxylase for oxidation of the C24 methyl group to a carboxylic acid. Tailoring enzymes may also be involved in the introduction of the cis-alkene at C8-C9.

Tailoring enzymes for modification of a product of the leptomycin PKS, a non-leptomycin PKS, or a chimeric PKS, can be those normally associated with leptomycin biosynthesis or "heterologous" tailoring enzymes. Tailoring enzymes can be expressed in the organism in which they are naturally produced, or as recombinant proteins in heterologous hosts. In some cases, the structure produced by the heterologous or hybrid PKS may be modified with different efficiencies by post-PKS tailoring enzymes from different sources. In such cases, post-PKS tailoring enzymes can be recruited from other pathways to obtain the desired compound. For example, the tailoring enzymes of the leptomycin PKS gene cluster can be expressed heterologously to modify polyketides produced by non-leptomycin synthases or can be inactivated in the Leptomycin producer.

Alternatively, the unmodified polyketide compounds can be produced in the recombinant host cell, and the desired modification (e.g., oxidation) steps carried out in vitro (e.g., using purified enzymes, isolated from native sources or recombinantly produced) or in vivo in a converting cell different from the host cell (e.g., by supplying the converting cell with the unmodified polyketide).

It will be apparent to the reader that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

The vectors used to perform the various operations to replace the enzymatic activity in the host PKS genes or to support mutations in these regions of the host PKS genes may be chosen to contain control sequences operably linked to the resulting coding sequences in a manner that expression of the coding sequences may be effected in an appropriate host. Suitable control sequences include those that function in eucaryotic and procaryotic host cells. If the cloning vectors employed to obtain PKS genes encoding derived PKS lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies.

Suitable control sequences for single cell cultures of various types of organisms are well known in the art. Control systems for expression in yeast are widely available and are routinely used. Control elements include promoters, optionally containing operator sequences, and other elements depending on the nature of the host, such as ribosome binding sites. Particularly useful promoters for procaryotic hosts include those from PKS gene clusters that result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433), can be used.

As noted, particularly useful control sequences are those which themselves, or with suitable regulatory systems, activate expression during transition from growth to stationary phase in the vegetative mycelium. The system contained in the plasmid identified as pCK7, i.e., the actI/actIII promoter pair and the actII-ORF4 (an activator gene), is particularly preferred. Particularly preferred hosts are those which lack their own means for producing polyketides so that a cleaner result is obtained. Illustrative control sequences, vectors, and host cells of these types include the modified *S. coelicolor* CH999 and vectors described in PCT publication WO 96/40968 and similar strains of *S. lividans*. See U.S. Pat. Nos. 5,672,491; 5,830,750, 5,843,718; and 6,177,262, each of which is incorporated herein by reference.

Other regulatory sequences may also be desirable which allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored, and this characteristic provides a built-in marker for screening cells successfully transformed by the present constructs.

The various PKS nucleotide sequences, or a mixture of such sequences, can be cloned into one or more recombinant vectors as individual cassettes, with separate control elements or under the control of a single promoter. The PKS subunits or components can include flanking restriction sites to allow for the easy deletion and insertion of other PKS subunits so that hybrid or chimeric PKSs can be generated. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

Thus, the present invention provides recombinant DNA molecules and vectors comprising those recombinant DNA molecules that encode at least a portion of the leptomycin PKS and that, when transformed into a host cell and the host cell is cultured under conditions that lead to the expression of said leptomycin PKS enzymes, results in the production of polyketides including but not limited to leptomycin and/or analogs or derivatives thereof in useful quantities. The present invention also provides recombinant host cells comprising those recombinant vectors.

Suitable culture conditions for production of polyketides using the cells of the invention will vary according to the host cell and the nature of the polyketide being produced, but will be know to those of skill in the art. See, for example, the examples below and WO 98/27203 "Production of Polyketides in Bacteria and Yeast" and WO 01/83803 "Overproduction Hosts For Biosynthesis of Polyketides."

The polyketide product produced by host cells of the invention can be recovered (i.e., separated from the producing cells and at least partially purified) using routine techniques (e.g., extraction from broth followed by chromatography).

The compositions, cells and methods of the invention may be directed to the preparation of an individual polyketide or a number of polyketides. The polyketide may or may not be novel, but the method of preparation permits a more convenient or alternative method of preparing it. It will be understood that the resulting polyketides may be further modified to convert them to other useful compounds. For example, an ester linkage may be added to produce a "pharmaceutically acceptable ester" (i.e., an ester that hydrolyzes under physiologically relevant conditions to produce a compound or a salt thereof). Illustrative examples of suitable ester groups include but are not limited to formates, acetates, propionates, butyrates, succinates, and ethylsuccinates.

The polyketide product can be modified by addition of a protecting group, for example to produce prodrug forms. A variety of protecting groups are disclosed, for example, in T. H. Greene and P. G. M. Wuts, Protective Groups in Organic Synthesis, Third Edition, John Wiley & Sons, New York (1999). Prodrugs are in general functional derivatives of the compounds that are readily convertible in vivo into the required compound. Conventional procedures for the selection and preparation of suitable prodrug derivatives are described, for example, in "Design of Prodrugs," H. Bundgaard ed., Elsevier, 1985.

Similarly, improvements in water solubility of a polyketide compound can be achieved by addition of groups containing solubilizing functionalities to the compound or by removal of hydrophobic groups from the compound, so as to decrease the lipophilicity of the compound. Typical groups containing solubilizing functionalities include, but are not limited to: 2-(dimethylaminoethyl)amino, piperidinyl, N-alkylpiperidinyl, hexahydropyranyl, furfuryl, tetrahydrofurfuryl, pyrrolidinyl, N-alkylpyrrolidinyl, piperazinylamino, N-alkylpiperazinyl, morpholinyl, N-alkylaziridinylmethyl, (1-azabicyclo[1.3.0]hex-1-yl)ethyl, 2-(N-methylpyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, and 3-(4-morpholino)-1-propyl.

In addition to post synthesis chemical or biosynthetic modifications, various polyketide forms or compositions can be produced, including but not limited to mixtures of polyketides, enantiomers, diastereomers, geometrical isomers, polymorphic crystalline forms and solvates, and combinations and mixtures thereof can be produced Many other modifications of polyketides produced according to the invention will be apparent to those of skill, and can be accomplished using techniques of pharmaceutical chemistry.

Prior to use the PKS product (whether modified or not) can be formulated for storage, stability or administration. For example, the polyketide products can be formulated as a "pharmaceutically acceptable salt." Suitable pharmaceutically acceptable salts of compounds include acid addition salts which may, for example, be formed by mixing a solution of the compound with a solution of a pharmaceutically acceptable acid such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

Prior to administration to a mammal the PKS product will be formulated as a pharmaceutical composition according to methods well known in the art, e.g., combination with a pharmaceutically acceptable carrier. The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

The composition may be administered in any suitable form such as solid, semisolid, or liquid form. See Pharmaceutical Dosage Forms and Drug Delivery Systems, 5$^{th}$ edition, Lippicott Williams & Wilkins (1991). In an embodiment, for illustration and not limitation, the polyketide is combined in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used.

EXAMPLES

The following Examples are intended to illustrate, but not limit, the scope of the invention.

Example 1

Gene Library Construction

Growth of Organism and Extraction of Genomic DNA

For genomic DNA extraction, a spore stock of *Streptomyces* sp ATCC 39366 (obtained from the American Type Culture Collection, Manassas, Va.) was inoculated into 35 ml of liquid R5 medium three days and grown in 30° C. A 10 ml portion of the cell suspension was centrifuged 5,000×g. The pellet was suspended into 3.5 ml of buffer I (Tris, 50 mM, pH7.5; 20 mM EDTA, 150 μg/ml RNase (Sigma-Aldrich) and 1 mg/ml of lysozyme (Sigma)). After incubation of the mixture at 37° C. for about 30 min, the salt concentration was adjusted by adding 850 μl of 5 M NaCl solution, then the mixture was extracted two times with phenol:chloroform: isoamyl alcohol (25:24:1, vol/vol) with gentle agitation followed by centrifugation for 10 min at 12,000×g. The genomic DNA in the supernatant was precipitated with 1 vol of isopropanol and redissolved in 800 μl of water.

Genomic Library Preparation

Approximately 10 μg of genomic DNA was partially digested with Sau3A1 (a series digestions with different dilutions of the enzyme) and the digested DNAs were run on an agarose gel with DNA standards. One of the conditions used was found to have generated fragments of size 30-45 kb. The DNA from this digestion was ligated with pSuperCos-1 (Stratagene), pre-linearized with BamHI and XbaI and the ligation mixture was packaged using a Gigapack XIII (Stragene) in vitro packaging Kit and the mixture was subsequently used for infection of *Escherichia coli* DH5α employing protocols supplied by the manufacturer.

Identification of Leptomycin Biosynthetic Gene Cluster

To find the gene cluster for leptomycin biosynthesis, cosmids from 475 *E. coli* transductants resulted from the above ligation mixture were sequenced using convergent primersT7cos (5'-CATAATACGACTCACTATAGGG) (SEQ ID NO:10) and T3cos-1 (5'-TTCCCCGAAAAGTGCCAC) (SEQ ID NO:11). After BLAST analysis, the sequences revealed that 4 cosmids carried DNA inserts with both ends encoding type I PKS (polyketide synthetase) genes. Restriction analysis of these four cosmids with BamHI showed 3 cosmids having overlapping inserts; the fourth cosmid (pKOS279-125.2L78) was distinct. Cosmid pKOS279-125.2L78 and pKOS279-125.3L71 from the 3 overlapping cosmids were sequenced. The incomplete sequences of pKOS279-125.2L78 revealed 6 complete modules and three incomplete modules.

From the 475 cosmids sequenced, also it was found that 16 cosmids carry inserts with PKS genes at one of their ends. While the above cosmids were under sequenced, DNA fragments encoding PKS genes from these 16 cosmids were pulled out by PCR and labeled with DIG (digoxigenin, Roche). The DIG-labeled PCR products were used to screen about 2000 *E. coli* transductants resulting from the ligation mixture of SuperCos-1 and partially-digested genomic DNA from the leptomycin producer. The in situ hybridization revealed up 89 positive transductants, and the cosmids in these clones were verified to contain PKS inserts by sequencing using T7cos and T3cos-1 primers (SEQ ID NO:57 and 58, respectively).

Figure 4A:
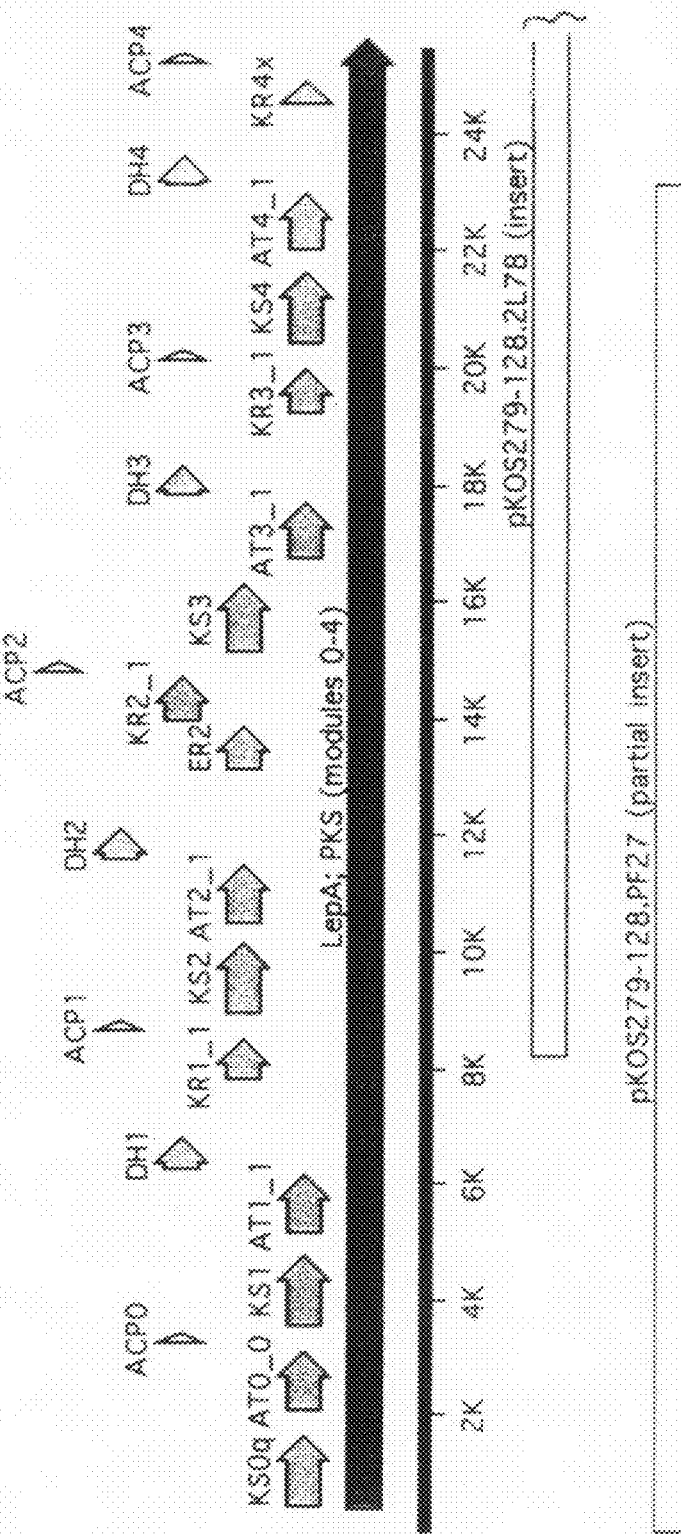
FIG. 4A shows the organization of the portion of the gene cluster comprising LepA.
Figure 4B:
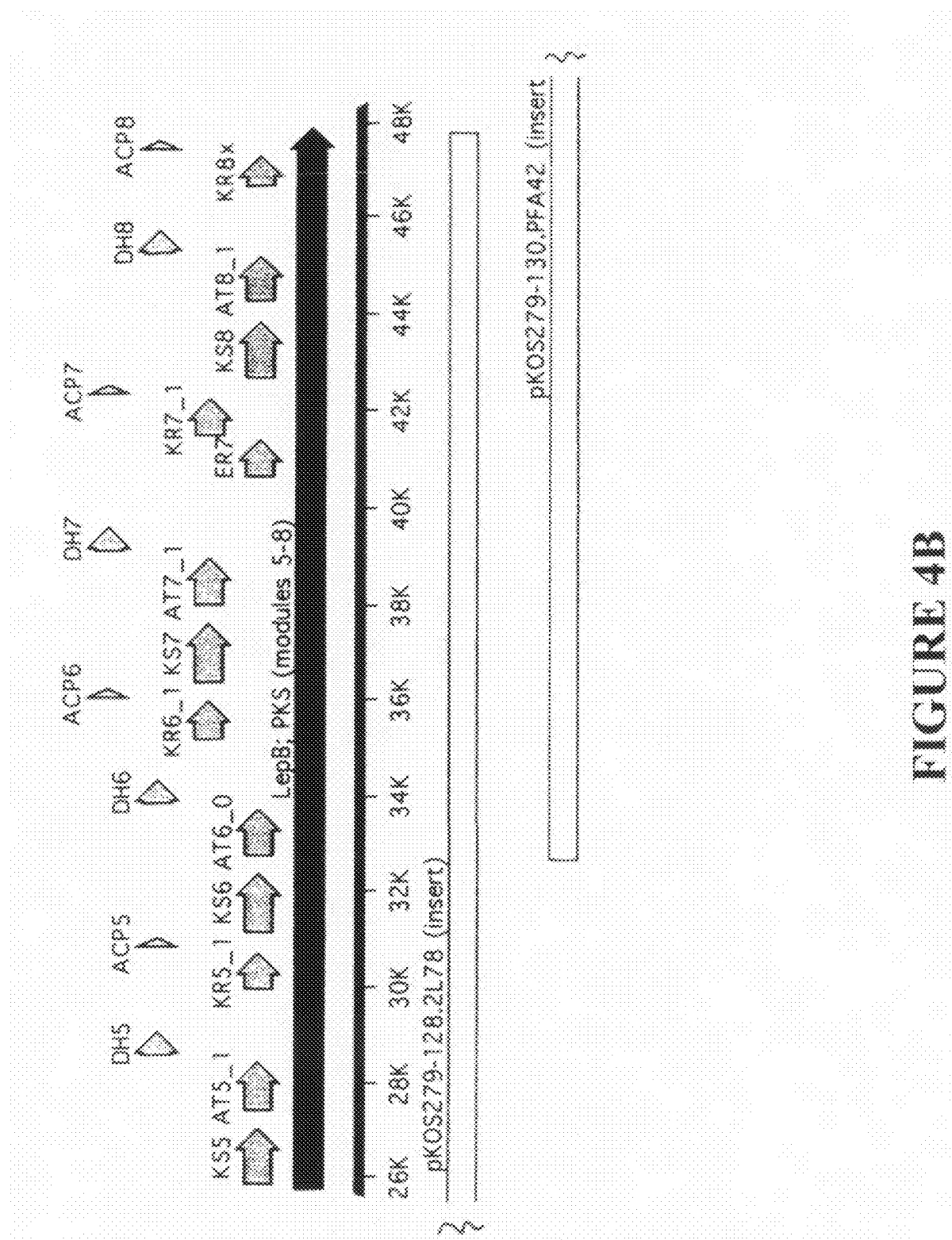
FIG. 4B shows the organization of the portion of the gene cluster comprising LepB.
Figure 4C:
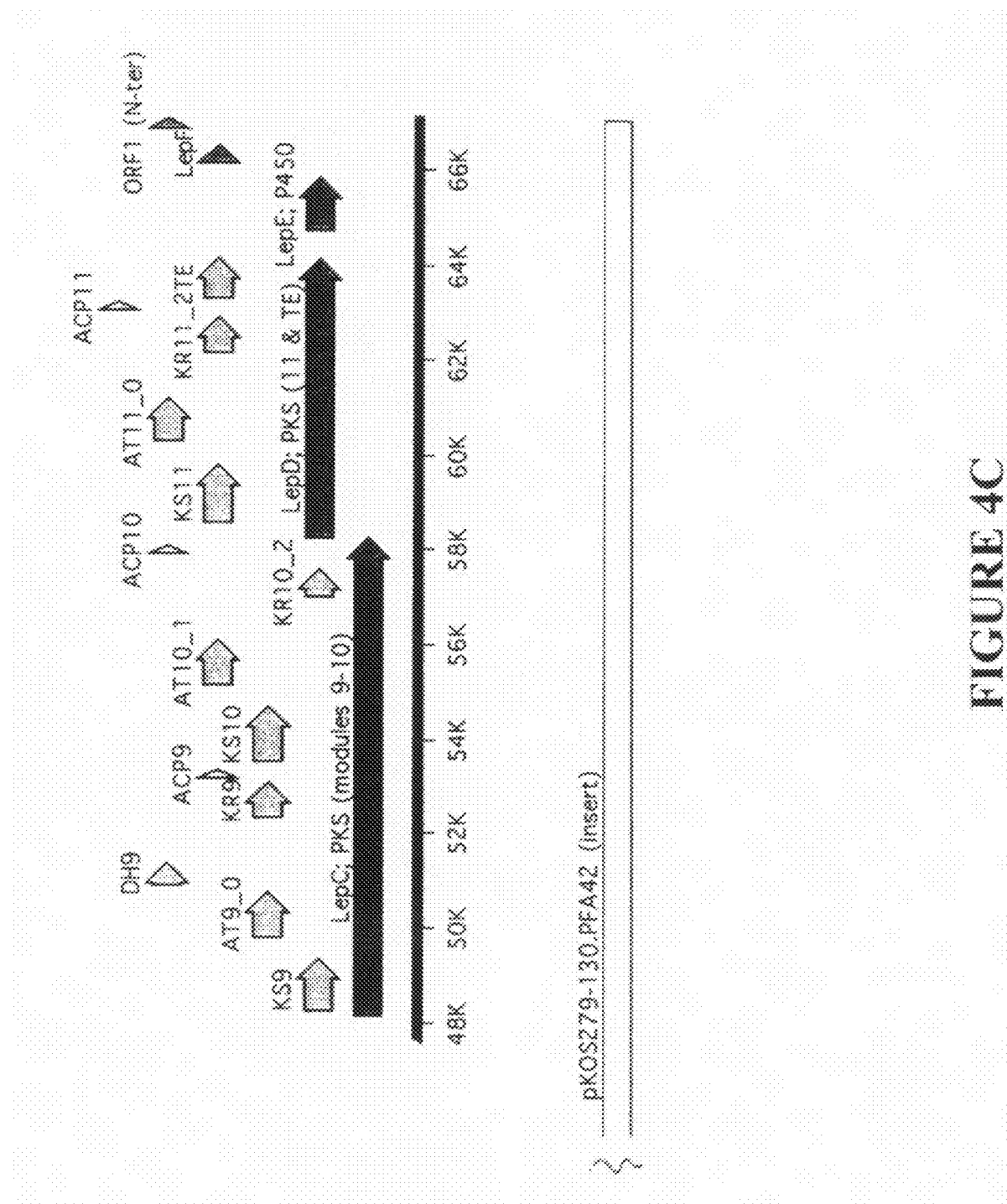
FIG. 4C shows the organization of the portion of the gene cluster comprising LepC, LepD, LepE, and LepF.

After DNA sequences of pKOS279-125.2L78 were available, these end sequences were analyzed using BLAST. DNA Blast revealed 3 interesting cosmids (pKOS279-128.PF26, pKOS279-128.PF27 and pKOS279-128.PF48. These 3 cosmids all have inserts extending to cover upstream of KR1ACP1 and reaching non-PKS genes (see FIG. 4).

All publications and patent documents cited herein are incorporated herein by reference as if each such publication or document was specifically and individually indicated to be incorporated herein by reference.

Although the present invention has been described in detail with reference to specific embodiments, those of skill in the art will recognize that modifications and improvements are within the scope and spirit of the invention. Citation of publications and patent documents is not intended as an admission that any such document is pertinent prior art, nor does it constitute any admission as to the contents or date of the same. The invention having now been described by way of written description, those of skill in the art will recognize that the invention can be practiced in a variety of embodiments and that the foregoing description are for purposes of illustration and not limitation of the following claims.

What is claimed is:

1. An isolated DNA molecule comprising a polynucleotide having a nucleotide sequence that is at least 95.0% identical to 58243 to 64170 of SEQ ID NO:3, wherein said polynucleotide encodes a polypeptide having thioesterase activity.

2. An isolated DNA molecule comprising a polynucleotide sequence encoding SEQ ID NO:7.

3. The isolated DNA molecule of claim 2, wherein said polynucleotide comprises nucleotides 58243 to 64170 of SEQ ID NO:3.

4. A recombinant polyketide synthase (PKS) comprising the isolated nucleic acid molecule of claim 2.

5. An isolated recombinant host cell comprising the PKS of claim 4.

6. A recombinant vector comprising the isolated nucleic acid molecule of claim 2.

7. An isolated recombinant host cell comprising the vector of claim 6.

8. A method of making an isolated polypeptide comprising:
   (a) culturing the isolated recombinant host cell of claim 5 or claim 7 under conditions such that said polypeptide is expressed; and
   (b) recovering said polypeptide.

9. The isolated DNA molecule of claim 2, wherein said nucleic acid sequence further comprises at least a portion of a PKS sequence.

10. The isolated DNA molecule of claim 9, wherein said nucleic acid sequence further comprises at least a portion of a second PKS sequence.

11. An isolated DNA molecule comprising the complete complementary sequence of the polynucleotide provided in claim 2.

* * * * *

SEQUENCE LISTING

```
<160> NUMBER OF SEQ ID NOS: 11

<210> SEQ ID NO 1
<211> LENGTH: 29467
<212> TYPE: DNA
<213> ORGANISM: Streptomyces ap. ATCC 39366

<400> SEQUENCE: 1
```

-continued

```
gatcacgggc aacgccggcc agggcgcgta cacggcggcc aacaccttcc tggacgccct    60
cgccgaacac cgccgcgcag ccgggctgcc cgccaacgcc ctggcctggg gactgtgggc   120
cgagggcagc gggatgaccc cgacacctcga ccacaccgac cgggcccgga tgtcccgggg   180
cgggatcgcg gcgctgccca ccgagaccgg actcgccctg ttcgacgccg cgttgcaccg   240
ggaccgccct tacacgatcc ccgcccgcct ggaccgcggc gcgctgcggg ccctggccgc   300
gagcggtgtg ctgcccgccg tactgcgcag cctcgtgcgt gtcccgccgc gcgtgccgc    360
cgcctccggc gacggcacgg acgcgtcgtc gtggccccgg cggatccggg aactcccggg   420
cgagcagcgg gaacgggcga tcaccgacct ggtgcgcggg caactcgccg ccgtcctcgg   480
acacgacgca cccgaacgac tcgacctcga ccgcgccttc cgcgaactgg gagtcgactc   540
gctgaccgca ctcgaactgc gcaaccggat caatgcgttc accggcctgc gactgcccgc   600
gacggtggtc ttcgaccacc ccagcggtac ggccctggtc gctcggatga tgcgcgagct   660
ggtcggtgcg gtgccgagcg agccgaccac gcccgtcgtc gcaccgaccg tgacggtcga   720
cgagccgatc gccgtcgtcg gcatcggctg tcgctatccg gcggtgtgg ccggtcccga    780
ggacctgtgg cgactggtcg cggccggcac ggacgcggtc ggcgacttcc ccgaggatcg   840
tggctgggac ctggcgaagc tgtacgaccc cgacccggac aaggtcggca aggtctacac   900
ccgtcggggc ggattcctct acgagtcggg ggagttcgac gccgagttct tcggcatctc   960
gccgcgcgag gcggcggcga tggacccgca gcagcggctg ctcctggaga ccgcgtggga  1020
ggcgttcgag cacgcgggcc tggaccccag gacgctgcgc gggagcaaca cggtgtgtt   1080
cgccggggtg atgtacaacg actacgcctc gcggctgcac cgcgcccccg acgggttcga  1140
gggcatgctg ttggccggca acgtgggcag cgtcgtgacc ggcagagtgt cctacgcgct  1200
gggcctggag gggccggcgg tcagcgtgga caccgcctgc tcgtcgtcgc tggtggcgct  1260
gcacctggcg gccaacgcgc tgcgtcgggg ggagtgcgat ctggcgctcg ccggtggggt  1320
gacggtgatg tccacccccga acgtcttcgt cgagttctcc cgacagcgcg gcctgtcggc  1380
ggacggccgt gccggtcgt tcgcggcggg cgcggacggg acgggttggg gcgagggtgt   1440
cgggctgctg gtggtggaac gactgtccga cgcgcggcgc aacgggcatc ccgtgctggc  1500
gctgctgcgt ggctcggcgg tcaaccagga cggcgcctcg aacgggctga ccgcgccgaa  1560
cggaccgtcc caggagcggg tgatccgggc ggcgttggcc ggtgcggggt tgtcggcgac  1620
ggacgtggac gcggtggagg cgcacggcac cgggacgacg ctgggcgacc cgatcgaggc  1680
gcaggcgttg ttggccacgt acgggcggga ccggccggcg gatcggccgc tgtggctggg  1740
ctcgatcaaa tcgaacatcg gcacacgca ggccgcggcg ggggcggccg gcctgatcaa   1800
gatgatcatg gcgatgcggc acggcgtact gcccgagaca ctgcacgtcg acgcgccgtc  1860
gccgcacgtg gactggtcga cgggacacgt cgagctgctg gccgaacgtc gaccgtggcc  1920
cgaggtcgac cgggcgcgcc gggccgccgt gtcgtcgttc gggatcagcg ggacgaacgc  1980
gcacgtgatc gtcgaacagg cgccggcggc cgaggcggtg gtgtcccggg acgagccggt  2040
gggtgtggcg ggcctggtgc cgtgggtgtt gtcggccagg accgccgacg gtctgcgggc  2100
gcaggcggcg cggttgcggg agtggtcggc gcggcatccg gaggcggatc cggtcgacgt  2160
ggggtggtcg ttggttcggg agcggtcggt tttcgatcgg cgggcggtgg tgggtggccg  2220
cgatccgggt gaactcgggg ctgggttgga caggttggcc gcgggtggcg gtattgccga  2280
cggtcggccg atgttttcgg gtcccggtcc ggtgttcgtg tttcccgggc aggggtcgca  2340
```

```
gtgggtgggg atggcggccg ggctgttgga gtgctcgccg gtatttgcgg aggcggtgac    2400
ggagtgcgcc gccgtgatgg atccgttggt ggcggattgg tcgttgttgg atgtgttgcg    2460
gggtgggtct gccggtgagt tggagcgggt ggatgttgtt cagccggtgc tgtttgcggt    2520
gatggtgggg cttgcgcggt ggtgggagtc gtgtggggtc aagccgggtg cggtcatcgg    2580
gcactcgcag ggggagatcg ctgccgcgca tgtggcgggt tatctgtcgc tggcggatgc    2640 ggtatggggtg gtcgtgttgc ggagtcgggc cctgctgggg gtcgcgtccg ccgggggcgg    2700
gatggtgtcc gtcggggtgt cggcggagcg tgctcgcgag ctggtcgccg gggatgaccg    2760
gctgtcgttg gcggcggtga acgggccgac gagtgtggtg ctttcgggtg atgtcgaagc    2820
gctgtcggtg gttgtcgagg cgtgcgagcg ggatggtgtg cgggctcggt ggattccggt    2880
ggattacgcg tcgcattcgg cgcggatgga ggccgtgcgg gacgaggtgg agcggctgtt    2940
ggcggatgtg acgccgcagg tgggccgcgt gccgatgtac tcgaccgtga gcggggaggt    3000
ggtcgtcgat cccgccgagt tgggcgggc gtactggttc gagaatctgc ggcgcacggt    3060
cgagcttgag cgggccgtgg gtgcggcggt cgcggatggg catggtgcgt tgtggagtg    3120 cagcccgcat ccggggctgg tggtgccgat ggggacacc ctggaggcgg ccggggtgga    3180
cggcgtcgtt ctggagacgt tgcggcgggg tgagggtggg cccgatcggc tggtcgccgc    3240
gctctcggcg gcgttcgtgg cgggtgtcgc ggtggactgg gccggaatgt tgccggggcg    3300
ccatgtcgag ctgccgacgt atgcgttcca gcggcggcgc tactggttga cgggtgggga    3360
acgtgcgggc gatccggccg ggttgggggct ggtcgcggcc gatcatccgc tgctgggggc    3420
tgtggtcggt tcggtgcggg acggggaact cctctacacc gggcggttgt ccgccgcgac    3480
gcacggctgg cttgcggacc acgcggtgtt cggctcggtg gtggtaccgg gacggccctt    3540
cgtcgagctg gcgtcgtggg tcggtgtcga ggccggttgc ccggtcgtcg acgaactcac    3600
gctgcatgcg cccctggtgc tgccggacgg ggtcggcatc cggcttcggg tggcggtggg    3660
cgcggcggat tcggcggggc gtcgggtggt ggagttccat tcgcggcccg aggatgcccc    3720
cgacgagcag tcgtggactc ggcatgcgac cggcacgctg ggtgccgcga gtgtgcccgg    3780
atccgcgtcg gccggggccg cggcgtgggc ggtctggccg ccggcggacg ccgaggtggt    3840
cgacccggag gccgtttacg agcgacttgc ggagcacggg tacgaatacg gccgattttt    3900
ccgggggttg cgggccgcat ggcggcgggg tgacgacttc ttcgccgagg tcgcgctgcc    3960
ggaggcggcc ggtcgggacg cgcacggcta cgacctgcat ccggcggtgc tggacgccgc    4020
gctgcatgtg gccgcggccg aggcggtggc ggagtcgggg gcgacgttgt tgccgttcgc    4080
ctggaccggg gtcgcactgc atgggccggg ggcgtcggtg cttcgggtga tgttgcggcg    4140
taccgggcgg gagacgctgg cggtcgacgt ggccgacgag cgtggtgttc cggtggcgtc    4200
ggtcgcgtcg ctgacgctgc ggccggtggc tgccgagcag ttggtggcgg ccgaggaagc    4260
gggccgcgag tggctttacc ggatggtctg ggagatcgcg gacgcgccgg tggcggagca    4320
cgtcgagggt gaacttcttg gttcggatga ggagtccgac gcgtcggcgg agcttgtggc    4380
gggcgggatt cggtggtga cccctgcggg cgccgaacag gtctccgagg tggggctgtt    4440
cgattgcccg cccgtggtcg gcgaagcccc cgaggaggtg gccggcgccg tgcatgcggt    4500 gctgccgcg gttcgggcgt gggtggcgga cgagcggttt gccggggcgc ggctggtggt    4560
tcgtacccgt ggcgcggttg ccacggatgc gcaggaccgg gtcggttctc ccgcgcatgc    4620
ggcgatctgg ggtctcgtgc gggtcgcgca gagcgagcat ccggggcgct tcgtcctggt    4680
cgatggggac gacgtcgatt cgggtgcggc gctgcgtgcg gcggtggcgt gcgggctgcc    4740
```

```
gcaggtggcg attcgcgaag gtgtggtgct ggcgccgcgc ctggtggggg cggtgcacga    4800
cacggcgctg gtgccgccgg cgccgggtgc ggatcaggcg tggcggatcg agtccgggac    4860
ggccgggacg ccggacgatc tggtggtgac ggcgcatccg gccgcctcgg cgccgttggc    4920
ggccgggcag gtgcgggtgg cggtgcgggc ggccggggtg aacttccgcg atgtgctgat    4980
cacgctcggc atgtacccgg ggcgggcggt ggtcggcgcc gaggcggccg gggtggtcgt    5040
ggaggtcggc ccgggcgtgt cggaaccggc cgtcggcgac cgggtgatgg gcttgttcga    5100
gggggcgttc gggccgcttg cggtggccga tcggcggctg ttggcccggg tgccggcggg    5160
ttggtcgttt gctcaggcgg cgtcggtgcc ggtggtcttc ctcaccgcgc tctacgggct    5220
gcacgatctg gccgggctgc ggtcgggtga atcggtgctg gtgcatgcgg ccacgggtgg    5280
ggtcggcatg gccgccaccc agctggcccg gcatcggggc gccgaggtgt acgcgaccgc    5340
gagtgcgacg aagtgggcca ccgtgcgcgg gctgggtgtt ccggacgaac ggatcgcctc    5400
gtctcgggac ctgtccttcg aacagcgctt cgcacgggcc acggacgggc gcgggatcga    5460
cgtggtgttg aactcgctgg cgggcgagtt caccgacgcg tcgttgcgac tcctggccga    5520
gggtggccgg ttcgtggaga tgggcaagac ggacgtccgg accgaggggc tgccggccgg    5580
ggtgcgctat cgggccttcg acctgatcga ggccggtccg gatcggatcg ccgagatgtt    5640
cgccgaactg gtcgacctct tcgagcgcgg tgtgctgcaa cccctgccga ttcggacctg    5700
ggacatccgt cgggcccgcg aggcgctgcg tttcctgggc caggcccggc atgtgggcaa    5760
ggtggtgctg accgtgccgc agccgctcgc ggccgacggc acggtcctga tcaccggcgg    5820
cacgggcacg ctgggtcgca gtctggcccg acacctggtc acgcggtggg gtgtgcgccg    5880
gctggtgctg accggccggg ccgggcccgc cgctcccggc gccgcgaac tggtcgcgga    5940 attggccgag tcgggtgccg acaccacgat cttggccttg cgatgcggcg gaccgggcgg    6000
cgaatggccg aagtgttgg ccgcgatccc ggccgaacac ccgttgaccg ccgtggtgca    6060
tgccgccgga acactcgacg acgcgccgat cgaggcgctg accccggagc gggtcgacca    6120
cgtgttgcgc cccaaggtgg acgccgccct cgtactggac gaactcaccc gggacgcgga    6180
cctggccgcg ttcgtgctgt tctcgtcggt ggccggcgta ctcggtgtgg ccggccaggg    6240
cggctatgca gcggggaacg cgttcctgga cggtctcgcc ggtcggcgcc gcgagcgggg    6300
gctgcccgcg accgctctgg cctggggcct gtgggcggaa cgcagcgcaa tgaccgcgca    6360
gttgggcgtc ggcgacctga agcgcctggc gcgcggcggc ctggtgccga tctcgaccgc    6420 ccagggggctc gccctgttcg acgccgcctg gcaggccgac gaggcggcgc tgatcccggc    6480
ccgcctggac cttgccgcac tgcgcgcaca ggcggcgacc cagccggtac atccgctgct    6540
gcgcggtctg gtcggcacca ccccgacccg ccggaacggc acacccttcgg aggcgccgtg    6600 ggcccgacgg ctcgcctcgg ccgcgcccgc cgagcgggtg acgtggcat tgcggctggt    6660 ccgggccgag gcggcggtgg tcctggggca cgagtcgatc gacggggtgc ggcccgaagt    6720
caccttccgc gacctcgggt tcgactcact gacgggtgtg gaactgcgca accgcgctgag    6780 cggcgccacc ggattgcggc tgccgtccac gctggtcttc gacttcccga ccccgctcgg    6840
cctggccggt ttcctggtcg ccgagtcggt cggcgagatg gacacggcgc cgaccgggcc    6900
ggttgccggg ggtgcggtgg tcgcggccga tccggtggtg atcgtcggga tgggctgccg    6960
attccccggg cgggtggact cggcggcggg tctgtgggac ctggtggccg cgggcggcga    7020
tgcgatcggg ccgttcccga ccgaccgtgg ctgggacgtc gacgcgctgt tcgatcccga    7080
```

```
tccggagcgg gtcggcaaga gctacgtccg taccggcgga ttcctctccg gggcggccga   7140
gttcgacgcc gagttcttcg gtgtgtcgcc gcgcgaggcg ttggcgatgg acccgcagca   7200
gcggctgctg ctggaaaccg cgtgggagac cttcgagcag gcgggcatcg atcccacctc   7260
gctccggggc agccggaccg gcgtcttcgc cgggatggcc ggccacgact acgcgaccgg   7320
gggcgcccgt tcgcaggccg gctggaggg ccacctgctg accgggaacg cggccagcgt   7380
ggcctcggga cgggtggcct acacgttcgg cctggagggg ccggcggtga ccgtggacac   7440
ggcgtgctcg tcgtcgctgg tggcgctgca cctggcggcc aacgcgctgc gggcggggga   7500
atgcgacctg cgcgctcgcc gcggggtgac cgcgatgtcc acgccggact tcttcctgga   7560
gttctcccgg cagcgcggac tgtccgtgga cggccgttgc aaggcgttcg cggccacggc   7620
ggacgggatg ggcgcggccg agggcgtggg cctgctcctg gtcgagcggc tgtcggatgc   7680
gcggcgcaac gggcattcgg tactggcggt ggtgcgtggg tcggcggtga accaggacgg   7740
cgcgtcgaat gggttgaccg cgccgaacgg gccgtcgcag cagcggtga tccgggcggc   7800
cctggccgac gccgggctgt ccgcggccga tgtggatgcg gtggaggcgc acgggaccgg   7860
cacgacgctc ggcgatccga tcgaggcgca ggcgttgctc gcgacctacg gcgggatcg   7920
ggcgccggat cggccgctgt ggttggggtc ggtgaagtcc aacatcgggc acacccaggc   7980
ggcggcgggt gtgccggggg tgatcaagat ggtctcggcg ctgcggcatg ggatgttgcc   8040
gcgcacgctg cacgtggacg agccgacgcc gcatgtggac tggtcggcgg gtggggtcga   8100
actgctcacg agccgcgcgg cgtggccgga ggccggggcg gtgcgtcggg cggggtgtc   8160
gtcgttcggg atcagcggga cgaacgcgca tgtgatcctg gagcaggcgg aggagagccc   8220
ggcgggttcg gtgccttcgg cgactcctcc ggtggccggg actccggtgt ggggcggtcg   8280
ggtgccctgg gtgttgtcgg cccggtccga accgctttg cgggcacagg ccgcgcggtt   8340
gcgggactgg ctggccgtac atcccgacgc cgatccgctc gatgtggggc ggtcgttggc   8400
gaccgggcgg gcggcgctcg atcaccgggc ggtggtgcat gggcgggacc tcgcggaatt   8460
gcgcctggcg gtcgcgaagt tggccgacag cgggccgggt gacgaggcgt cgatcgtcgg   8520
ctcggtctcc gccgccggtc cggttttcgt gttttccgggg caggggtcgc agtgggtggg   8580
gatggcggcc gggttgttgg agtgttcgcc ggtgtttgcg ggtgtggttg ccagtgtgc   8640
tgcggtgatg gatccgttgg tggcggattg gtcgttgttg gatgtgttgc ggggtgggtc   8700
tgccggtggt gaggcgttgg cggagcgggt ggatgtggtt cagccggcgt tgttcgtggt   8760
gatggtgggg cttgcgcggt ggtgggagtc gtgtggggtc aagccgggtg cggtgatcgg   8820
acactcacag ggggagatcg cggctgcgca tgtggcggga tatctgtcgc tggcggatgc   8880
ggtgcggggtg gttgtgctgc ggagtcgggc gttgctcggg gttgcgtctt ccggtggcgg   8940
gatggtgtcg gtgggtgtgt ccgccgatcg ggcccgggag ctggtcgccg aggacgaccg   9000
gttgtcgctg cgggccgtga acgggccgac gagtgtggtg cttcgggtg atgtcgaagc   9060
gctggccgtg gttgtcgacg gctgtgagcg ggacggggtc cgggctcggt ggattccggt   9120
ggattacgcg tcgcattcgg cgcggatgga ggccgtgcgg gacgaggtgg agcggctgtt   9180
ggcggatgtg acgccgcagg cgggccgcgt gccgatgtac tccacggtga gtgggggca   9240
cgttaccgac ccgagtgtgc tcggtggttc gtactggttc gacaatcgc ggcgtacggt   9300
cgagttggag cgggccgtcg gagcggcggt tgtcgacggg cattcggtct tcgtcgagtg   9360
cagtccgcat ccggggctgg tggtgccact gggggacacc ctggaggcgg ccggggtgga   9420
tggcgtcgtt ctggagacgc tgcggcgggg cgagggcggt cccgatcggc tggtcggcgc   9480
```

-continued

| | |
|---|---|
| gctttcggcg gcgttccgga gcggtctggc cgtggactgg gccgggtccg ggatggtgcc | 9540 |
| ggggcggcgg gtcgagctgc cgacctatgc cttccagcgg cggcggtact gggtcgagcc | 9600 |
| cggcgagagg gccggcgggg tcgggtgggg gcagttcacg gtcgaacatc cggtgctggg | 9660 |
| cgccggggtc gatctggccg acggagccgg gacggtcttc accggcggc tgtccgcggc | 9720 |
| ctcgcacggg tggctcgcgg agcatgtggt gctcggcacg gtgatcgcgc ccggcacggc | 9780 |
| gttcgtcgac ctggcgctgc gtgcggggc gacggtcggc cgggcgacgg tcgaggaact | 9840 |
| gaccctgcac gcgccgctga tcctgcccga cgcgggcggt gtacggattc aggtccgggt | 9900 |
| cggcgcaccc gacgccgccg ggtcggatc ggtggagatc cattcccgac cggaggacgc | 9960 |
| ggccggcgac gagccatgga cccggcacgc ctccggacc ctgaccgcga ccgacctcga | 10020 |
| cccggcggac gtgccacgg aggcggcgat ctggccgccc gcgggcagta cgccggtcga | 10080 |
| tctggacgga gcctacgagc gactggccac ggccggattc gagtacggtc ccgccttcca | 10140 |
| ggggctgcga gccctgtggc ggcgcggcgc cgagtcgttc gccgagatcg aactcgcgga | 10200 |
| cgacgcacgg caggaggccg aacgctacga ggtgcatccc gcgctgttgg atgcggccgt | 10260 |
| gcatgcgctg gggatggagc cgacggcgga ggttgcgccg gatgaggcgc ggattgcctt | 10320 |
| ctcctggcga ggggttcggc tggttgccgc cggagcgggg cggttgcggg tcggctggc | 10380 |
| accggtgggc tcgacgcgg tgtcgttgtg gctgagcgac atggacggtg agccggtcgg | 10440 |
| gtcggtccgg gccctgaccg tgcggccggt cgcggccgag cggctgcgtc cggctggggc | 10500 |
| gccgccgcgc gactcgatgt tccgggtgga gtggcggccg tgtcgggcg acgagtcggg | 10560 |
| cgtggcggtt cgctgggcgg tggtgggcgc ggcggactcc gggccgcttg cccggctggt | 10620 |
| ggcggcgtat ccgatgtgc cggtgtaccg cagtgtggtc gaggcggccg gggatgtggc | 10680 |
| ggcgggaccg cccgatgtcg tggtggtggg cgtgggcgag ccgactgtt cggaggggtc | 10740 |
| ggtcgagcgc actcggcggg tgcttgcgga cgtgctggcg tggatgcagg actggctggc | 10800 |
| cgactcccgc ttcgcggcga cgcgcctggt cgtggtgacc tccggggccg tcgccgccga | 10860 |
| cgtggacgcc gaccccgacg agcgggtggc ggacctggcc ggcgcggcgg tgtggggtt | 10920 |
| gttgcgctcg gcccagtccg aacaccccga ccgatgcacg ctggtcgacc tcgacgagga | 10980 |
| cgcggcgtcg attgacgcct ggccggcgat tcttgcctcc gccgagcgc aactcgccgt | 11040 |
| ccggatgggc cgattccggg tgcctcggct ggccagggtg actgccgggg cggcgagcc | 11100 |
| ggtcgccttc gcgcccgacg gcacggtgtt ggtcaccggt gccaccggcg gcctgggcgc | 11160 |
| cctggtggcc cggcacctgg tgaccgcgca cggcgtgcgc cgacttctgc tgctgtcccg | 11220 |
| ccggggcgcg gccgcacccg gcgcggccga actggtcgag gacctgaccg cgcaggggcc | 11280 |
| ggaggtcacc ctcgccgcct gcgatcgtgc cgcgctggcc gccgagttgg cgcgtatccc | 11340 |
| ggccgagcac gcgctgaccg gcgtgatcca caccgccgga gtggtggacg acgccaccat | 11400 |
| cgcgaacctg accgatgcgc acatggaaca cgcgctgcgc cccaaggcgg acgccgcgtt | 11460 |
| ccatctggac gagttgaccc gggacgtgaa cccggccgca ttcgtcctgt tctcctccgg | 11520 |
| ggccaccacc ttcggtggcc cgggacaggg caactacgcg gcggccaacg ccttcctgga | 11580 |
| cggcctggcc cggcagcgcc gcgaccgcg cctgcccggg atctcgctgg cctgggcct | 11640 |
| gtgggcgggc gcgcagggga tgggcgggcg gctgagcgag gccgacctgg cccgctggc | 11700 |
| ccggaccggc gcggtggcga tgccggcggc cgaggcactg cggttgttcg atatcgcgct | 11760 |
| gggccggccc gaggcggccc tggtgccggc acacctggac ctcccggcga tgcgggcgga | 11820 |

```
tgccggtgct cgacccgcgc tgttccgcga gttgctcggg atcggtacgc gacgggcggc    11880
agtgggcgcg ggcgggtcgg cgctgacccg gcggctgggc gggatgtctc cggccgagcg    11940
ggagcaggcg gtcctggacg tggtgcggac cgaggccgcg aacacgctgg gacacgagtc    12000
ggccggggcg gtgtcggccg ggcgagcgtt caaggagctg gggttcgact cgctgaccgg    12060
ggtggaactg cgcaaccggt tgaacaccgc gaccgggctg cggttgccgt ccacgctggt    12120
cttcgactac ccgacgccgg cggggctggc ggcgttcctg gtcgccgagt tggtcggtcg    12180
ttcggtacag gcggtgccgg tgccgccggt cggtgggcgg cacggggacg ccgacgatgc    12240
gatcgtgatc gtcggcatgg gctgccggtt cccgggcggg gtggcctcgc cggaggacct    12300
gtggaatctg ctggcctcgg gtggggacgc gatcggaccg ttcccgacgg accggggatg    12360
ggacctggcc gggctgttcg accccgatcc cgagcgggcc gggaagagct acgtggaatc    12420
gggcggattc ctgtatggga tcggcgagtt cgacgcggag ttcttcggga tctcgccgcg    12480
tgaggcgttg gcgatggatc cgcagcagcg gttgctcctg gagacggcgt gggagacgtt    12540
cgagcgggcg ggcatcgatc cgacctcgct gcgcggcagc cggaccgggg ttttcgccgg    12600
ggtgatcgac aacgactacg cgcccgggt gaaccaggtg ccggacgagg tcagggcta    12660 tctgggctac ggcagttcgg ccagcatcgc gtccgggcgg gtctcgtacg tcctgggcct    12720
ggagggcccg gcggtcagta tcgacaccgc gtgctcgtcg tccctggtcg cgctgcacct    12780
ggcggtgaac gcggtgcggt cgggcgaatg cgaactggcc ctggccggtg gtgtgacggc    12840 gatgccacc accgagttct tcgtggagtt ctcccgacag cggggcctgt cgccggacgg    12900
ccgctgcaag gcgttcgcgg cggcggcgga cgggatgggc gcggccgagg gcatcgggct    12960
ggtgctggtg gagcggttgt cggatgcgcg gcgccatggg cattcggtac tggcggtggt    13020
gcgtgggtcg gcggtgaacc aggacggcgc gtcgaatggg ttgaccgcgc cgaacgggcc    13080
gtcgcagcag cgggtgatcc ggcaggcgtt gggtgctgcg ggcttgtctg cggcggatgt    13140
ggatgcggtg gaggcgcacg ggaccgggac gacgttgggt gatccgatcg aggcgcaggc    13200
gttgttggcg acctatgggc aggatcggcc ggggatcgg ccgctgtggt tggggtcggt    13260
gaagtcgaat atcgggcaca cgcaggcggc tgcgggtgtg ccggggtga tcaagatggt    13320 gttggcgctg cggcatgggg tgttgcctcg gacgttgcat gtggacgagc cgacgccgca    13380
tgtggattgg tcggccgggc gggtcgaggt gttggcggac gaggtggcgt ggccggcagg    13440
ggagcgggtg cgccgggcgg gtgtgtcgtc cttcggaatc agcgggacga acgtgcacgt    13500
ggtcctggag gaggcgccgg cggacgccgc cgagcctgcg cccgccgcgc cggaggtccc    13560
gggcgtcggc ggcgtgctgc cctgggtggt gtcggcgcgc accgaggccg ggctgcgggc    13620
gcaggcggcg cggttgcggg attgggtgag cgaacatccg gacgccgaac cgacggatgt    13680
cgcacggtcg ttggtggtcg ggcgagcggt gttggacgtg cgcgcggtgg tgcgcgggcg    13740
ggaatccggc gaacttgtcg ccggcctgga cgagttggcg cgggccgggg tgggagaccc    13800
cggctcgctg gtgagcggct cggatccggt gttcgtgttt ccggggcagg ggtcgcagtg    13860 ggtgggatg gcgccgggt tgttggagtg ttcgccggtg tttgcgggtg tggttgccga    13920
gtgtgctgcg gtgatggatc cgttggtggc ggattggtcg ttgttggatg tgttgcgggg    13980
tgggtctgcc ggtgagttgg agcgggtgga tgttgttcag ccggtgctgt ttgcggtgat    14040 ggtgggggctt gcgcggtggt gggagtcgtg tggggtcaag ccgggtgcgg tgatcgggca    14100
ctcgcagggg gagattgcgg ctgcgcacat cgcgggttat ctgtcgctgg cggatgcggt    14160
gcgggtggtt gtgctgcgga gtcgggctct gctgggggtt gcgtcttccg gtggcgggat    14220
```

```
ggtttcggtc ggggtgtctg cggagcgggc gcgggagttg gttgccggag ctgacgggtt    14280
gtcgttggcg gcggtgaacg ggccgacgag tgtggtgctt tcgggtgatg tcgaagcgct    14340
gtcggtggtt gtcgaggcgt gcgagcggga tggtgtgcgg gctcggtgga ttccggtgga    14400
ttacgcgtcg cattcggcgc ggatggaggc cgtgcgggac gaggtggagc ggctgttggc    14460
ggatgtgacg ccgcaggtgg gctgcgtgcc gatgtactcg accctgaccg gtgcgccgat    14520
cgccgatccc gccgagttgg gcggggcgta ctggttcgaa aacctgcggc gcacggtcga    14580
gttggagcgg gcggtcggtg cggcagtggc ggatgggcgc accgtgttcg tcgagtgcag    14640
tccgcatccg gggctggtgg tgccgctggg ggacaccctg gaggcggccg gggtggatgg    14700
cgcggttctg gagacgttgc ggcggggtga aggtgggccc gatcggctgg tcgccgcgct    14760
ctcggcggcg ttcgtgcgtg gtctggcggt ggattgggcc gggttgatcg tcggtgctcg    14820
ggtggagttg ccgacctacg ccttccaacg acggcgctat tggttggacg acggggcgcg    14880
gtcgggggat ccgggcgggt tgggactggc cgcggtcgca catccctgc tgggtgcggc    14940
ggtacggccg gcgcagggcg cggggttgtt gttcaccgga cggttgtcga cggcgaccca    15000
cccgtggctc gcggatcatg tggtgctcgg ctcgacgatc gtgcccggca cggtgttcgt    15060
ggacctggcg ctgtgggccg gggccgaggc ggagtgcccg gtggtggacg aactgaccct    15120
gcacaccccg ctggtgctgc cggaacacgg cggcgtgcat gtacaggtga ccgtcgacgg    15180
gccggacgcc gccggggccc gggcggtcgc ggtgtactcc cggccggagg acgctcccgg    15240
cgaggagccg tggaccccgg cacgccgtcgg tgccctcgtt gccgacgccg atacgggtgc    15300
cgctcccgac gcggctgcgg aggcgtggcc gccggtcggc gcgaagccga tcgaggtggc    15360
ggacttctat gcgcggctgg tggagtccgg ggtcgactac gggccggcgt ttcgcgggat    15420
gcgggccgcc tggcggcgcg gggacgagct gttcgccgat gtggcgctgc cggccgagga    15480
ggagcgcgac gcacaccgct tcggggtaca tccggcgctg ctcgacgcgg gcgtgcagac    15540
cctgcgggtg gatccggggc aggtcgacga ggacgacatc cgggtggcct tctcctggca    15600
cggggtgcgc ctcttcgcgg ccggcgtgac ccggctgcgg gtgtcgtgcg tgccgtcggg    15660
cgagggtgcg gtgtcgttgc ggatcacgga cgagaccgga cgggcggtcg ccgcgatcga    15720
ggcgttgacg gtgcgggcga tctcggccga ccagctacgg cgggccggcg gcgggcggga    15780
cgtgctgtac cggctcgcgt ggcgggcatc ggcggttccc gtaccggtgg cgacgcctcg    15840
tgtggcggtg gtcggcgggt gggatctgcc cggtctgggc gggttggtgg accggtatcc    15900
gggctttgcc gaacttgctt cgtgtgaccc gccgttgccc gatctggtac tgctcccggt    15960
tggtgatccg gatgcggatg tgccgttctc cgagcggcgt atgcgggagg tgacggcgga    16020
actgatcggg cggctggagg cgtttctcgg cgacgaacgg ttcgcggcgg cccgggtggt    16080
cgtggtgact cgttcggcgg tgctcgtgga cgggacgcg gggctcgggg acccggcgtc    16140
ggcgtcggtc tggggagtgg tccgggcggc gcaggccggg catccggggc ggatcgtgct    16200
ggtcgacctg gacgacgagc cggcttcggc ggcggctttg gcggcggtgg cctcggccgg    16260
tggtgagccg cagttcgcgg tgcgcggtgg tcgggtgtcg gtaccgagac tggagcggat    16320
tccggcctcc ggcggagcac ggtcggcggt gggaccggc acggtgttga tcgccggtgc    16380
ggaccgggcg gtcggcgcgg gggtggccga gcatctggcc ggggcgtacg gggtgggccg    16440
gttcgtgttg ttgtccgtgg atccttcggg tgcggggccg accgaactgg ccgcccggct    16500
gggtgaggcc ggtgccgagg tcgtctcggc ggcctgggac gggcacgatc cgggcgtgct    16560
```

```
tgccgcgctt gtgaccgaac accggccggc gggcgtggtg gacgcgtcgg gcgagtcgga    16620
tgcagcctgg gccctgcacg agctgaccgc cgacgtggac ccggcgttct tcgtgctgtt    16680
ctcgtcggcg gcgagcctgc tcggttcgtc ggcgcatgcg gccacggccg gggtggatgc    16740
cttccacgat gcgctggccg cacatcggcg ggcgagtggg ctgcccgggg tgtcgcttgc    16800
gtgcgggacg gatccgctgc cggggctgcc cgacctgttc gacgaggcga tacgccggga    16860
ggacgccgtg ttggtttcgg cgtcgacgga tctcaccggg cccgcgtcga cgtcaccatt    16920
gttgccctcc cggaacggtc gtggcgcgac caactccgcc gagacctcga tcgaggcgga    16980
cggcgaggcc ctggcccggc gcctggcggc gttgtccgag gaggagcgcg agcgcgaact    17040
ggtcggcctg gtacgggccc aggccgcggc ggtgctcggg catgccggca tcggcgagat    17100
cggacccgaa cgggcgttca aggaggtcgg gttcgactcg ctcaccgcgg tggaactgcg    17160
caaccggctg atccggggca ccggggtcgg cctgcgctcc accctcgtct tcgacttccc    17220
cacgccgcga atactggccc gccacctgag cggccggctg gtcgaggcgg catccccgat    17280
cggtgcgctg ctggccgatc tggaccgatt cgagggcgag ttgcacgcgg tgctcggcga    17340
ggcggaggcc cgcgaccggc tggccgagcg gctgcgtcgg ctgttggccg actgtaccgc    17400
gccggacgag agcgccccg ccgccgacga tgtctcggac gtgcagtcgg ccaccgacga    17460
cgagttgttc tcgctcgtcg accagggctt cgaatgaccc ggcccatcca cgcatacgac    17520
cgtgtcggca aggagtagag gcaacgtggc tgagtcggaa gagaaactgc gctcgtacct    17580
gcggaaggcc atcaccgatg cgcgcgacgc gcatcgccgg gtacgcgagt tggaggaccg    17640
gcagcgcgag ccgatcgcga tcgtgggcat ggcctgccgc ttccccggcg gtttgggtac    17700
gccggaggac ctgtggcggt tcgtcgtcga aggcggcgat gcgatcggcg agttcccgac    17760
cgaccggggc tgggacctcg acggcctgta cgacccggat cccgaccggc cgggcacgtc    17820
gtacgtccgc gagggcggat tcctgtacga cgtcgccgac ttcgacgccg agttcttcgg    17880
catctcgccc cgcgaggcgg cggcgatgga cccgcagcag cgactgcttc tggagacctc    17940 ttggaggcc gtggaacgcg cgggcatcga cccgacgtcg ctgcggcaca gccggaccgg    18000
gatctacacc gggatcaacg gcctcgacta cacgaccgtg ttggcccgca ccgccaaggg    18060
ccgggacggc acgctcggca tggccaacgg ggccagcctg ctggcgggtc gggtggcgta    18120
catcctcggc ctggagggc cggcggtgac cgtggacacg gcgtgttcgt cgtccctggt    18180
ggcactgcac ctggcgagca acgcactgcg gtcgggggaa tgcgacctgg ccctggccgg    18240
cggtgcgacg gtgatgtgca cgccggagat cttcgtcaac ttcagccggc agcgcggact    18300
ggcccgcgac ggccgatgca agccgttctc ggcggcggcc gacgggttca tcctctccga    18360
cggcgcgggc ctgttcctga tcgaacggct ctccgacgcg cggcgcaacg gacatccggt    18420
actggccgtg ctgcgcggtt cggcgatcaa ccaggacggc gcgtcgaacg gctgaccgc    18480 gccgaacggc ccgcccagg agcgggtgat ccggcaggcc ctgcagagcg ccgggttggt    18540
gaccggtgac gtggacgccg tggaggcaca cggcaccggg accacgctcg gcgaccccat    18600
cgaggcgcac gcgctgttgg cgacctacgg gcaggatcgg cccgcggatc ggccgctgag    18660
gctcgggtcg atcaagtcca acatcggaca cacccaggcc gccgcggggg tggccgggat    18720
gatcaagatg gtgttggccc tgcggcacgg cgtgctgccc aggacgctgc acgtcgacgc    18780
gccctcgccg cacatcgact ggtcggccgg gcgggtggaa ctgctcacgg agcccgtgcc    18840
gtggccgagg tcgaccggc cgcgccggc cggtgtctcg tcgttcgggg cgagcgggac    18900
gaacgcgcac gtggtggtgg aggaggcgcc gtcggacggc gacgacggtg tcgtggaggt    18960
```

```
gcccgcgccc acgggcatcg gcagtgtcct gccgtgggtg ttgtcggccc gatccgaggc    19020
ggcgttgcgc gcgcaggcgg ggcgattgcg ggactggctg gccgagcacc ccgaggcgga    19080
tccggtcgac gtgggccggt cgttggcggt ggggcgtgcg gtgctggaac gtcgcgccgt    19140
ggtgcgcggg cggatgtcg ccgaactcgc cgtcgggatc ggcgaggtgg ccgaccgcgg     19200
agaactcgcc ggtgggcggc cgatgttcgc cggacccggt ccggtgttcg tgtttccggg    19260
gcaggggtcg cagtgggtgg ggatggcggc cgggttgttg gagtgttcgc cggtgtttgc    19320
gggtgtggtt gccgagtgtg ctgccggtgat ggatccgttg gtggcggatt ggtcgttgtt   19380
ggatgtgttg cggggtgggt ctgccggtgg tgaggcgttg gcggagcggg tggatgtggt    19440
tcagccggcg ttgttcgcgg tgatggtggg gcttgcgcgg tggtgggagt cgtgtggggt    19500
caagccgggt gcggtgatcg gacactcaca gggggagatc gcggctgcgc atgtggcggg    19560
atatctgtcg ctggcggatg cggtacggat cgtggtgttc cgcagtcggg cgctgcgcgg    19620
gatcgcggcg gccggtggcg gcatggtctc cgtgggcgtg tccgtcgagc gtgccgagga    19680
actggtggcc ggctctgccg ggttgtcgct cgcggccgtc aacgggccgc agagcgtggt    19740
gctttccggc gaccgtgagg cactggccgc cgtcgtcgac gcgtgcgagc gcgagggtgc    19800
gcgagcccgg tggatccccg tggactacgc gtcgcattcc gcgcacatgg aggtggtccg    19860
ggacgaggtc gagcgtttgt cggccgaggt gacgccgcgg gcgggtcggg tgccgatgta    19920
ctcgacgctg accggggaag tcgtcacgga cccggccgag ttgggcgccg gctactggtt    19980
cgagaacctg cgcgggacgg tacgctgac caccgcagtg ggggcagccg ttgccgacgg     20040
acacgtcgcc ttcgtcgagt gcagcccgca tccgggcctg gtcgtgccgc tcgcggacac    20100
cctcgatgag ctgggcgtcg acgacggcac ggtcctggag acgttacggc gggacgacgg    20160
cggcccgat cggctggtcg ccgcgctctc ggcggcgttc gtggcgggtg tgccggtgga     20220
ctgggccgca ctgtttccgg gcgaggggcg ggccgacctg cccacgtacg ccttccaaca    20280
tcggcgctat tgggccgagg ccgaatcgcc cgcaggcggc ggcgtggcct gggggcagcg    20340
cgcggtgacg catccggtac tcggcgccgc cgtcgacctg gccggcgacg cgggcaccgt    20400
gttcaccggg cggctgtcga cgaccgccca accgtggctg gccgaccacg ccgtgctcgg    20460
cacggtgatc gtgcccggga cggcgttcct ggacctggtc ctgcgggccg agccgaggt     20520
cggctacccg gcgatcgagg aactgaccct gcacacgccg ctcgtgctgc cggacgcctc    20580
gggcgtcctg gtacaggtcg tggtcggtgc cgcggacggc gacggcggcg acggcggcga    20640
cggggcccgg acgtcgatg tgcactcgcg ggccgaggac gcgccgccgg accacccgtg     20700
gacccggcac gcctcggggg tgctggtcgc ggcgggcgag gagcgggccg aggacgcgcc    20760
ggccgggcgg tggccgccga ccggtgccga ggtggtgggg gtcgacgacg cctacgagcg    20820
gctggcggtg gcgggcttcg actacggccc cgtgttccag gggctgcggt cggtccgggc    20880
gcgaggcgac gagttgttcg ccgaggtgga gttgccggag gaggggcacg cggacgcgga    20940
ccggttcgcg gtgcacccgg cgctgctcga tgccgcgttg cacccgctgg tggtcgcggc    21000
cggtgccgac gcgccggtcg tggccgggct gccgttcgtg tggcacggca ttcgggcggg    21060
tgttccgggg gcgcgacggt tgcggttcg gctggtgcgc tcggcgtcgg ggtcggcgtc    21120
ggggtcggct gcgggctcgg actcggcttc cggcgaggtc tcggtccggg cgtgggacga    21180
gggcggccgg gaggtggtgg cgatcgagtc gctgaccatt cgcccggtct cggcggacgg    21240
gttgcggacg cccgatgctt tggtccgcga ctccctgttc acgctcgcgt ggaccgcgtt    21300
```

```
ggagctaccg gacgtcgatg acgacgtgcc gaacgcgacc ctgctgggcg gcgacggtgc   21360
ggccgatctc gccgcgctgg tggctgccat ggacaccgga acggacgtac cggctctggt   21420
ggctctgccc gtatcggtcg acgacgcgga ccccgtggcg gcggcgcaca cggccggccg   21480
gcaggtgctg gcggtactcc gggactggct ggcggacgag cggttcgccg actctcggct   21540
ggtgttcgtc acctccggcg cggtcgcggt cgccgacgag caggtacgtc cggcctcggc   21600
ggctgtctgg ggcctggtcc gctccgccca gtccgaacac ccggggcgct tcgtcctggt   21660
ggacgcggac tccgtcgccg accccggccc ggagttcgac cgggccctgc ggaccggtgc   21720
ggaccagctg atcctgcgag atggaacggc cctgataccg aggctggttc gagccccggc   21780
ggacggcgga tcgggcggat tcgtgcccgc tgccgacggc acggtcctga tcaccggcgg   21840
caccggcacc ctgggcacgc tgcttgcccg gcacctggtc accgaacacg cgtgcgcccg   21900
gctcctgttg ctcagtcggc gcggcggtac ggccgccggc gcgacggacc tggtcgcgga   21960
actgccgcg ttcggtgccg aggtgacctg cgtggccggg gacgccgcag accgcgccac   22020
gctggagcgg gtgttggcgg acatccccgc cgaacacccg ctgacggcgg tgatccacgc   22080
ggcgggtgtg gtggacgacg gcgtcgtaca gtccctcacc gccgaccggc tggacgcggt   22140
gttgcgccct aaggtggacg ccgcgtggaa cctgcacgag gcgacccggc acctggacct   22200
gaccgcgttt gtgctgttct cctctgcggc gggtgtgctc ggaaacccg gccagggcaa   22260
ctacgcggcg gccaacgcct ttctcgacgc gctcgcacgc cgccggcgcc gtgagggcct   22320
gcccggcagc tcgttggcgt ggggctggtg ggcgccgacc agcgagatga ccgcggggct   22380
cggcgacgcc gaccggcagc ggatggcgcg tttgggtgta ctgcccctgg cgccggaaca   22440
ggggttggcc ctgttcgacg cggcgacgaa ccatgccgaa ccgacaccga ccgtggtccg   22500
gatggacctc gcggtgctac gcaccgccgg atcggtggtg cccacgctgc tgcgcggtct   22560
ggcccgggtg cccaaccggc gggctgcgac ggcgggttcg gtggccgagc tgcgccgtcg   22620
tccggccggc gtatcggcct tcgactggga gcagacgctg atccgggcgg tgtgcgtgca   22680
tgccgccgcc gtcatcggcc acgccgacgc gaccgagatc gatgagacac gggcgttccg   22740
cgacctgggc ttcgattcgc tcacaggtct ggagctgcgc aatcgactga acacggcaac   22800
cggactgcgg ctgcccgcca cgctggtctt cgactacccc agcccggtgg tcctgggccg   22860
gtggttgcgt gatcggctcg ccgaggagga cgccgggggc ccggtcggct cgaccctcgg   22920
agcgcaggtg gtgtcgccgg tcggttccga cgccggcgag gactcgatcg tgatcgtcgg   22980
catgggctgc cggttcccg gcgggatcac cgcgcccgaa cacctgtggg acgtggtggc   23040
cggtggggtg gacaccctca ccgacttccc caccgatcgt ggctgggatg tcgagcgcat   23100
cttcgacccg gacccggacc gacccggcag cacctacgtg cgcaccggcg gattcgtgga   23160
ctcggccgcc gacttcgacc cggacctctt cgggatctcg ccgcgtgagg cgttggcgat   23220
ggatccgcag cagcgattgc tcctggagac ggcgtgggag acgttcgagc gggcgggcat   23280
cgatccgacc tcgctgcgcg gcagccggac cggggttttc gccggcgcca tctactacga   23340
ctacgcgggt ggccggctgc ggaaggtgcc ggacgaactg gaaggctaca tcggcaacgg   23400
caatgtgggc agcgtcgcct cgggccgggt ggcctacacg ttcggtctgg aggggccggc   23460
ggtcaccgtg gacacggcgt gctcgtcgtc cctggtggcg ctgcacctgg cggtgaacgc   23520
ggtgcggtcg ggcgagtgtg aactggccct ggcgggtggc gtcaccgtga tgtcgacgcc   23580
cagcgtcttc ctcgacttct cccggcagcg cggcctgtcg tccgacgcc ggtgccgtc    23640
gttcgcggcg gcggcggacg gcaccggggtg gggtgagggt gtcggggttgg tgctggtgga   23700
```

```
gcggttgtcg gatgcgcggc gcaatgggca tccggttctg gcggtggtgc gtgggtcggc   23760
ggtgaaccag gacggcgcgt cgaatggttt gaccgcgccg aacgggccgt cgcagcagcg   23820
ggtgatccgg caggcgttgg gcagcgccgg gttgtcgccc gccgatgtgg acgccgtgga   23880
ggcgcacgga accgggacga cgttgggtga tccgatcgag gcgcaggcgt tgttggcgac   23940
ctatgggcag gatcggccgg gggatcgccc gctgtggctc gggtcggtca agtccaacct   24000
cgggcacacg caggcggctg cgggtgtggc cggggtgatc aagatggtgt tggcgctgcg   24060
gcatggggtg ttgcctcgga cgttgcatgt ggacgagccg acgccgcatg tggattggtc   24120
ggccgggcgg gtcgaggtgt tggcggacga ggtggcgtgg ccggcggggg agcgggtgcg   24180
ccgggcgggt gtgtcgtcct tcggaatcag cgggacgaat gcacacgtgg tgctggaaga   24240
gccgccgccg gtgaccgaag tgccggatgt ggccgtcgag tccgggctgg gcgggcggca   24300
cacctgggtg gtgtcggcgc ggtccgaggc agcggtacgg gaacaggcgg cccggctgcg   24360
cgactgggtc acggcccgtc cggatctcga tccggcgcac gtggcccggt cgttggtgtg   24420
cgaacgggcg ctgttcggcc atcgggcggt ggtctccggc gccgatctcg ccgagctggc   24480
cgatgggttg tccgccgtgg cggcgggcgc cgagggcgcg tggtcggtg cggtgggtcg   24540 cgggccgggg aagacggccg tgctgtgcac gggtcagggg gtgcgggcgc tcggtatagg   24600
ccgcgaactt cacgcggcgt tcccggtgtt cgccggcgcc ctggacgagg tgtgtgcggc   24660
cttcgacgat gtggtgccgt tctcggtgcg ggacgtcgtg ctcggtgccg aagggggtgtc   24720 ggatgccgac gcgcaggaca ccggggtggc ccagccggcg ctgttcgcgt tcgaggtggc   24780
gctgtaccgg ctgtgggcct cgtgggggca ggcgcccgac ttcgtggtgg ggcattcgct   24840
cggcgagatc gttgcggcgc atgtggcggg agtgttctcg ctcgcggatg cggtggtctt   24900
cgtcgcggcg cgggctcggt tgatgagtgc gctgccgagt ggagggggcga tgctcgccgt   24960 cggtgcgagc gaggccgagg tggcggcgtc gtgcccggcc gaggtgacga tcgcagcggt   25020
gaacggcccg gcgagtgtgg tggtttccgg acccgccgag gcggtggccg cgctcgaacc   25080
ggactgcgtg atgcgcgggt ggcggatctc gcgcctgtcg gtgtcgcacg ccttccactc   25140
ggcgctgatg caaccgatgt tggccgaact ccgcgaggtg ctgaccgggt tgacctacgg   25200
cacgcccgag atcgcggtgg tgtcggacac caccggggcgg gttgcgggcg ccgaagagtt   25260
ggctgatccc gagtactggg tgcggcacgt acgccgcgcg gtgcgcttcg gggatgcgat   25320
cgccacgctg cgcgccgaag gggtacggac cttcgtggag atcgggccgg aggcggcgtt   25380
gaccgcgatg gtggtcgagg gcacggccgg cgcggaggac gtggccgccg tagcgacccg   25440
gcgtcggggt cgagcggccg tgtcgagtgt ggtggaggcg ctcgcccggg tgttcgtgca   25500
cggcgcgacg gtggattggg ccgcgttgtc caccggttcc gggcccgggg gacgggtgga   25560
tctgccgacc tacgccttcg agcggcgcgc cttctggttg cacgccggtg tggacgcggg   25620
cgacgcggtc gggctggggc agggtgtggt ggaccatccg ctgctcggtg cggtcgtggg   25680
cctggcggac gaccagggcg tcctgttcac cggccggttg gccctggaca cccatccgtg   25740
gttggccgaa cacaccgtct tgggcacggt attgctgccg ggcacggcat tcctggagct   25800
ggccctgcac gtcggccgcc tcctggactg cgcgcgggtc gacgagctga ccctgtcggc   25860
cccgctggcg ctgccgtcga cgggcggtgt gcaggtccag gtccgagtcg gtgtaccgga   25920
ggagagcggg acacggacga tcacggtgca tgcccgcccg gattcggcgg aggaggcgcc   25980
ttggacgctg cacgccgccg gggccctggg tccatcagcc gaggtggatg caccctcgga   26040
```

-continued

```
tgccgcgagt tggccgcctg ccgatgcgac cgcgatggac tcggcggggc tgtatccctg    26100
gttcgccgag accggcgtcg actacggacc ctcgttccgg ggcgtacaag cgacctggcg    26160
ccgtgatgac gaggtgttcg cggagatcgt gctcgcggcc gacgaccegg ccgccgacgg    26220 ccggttcgag ctgcaccccg cgctgttcga cgccgcgttg cacccgctgg gcctgaccct    26280
gctcgacgcg gcggagccgc gcctgcggct gccgttctcc tggcgcggag tggcgctgca    26340
cacgtccggg gctcgcacgt tgcgggttcg gctgcgtccc accgggcccg acaccatcgc    26400
ggtgacggcc accgacgaga cgggtcgacc ggtggtcgcg gtcgaggccc tggcggtgcg    26460
cgaaccctcg cgggaccgac tgccacgacc cgacgcgaac gcgggcgagt tgttcgagcc    26520
gcagtggacg ccgctgtcac cggcggacac ggcggacatg gcggacacgc tcggggcggt    26580
ggtgggcggc cccgaactcg cctcgacagc caccegatte ggtgccacac atcccctga    26640 cctggccgcc ctggccgaat cggcaatccc cgagacggtc ctgtacgacc tggtcaccgc    26700
cgttcccggc gtatccgccg aagccgtaca ccaagccgcc gcccaagcgc tggacctggc    26760
ccgatcctgg ctcgccgacg agcgcttcga gtcggcccgc ctgatcgtgc gcacccgaca    26820
cgcggtcgcc gccgccgaag cgacgcgcc ggacccggcc gccgccgcga cccatggcct    26880
gtttcgtacc gcctgctccg aacaccccga gcggttcgcg ctcgtcgacg ccgacgacct    26940
cgacgaggtc tcgcccgagg ccatcgccgc cgtcgtggtc gagcccgagg cggccgtgcg    27000
ggccggtcgc gtcctggttc cgcgcctgcg ccgagcggcc gtggcgccca aggccgactt    27060
cggcttcgcc gccgaaggca ccgttctgat caccggtggc accggagcac tgggccggca    27120
ggtcgcccgg cacctggtgc gcgtacacgg ggtgcgccgc ctcctcctgc tctcccgtcg    27180
cggcgacgaa gccccccgagg ccgccgagtt gcgggccgaa ctgatcgagg ccggcgcgca    27240
cgtcaccttc gccgccggag acgctgccga acgtggcgtg ctggccgacg tgttggccgc    27300
gatcccggcc gcccacccgc tgaccggcgt ggtgcacctg gccggggtga ccgacgacgg    27360
gctggtcggg acgctgaccc ccgagcggct ggcggcggtg ttgcgcccca agatcgacgc    27420
ggcgctgcac ctggacgaac tcaccgccga cgccgacctg tcggcgttcg tcctgttctc    27480
ctcggccgcc ggtccggtcg gcaaccccgg ccaggccaac tacgcggcgg ccaatgtcgc    27540
cctcgacgcg ctggcccgcc ggcgccgagc gcgcggccga ccggccgtgt cgttgcagtg    27600
ggggttgtgg gccgaacgca gtgcgctgac cgcgacgatg agcgcgaccg atcggcgccg    27660
ggcggccggc gcgggtgtgc gggcgttgtc cgtggagcag ggcctcgcac tgctggacgc    27720
ggcggccggg cggcccgagg cggtgctgac gccgctgcgc ctcgatccgg cgatcctgcg    27780
cggtccggag gagcgggtgg cgcccgtgtt gcgcgggctg gtgccgaccc gggcccggcg    27840
tgcgccggcc cgtacctcgg acaccgcccg ctcactggtg cgccgattgg ccgcgttgcc    27900
cgaggccgag caggaccggc tgttggtcga cctggtccgt acccacgcgg ccggtgtgct    27960
cggccacgcg gacgcgcgca cgatcgaccc ggaccgcgcg ttcggcgaac tgggcctgga    28020
ctcgctggcg gcgttggaac tgcgcacccg gttgagcacg gcggtcgggc tgcgcctgcc    28080
cgccacgatg ttgttcgacc atccgtgcgc gcgtgccgtg ggcgtacacc tgcgcgcgca    28140
actgctcgac gcgccgacac ccgggcgggc ggcgggtgtc gcccggccgg tgtcggacga    28200
gccggtcgcg gtggtggcga tcagctgccg cttccccggc ggcgtcgcga gcccgaggga    28260
cctgtggcgg ctggtgtcgg aacacaccga cgccatctcg gagttcccgc aggatcgggg    28320
ctgggacctg gccgagctgt tccacccgga ccccgaacat gccggtacct cgtatgtaag    28380
cgagggcgga ttccttacg aggcaaccga gttcgacccg gagttcttcg gcatctcgcc    28440
```

```
gcgcgaggcg ctggccatgg acccgcagca gcggttgctc ctggaggcgt cctgggaggc    28500
gatcgagcgc gccggcgtgg atcccaggtc gctgcgcggc agtcgtaccg gggtgtacgc    28560
gggcctgatg tacgccgact acgcgtcgcg ggtgggcagc gcgccgaagg gcgtggacgg    28620
gtatctcggc aacggcagcg cgggcagtat cgcgtccggg cgggtggcct acacgctggg    28680
tctggagggg cccgcggtga ccgtggacac cgcctgctcg tcgtccttgg tcgcactgca    28740
cctggcggcc aacgcactgc gccagggtga gtgtgatctg gcgctggcgg gcggggtgac    28800
ggtgatgtcc agcccggcca cgttcgtcga gttctcccgg cagcgcggcc tggccccgga    28860
tgcgcggtgc aagtcgttcg cggccggcgc cgacggtacc tcgtggtccg agggcatcgg    28920
tctgctcctg gtggaacgcc tgtcggacgc gcgccggttg ggccatccgg tgctggccgt    28980
ggtgcgcggc agtgcgatca accaggacgg cgccagcaac ggcctggccg cgcccaacgg    29040
gctcgcccag gagcgggtga tccgggatgc gctcgcgcac gccgagttgc gtccgtccga    29100
cgtggacgcg gtggaggcgc acggcaccgg cacgccgctg ggcgacccga tcgaggcgcg    29160
cgccctgctc gccacctacg gcaggaccgg ccggcggat cggccgttgt ggctggggtc    29220
ggtcaagtcc aacctcgggc acacccaggc ggcgcgggc gtggccggcg tgatcaagat    29280
gatcatggcg atgcggcatg ccgaactgcc cgggacgctg cacgtggacg ccccctcacc    29340
gcacgtggac tggtcggcgg gggcggtgtc gctgctcacc gccgcgaccc cgtggccgca    29400
gaccgggcgt ccgcgccgtg cggggtgtc gtcgttcggg atcagcggga ccaacgcgca    29460
cgtgatc                                                             29467

<210> SEQ ID NO 2
<211> LENGTH: 9726
<212> TYPE: DNA
<213> ORGANISM: Streptomyces ap. ATCC 39366

<400> SEQUENCE: 2
gatccgcgac tgcgacgcgg cactcgcgcc gcacaccgac tggtcgctgc tcgccgtgct      60
gcgcggcgag cccgacgcgc cgccgctcga ccgggtcgac gtggtgcaac cggtgttgtt     120
cgcggtgatg gtcgcgctcg ccgaactgtg gcgctcgctg ggcgtacggc cggcttcggt     180
ggtcggccac tcgcagggcg agatcgccgc gcccacatc gcgggcgcgc tcaccctcga     240
cgacgcggcc cggatcgtcg cactgcgcag ccgcgccctg cgcgggttgt ccggcgacgg     300
cgggatgatg tccgtcgcgg ccggcccgga gcagatcgcc cgattgctcg acggattcgc     360
ggaccggctc ggcatcgccg ccgtcaacgg cccgccgcc gtggtgattt ccggcgcggc     420
cgacgcgctc gccgaactgc acgcccactg cgaggcggac gggatccgcg cccgggtgct     480
cccggtcgac tacgcctcgc actccgccca gtcgagcag gtccgcgagg aactgctcgc     540
cgccctgggc gagatcgtgc ccacgccgac caccgacgcg gtcttctact cctcggtcac     600
cggcgaaccc gtcgagggca ccgcgctcga cgccgagtac tggtaccgca acctgcgcgc     660
caccgtcgcc ttcgacccggg ccaccgatgc cctgctgcgg gacggccaca cggtgttcgt     720
cgagaccagc ccgcatccgg tccttgcgcc cgccgtcgag gatagtgccc agcgcgccgg     780 tacgacgtg acggtcgtgg gcagcctcca gcgcgacacc gacaccctcg cccgtttcct     840
caccgccgcg gccggcctgc acgtgcacgg cgtcccggtg gactggtccg cgacccacgc     900
cggacaccgg ccccggccgg tcgacctgcc cacctacgca ttccaacgcg agcgctactg     960
gctggaggcg ggcaagacgc ccaccgacgc ggccggcctc ggcctgcacc cggcggcaca    1020
```

-continued

| | | | | | |
|---|---|---|---|---|---|
| ccccctgttg | ggcgcggccg | tggtacccgc | cgagggcgac | cggcacatcc | tcaccggccg | 1080 |
| catctcgctg | cgcacccacc | cctggctcgc | cgaccacacg | atcctggaca | cggtgctgct | 1140 |
| cccgggcacc | gcgttcgtcg | aactcgccct | ccaggcgggc | gatcgggccg | actgtgacct | 1200 |
| gatcgaggag | ctgaccgtcg | aggccccgct | gcggctcacc | gacaccggcg | ccgtacacct | 1260 |
| gcaggtgttg | ctggacgagc | cggacgagca | gggccgccga | gcgctgacca | tccactcccg | 1320 |
| agccgacgac | gcgcccgcgg | agcagacgtg | gacgcggcac | gcgagcgggg | tactggcgcc | 1380 |
| ggtcgcggac | ggcctcgacg | ccgtgccggc | gaccgacgcc | gcgtggccgc | ccgccggggc | 1440 |
| cgtcgcgctg | gacgtggacg | ggctgtacga | gcggttggcc | gggcagggct | accggtacgg | 1500 |
| accggccttc | cgggcggtgc | gggccgcgtg | gcgcctgggc | gatacggtcc | tggccgaggt | 1560 |
| cgcgccgggc | gacgaggcgc | acggcgcacg | ggacttcgcg | ctgcacccgg | ccctgctgga | 1620 |
| cgccgcgctg | cacgccgccg | gcgccgccga | cagcggaaca | tccggcgggg | acggtgccat | 1680 |
| cggcctaccc | ttcgcctgga | ccgacgtacg | cctgcacgcc | gtcggcgccg | ccgcgctccg | 1740 |
| ggtccgcctg | gaacgccgcg | gcccggacac | cgtcggcctc | gaactcaccg | atcacaccgg | 1800 |
| cgccttggtc | gccaccgtcg | gtgccctggt | cggccgcccc | gcgaccgccg | accggctcgc | 1860 |
| gcccgccgcc | gacccggccc | accgcgacct | ccaccacgtc | gactggtccc | gctgcccac | 1920 |
| tcccaccgaa | accagcaccg | cccgctggtc | gttgctcggc | ccggacgaac | tggaggcggt | 1980 |
| ggccgggctg | cgcgccgccg | gcgccgaagt | gcacgcgaac | gggaaccccg | accccgccga | 2040 |
| cgtactgctg | atcacctgcg | ccggccggac | cggggacgac | gtcccccgaag | ccgcccgggc | 2100 |
| cgccacacac | cgcgtactcg | acctgctcca | gcgcgcactg | accgacccac | gcctcaccgc | 2160 |
| atgcaccctg | gtcgtgctga | cccggggcgc | agtacccggg | caccacggcg | aggacgtgtg | 2220 |
| cgacctggtc | gccgcgccga | tcgtgggcct | ggtccgctcc | gcgcagaccg | aacacccggg | 2280 |
| ccggatcgtg | ctggtcgacc | tggacgacca | cgccgactcc | ttcgccgcgc | tgcgcgccgc | 2340 |
| cgtcgtcacc | gacgtcggcg | aaccgcaact | ggccatccgc | acgggcaccg | tgtccgcacc | 2400 |
| ccgactgatc | cgcaccggca | ccgaaccgcg | cctgagcccg | cccgccggcg | ccccggcctg | 2460 |
| gcggctcgac | ctgctcggcg | gtggcaccct | ggaccggctc | gcgctgctcc | cgaacgccga | 2520 |
| cgcggcggtc | ccgctcgcgc | ccggacaggt | ccggatcgcc | gtccgcgccg | ccgggctgaa | 2580 |
| cttccgcgac | gtcgtggtcg | ccctcggcat | ggtcaccgac | accgcccgc | ccggcggcga | 2640 |
| gggggccgga | atcgtagtgg | aggtcggccc | cgatgtgccc | gaactcgtcc | cgggcgaccg | 2700 |
| ggtgatgggc | ctgttcggcg | gcggcaccgg | accgattacc | gtggccgacc | accggctgct | 2760 |
| cgcgccgatc | cccaccggct | ggacctacgc | ccaggccgcg | gccgtcccgg | tggtgttcct | 2820 |
| gaccgcctac | tacggcctgg | ccgacctcgg | cgggctgcgc | gccggcgaat | cgctgctcgt | 2880 |
| ccacgccgcc | accggcggag | tgggcatggc | ggccgtgcaa | ctggcccggc | actggaacgt | 2940 |
| ggaggtgttc | ggcaccgcct | cgcccggcaa | atgggccacc | ctgcgcggcc | agggcgtgga | 3000 |
| cgacgcgcat | ctggcgtcct | cgcgcgatct | cgacttcgcg | caccggttcg | gcgaggtcga | 3060 |
| cgtggtgctc | aactcgctcg | cgcacgaatt | cgtcgacgcc | tcactgcggt | tgctcgcgcc | 3120 |
| cggcggccga | ttcctggaga | tgggcaagac | cgacatccgc | gaccgggacg | aggtgcttgc | 3180 |
| cgcccatccg | ggccgcgact | accgggcgtt | cgacctgatg | gacgcggggc | cggagcggat | 3240 |
| ccgggagatg | ctggccgacc | tgtaccggct | cttcgagacc | ggcgtgctgc | accgctgcc | 3300 |
| cgtgaccccg | tgggatgtgc | gcggtgcggt | cggcgcgttc | cggcacctga | gccaggcccg | 3360 |
| gcacaccggc | aagatcgtgc | tgaccctgcc | gcccaccctc | ggcgccgctc | ccgacccgga | 3420 |

-continued

```
gggcacggtc ctgatcaccg gcggcaccgg caccctcggc ggcctgctcg cccgccacct    3480
cgtacgcacc gccggggtac gacacctgct cctgatcggc cggcgcggcc cggccgccga    3540
cggcgcggcc gagttgtccg ccgaactgac cgcgctcggc gcccgggtga ccatcgcggc    3600
ctgcgacgcc gccgaccgtg cggcgctggc cgcgctgctc gccgacatcc cggccgaaca    3660
cgcgctcacc tcggtgatcc acgccgccgg cgtgatcgac gacgcggcgc tgaccgcgct    3720
cacccccgag cggctggacc gggtgctgcg cccgaaactg cacgccgcct ggaacctgca    3780
cgagctgacc cgcgacctcg acctggccga gttcgtgctg ttctcctcga tggccggcac    3840
cttcggcggc gccggacagg ccaactacgc cgccgcgaac gccttcctgg acgcgctcgc    3900
ccagcaccgc cgagcccgcg gcctggccgc gaccgcggcc gcctggggtc tgtgggcgca    3960
ggccagcggg atgaccggac acctgggcgc cgaggacctg gaccgcattg cccgcaccgg    4020
cgtcgccgcg ctggagaccg cccacgcact caccctgtac gacgcgctcc gcgcggccga    4080
ccgccccacg atcgtgcccg cccgcctgga cccgcacgcg ctgcgcgccg ccgccccgac    4140
cgtacccgca ctgctgcgcg acctggtgcg cgacctggtg cgcccgcgcg gacgccgcgc    4200
cgccgccgac accgcgccgg acgccgcgtc cctggccgag cggctggccc gactgccgga    4260
ggagcggcgc cggcagacgc tgctgaccct cgtccgcacc gagaccgccg ccgtcctggg    4320
ccacgccacc ccggacgcgg tcgccccgct gcgcccgttc aaggccctcg gcttcgactc    4380
gctcacgtcg gtcgaactgc gcaaccgcat cggtgcggcg accggcctgc gcctgccgt     4440
caccctggtc ttcgaccacc cgaccccgca ggccctcgcc gaccacgtcg gcgccgaact    4500
cctgggcgta gcgcccgtgg tcgtcgaacc cgagcgaccc gccgcacaca ccgacgacga    4560
cccgatcgtg atcgtgagcg tcggctgccg ctacccgggc ggggtggccg gacaggacga    4620
gatgtggcgg atgctcgccg agggcaccga caccatcggg cccttccccc aagaccgggg    4680
ttgggagttg gacacactct tcgacccgga ccccgaccgg gtgggcaagt cgtacgtccg    4740
tgaaggcgga ttcgtcgccg acgcggtgca cttcgacgcc gagttcttcg ggatctcgcc    4800
ccgcgaggcg acctcgatgg acccgcagca gcggctcctg ttggagaccg cgtgggaaac    4860
gttcgagcag gccggcatcg accccaccac gctgcgcggc agcggcacgg cgtgttcgt     4920
cggggccatg gcgcaggact accacggcac ttcgcaggcg atggccgagg ccaggaggg     4980
ctacctgctg accgggaccg ccaccagcgt gatctccggc cgggtctcct acgtcctggg    5040
cctggagggg ccggcggtga ccgtggacac cgcgtgctcg tcatccctgg tcgccctgca    5100
ccttgcggcg aacgcactgc gtgcgggtga gtgcgatctc gcgcttgcgg gcggggtggc    5160
ggtgttgacg tcgccgcagg cgttcatcga gttcagccgg cagcgcggac tggccgcgga    5220
cgggcgctgc aagcccttcg cggcggcggc caacggcacc ggctggggcg agggtgtcgg    5280
cctggtactc gtcgagcggc tgtccgacgc gcgccggcgc gggcatccgg tgctggccgt    5340
ggtgcgcggc tcggcggtca accaggacgg cgcctcgaac gggctgaccg cacccaacgg    5400
cccctcgcaa cagcgggtga tccgacaggc ggttgcgcaa cgcgggcctgc tcgcgacgga    5460
cgtcgacgcg gtcgaggcgc acggcaccgg gaccacgctc ggcgacccga tcgaggcgca    5520
ggcgctgctg gcgacctacg gcaggaccgg ccggcgcaa cggccgctgt ggctgggtc     5580
ggtcaagtcc aacatcgggc acactcaggc cgcgcggggg gtcgccgggg tgatcaagat    5640
ggtgctcgcg ctgcggcacg ggacgttgcc gccgacgttg cacgtggacg cgcccacgcc    5700
gcatgtggac tgggcgtcgg gacaggtgcg gctgctcacc gagccggtgg cgtggccggc    5760
```

```
gggggaacgg gtgcgtcggg ccgggatctc ctcgttcggg gtgagcggga ccaacgcgca   5820
cgtgatcatc gagcaggcgc cggcggaggg cgcggtcgat gccgcgccgg tcgatgccgc   5880
gccggccgcc gcgctcgggg ggatcgtgcc gtgggtggtg tccgcgcgat cccaggccgg   5940
gttgcgggcg caggcggcgc ggctgcggga ctggccgcc gtgcatccgg agtttgcccc    6000
ggccgacgtg gccgcctcgc tggtgcgcgg cgggcggtg ttcgagcggc gcgcagtggt    6060
ccggggtcgg gataccgacg aactggtcgc cgcactcgct gagttggtcg actcgtcggc   6120
aacgggcgag gcgccgacgg cgatcgggcc cgggccggtg ttcgtcttcc ccggccaggg   6180
atcgcaatgg gtgggcatgg cggcggagtt gctgacgtgc tgcccggtct cgcggagac    6240
cgtcacgcag tgcgccgagg tgatggaccc gctgctgccg ggctgggcgc tgctcgacgt   6300
gctgcgcggc accgacgacg agacggccga actgctgcgc cgggtcgagg tggtgcaacc   6360
cgtgctgttc gcggtgatgg tgggtctggc ccgctggtgg gagtcgtgcg gggtgcgacc   6420
ggccgcggta tcgggcact cccagggcga gatcgccgcc gcgtacatag ccggccacct    6480
gaccctgccg gacgccgccc ggatcgccgc gctgcggatc cgcgcggtgc aggccgccga   6540
catgatccgc ggcgcgatgg tggctgtcgc ggtatccgcc ctgcgggccg aggagttgat   6600
cacccgcacc ggcaccgggg acctggtcaa cgtgggcggg atcaacaagc ccgaccaaca   6660
ccgtgtgtcc ggcgacaccg acgccttggc cctgatcgtg gccgactgcg agcgcgaggg   6720
tgtacgggcg cgctggatcc cggccgcgta ctcctcgcac tcgccgcaga tggacgctgt   6780
acgcggcgac ctggaacgcc tgctcgcggg catccaaccc accccggg gggtgccgat     6840
gtactccacg gtcaccggcg gccgactcgc cgacgacgcg ctgctcgaca tcgactactg   6900
gttcgagaac atgcggcgca ccgtgcggtt cgaggaggcg atcggcgcgg cggcggccga   6960
cggacacacc gtgttcctcg aatgcagctc gcaccccggc ctggtggtgc cgctcggcga   7020
caccctggac tcgctcggcg tgcacggcgc caccctggag acgctgcgcc gcgcggacgg   7080
cggcgccgat cggctgctcg ccgcgctctc cgcgatgttc gtgcacggcg gcgcggtgga   7140
ctgggccggg ctgctaccgg gtcgccgggt cgcgctgccc acgtacgcct tccagcgtcg   7200
gcggcactgg gtggagcccg tcggaccggc ccgagggggc gtcggctggg ggcagttcgc   7260
ggtggagcac ccgatcctgg gcgccggggt cgacctggcc gacggctcgg cgaccgtgtt   7320
caccgggcgc ctggacacca ccacacacgg ttggctcgcc gaccacctcg tgctcggcga   7380
agtcctggtc ccgggcacgg tgttcgtgga cctggcgctg cgcgcgggcg cgcccctcgg   7440
ctgtgcggtg gtcgaggagt tggccctgca cgagccgctg tgttgccgg acgcggacgg    7500
ggtgcggatc caggtcaccg tcgaggcacc ggacgacgcg ggtacgcggg cgctgaccat   7560
acactcccgg cccgaggacg cgcccgccgc cgagccgtgg acccgacacg cctcgggcac   7620
ggtggccccc ggcgcgcacc ggccgcagca ggagtccggg ccatggccgc cgatcggggc   7680
gacgccgctg gacgtggcgg acgtatattt gcggttgacc gaactgggcc tgggctacgg   7740
cccgacgctc gccggactgc gggccgcgtg gcggcgcggc gacgacctgt tcgccgaggt   7800
cgcgcgcacc gccgacggcg aacgtggcac cgcccgcttc ggcctgcacc cggccctgct   7860
cgatgcggcc ctgcacgggc ttgccccgg ctcggcaccc ggcggcgcac ctaccgaggt    7920
gcggctggcc ggcgcctggc gcggggtgac gctgggcggc gatgccggta ccgccggccg   7980
gattcggctg cggggcgtcg acggggacgg cgtcgaggtc gaactggccg acgaggcagg   8040
tcgatccatg gccggatcg agtcggtggc gctgcggcca tggagcgcgg ggcaggtgcg    8100
ggcggccggg cgggcccgac cgtggttgac ccgctgggag tgggcccggg tcgagccgac   8160
```

```
cgacccggcg gcggcaggag gtcgctgggc cgtgctcggt gcgcgggctt gggacggggt   8220
gccggcctat gcgaccgccg ccgaactgat cgcggccgtc gaggtcggcg tcccggttcc   8280
ggatctggtc gcgctgcccg tgcggatcga cccggccggc gggctcgatc cggaggcgat   8340
ccgggccacg atccgggcgg tgcgcgagac cctgcggcag tggcgggccg agccgcggct   8400
ggcggcctcc cgcctggtcg tggtgaccca cgacgcggtc tcggcgcggc ccgaggaccg   8460
ggtcaccgat ccgggcgcgg cggcggtgtg gggcgtggtc cgggcggccc gggcggcgga   8520
ccccgagcgg ttcgtgctcg ccgacgtgga cggggaggac gggtcctggc cggtgctgct   8580
ggccgaagcg tccgccggtc gcgccgagtt cgcgatccgc gcgggcacgg tactgctgcc   8640
gggcctggcc cgggtaccgg cgggcgagac cggcacggcg gcttcccga ccgacggcac   8700 ggtattggtc actgtcgcga ccgacccgac cgacccgacc gacggcaccg acccggtcgg   8760
cacactgctg gctcggcacc tggtgaccgc ccacggagtg cgccggctga tcctggccgg   8820
cgggcccgcc gccgggatgc cgcttgcccg ggaactggcc gcgcagggcg cggagatcca   8880
cgtggtcgtc tgcgacgtga ccgaccgcac cgaactggcg aagctgctgg ccacgatccc   8940
cgagcacagc ccgctgaccg ccgtggtgca caccgccggg ctcggccggt cgcacaccga   9000
ggccatgctg cgggcccggg tggacgcggc cgtacacctg cacgaactca cccgcgacgc   9060
cgacctgtcc gccttcgtgc tctgcaccgc cctggacggc gtactcgccg accccgggcg   9120
cggcgaacac gcggccggcg acgccttcct ggacgccctg gcccggcacc ggcacgccgc   9180
cgggctgccc gcgctcgcgc tggcctgggc accgggggcc gaaccggtcg ccgggctgct   9240
gccgttgccc ggcgagcagg ccacggtcct gttcgaccgg gccctcgggc tgcccgaacc   9300
ggccctgatc ccgctcgcgc cggacacctc ggcgctgcgc cgggccgaac cgggcgcact   9360
gccggcgctg ttgaccacgc tggtggccga cccgaaccac cgcgtcggcg ccgccgccga   9420
ggcggcgccc gcactgatcg gccgactgct cgccctgccg gacgacgagc gggaaagcgt   9480
cctggtcgac ctggttcgcg gctgcgccgc ccgcgatcctc ggtcatgccg atccgaccgc   9540
gatcgagacg ggagcggcgt tcaaggatct cggcttcgac tcgctgaccg ccctggagat   9600
gcgcaaccga ctgcgcgccg cgctgggcct gaccctgccg gccacgctga tcttcagcca   9660
ccccaacgcg gcggccctgg gccggcacct gcacggcctg ctgcgccgcg agcacggggt   9720
ctcgtg                                                               9726

<210> SEQ ID NO 3
<211> LENGTH: 67167
<212> TYPE: DNA
<213> ORGANISM: Streptomyces sp. ATCC 39366

<400> SEQUENCE: 3
cggtgggctc gggtgagaaa aaattagtcc gaatcgatgc gctcccgtgc tgttgcgcat     60
gtgaccgata tgtaagcgac atgtgaacgt tcgtcgcaag caggtgcgtt cgcccccgcc    120
ggcgggtcgt cgggaccgcg cgcgcggggcg tgcgagccgg gtgcgcggcc ggtctgatca    180
agggttctcg cgcgtcgacg acgcaggtcg aaggcgggcg tgcgcggggc gttcgcgcac    240
tacaccaggt gacccgaatg gttcaaccgc gccgtcgaaa gcgcccgaac ggggcctgaa    300 ttcaccccctt gcggccgatc gacccggtac tccaatgtgt tgatctgtgt tcgtccgtgt    360
actcaacgta tgcaggtcat ggagcgcgga atgacggaat tcaacgccga tgcccatcgc    420
gcacaccccg cgccggaaga cgcggtggcc atcgtcgggt tggcctgccg actccccggc    480
```

-continued

| | |
|---|---|
| gccgacggcc ccgacgagtt ctgggacctg ctgagcaacg gacgcgacac gatcaccgaa | 540 |
| gtgccccgcc atcgccggga cgcgagagcg gcggacgaca cgaatcgaac ggccggcgga | 600 |
| tcccccacc cagccgcgaa ccgaccgcga agaggcggat tcctggacgc ggtggaccgg | 660 |
| ttcgacgccg ccttcttcgg catcaccccg ggcgaggccg ccctgatcga cccgcaacag | 720 |
| cgcctgatgc tcgaactgtg ctgggaggcc ctggaacacg cgggcatccc gccgacccgg | 780 |
| attcggggca gcgccaccgg ggtgttcgcc ggcgcgatct gggacgacta cgccaccctg | 840 |
| ctgcgccgcg ccggcgtcga gcccggcccc cgacacgcca ccggcctgca ccgcagcatg | 900 |
| atcgccaacc gggtctcgta caccctcggc ctgcgcggcc ccagcatgac ggtggacgcg | 960 |
| gcccagtcct cgtccctggt cgcggtacac ctggccggcg agagcctgcg ccggggcgag | 1020 |
| tcgacactgg ccctggtcgg cggggtcaac ctggacctgg ttcccgacca cgacggcgac | 1080 |
| gcggccaagt tcggcgggct ctccccgcag ggccgctgct tcaccttcga cgcccgggcc | 1140 |
| gacggctacg tgcgcggcga gggcggcgcg gtggtggtgc tcaagccgct gtcccgggcg | 1200 |
| ctggccgacg gcgacgtcgt gcacggcgtg atccgcggca gcgcgatgaa caacgacggg | 1260 |
| ggcgcgacg cgctgaccgc gccggacccc cgggcccagg cggaggtgat ccggctggcc | 1320 |
| cggcggcggg ccggggtcgc cgcgtccgcc gtccaatacg tcgaactgca cggcacgggc | 1380 |
| accccgtcg gcgacccgat cgaagccgcc gcactcggtg cggcgctcgg caccgagcgg | 1440 |
| gcgaaccggc cgccgctggc cgtcggttcg gtcaagacca acgtcgggca cctggagggt | 1500 |
| gcggccggca tcgtcggcct ggtcaagacg cgtgttggcga tccgacaccg gcggctcccg | 1560 |
| gcaagcctga acttcgccga accccatccg cgaatcccgt tgggcgaact gggcctgcgg | 1620 |
| gtgcagacgg cggagggtga ctggccctgc ccggacgaaa ccctgatcgc cggggtgagt | 1680 |
| tcgttcggga tgggtgggac caactgccat gtggtgctcg cggaggcgga gcccgcggat | 1740 |
| ggggtgggc cgtcggtcgc gtcggcgccc tcgggtgggt cggatccggg catggagtcc | 1800 |
| gccaccggcc cggtgccttc ggacgcggtt gccgtgccga tctccggtgt cgacgccgac | 1860 |
| gggcttcggg cccaggccgg gcggtggcac ggccatgtac gcgaacatcc cgacgtggcg | 1920 |
| ccggccgacc tcggctactc ggccgccacc acccggaccg cgtttgccgc ccgcgccgtc | 1980 |
| gtcctcgctc gcgaccacgc cgaactcctc gccgggctcg acgcgttacg cggagccggc | 2040 |
| gcggatccac acctggtccg agccgacgcg caacccggcc gcaccgcctt cctgttcacc | 2100 |
| ggacagggca gccaacgccc ggccatggcg caagagtcgt acgcccgcca cgccgtcttc | 2160 |
| gcggcggcct tcgacgccgc ctgcgcccac ctggacccac acctgccgcg cccgctgcgc | 2220 |
| gaggtgttgt tcgcgtcgcc cgacagcccg gacgcggcgc tcgtgcaccg caccgagtac | 2280 |
| acccaacccg cgctgttcgc cgtcgaggtc gcgctgtacc ggctgttcga gcactgggga | 2340 |
| gtgacccccgg acctgctgct cggccactcg atcggcgagc tgtgcgccgc gcatgtggcc | 2400 |
| ggcgtctggt ccctgcccga cgcgtgtgcg ctggtcgcgg cccggggtcg gctgatgcag | 2460 |
| gaactgccgg acggcgggc gatggtgtcg ctgcgggtcg ccgaggacga cgtgctcgcc | 2520 |
| tcgctcgaac cggtccgcga ccgggtctcg atcgcggcct caacgggcc gctggccacg | 2580 |
| gtgatatcgg gcgaccggga cgcggtcctg gacgtcgcgg ccggctggcg ggcacagggc | 2640 |
| cacaagacca cccgactgcg ggtcgcacac gccttccact caccgcgcat ggacgcgatg | 2700 |
| acggacgcct tcgccgaggt ggccgccggg ttgaccgctc gggcacccac cctgcccgtc | 2760 |
| gtgtcgaacc tgaccggcct gccgctgacc gccgaacagg cctgctcccc ggactactgg | 2820 |
| gtccgccatg tacggcacac cgtgcgcttc cacgacggag tgcgccggct gcgcgcggaa | 2880 |

-continued

```
ggcgcgacga tactgctcga actgggcccg gacggcagcc tgtcggcggc ggcccggacc    2940
tgcctgctcg acggcgagcg ggacaccgtg ccacgatcc cgacgctgcg ccgcaaccgc     3000
cccgagacgc acgcgttgac cacgcgcgtg gcccgcctgt acgccaacgg cgtggacccg    3060
gactgggagc gggtgttcgc ggggcgcggg gcgcgccggg tcgcgttgcc cacgtacgcc    3120
ttccgacgcg cacgccactg gccggtgcc tcggcggaag ccgccgacac cgccgtgccg     3180
gacgaatcgc tcgccgtggt accgacgttg gccgagcggt tggccgccct gtccgctgtc    3240
gagcagcatc ggatcctgct cgacctgatc cgggcacacg cgaccgcggt cctgggcccc    3300
ggcgcgacca cgaccgtcga acccgaccgc acctaccgcg aatcgggcct ggactcgctc    3360
ggcaccgtcg aactgatcac caggctggcc cgggacaccg gcctcgacct gccccgacc    3420 acggtcttcg accacccac acccaccgcg ctcgcccacc acctgcgcac ccgggcgctc    3480
gacctgcccg tgccgacccg ccccggccg acacccgggc cggcccgcgc cgacgaaccg    3540
atcgccatcg tggcaatggg ctgccggttg cccgcgcgg tgcgcacccc cgaggacctg     3600
tggcggctgg tcgcggacgg cgtggacgcg atcacggcct tccccaccga ccgcggctgg    3660
gacctggacc ggctccacca cgacgacccg gaccgacccg gcaccagcta tgtacgatcc    3720
ggcggattcc tggaccgcgc gggcgacttc gacgcggagt tcttcgggat cggcccgcgc    3780
gaggcgctgg ccatggaccc gcagcaacgg ctgctcctgg agacctcctg ggaggcgatc    3840
gaacgcgccg gactcgaccc gagcacgctg cgcggcgagc gggtgggggt gttcgtcggc    3900
gccaccgcgc aggaatacgg cccgcgcatg cacgaatcca ccgacgccct cgccgggttc    3960
ctgctgaccg gcaccacgcc cagcgtcgcg tccgggcgga tcgcatacac cctcggcctg    4020
tcgggcccgc cgctcaccgt cgacaccgcc tgctcgtcct cgctggtcgc ggtgcacctg    4080
gccgcccgtt cgctggcgag cggggaatgt gcgctggccc tggcgggcgg cgccaccgtg    4140
atggccggtc ccggcatgtt cgtcgagttc gcccggcagc gcggcttggc ccccgacggt    4200
cgttgcaagc cgttctcggc ggacgccgac ggcacggcct gggccgaggg cgtcggcgtg    4260
ctcctgctga aacgcctgtc cgacgcgcgc cgcaacggcc atcccgtact cgccgtgctg    4320
cgcggctcgg cgatcaacca ggacggggcc agcaacgggc tcagcgcgcc caacgggacc    4380
gcccagcagc gggtgatccg ggacgcgctg ccgccgccg ggctcgatcc gcaagacgtc     4440
gacctggtcg aggcacacgg caccgggaca ccgctgggcg acccgatcga ggcgcaggcg    4500
ctgctggcga cgtacgggcg cgatcgggcc gccgatcggc cgctgctgct cggctcggtg    4560
aagtccaaca tcggccacac ccaggccgcg gcgggtgtgg ccgggctgat caagaccgtg    4620
ctggccctgc gacacggcgc gataccgggg acgctgcacc tgcgcgaacc gtcgccccac    4680
gtgcggtggt cggacggggc gatcacgctg ccgacgacga ccacggactg gcccgcgtac    4740
gaccgtccgc gccgcgcggc ggtgtcgtcg ttcgggatca gcgggacgaa cgcgcacgtg    4800
atcgtggagg aggcgggcgg gggcgcggag ataccggggc ctgcccctgc ccgcgggctt    4860
gcgtccgccg gtgtcgccga ccccgtgccg ctggtggttt ccgcgcggag cgaggccgcg    4920
ttgcgggggc aggcggagca gcttgcggga ctgctgcgag cggcggacgc tccggccctg    4980
gccgatgtcg gatattcgct gctgcgcggc cgggccgggt tcgagtacac cgccgtgata    5040
ccggcgcgca cccacgccga ggcgctgcac gggttgaccg cgctcgccgc cgatcgaccc    5100
gccgaccggc tgatccgggg cggcgccgcg cgggcccggg gcgggaccgt gttcgtcttc    5160
cccgggcagg gcacccagtg gtccgggatg gcgctggaac tccttgacac cagcgagccg    5220
```

-continued

```
ttcgccgcct ccatgcgggc ctgcaccgac gcgctcgacc cgtacgccgt cgactggtcg    5280
ctgctcgacg tgctccgcga acccgggacg ccggggttga cgcgcgtcga tgtcgtgcag    5340
ccggcgctgt tcgcggtgat ggtctcgctg gccgcgctgt ggcgctcgat cgggatcgaa    5400
ccgcaggccg tggtcggcca ctcgcagggc gagatcgccg ccgcgtacgt cgcgggcgca    5460
ctgtccctgg ccgacgccgc caaggtggtc gccctgcgca gccgggcact ggtcgcggcg    5520
gcgggcagcg gcgggatggc ctccgtgtcg ctgcccgccg aacaggtcgc cgcgctgctc    5580
gaaccctggg ccggccgact cggcgtggcc gccgtcaacg ggccgagcgc caccgtggtc    5640
agcggcgaca ccgcggcact ggacacgttc ctggaccgat gcgcggcgga cgacctgcgg    5700
gcccggcgga tccccgtcga ctacgcgtcg cactccgtgc acatggagga gatccgcgat    5760
cgactcctga ccgacctggc cgacgtgacc ccgcgagccg cgtcgacagc cttctactcc    5820
accctgaccg gcggtcgcat ggccgacacg agcggcctcg acgccgacta ctggtaccgc    5880
aacctgcgtc gaacggtgcg atacgagacg gccgttcggg cattgagcga ggacggtcac    5940
cggctgttcg tcgaggtcgg cccgcacccc gtgctcacgc tcggtaccca ggaaacgttg    6000
gacgcgtgcg gcagcggcgg caccacgatc ggcacgctga ccgcgacga cggcggccgg    6060 gcccgctttc tggttgcggt ggcggaggcc gtcgcgcacg gcgcccggcc cgacgccgaa    6120
gcgctgttcg acccgcccgg aaccggagtg cgggcggttg ccctgcccac ctacgcgttc    6180
caacaccgcc gctactggct gaccccgcgt gaggcggctc ccgagggtac ggctgccctc    6240
ggtctgacgc cgatctccca tccgctgctc ggcgcgcttg gcgcgctcgg cgtcgagccg    6300
gatggcacgg tgatcgcgac cggtcggatc tcgctgcggg agttgccgtg gctggcggac    6360
cacgcggtcg cggacaccgt ggtgttgccg gggaccgcgt ttctcgaact ggccctgtgc    6420
gtcggggagt ccgtgggtgc tccgcaggtc gaggaactga ccctggagag cccgctgctc    6480
ttgcccgaga ccggtgacgt gtacctgcgg gttgccgtgg ccccggcgga cgaggcgcgg    6540
cgacgggcgg tcaccatcca ctcccggcgt gcgggtgggg gcggtgccga tgcggagcgg    6600
gagtcgtggg ttcggcatgc gggcgggctg ctcgttgatt cggtgcggga ggtggacgac    6660
ggcggcagtg gtgggctcac ccagtggccg ccgcccggtg ccgatgtgct cgatctcgcc    6720
gatgcctacc cggtgttggc ggggctcggt tacggctacg ggccggcctt tcggggactg    6780
cgtgcggctt ggcgcggggc cggcggcgaa ctcttcgccg aggtgcggct gccggatgaa    6840
ctgcgggaat cggagtcggg ggtggtgggg cccgagttcg ggattcaccc ggcgctcttg    6900
gacgcggcac tgcatccgtt gctttcgtcg ctttcgttga cttcgttgtc gtcgacgcgg    6960
gacggaccgg cgggtgcgcc gccgcgtatt ccgttctcgc tggcggacgt gcggctgtac    7020
gccaccgggg ccgacatgtt gcgggtacgg ctgcgccggg cggatggcgg ggccgcggcg    7080
ctcacggttg ccgacggcgt cggtgcgccg gtcctgtcca tcggtgcgct caccctgcgc    7140
gaactgcctg cggacgggct gatcgcgcg gaacccgggc cgggcgaggc gatgttcgac    7200
ctgcgctgga tcgccggatc gatcccggcg gagccgacgg gtctcgggta tgcgttcatc    7260
ggggacgacc tcgcctgggg cgacggcgag gtgtatccga gcctcgcgga tctcgatgcg    7320
cgactgctcg cgacggggga acccacgccc gacgtggtgt tcgccgccgc accggtgggg    7380
gtggacgacg acgtcccggg cgccgcgcac gacagcgcgc gctgggcgtt ggacctggtc    7440
gggggttggc ttgccggcga gcggtcgagt gcggcgcggc tggtcgtggt caccccgtggt    7500 gcggttgctg ctcggaccgg tgacgcgctg tccgggctgc ccgcagcccc cgtatggggg    7560
ctgttgcgga ccgcgcagtc cgaacacccc gatcgtttcg tgctgatcga cctggacgat    7620
```

```
gcggtgcgat ccccttccgc gctgcttggc gcggccgttg cgggtgaacc tcaactcgcc    7680
ctgcgtgacg gggtggttca tctaccccgc atggtggcgg tggattcggc ggacgcgcag    7740
gtgactcgac gccgacccga tccgaacggg accgcgctga tcaccggtgg caccggcacc    7800
ctgggtgcgc tgatcgcccg ccggctggcc gccgaacacg gcatccggca cctgctcctg    7860
ctcggacgtg cgggtcggga ggcccccggc gccgaggagt tgatcgccga actcggcgcg    7920
ctcggcgccc gggtgaccgt ggccgcgtgc gacgtcgccg accgggccgc gctccgccgc    7980
gtgatcgagg acatccccgc cgagcacccg cccacgatcg tcgtacacgc cgccggtgtg    8040
ctcgacgacg cgacgctgtt gtcgttgacc ccggatcggc tcgacgcggt gctgcgcccc    8100
aaggtggacg cggcctggca tctgcacgag ctgacccgag cggcgaaccc ggcggcgttc    8160
gtgctgtttt cgtccatcac cgcgatcacg ggcaacgccg gccagggcgc gtacacggcg    8220
gccaacacct tcctggacgc cctcgccgaa caccgccgcg cagccgggct gcccgccaac    8280
gccctggcct ggggactgtg ggccgagggc agcgggatga cccgacacct cgaccacacc    8340
gaccgggccc ggatgtcccg gggcgggatc gcggcgctgc ccaccgagac cggactcgcc    8400
ctgttcgacg ccgcgttgca ccgggaccgc ccgtacacga tccccgcccg cctggaccgc    8460
ggcgcgctgc gggccctggc cgcgagcggt gtgctgcccg ccgtactgcg cagcctcgtg    8520
cgtgtcccgc cgccgcgtgc cgccgcctcc ggcgacggca cggacgcgtc gtcgtggccc    8580
cggcggatcc gggaactccc gggcgagcag cgggaacggg cgatcaccga cctggtgcgc    8640
gggcaactcg ccgccgtcct cggacacgac gcacccgaac gactcgacct cgaccgcgcc    8700
ttccgcgaac tgggagtcga ctcgctgacc gcactcgaac tgcgcaaccg gatcaatgcg    8760
ttcaccggcc tgcgactgcc cgcgacggtg gtcttcgacc accccagcgg tacgccctg    8820 gtcgctcgga tgatgcgcga gctggtcggt cggtgccga gcgagccgac cacgcccgtc    8880
gtcgcaccga ccgtgacggt cgacgagccg atcgccgtcg tcggcatcgg ctgtcgctat    8940
ccgggcggtg tggccggtcc cgaggacctg tggcgactgg tcgcggccgg cacggacgcg    9000
gtcggcgact tccccgagga tcgtggctgg gacctggcga agctgtacga ccccgacccg    9060
gacaaggtcg gcaaggtcta caccgtcgg ggcggattcc tctacgagtc ggggagttc     9120 gacgccgagt tcttcggcat ctcgccgcgc gaggcggcgg cgatggaccc gcagcagcgg    9180
ctgctcctgg agaccgcgtg ggaggcgttc gagcacgcgg gcctggaccc caggacgctg    9240
cgcgggagca acacggtgt gttcgccggg gtgatgtaca acgactacgc ctcgcggctg    9300
caccgcgccc ccgacgggtt cgagggcatg ctgttggccg gcaacgtggg cagcgtcgtg    9360
accggcagag tgtcctacgc gctgggcctg gaggggccgg cggtcagcgt ggacaccgcc    9420
tgctcgtcgt cgctggtggc gctgcacctg gcggccaacg cgctgcggtc ggggagtgc    9480 gatctggcgc tcgccggtgg ggtgacggtg atgtccaccc cgaacgtctt cgtcgagttc    9540
tcccgacagc gcggcctgtc ggcggacggc cggtgccggt cgttcgcggc gggcgcggac    9600 gggacggggtt ggggcgaggg tgtcgggctg ctggtggtgg aacgactgtc cgacgcgcgg    9660
cgcaacgggc atcccgtgct ggcgctgctg cgtggctcgg cggtcaacca ggacggcgcc    9720
tcgaacgggc tgaccgcgcc gaacggaccg tcccaggagc gggtgatccg gcggcgttg     9780 gccggtgcgc ggttgtcggc gacggacgtg gacgcggtgg aggcgcacgg caccgggacg    9840
acgctgggcg acccgatcga ggcgcaggcg ttgttggcca cgtacgggcg ggaccggccg    9900
gcggatcggc cgctgtggct gggctcgatc aaatcgaaca tcgggcacac gcaggccgcg    9960
```

```
gcggggcgg ccggcctgat caagatgatc atggcgatgc ggcacggcgt actgcccgag      10020
acactgcacg tcgacgcgcc gtcgccgcac gtggactggt cgacgggaca cgtcgagctg      10080
ctggccgaac gtcgaccgtg gcccgaggtc gaccgggcgc gccgggccgc cgtgtcgtcg      10140
ttcgggatca gcgggacgaa cgcgcacgtg atcgtcgaac aggcgccggc ggccgaggcg      10200
gtggtgtccc gggacgagcc ggtgggtgtg gcgggcctgg tgccgtgggt gttgtcggcc      10260
aggaccgccg acggtctgcg ggcgcaggcg gcgcggttgc gggagtggtc ggcgcggcat      10320
ccggaggcgg atccggtcga cgtggggtgg tcgttggttc gggagcggtc ggttttcgat      10380
cggcgggcgg tggtcggtgg ccgcgatccg ggtgaactcg ggctgggtt ggacaggttg       10440
gccgcgggtg gcggtattgc cgacggtcgg ccgatgtttt cgggtcccgg tccggtgttc      10500
gtgtttcccg gcaggggtc gcagtgggtg gggatggcgg ccgggctgtt ggagtgctcg       10560
ccggtatttg cggaggcggt gacggagtgc gccgccgtga tggatccgtt ggtggcggat      10620
tggtcgttgt tggatgtgtt gcggggtggg tctgccggtg agttggagcg ggtggatgtt      10680
gttcagccgg tgctgtttgc ggtgatggtg gggcttgcgc ggtggtggga gtcgtgtggg      10740
gtcaagccgg gtgcggtcat cgggcactcg caggggagga tcgctgccgc gcatgtggcg      10800
ggttatctgt cgctggcgga tgcggtatgg gtggtcgtgt tgcggagtcg ggccctgctg      10860
ggggtcgcgt ccgccggggg cgggatggtg tccgtcgggg tgtcggcgga gcgtgctcgc      10920
gagctggtcg ccggggatga ccggctgtcg ttggcggcgg tgaacgggcc gacgagtgtg      10980
gtgctttcgg gtgatgtcga agcgctgtcg gtggttgtcg aggcgtgcga gcgggatggt      11040
gtgcgggctc ggtggattcc ggtggattac gcgtcgcatt cggcgcggat ggaggccgtg      11100
cgggacgagg tggagcggct gttgcggat gtgacgccgc aggtgggccg cgtgccgatg       11160
tactcgaccg tgagcgggga ggtggtcgtc gatcccgccg agttgggcgg ggcgtactgg      11220
ttcgagaatc tgcggcgcac ggtcgagctt gagcgggccg tgggtgcggc ggtcgcggat      11280
gggcatggtg cgtttgtgga gtgcagcccg catccggggc tggtggtgcc gatgggggac      11340
accctggagg cggccgggt ggacggcgtc gttctggaga cgttgcggcg gggtgagggt       11400
gggcccgatc ggctggtcgc cgcgctctcg gcggcgttcg tggcgggtgt cgcggtggac      11460
tgggccggaa tgttgccggg gcgccatgtc gagctgccga cgtatgcgtt ccagcggcgg      11520
cgctactggt tgacgggtgg ggaacgtgcg ggcgatccgg ccgggttggg gctggtcgcg      11580
gccgatcatc cgctgctggg ggctgtggtc ggttcggtgc gggacgggga actcctctac      11640
accgggcggt tgtccgccgc gacgcacggc tggcttgcgg accacgcggt gttcggctcg      11700
gtggtggtac cggggacggc cttcgtcgag ctggcgtcgt gggtcggtgt cgaggccggt      11760
tgcccggtcg tcgacgaact cacgctgcat gcgcccctgg tgctgccgga cggggtcggc      11820
atccggcttc gggtggcggt gggcgcggcg gattcggcgg ggcgtcgggt ggtggagttc      11880
cattcgcggc ccgaggatgc ccccgacgag cagtcgtgga ctcggcatgc gaccggcacg      11940
ctgggtgccg cgagtgtgcc cggatccgcg tcgccggggg ccgcggcgtg ggcggtctgg      12000
ccgccggcgg acgccgaggt ggtcgacccg gaggccgttt acgagcgact tgcggagcac      12060
gggtacgaat acgggccgat tttccggggg ttgcgggccg catggcggcg gggtgacgac      12120
ttcttcgccg aggtcgcgct gccggaggcg gccggtcggg acgcgcacgg ctacgacctg      12180
catccggcgg tgctggacgc cgcgctgcat gtggccgcg ccgaggcggt ggcggagtcg        12240
gggcgacgt tgttgccgtt cgcctggacc ggggtcgcac tgcatgggcc ggggggcgtcg      12300
gtgcttcggg tgatgttgcg gcgtaccggg cgggagacgc tggcggtcga cgtggccgac      12360
```

```
gagcgtggtg ttccggtggc gtcggtcgcg tcgctgacgc tgcggccggt ggctgccgag    12420
cagttggtgg cggccgagga agcgggccgc gagtggcttt accggatggt ctgggagatc    12480
gcggacgcgc cggtggcgga gcacgtcgag ggtgaacttc ttggttcgga tgaggagtcc    12540
gacgcgtcgg cggagcttgt ggcgggcggg attcgggtgg tgacccctgc gggcgccgaa    12600
caggtctccg aggtggggct gttcgattgc ccgcccgtgg tcggcgaagc ccccgaggag    12660
gtggccggcg ccgtgcatgc ggtgctggcc gcggttcggg cgtgggtggc ggacgagcgg    12720
tttgccgggg cgcggctggt ggttcgtacc cgtggcgcgg ttgccacgga tgcgcaggac    12780
cgggtcggtt ctcccgcgca tgcggcgatc tggggtctcg tgcgggtcgc gcagagcgag    12840
catccggggc gcttcgtcct ggtcgatggg gacgacgtcg attcgggtgc ggcgctgcgt    12900
gcggcggtgg cgtgcgggct gccgcaggtg gcgattcgcg aaggtgtggt gctggcgccg    12960
cgcctggtgg gggcggtgca cgacacgcgc ctggtgccgc cggcgccggg tgcggatcag    13020
gcgtggcgga tcgagtccgg gacggccggg acgccggacg atctggtggt gacggcgcat    13080
ccggccgcct cggcgccgtt ggcggccggg caggtgcggg tggcggtgcg ggcggccggg    13140
gtgaacttcc gcgatgtgct gatcacgctc ggcatgtacc cggggcgggc ggtggtcggc    13200
gccgaggcgg ccggggtggt cgtggaggtc ggcccggggcg tgtcggaacc ggccgtcggc    13260
gaccgggtga tgggcttgtt cgagggggcg ttcgggccgc ttgcggtggc cgatcggcgg    13320
ctgttggccc gggtgccggc gggttggtcg tttgctcagg cggcgtcggt gccggtggtc    13380
ttcctcaccg cgctctacgg gctgcacgat ctggccgggc tgcggtcggg tgaatcggtg    13440
ctggtgcatg cggccacggg tggggtcggc atggccgcca cccagctggc ccggcatcgg    13500
ggcgccgagg tgtacgcgac cgcgagtgcg acgaagtggg ccaccgtgcg cgggctgggt    13560
gttccggacg aacggatcgc ctcgtctcgg gacctgtcct tcgaacagcg cttcgcacgg    13620
gccacggacg ggcgcgggat cgacgtggtg ttgaactcgc tggcgggcga gttcaccgac    13680
gcgtcgttgc gactcctggc cgagggtggc cggttcgtgg agatgggcaa gacggacgtc    13740
cggaccgagg ggctgccggc cggggtgcgc tatcgggcct tcgacctgat cgaggccggt    13800
ccggatcgga tcgccgagat gttcgccgaa ctggtcgacc tcttcgagcg cggtgtgctg    13860
caacccctgc cgattcggac ctgggacatc cgtcgggccc gcgaggcgct gcgtttcctg    13920
ggccaggccc ggcatgtggg caaggtggtg ctgaccgtgc cgcagccgct cgcggccgac    13980
ggcacggtcc tgatcaccgg cggcacgggc acgctgggtc gcagtctggc ccgacacctg    14040
gtcacgcggt ggggtgtgcg ccggctggtg ctgaccggcc gggccgggcc cgccgctccc    14100
ggcgccgccg aactggtcgc ggaattggcc gagtcgggtg ccgacaccac gatcgtggcc    14160
tgcgatgcgg cggaccgggc ggcgatggcc gaggtgttgg ccgcgatccc ggccgaacac    14220
ccgttgaccg ccgtggtgca tgccgccgga acactcgacg acgcgccgat cgaggcgctg    14280
accccggagc gggtcgacca cgtgttgcgg cccaaggtgg acgccgccct cgtactggac    14340
gaactcaccc gggacgcgga cctggccgcg ttcgtgctgt tctcgtcggt ggccggcgta    14400
ctcggtgtgg ccggccaggg cggctatgca gcggggaacg cgttcctgga cggtctcgcc    14460
ggtcggcgcc gcgagcgggg gctgcccgcg accgctctgg cctggggcct gtgggcggaa    14520
cgcagcgcaa tgaccgcgca gttgggcgtc ggcgacctga agcgcctggc gcgcggcggc    14580
ctggtgccga tctcgaccgc ccaggggctc gccctgttcg acgccgcctg gcaggccgac    14640
gaggcggcgc tgatcccggc ccgcctggac cttgccgcac tgcgcgcaca ggcggcgacc    14700
```

```
cagccggtac atccgctgct gcgcggtctg gtcggcacca ccccgacccg ccggaacggc    14760
acaccttcgg aggcgccgtg ggcccgacgg ctcgcctcgg ccgcgcccgc cgagcgggtg    14820
gacgtggcat tgcggctggt ccgggccgag gcggcggtgg tcctggggca cgagtcgatc    14880
gacggggtgc ggcccgaagt caccttccgc gacctcgggt tcgactcact gacgggtgtg    14940
gaactgcgca accggctgag cggcgccacc ggattgcggc tgccgtccac gctggtcttc    15000
gacttcccga ccccgctcgg cctggccggt ttcctggtcg ccgagtcggt cggcgagatg    15060
gacacgcgcc cgaccgggcc ggttgccggg ggtgcggtgg tcgcggccga tccggtggtg    15120
atcgtcggga tgggctgccg attcccgggc ggggtggact cggcggcggg tctgtgggac    15180
ctggtggccg cgggcggcga tgcgatcggg ccgttcccga ccgaccgtgg ctgggacgtc    15240
gacgcgctgt tcgatcccga tccggagcgg gtcggcaaga gctacgtccg taccggcgga    15300
ttcctctccg gggcggccga gttcgacgcc gagttcttcg gtgtgtcgcc gcgcgaggcg    15360
ttggcgatgg acccgcagca gcggctgctg ctggaaaccg cgtgggagac cttcgagcag    15420
gcgggcatcg atcccacctc gctccggggc agccggaccg gcgtcttcgc cgggatggcc    15480
ggccacgact acgcgaccgg gggcgcccgt tcgcaggccg ggctggaggg ccacctgctg    15540
accgggaacg cggccagcgt ggcctcggga cgggtggcct acacgttcgg cctggagggg    15600
ccggcggtga ccgtggacac ggcgtgctcg tcgtcgctgg tggcgctgca cctggcggcc    15660
aacgcgctgc gggcggggga atgcgacctg cgcctcgccg gcggggtgac cgcgatgtcc    15720
acgccggact tcttcctgga gttctcccgg cagcgcggac tgtccgtgga cggccgttgc    15780
aaggcgttcg cggccacggc ggacgggatg ggcgcggccg agggcgtggg cctgctcctg    15840
gtcgagcggc tgtcggatgc gcggcgcaac gggcattcgg tactggcggt ggtgcgtggg    15900
tcggcggtga accaggacgg cgcgtcgaat gggttgaccg cgccgaacgg gccgtcgcag    15960
cagcgggtga tccgggcggc cctggccgac gccgggctgt ccgcggccga tgtggatgcg    16020
gtggaggcgc acgggaccgg cacgacgctc ggcgatccga tcgaggcgca ggcgttgctc    16080
gcgacctacg gcgcggatcg ggcgccggat cggccgctgt ggttgggctc ggtgaagtcc    16140
aacatcgggc acacccaggc ggcggcgggt gtggccgggg tgatcaagat ggtctcggcg    16200
ctgcggcatg ggatgttgcc gcgcacgctg cacgtggacg agccgacgcc gcatgtggac    16260
tggtcggcgg gtggggtcga actgctcacg agcgcgcggg cgtggccgga ggccgggcgg    16320
gtgcgtcggg cggggtgtc gtcgttcggg atcagcggga cgaacgcgca tgtgatcctg    16380
gagcaggcgg aggagagccc ggcggttcg gtgccttcgg cgactcctcc ggtggccggg    16440
actccggtgt ggggcggtcg ggtgccctgg gtgttgtcgg cccggtccga acccgctttg    16500
cgggcacagg ccgcgcggtt gcgggactgg ctggccgtac atcccgacgc cgatccgctc    16560 gatgtgggc ggtcgttggc gaccgggcgg gcggcgctcg atcaccgggc ggtggtgcat    16620
gggcgggacc tcgcggaatt gcgcctggcg gtcgcgaagt tggccgacag cgggccgggt    16680
gacgaggcgt cgatcgtcgg ctcggtctcc gccgccggtc cggttttcgt gtttccgggg    16740
caggggtcgc agtgggtggg gatggcggcc gggttgttgg agtgttcgcc ggtgtttgcg    16800
ggtgtggttg ccgagtgtgc tgcggtgatg gatccgttgg tggcggattg gtcgttgttg    16860
gatgtgttgc ggggtgggtc tgccggtggt gaggcgttgg cggagcgggt ggatgtggtt    16920
cagccggcgt tgttcgtggt gatggtgggg cttgcgcggt ggtgggagtc gtgtgggtc    16980 aagccgggtg cggtgatcgg acactcacag ggggagatcg cggctgcgca tgtggcggga    17040
tatctgtcgc tggcggatgc ggtgcgggtg gttgtgctgc ggagtcgggc gttgctcggg    17100
```

```
gttgcgtctt ccggtggcgg gatggtgtcg gtgggtgtgt ccgccgatcg ggcccgggag   17160
ctggtcgccg aggacgaccg gttgtcgctg gcggccgtga acgggccgac gagtgtggtg   17220
ctttcgggtg atgtcgaagc gctggccgtg gttgtcgacg gctgtgagcg ggacggggtc   17280
cgggctcggt ggattccggt ggattacgcg tcgcattcgg cgcggatgga ggccgtgcgg   17340
gacgaggtgg agcggctgtt ggcggatgtg acgccgcagg cgggccgcgt gccgatgtac   17400
tccacggtga gtgggggggca cgttaccgac ccgagtgtgc tcggtggttc gtactggttc   17460
gacaatctgc ggcgtacggt cgagttggag cgggccgtcg gagcggcggt tgtcgacggg   17520
cattcggtct tcgtcgagtg cagtccgcat ccggggctgg tggtgccact gggggacacc   17580
ctggaggcgg ccggggtgga tggcgtcgtt ctggagacgc tgcggcgggg cgagggcggt   17640
cccgatcggc tggtcggcgc gctttcggcg gcgttccgga gcggtctggc cgtggactgg   17700
gccgggtccg ggatggtgcc ggggcggcgg gtcgagctgc cgacctatgc cttccagcgg   17760
cggcggtact gggtcgagcc cggcgagagg gccggcgggg tcgggtgggg gcagttcacg   17820
gtcgaacatc cggtgctggg cgccggggtc gatctggccg acggagccgg gacggtcttc   17880
accgggcggc tgtccgcggc ctcgcacggg tggctcgcgg agcatgtggt gctcggcacg   17940
gtgatcgcgc ccggcacggc gttcgtcgac ctggcgctgc gtgcggggc gacggtcggc   18000 cgggcgacgg tcgaggaact gaccctgcac gcgccgctga tcctgcccga cgcgggcggt   18060
gtacggattc aggtccgggt cggcgcaccc gacgccgccg gggtcggatc ggtggagatc   18120
cattcccgac cggaggacgc ggccggcgac gagccatgga cccggcacgc ctccgggacc   18180
ctgaccgcga ccgacctcga cccggcggac gtggccacgg aggcggcgat ctggccgccc   18240
gcgggcagta cgccggtcga tctggacgga gcctacgagc gactgccac ggccggattc   18300 gagtacggtc ccgccttcca ggggctgcga gccctgtggc ggcgcggcgc cgagtcgttc   18360
gccgagatcg aactcgcgga cgacgcacgg caggaggccg aacgctacga ggtgcatccc   18420
gcgctgttgg atgcggccgt gcatgcgctg gggatggagc cgacggcgga ggttgcgccg   18480
gatgaggcgc ggattgcctt ctcctggcga ggggttcggc tggttgccgc cggagcgggg   18540
cggttgcggg tgcggctggc accggtgggc tcggacgcgg tgtcgttgtg gctgagcgac   18600
atggacggtg agccggtcgg gtcggtccgg gccctgaccg tgcggccggt cgcggccgag   18660
cggctgcgtc cggctggggc gccgccgcgc gactcgatgt tccgggtgga gtggcggccg   18720
gtgtcgggcg acgagtcggg cgtggcggtt cgctgggcgg tggtgggcgc ggcggactcc   18780
gggccgcttg cccggctggt ggcggcgtat ccggatgtgc cggtgtaccg cagtgtggtc   18840
gaggcggccg gggatgtggc ggcgggaccg cccgatgtcg tggtggtggg cgtgggcgag   18900
gccgactgtt cggaggggtc ggtcgagcgc actcggcggg tgcttgcgga cgtgctggcg   18960
tggatgcagg actggctggc cgactcccgc ttcgcggcga cgcgcctggt cgtggtgacc   19020
tccggggccg tcgccgccga cgtggacgcc gaccccgacg agcgggtggc ggacctggcc   19080
ggcgcggcgg tgtgggggtt gttgcgctcg gcccagtccg aacacccga ccgatgcacg   19140 ctggtcgacc tcgacgagga cgcggcgtcg attgacgcct ggccggcgat tcttgcctcc   19200
gccgagccgc aactcgccgt ccggatgggc cgattccggg tgcctcggct ggccagggtg   19260
actgccgggg gcggcgagcc ggtcgccttc gcgcccgacg gcacggtgtt ggtcaccggt   19320
gccaccggcg gcctgggcgc cctggtggcc cggcacctgg tgaccgcgca cggcgtgcgc   19380
cgacttctgc tgctgtcccg ccggggcgcg gccgcacccg gcgcggccga actggtcgag   19440
```

```
gacctgaccg cgcaggggc ggaggtcacc ctcgccgcct gcgatctggc cgatcgtgcc    19500
gcgctggccg ccgagttggc gcgtatcccg gccgagcacg cgctgaccgg cgtgatccac    19560
accgccggag tggtggacga cgccaccatc gcgaacctga ccgatgcgca catggaacac    19620
gcgctgcgcc ccaaggcgga cgccgcgttc catctggacg agttgacccg ggacgtgaac    19680
ccggccgcat tcgtcctgtt ctcctccggg gccaccacct tcggtggccc gggacagggc    19740
aactacgcgg cggccaacgc cttcctggac ggcctggccc ggcagcgccg cgaccgcggc    19800
ctgcccggga tctcgctggc ctggggcctg tgggcgggcg cgcaggggat gggcgggcgg    19860
ctgagcgagg ccgacctggc ccgctgggcc cggaccggcg cggtggcgat gccggcggcc    19920
gaggcactgc ggttgttcga tatcgcgctg ggccggcccg aggcggccct ggtgccggca    19980
cacctggacc tcccggcgat gcgggcggat gccggtgctc gacccgcgct gttccgcgag    20040
ttgctcggga tcggtacgcg acgggcggca gtgggcgcgg gcgggtcggc gctgacccgg    20100
cggctggcgg ggatgtctcc ggccgagcgg gagcaggcgg tcctggacgt ggtgcggacc    20160
gaggccgcga acacgctggg acacgagtcg gccggggcgg tgtcggccgg gcgagcgttc    20220
aaggagctgg ggttcgactc gctgaccggg gtggaactgc gcaaccggtt gaacaccgcg    20280
accgggctgc ggttgccgtc cacgctggtc ttcgactacc cgacgccggc ggggctggcg    20340
gcgttcctgg tcgccgagtt ggtcggtcgt tcggtacagg cggtgccggt gccgccggtc    20400
ggtgggcggc acggggacgc cgacgatgcg atcgtgatcg tcggcatggg ctgccggttc    20460
ccgggcgggg tggcctcgcc ggaggacctg tggaatctgc tggcctcggg tggggacgcg    20520
atcggaccgt tcccgacgga ccggggatgg gacctggccg ggctgttcga ccccgatccc    20580
gagcgggccg ggaagagcta cgtggaatcg ggcggattcc tgtatgggat cggcgagttc    20640
gacgcggagt tcttcgggat ctcgccgcgt gaggcgttgg cgatggatcc gcagcagcgg    20700
ttgctcctgg agacggcgtg ggagacgttc gagcgggcgg gcatcgatcc gacctcgctg    20760
cgcggcagcc ggaccggggt tttcgccggg gtgatcgaca cgactacgg cgcccgggtg    20820
aaccaggtgc cggacgaggt cgagggctat ctgggctacg gcagttcggc cagcatcgcg    20880
tccgggcggg tctcgtacgt cctgggcctg gagggcccgg cggtcagtat cgacaccgcg    20940
tgctcgtcgt ccctggtcgc gctgcacctg gcggtgaacg cggtgcggtc gggcgaatgc    21000
gaactggccc tggccggtgg tgtgacggcg atggccacca ccgagttctt cgtggagttc    21060
tcccgacagc ggggcctgtc gccggacggc cgctgcaagg cgttcgcggc ggcggcggac    21120
gggatgggcg cggccgaggg catcgggctg gtgctggtgg agcggttgtc ggatgcgcgg    21180
cgccatgggc attcggtact ggcggtggtg cgtgggtcgg cggtgaacca ggacggcgcg    21240
tcgaatgggt tgaccgcgcc gaacgggccg tcgcagcagc gggtgatccg gcaggcgttg    21300
ggtgctgcgg gcttgtctgc ggcggatgtg gatgcggtgg aggcgcacgg gaccgggacg    21360
acgttgggtg atccgatcga ggcgcaggcg ttgttggcga cctatgggca ggatcggccg    21420
ggggatcggc cgctgtggtt ggggtcggtg aagtcgaata tcgggcacac gcaggcggct    21480
gcgggtgtgg ccggggtgat caagatggtg ttggcgctgc ggcatgggt gttgcctcgg    21540
acgttgcatg tggacgagcc gacgccgcat gtggattggt cggccgggcg ggtcgaggtg    21600
ttggcggacg aggtggcgtg gccggcaggg gagcgggtgc gccggcggg tgtgtcgtcc    21660
ttcggaatca gcgggacgaa cgtgcacgtg gtcctggagg aggcgccggc ggacgccgcc    21720
gagcctgcgc ccgccgcgcc ggaggtcccg ggcgtcggcg gcgtgctgcc ctgggtggtg    21780
tcggcgcgca ccgaggccgg gctgcgggcg caggcggcgc ggttgcggga ttgggtgagc    21840
```

```
gaacatccgg acgccgaacc gacggatgtc gcacggtcgt tggtggtcgg gcgagcggtg    21900
ttggacgtgc gcgcggtggt gcgcgggcgg gaatccggcg aacttgtcgc cggcctggac    21960
gagttggcgc gggccggggt gggagacccc ggctcgctgg tgagcggctc ggatccggtg    22020
ttcgtgtttc cggggcaggg gtcgcagtgg gtggggatgg cggccgggtt gttggagtgt    22080
tcgccggtgt ttgcgggtgt ggttgccgag tgtgctgcgg tgatggatcc gttggtggcg    22140
gattggtcgt tgttggatgt gttgcggggt gggtctgccg gtgagttgga gcgggtggat    22200
gttgttcagc cggtgctgtt tgcggtgatg gtggggcttg cgcggtggtg ggagtcgtgt    22260
ggggtcaagc cgggtgcggt gatcgggcac tcgcaggggg agattgcggc tgcgcacatc    22320
gcgggttatc tgtcgctggc ggatgcggtg cgggtggttg tgctgcggag tcgggctctg    22380
ctgggggttg cgtcttccgg tggcgggatg gtttcggtcg gggtgtctgc ggagcgggcg    22440
cgggagttgg ttgccggagc tgacgggttg tcgttggcgg cggtgaacgg gccgacgagt    22500
gtggtgcttt cgggtgatgt cgaagcgctg tcggtggttg tcgaggcgtg cgagcgggat    22560
ggtgtgcggg ctcggtggat tccggtggat tacgcgtcgc attcggcgcg gatggaggcc    22620
gtgcgggacg aggtggagcg gctgttggcg gatgtgacgc cgcaggtggg ctgcgtgccg    22680
atgtactcga ccctgaccgg tgcgccgatc gccgatcccg ccgagttggg cggggcgtac    22740
tggttcgaaa acctgcggcg cacggtcgag ttggagcggg cggtcggtgc ggcagtggcg    22800
gatgggcgca ccgtgttcgt cgagtgcagt ccgcatccgg ggctggtggt gccgctgggg    22860
gacaccctgg aggcggccgg ggtggatggc gcggttctgg agacgttgcg gcggggtgaa    22920
ggtgggcccg atcggctggt cgccgcgctc tcggcggcgt tcgtgcgtgg tctggcggtg    22980
gattgggccg ggttgatcgt cggtgctcgg gtggagttgc cgacctacgc cttccaacga    23040
cggcgctatt ggttggacga cggggcgcgg tcggggatc cgggcgggtt gggactggcc    23100
gcggtcgcac atccctgct gggtgcggcg gtacggccgg cgcagggcgc ggggttgttg    23160
ttcaccggac ggttgtcgac ggcgacccac ccgtggctcg cggatcatgt ggtgctcggc    23220
tcgacgatcg tgcccggcac ggtgttcgtg gacctggcgc tgtgggccgg ggccgaggcg    23280
gagtgcccgg tggtggacga actgaccctg cacaccccgc tggtgctgcc ggaacacggc    23340
ggcgtgcatg tacaggtgac cgtcgacggg ccggacgccg ccggggcccg ggcggtcgcg    23400
gtgtactccc ggccggagga cgctcccggc gaggagccgt ggacccggca cgccgtcggt    23460
gccctcgttg ccgacgccga tacggtgcc gctcccgacg cggctgcgga ggcgtggccg    23520
ccggtcggcg cgaagccgat cgaggtggcg gacttctatg cgcggctggt ggagtccggg    23580
gtcgactacg gccggcgtt tcgcgggatg cgggccgcct ggcggcgcgg ggacgagctg    23640
ttcgccgatg tggcgctgcc ggccgaggag gagcgcgacg cacaccgctt cggggtacat    23700
ccggcgctgc tcgacgcggg cgtgcagacc ctgcgggtgg atccggggca ggtcgacgag    23760
gacgacatcc gggtggcctt ctcctggcac ggggtgcggc tcttcgcggc cggcgtgacc    23820
cggctgcggg tgtcgtgcgt gccgtcgggc gagggtgcgg tgtcgttgcg gatcacggac    23880
gagaccggac gggcggtcgc cgcgatcgag gcgttgacgg tgcgggcgat ctcggccgac    23940
cagctacggc gggccggcgg cgggcgggac gtgctgtacc ggctcgcgtg gcgggcatcg    24000
gcggttcccg taccggtggc gacgcctcgt gtggcggtgg tcggcgggtg ggatctgccc    24060
ggtctgggcg ggttggtgga ccggtatccg ggctttgccg aacttgcttc gtgtgacccg    24120
ccgttgcccg atctggtact gctcccggtt ggtgatccgg atgcggatgt gccgttctcc    24180
```

```
gagcggcgta tgcgggaggt gacggcggaa ctgatcgggc ggctggaggc gtttctcggc   24240
gacgaacggt tcgcggcggc ccgggtggtc gtggtgactc gttcggcggt gctcgtggac   24300
ggggacgcgg ggctcgggga cccggcgtcg gcgtcggtct ggggagtggt ccggtcggcg   24360
caggccgggc atccggggcg gatcgtgctg gtcgacctgg acgacgagcc ggcttcggcg   24420
gcggctttgg cggcgtggc ctcggccggt ggtgagccgc agttcgcggt gcgcggtggt   24480
cgggtgtcgg taccgagact ggagcggatt ccggcctccg gcggagcacg gtcggcggtg   24540
gggaccggca cggtgttgat cgccggtgcg gaccgggcgg tcggcgcggg ggtggccgag   24600
catctggccg gggcgtacgg ggtgggccgg ttcgtgttgt tgtccgtgga tccttcgggt   24660
gcggggccga ccgaactggc cgcccggctg ggtgaggccg gtgccgaggt cgtctcggcg   24720
gcctgggacg ggcacgatcc gggcgtgctt gccgcgcttg tgaccgaaca ccggccggcg   24780
ggcgtggtgg acgcgtcggg cgagtcggat gcagcctggg ccctgcacga gctgaccgcc   24840
gacgtggacc cggcgttctt cgtgctgttc tcgtcggcgg cgagcctgct cggttcgtcg   24900
gcgcatgcgg ccacggccgg ggtggatgcc ttccacgatg cgctggccgc acatcggcgg   24960
gcgagtgggc tgcccggggt gtcgcttgcg tgcgggacgg atccgctgcc ggggctgccc   25020
gacctgttcg acgaggcgat acgccgggag gacgccgtgt tggtttcggc gtcgacggat   25080
ctcaccgggc ccgcgtcgac gtcaccattg ttgccctccc ggaacggtcg tggcgcgacc   25140
aactccgccg agacctcgat cgaggcggac ggcgaggccc tggcccggcg cctggcggcg   25200
ttgtccgagg aggagcgcga gcgcgaactg gtcggcctgg tacgggccca ggccgcggcg   25260
gtgctcgggc atgccggcat cggcgagatc ggacccgaac gggcgttcaa ggaggtcggg   25320
ttcgactcgc tcaccgcggt ggaactgcgc aaccggctga tccggggcac cggggtcggc   25380
ctgcgctcca ccctcgtctt cgacttcccc acgccgcgaa tactggcccg ccacctgagc   25440
ggccggctgg tcgaggcggc atccccgatc ggtgcgctgc tggccgatct ggaccgattc   25500
gagggcgagt tgcacgcggt gctcggcgag gcggaggccc gcgaccggct ggccgagcgg   25560
ctgcgtcggc tgttggccga ctgtaccgcg ccggacgaga gcgcccccgc cgccgacgat   25620
gtctcggacg tgcagtcggc caccgacgac gagttgttct cgctcgtcga ccagggcttc   25680
gaatgacccg gcccatccac gcatacgacc gtgtcggcaa ggagtagagg caacgtggct   25740
gagtcggaag agaaactgcg ctcgtacctg cggaaggcca tcaccgatgc gcgcgacgcg   25800
catcgccggg tacgcgagtt ggaggaccgg cagcgcgagc cgatcgcgat cgtgggcatg   25860
gcctgccgct tccccggcgg tttgggtacg ccggaggacc tgtggcggtt cgtcgtcgaa   25920
ggcggcgatg cgatcggcga gttcccgacc gaccggggct gggacctcga cggcctgtac   25980
gacccggatc ccgaccggcc gggcacgtcg tacgtccgcg agggcggatt cctgtacgac   26040
gtcgccgact tcgacgccga gttcttcggc atctcgcccc gcgaggcggc ggcgatggac   26100
ccgcagcagc gactgcttct ggagacctct tgggaggccg tggaacgcgc gggcatcgac   26160
ccgacgtcgc tgcggcacag ccggaccggg atctacaccg ggatcaacgg cctcgactac   26220
acgaccgtgt tggcccgcac cgccaagggc cgggacggca cgctcggcat ggccaacggg   26280
gccagcctgc tggcgggtcg ggtggcgtac atcctcggcc tggagggggcc ggcggtgacc   26340 gtggacacgg cgtgttcgtc gtccctggtg gcactgcacc tggcgagcaa cgcactgcgg   26400 tcggggggaat gcgacctggc cctggccggc ggtgcgacgg tgatgtgcac gccggagatc   26460
ttcgtcaact tcagccggca gcgcggactg gcccgcgacg gccgatgcaa gccgttctcg   26520
gcggcggccg acgggttcat cctctccgac ggcgcgggcc tgttcctgat cgaacggctc   26580
```

```
tccgacgcgc ggcgcaacgg acatccggta ctggccgtgc tgcgcggttc ggcgatcaac   26640
caggacggcg cgtcgaacgg gctgaccgcg ccgaacggcc cggcccagga gcgggtgatc   26700
cggcaggccc tgcagagcgc cgggttggtg accggtgacg tggacgccgt ggaggcacac   26760
ggcaccggga ccacgctcgg cgaccccatc gaggcgcacg cgctgttggc gacctacggg   26820
caggatcggc ccgcggatcg gccgctgagg ctcgggtcga tcaagtccaa catcggacac   26880
acccaggccg ccgcgggggt ggccgggatg atcaagatgg tgttggccct gcggcacggc   26940
gtgctgccca ggacgctgca cgtcgacgcg ccctcgccgc acatcgactg gtcggccggg   27000
cgggtggaac tgctcacgga gcccgtgccg tggccgaggt cggaccggcc gcgccgggcc   27060
ggtgtctcgt cgttcggggc gagcgggacg aacgcgcacg tggtggtgga ggaggcgccg   27120
tcggacggcg acgacggtgt cgtggaggtg cccgcgccca cgggcatcgg cagtgtcctg   27180
ccgtgggtgt tgtcggcccg atccgaggcg gcgttgcgcg cgcaggcggg gcgattgcgg   27240
gactggctgg ccgagcaccc cgaggcggat ccggtcgacg tgggccggtc gttggcggtg   27300
gggcgtgcgg tgctggaacg tcgcgccgtg gtgcgcgggc gggatgtcgc cgaactcgcc   27360
gtcgggatcg gcgaggtggc cgaccgcgga gaactcgccg gtgggcggcc gatgttcgcc   27420
ggacccggtc cggtgttcgt gtttccgggg caggggtcgc agtgggtggg gatggcggcc   27480
gggttgttgg agtgttcgcc ggtgtttgcg ggtgtggttg ccgagtgtgc tgcggtgatg   27540
gatccgttgg tggcggattg gtcgttgttg gatgtgttgc ggggtgggtc tgccggtggt   27600
gaggcgttgg cggagcgggt ggatgtggtt cagccggcgt tgttcgcggt gatggtgggg   27660
cttgcgcggt ggtgggagtc gtgtgggggtc aagccgggtg cggtgatcgg acactcacag   27720
ggggagatcg cggctgcgca tgtggcggga tatctgtcgc tggcggatgc ggtacggatc   27780
gtggtgttcc gcagtcgggc gctgcgcggg atcgcggcgg ccgtggcgg catggtctcc   27840 gtgggcgtgt ccgtcgagcg tgccgaggaa ctggtgccg gctctgccgg gttgtcgctc   27900
gcggccgtca acgggccgca gagcgtggtg ctttccggcg accgtgaggc actggccgcc   27960
gtcgtcgacg cgtgcgagcg cgagggtgcg cgagcccggt ggatcccggtg ggactacgcg   28020 tcgcattccg cgcacatgga ggtggtccgg gacgaggtcg agcgtttgtc ggccgaggtg   28080
acgccgcggg cgggtcgggt gccgatgtac tcgacgctga ccggggaagt cgtcacggac   28140
ccggccgagt tgggcgccgg ctactggttc gagaacctgc gcgggacggt acggctgacc   28200
accgcagtgg gggcagccgt tgccgacgga cacgtcgcct tcgtcgagtg cagcccgcat   28260
ccgggcctgg tcgtgccgct cgcggacacc ctcgatgagc tgggcgtcga cgacggcacg   28320
gtcctggaga cgttacggcg ggacgacggc ggccccgatc ggctggtcgc cgcgctctcg   28380
gcggcgttcg tggcgggtgt gccggtggac tgggccgcac tgtttccggg cgaggggcgg   28440
gccgacctgc ccacgtacgc cttccaacat cggcgctatt gggccgaggc cgaatcgccc   28500
gcaggcggcg gcgtggcctg ggggcagcgc gcggtgacgc atccggtact cggcgccgcc   28560
gtcgacctgg ccggcgacgc gggcaccgtg ttcaccgggc ggctgtcgac gaccgcccaa   28620
ccgtggctgg ccgaccacgc cgtgctcggc acggtgatcg tgcccgggac ggcgttcctg   28680
gacctggtcc tgcgggccgg agccgaggtc ggctacccgg cgatcgagga actgaccctg   28740
cacacgccgc tcgtgctgcc ggacgcctcg ggcgtcctgg tacaggtcgt ggtcggtgcc   28800
gcggacggcg acggcggcga cggcggcgac ggggcccgga cggtcgatgt gcactcgcgg   28860
gccgaggacg cgccgccgga ccacccgtgg acccggcacg cctcgggggt gctggtcgcg   28920
```

```
gcgggcgagg agcgggccga ggacgcgccg gccgggcggt ggccgccgac cggtgccgag   28980
gtggtgggggg tcgacgacgc ctacgagcgg ctggcggtgg cgggcttcga ctacggcccc   29040
gtgttccagg ggctgcggtc ggtccggcg cgaggcgacg agttgttcgc cgaggtggag   29100
ttgccggagg aggggcacgc ggacgcggac cggttcgcgg tgcacccggc gctgctcgat   29160
gccgcgttgc acccgctggt ggtcgcgccc ggtgccgacg cgccggtcgt ggccgggctg   29220
ccgttcgtgt ggcacggcat tcgggcgggt gttcccgggg cgcgacggtt gcggttcgg   29280
ctggtgcgct cggcgtcggg gtcggcgtcg gggtcggctg cgggctcgga ctcggcttcc   29340
ggcgaggtgt cggtccgggc gtgggacgag ggcggccggg aggtggtggc gatcgagtcg   29400
ctgaccattc gcccggtctc ggcggacggg ttgcggacgc ccgatgcttt ggtccgcgac   29460
tccctgttca cgctcgcgtg gaccgcgttg gagctaccgg acgtcgatga cgacgtgccg   29520
aacgcgaccc tgctgggcgg cgacggtgcg gccgatctcg ccgcgctggt ggctgccatg   29580
gacaccggaa cggacgtacc ggctctggtg gctctgcccg tatcggtcga cgacgcggac   29640
cccgtggcgg cggcgcacac ggccggccgg caggtgctgg cggtactccg ggactggctg   29700
gcggacgagc ggttcgccga ctctcggctg gtgttcgtca cctccggcgc ggtcgcggtc   29760
gccgacgagc aggtacgtcc ggcctcggcg gctgtctggg gcctggtccg ctccgcccag   29820
tccgaacacc cggggcgctt cgtcctggtg gacgcggact ccgtcgccga ccccggcccg   29880
gagttcgacc gggccctgcg gaccggtgcg gaccagctga tcctgcgaga tggaacggcc   29940
ctgataccga ggctggttcg agcccgcgcg gacggcggat cgggcggatt cgtgcccgct   30000
gccgacggca cggtcctgat caccggcggc accggcaccc tgggcacgct gcttgcccgg   30060
cacctggtca ccgaacacgg cgtgcgccgg ctcctgttgc tcagtcggcg cggcggtacg   30120
gccgccggcg cgacggacct ggtcgcggaa ctcgccgcgt tcggtgccga ggtgacctgc   30180
gtggccgggg acgccgcaga ccgcgccacg ctggagcggg tgttggcgga catccccgcc   30240
gaacacccgc tgacggcggt gatccacgcg gcgggtgtgg tggacgacgg cgtcgtacag   30300
tccctcaccg ccgaccggct ggacgcggtg ttgcgcccta aggtggacgc cgcgtggaac   30360
ctgcacgagg cgacccggca cctggacctg accgcgtttg tgctgttctc ctctgcggcg   30420
ggtgtgctcg gaaaccccgg ccagggcaac tacgcggcgg ccaacgccct tctcgacgcg   30480
ctcgcacgcc gccggcgccg tgagggcctg cccggcagct cgttggcgtg gggctggtgg   30540
gcgccgacca gcgagatgac cgcggggctc ggcgacgccg accggcagcg gatgcgcgt   30600
ttgggtgtac tgcccctggc gccggaacag gggttggccc tgttcgacgc ggcgacgaac   30660
catgccgaac cgacaccgac cgtggtccgg atggacctcg cggtgctacg caccgccgga   30720
tcgttggtgc ccacgctgct gcgcggtctg gcccgggtgc caaccggcg ggctgcgacg   30780
gcgggttcgg tggccgagct gcgccgtcgt ccggccggcg tatcggcctt cgactgggag   30840
cagacgctga tccgggcggt gtgcgtgcat ccgccgccg tcatcggcca cgccgacgcg   30900
accgagatcg atgagacacg ggcgttccgc gacctgggct tcgattcgct cacaggtctg   30960
gagctgcgca atcgactgaa cacggcaacc ggactgcggc tgcccgccac gctggtcttc   31020
gactacccca gcccggtggt cctgggccgg tggttgcgtg atcggctcgc cgaggaggac   31080
gccggggggcc cggtcggctc gaccctcgga gcgcaggtgg tgtcgccggt cggttccgac   31140
gccgcgagg actcgatcgt gatcgtcggc atgggctgcc ggttccccgg cgggatcacc   31200
gcgcccgaac acctgtggga cgtggtggcc ggtgggggtgg acaccctcac cgacttcccc   31260
accgatcgtg gctgggatgt cgagcgcatc ttcgacccgg acccggaccg acccggcagc   31320
```

-continued

```
acctacgtgc gcaccggcgg attcgtggac tcggccgccg acttcgaccc ggacctcttc    31380
gggatctcgc cgcgtgaggc gttggcgatg gatccgcagc agcgattgct cctggagacg    31440
gcgtgggaga cgttcgagcg ggcgggcatc gatccgacct cgctgcgcgg cagccggacc    31500
ggggttttcg ccggcgccat ctactacgac tacgcgggtg gccggctgcg gaaggtgccg    31560
gacgaactgg aaggctacat cggcaacggc aatgtgggca gctcgcctc gggccgggtg     31620
gcctacacgt tcggtctgga ggggccggcg gtcaccgtgg acacggcgtg ctcgtcgtcc    31680
ctggtggcgt gcacctggc ggtgaacgcg gtgcggtcgg gcgagtgtga actggccctg     31740
gcgggtggcg tcaccgtgat gtcgacgccc agcgtcttcc tcgacttctc ccggcagcgc    31800
ggcctgtcgt ccgacggccg gtgccggtcg ttcgcggcgg cggcggacgg caccgggtgg    31860
ggtgagggtg tcgggttggt gctggtggag cggttgtcgg atgcgcggcg caatgggcat    31920
ccggttctgg cggtggtgcg tgggtcggcg gtgaaccagg acggcgcgtc gaatggtttg    31980
accgcgccga acgggccgtc gcagcagcgg gtgatccggc aggcgttggg cagcgccggg    32040
ttgtcgcccg ccgatgtgga cgccgtggag gcgcacggaa ccgggacgac gttgggtgat    32100
ccgatcgagg cgcaggcgtt gttggcgacc tatgggcagg atcggccggg ggatcggccg    32160
ctgtggctcg ggtcggtcaa gtccaacctc gggcacacgc aggcggctgc gggtgtggcc    32220
ggggtgatca agatggtgtt ggcgctgcgg catgggtgt tgcctcggac gttgcatgtg      32280
gacgagccga cgccgcatgt ggattggtcg gccgggcggg tcgaggtgtt ggcggacgag    32340
gtggcgtggc cggcggggga gcgggtgcgc cgggcgggtg tgtcgtcctt cggaatcagc    32400
gggacgaatg cacacgtggt gctgaagag ccgccgccgg tgaccgaagt gccggatgtg      32460
gccgtcgagt ccgggctggg cggcggcac acctgggtgg tgtcggcgcg gtccgaggca     32520
gcggtacggg aacaggcggc ccggctgcgc gactgggtca cggcccgtcc ggatctcgat    32580
ccggcgcacg tggcccggtc gttggtgtgc gaacgggcg tgttcggcca tcgggcggtg     32640
gtctccggcg ccgatctcgc cgagctggcc gatgggttgt ccgccgtggc ggcgggcgcc    32700
gagggcgcgg tggtcggtgc ggtgggtcgc gggccgggga agacgccgt gctgtgcacg     32760
ggtcagggg tgcgggcgct cggtataggc cgcgaacttc acgcggcgtt cccggtgttc      32820
gccggcgccc tggacgaggt gtgtgcggcc ttcgacgatg tggtgccgtt ctcggtgcgg    32880
gacgtcgtgc tcggtgccga aggggtgtcg gatgccgacg cgcaggacac cggggtggcc    32940
cagccggcgc tgttcgcgtt cgaggtgcg ctgtaccggc tgtgggcctc gtgggggcag      33000
gcgcccgact tcgtggtggg gcattcgctc ggcgagatcg ttgcggcgca tgtggcggga    33060
gtgttctcgc tcgcggatgc ggtggtcttc gtcgcggcgc gggctcggtt gatgagtgcg    33120
ctgccgagtg gaggggcgat gctcgccgtc ggtgcgagcg aggccgaggt ggcggcgtcg    33180
tgcccggccg aggtgacgat cgcagcggtg aacggcccgg cgagtgtggt ggtttccgga    33240
cccgccgagg cggtggccgc gctcgaaccg gactgcgtga tgcgcgggtg gcggatctcg    33300
cgcctgtcgg tgtcgcacgc cttccactcg gcgctgatgc aaccgatgtt ggccgaactc    33360
cgcgaggtgc tgaccgggtt gacctacggc acgcccgaga tcgcggtggt gtcggacacc    33420
accgggcggt tgcgggcgc cgaagagttg gctgatcccg agtactgggt gcggcacgta    33480
cgccgcgcgg tgcgcttcgg ggatgcgatc gccacgctgc gcgccgaagg ggtacggacc    33540
ttcgtggaga tcgggccgga ggcggcgttg accgcgatgg tggtcgaggg cacggccggc    33600
gcggaggacg tggccgccgt agcgacccgg cgtcggggtc gagcggccgt gtcgagtgtg    33660
```

```
gtggaggcgc tcgcccgggt gttcgtgcac ggcgcgacgg tggattgggc cgcgttgtcc   33720
accggttccg ggcccggggg acgggtggat ctgccgacct acgccttcga gcggcggcgc   33780
ttctggttgc acgccggtgt ggacgcgggc gacgcggtcg ggctggggca gggtgtggtg   33840
gaccatccgc tgctcggtgc ggtcgtgggc ctggcggacg accagggcgt cctgttcacc   33900
ggccggttgg ccctggacac ccatccgtgg ttggccgaac acaccgtctt gggcacggta   33960
ttgctgccgg gcacggcatt cctggagctg gccctgcacg tcggccgcct cctggactgc   34020
gcgcgggtcg acgagctgac cctgtcggcc ccgctggcgc tgccgtcgac gggcggtgtg   34080
caggtccagg tccgagtcgg tgtaccggag gagagcggga cacggacgat cacggtgcat   34140
gcccgcccgg attcggcgga ggaggcgcct tggacgctgc acgccgccgg ggccctgggt   34200
ccatcagccg aggtggatgc accctcggat gccgcgagtt ggccgcctgc cgatgcgacc   34260
gcgatggact cggcggggct gtatccctgg ttcgccgaga ccggcgtcga ctacggaccc   34320
tcgttccggg gcgtacaagc gacctggcgc cgtgatgacg aggtgttcgc ggagatcgtg   34380
ctcgcggccg acgacccggc cgccgacggc cggttcgagc tgcaccccgc gctgttcgac   34440
gccgcgttgc acccgctggg cctgaccctg ctcgacgcgg cggagccgcg cctgcggctg   34500
ccgttctcct ggcgcggagt ggcgctgcac acgtccgggg ctcgcacgtt gcgggttcgg   34560
ctgcgtccca ccgggcccga caccatcgcg gtgacggcca ccgacgagac gggtcgaccg   34620
gtggtcgcgg tcgaggccct ggcggtgcgc gaaccctcgc gggaccgact gccacgaccc   34680
gacgcgaacg cgggcgagtt gttcgagccg cagtggacgc cgctgtcacc ggcggacacg   34740
gcggacatgg cggacacgct cggggcggtg gtgggcggcc ccgaactcgc ctcgacagcc   34800
acccgattcg gtgccacaca tcaccctgac ctggccgccc tggccgaatc ggcaatcccc   34860
gagacggtcc tgtacgacct ggtcaccgcc gttcccggcg tatccgccga agccgtacac   34920
caagccgccg cccaagcgct ggacctggcc cgatcctggc tcgccgacga gcgcttcgag   34980
tcggcccgcc tgatcgtgcg caccccgacac gcggtcgccg ccgccgaagg cgacgcgccg   35040
gacccggccg ccgccgcgac ccatggcctg tttcgtaccg cctgctccga acaccccgag   35100
cggttcgcgc tcgtcgacgc cgacgacctc gacgaggtct cgcccgaggc catcgccgcc   35160
gtcgtggtcg agcccgaggc ggccgtgcgg gccggtcgcg tcctggttcc gcgcctgcgc   35220
cgagcggccg tggcgcccaa ggccgacttc ggcttcgccg ccgaaggcac cgttctgatc   35280
accggtggca ccgagcacac tgggcggcag gtcgcccgcc acctggtgcg cgtacacggg   35340
gtgcgccgcc tcctcctgct ctcccgtcgc ggcgacgaag cccccgaggc cgccgagttg   35400
cgggccgaac tgatcgaggc cggcgcgcac gtcaccttcg ccgccggaga cgctgccgaa   35460
cgtgcgctgc tggccgacgt gttggccgcg atcccgccg cccacccgct gaccggcgtg   35520
gtgcacctgg ccggggtgac cgacgacggg ctggtcggga cgctgacccc cgagcggctg   35580
gcggcggtgt tgcgccccaa gatcgacgcg gcgctgcacc tggacgaact caccgccgac   35640
gccgacctgt cggcgttcgt cctgttctcc tcggccgccg gtccggtcgg caaccccggc   35700
caggccaact acgcggcggc caatgtcgcc ctcgacgcgc tggcccgccg cgccgagccg   35760
ccggccgac cggccgtgtc gttgcagtgg gggttgtggg ccgaacgcag tgcgctgacc   35820
gcgacgatga gcgcgaccga tcggcgccgg cggccggccc cgggtgtgcg ggcgttgtcc   35880
gtggagcagg gcctcgcact gctggacgcg ggccgggc gcccgaggc ggtgctgacg   35940
ccgctgcgcg tcgatccggc gatcctgcgc ggtccggagg agcgggtggc gcccgtgttg   36000
cgcgggctgg tgccgacccg ggcccggcgt gcgccggccc gtacctcgga caccgcccgc   36060
```

```
tcactggtgc gccgattggc cgcgttgccc gaggccgagc aggaccggct gttggtcgac    36120
ctggtccgta cccacgcggc cggtgtgctc ggccacgccg acgcgcgcac gatcgacccg    36180
gaccgcgcgt tcggcgaact gggcctggac tcgctggcgg cgttggaact gcgcacccgg    36240
ttgagcacgg cggtcgggct gcgcctgccc gccacgatgt tgttcgacca tccgtgcgcg    36300
cgtgccgtgg gcgtacacct gcgcgcgcaa ctgctcgacg cgccgacacc cgggcgggcg    36360
gcgggtgtcg cccggccggt gtcggacgag ccggtcgcgg tggtggcgat cagctgccgc    36420
ttccccggcg cgtcgcgag ccccgaggac ctgtggcggc tggtgtcgga acacaccgac    36480
gccatctcgg agttcccgca ggatcggggc tgggacctgg ccgagctgtt ccacccggac    36540
cccgaacatg ccggtacctc gtatgtaagc gagggcggat tcctttacga ggcaaccgag    36600
ttcgacccgg agttcttcgg catctcgccg cgcgaggcgc tggccatgga cccgcagcag    36660
cggttgctcc tggaggcgtc ctgggaggcg atcgagcgcg ccggcgtgga tcccaggtcg    36720
ctgcgcggca gtcgtaccgg ggtgtacgcg ggcctgatgt acgccgacta cgcgtcgcgg    36780
ctgggcagcg cgccggaggg cgtggacggc tatctcggca acggcagcgc gggcagtatc    36840
gcgtccgggc gggtggccta cacgctgggt ctggaggggc ccgcggtgac cgtggacacc    36900
gcctgctcgt cgtccttggt cgcactgcac ctggcggcca acgcactgcg ccagggtgag    36960
tgtgatctgg cgctggcggg cggggtgacg gtgatgtcca gcccggccac gttcgtcgag    37020
ttctcccggc agcgcggcct ggccccggat gcgcggtgca agtcgttcgc ggccggcgcc    37080
gacggtacct cgtggtccga gggcatcggt ctgctcctgg tggaacgcct gtcggacgcg    37140
cgccggttgg gccatccggt gctggccgtg gtgcgcggca gtgcgatcaa ccaggacggc    37200
gccagcaacg gcctggccgc gcccaacggg ctcgcccagg agcgggtgat ccgggatgcg    37260
ctcgcgcacg ccgagttgcg tccgtccgac gtggacgcgg tggaggcgca cggcaccggc    37320
acgccgctgg gcgaccccgat cgaggcgcgc gccctgctcg ccacctacgg gcaggaccgg    37380
ccggcggatc ggccgttgtg gctggggtcg gtcaagtcca acctcgggca cacccaggcg    37440
gcggcgggcg tggccggcgt gatcaagatg atcatggcga tgcggcatgc cgaactgccc    37500
gggacgctgc acgtggacgc cccctcaccg cacgtggact ggtcggcggg ggcggtgtcg    37560
ctgctcaccg ccgcgacccc gtggccgcag accgggcgtc cgcgccgtgc gggggtgtcg    37620
tcgttcggga tcagcgggac caacgcgcac gtgatcctgg aacagggcga ccccgccccg    37680
accgcgcccg ccgaaccggc accggcgtcg gcgcctttgg ccgcgctggc gtggccactg    37740
tccggggcga gcgcggtggc actgcgcggg caggccgagc ggctgcgcgc acatctggac    37800
gcgcaccccg agtacgggcc ggtcgacatc gcgcacgcgc tcgtcggcgg ccgatcccgg    37860
ttcgaacacc gcgccgtggt ggtcgccgag gacgcggcgg gcctgcgggc cgggctggac    37920
gcgctgagcg ccgaccggcc cgacgcgcg gtgccggtgg gcgtggccgg cgaacccggc    37980
cggatcgcct tcgtgttcgg cggacagggt tcgcagtggc ccggcatggg cgcccgactg    38040
ctcaccgagt cgccggtctt cgccgccggg atccgcgact gcgacgcggc actcgcgccg    38100
cacaccgact ggtcgctgct cgccgtgctg cgcggcgagc ccgacgcgcc gccgctcgac    38160
cgggtcgacg tggtgcaacc ggtgttgttc gcggtgatgg tcgcgctcgc cgaactgtgg    38220
cgctcgctgg gcgtacggcc ggcttcggtg gtcggccact cgcagggcga gatcgccgcc    38280
gcccacatcg cggcgcgct cacccctcgac gacgcggccc ggatcgtcgc actgcgcagc    38340
cgcgccctgc gcgggttgtc cggcgacggc gggatgatgt ccgtcgcggc cggccgggag    38400
```

```
cagatcgccc gattgctcga cggattcgcg gaccggctcg gcatcgccgc cgtcaacggc   38460
cccgccgccg tggtgatttc cggcgcggcc gacgcgctcg ccgaactgca cgcccactgc   38520
gaggcggacg ggatccgcgc ccgggtgctc ccggtcgact acgcctcgca ctccgcccag   38580
gtcgagcagg tccgcgagga actgctcgcc gccctgggcg agatcgtgcc cacgccgacc   38640
accgacgcgg tcttctactc ctcggtcacc ggcgaacccg tcgagggcac cgcgctcgac   38700
gccgagtact ggtaccgcaa cctgcgcgcc accgtcgcct tcgaccgggc caccgatgcc   38760
ctgctgcggg acggcacac ggtgttcgtc gagaccagcc cgcatccggt ccttgcgccc   38820
gccgtcgagg atagtgccca gcgcgccggt acggacgtga cggtcgtggg cagcctccag   38880
cgcgacaccg acaccctcgc ccgtttcctc accgccgcgg ccggcctgca cgtgcacggc   38940
gtcccggtgg actggtccgc gacccacgcc ggacaccggc cccggccggt cgacctgccc   39000
acctacgcat tccaacgcga gcgctactgg ctggaggcgg gcaagacgcc caccgacgcg   39060
gccggcctcg gcctgcaccc ggcggcacac ccctgttgg gcgcggccgt ggtaccgcc   39120 gagggcgacc ggcacatcct caccggccgc atctcgctgc gcacccaccc ctggctcgcc   39180
gaccacacga tcctggacac ggtgctgctc ccgggcaccg cgttcgtcga actcgccctc   39240
caggcgggcg atcgggccga ctgtgacctg atcgaggagc tgaccgtcga ggccccgctg   39300
cggctcaccg acaccggcgc cgtacacctg caggtgttgc tggacgagcc ggacgagcag   39360
ggccgccgag cgctgaccat ccactcccga gccgacgacg cgcccgcgga gcagacgtgg   39420
acgcggcacg cgagcggggt actggcgccg gtcgcggacg gcctcgacgc cgtgccggcg   39480
accgacgccg cgtggccgcc cgccggggcc gtcgcgctgg acgtggacgg gctgtacgag   39540
cggttggccg ggcagggcta ccggtacgga ccggccttcc gggcggtgcg ggccgcgtgg   39600
cgcctgggcg atacggtcct ggccgaggtc gcgccgggcg acgaggcgca cggcgcacgg   39660
gacttcgcgc tgcacccggc cctgctggac gccgcgctgc acgccgccgg cgccgccgac   39720
agcggaacat ccggcgggga cggtgccatc ggcctaccct tcgcctggac cgacgtacgc   39780
ctgcacgccg tcggcgccgc cgcgctccgg gtccgcctgg aacgccgcgg cccggacacc   39840
gtcggcctcg aactcaccga tcacaccggc gccttggtcg ccaccgtcgg tgccctggtc   39900
ggccgccccg cgaccgccga ccggctcgcg cccgccgccg accggccca ccgcgacctc   39960 caccacgtcg actggtcccc gctgcccact cccaccgaac ccagcaccgc ccgctggtcg   40020
ttgctcggcc cggacgaact ggaggcggtg gccgggctgc gcgccgccgg cgccgaggtg   40080
cacgcggacg gcgaccccga ccccgccgac gtactgctga tcacctgcgc cggccggacc   40140
ggggacgacg tccccgaagc cgcccggccc gccacacacc gcgtactcga cctgctccag   40200
cgcgcactga ccgaccacg cctcaccgca tgcaccctgg tcgtgctgac ccggggcgca   40260
gtacccgggc accacggcga ggacgtgtgc gacctggtcg ccgcgccgat cgtgggcctg   40320
gtccgctccg cgcagaccga acacccgggc cggatcgtgt tggtcgacct ggacgaccac   40380
gccgactcct tcgccgcgct gcgcgccgcc gtcgtcaccg acgtcggcga accgcaactg   40440
gccatccgca cggcaccgt gtccgcaccc cgactgatcc gcaccggcac cgaaccgcgc   40500
ctgagcccgc ccgccggcgc cccggcctgg cggctcgacc tgctcggcgg tggcaccctg   40560
gaccggctcg cgctgctccc gaacgccgac gcggcggtcc cgctcgcgcc cggacaggtc   40620
cggatcgccc tccgcgccgc cgggctgaac ttccgcgacg tcgtggtcgc cctcggcatg   40680
gtcaccgaca cccgccgcc cggcggcgag ggggccggaa tcgtagtgga ggtcggcccc   40740
gatgtgcccg aactcgtccc gggcgaccgg gtgatgggcc tgttcggcgg cggcaccgga   40800
```

-continued

```
ccgattaccg tggccgacca ccggctgctc gcgccgatcc ccaccggctg gacctacgcc    40860
caggccgcgg ccgtcccggt ggtgttcctg accgcctact acggcctggc cgacctcggc    40920
gggctgcgcg ccggcgaatc gctgctcgtc cacgccgcca ccggcggagt gggcatggcc    40980
gccgtgcaac tggcccggca ctggaacgtg gaggtgttcg gcaccgcctc gcccggcaaa    41040
tgggccaccc tgcgcggcca gggcgtggac gacgcgcatc tggcgtcctc gcgcgatctc    41100
gacttcgcgc accggttcgg cgaggtcgac gtggtgctca actcgctcgc gcacgaattc    41160
gtcgacgcct cactgcggtt gctcgcgccc ggcggccgat tcctggagat gggcaagacc    41220
gacatccgcg accgggacga ggtgcttgcc gcccatccgg ccgcgacta ccggcgttc    41280 gacctgatgg acgcggggcc ggagcggatc cgggagatgc tggccgacct gtaccggctc    41340
ttcgagaccg gcgtgctgca cccgctgccc gtgaccccgt gggatgtgcg cggtgcggtc    41400
ggcgcgttcc ggcacctgag ccaggcccgg cacaccggca agatcgtgct gaccctgccg    41460
cccaccctcg gcgccgctcc cgacccggag ggcacggtcc tgatcaccgg cggcaccggc    41520
accctcggcg gcctgctcgc ccgccacctc gtacgcaccg ccggggtacg acacctgctc    41580
ctgatcggcc ggcgcggccc ggccgccgac ggcgcggccg agttgtccgc cgaactgacc    41640
gcgctcggcg cccgggtgac catcgcggcc tgcgacgccg ccgaccgtgc ggcgctggcc    41700
gcgctgctcg ccgacatccc ggccgaacac gcgctcacct cggtgatcca cgccgccggc    41760
gtgatcgacg acgcggcgct gaccgcgctc accccgagc ggctggaccg ggtgctgcgc    41820
ccgaaactgc acgccgcctg gaacctgcac gagctgaccc gcgacctcga cctggccgag    41880
ttcgtgctgt tctcctcgat ggccggcacc ttcggcggcg ccggacaggc caactacgcc    41940
gccgcgaacg ccttcctgga cgcgctcgcc cagcaccgcc gagcccgcgg cctggccgcg    42000
accgcggccg cctggggtct gtgggcgcag gccagcggga tgaccggaca cctgggcgcc    42060
gaggacctgg accgcattgc ccgcaccggc gtcgccgcgc tggagaccgc ccacgcactc    42120
accctgtacg acgcgctccg cgcggccgac cgccccacga tcgtgcccgc ccgcctggac    42180
ccggacgcgc tgcgcgccgc cgccccgacc gtacccgcac tgctgcgcga cctggtgcgc    42240
gacctggtgc gcccgcgcgg acgccgcgcc gccgccgaca ccgcgccgga cgccgcgtcc    42300
ctggccgagc ggctggcccg actgcccgag gagcggcgcc ggcagacgct gctgaccctc    42360
gtccgcaccg agaccgccgc cgtcctgggc cacgccaccc cggacgcggt cgccccgctg    42420
cgcccgttca aggccctcgg cttcgactcg ctcacgtcgg tcgaactgcg caaccgcatc    42480
ggtgcggcga ccggcctgcg cctgcccgtc accctggtct tcgaccaccc gaccccgcag    42540
gccctcgccc accacgtcgg cgccgaactc ctgggcgtag cgcccgtggt cgtcgaaccc    42600
gagcgacccg ccgcacacac cgacgacgac ccgatcgtga tcgtgagcgt cggctgccgc    42660
tacccgggcg gggtggccgg acaggacgag atgtggcgga tgctcgccga gggcaccgac    42720
accatcgggc ccttcccccca agaccggggt tgggagttgg acacactctt cgacccggac    42780
cccgaccggg tgggcaagtc gtacgtccgt gaaggcggat tcgtcgccga cgcggtgcac    42840
ttcgacgccg agttcttcgg gatctcgccc cgcgaggcga cctcgatgga cccgcagcag    42900 cggctccctgt tggagaccgc gtgggaaacg ttcgagcagg ccggcatcga ccccaccacg    42960
ctgcgcggca gcggcacggg cgtgttcgtc ggggccatgg cgcaggacta ccacggcact    43020
tcgcaggcga tggccgaggg ccaggagggc tacctgctga ccgggaccgc caccagcgtg    43080
atctccggcc gggtctccta cgtcctgggc ctggaggggc cggcggtgac cgtggacacc    43140
```

```
gcgtgctcgt catccctggt cgccctgcac cttgcggcga acgcactgcg tgcgggtgag   43200
tgcgatctcg cgcttgcggg cggggtggcg gtgttgacgt cgccgcaggc gttcatcgag   43260
ttcagccggc agcgcggact ggccgcggac gggcgctgca agcccttcgc ggcggcggcc   43320
aacggcaccg gctgggcga gggtgtcggc ctggtactcg tcgagcggct gtccgacgcg   43380
cgccggcgcg ggcatccggt gctggccgtg gtgcgcggct cggcggtcaa ccaggacggc   43440
gcctcgaacg ggctgaccgc acccaacggc ccctcgcaac agcgggtgat ccgacaggcg   43500
ttgcgcaacg cgggcctgct cgcgacggac gtcgacgcgg tcgaggcgca cggcaccggg   43560
accacgctcg gcgacccgat cgaggcgcag gcgctgctgg cgacctacgg gcaggaccgg   43620
ccggcgcaac ggccgctgtg gctggggtcg gtcaagtcca acatcgggca cactcaggcc   43680
gcggcggggg tcgccggggt gatcaagatg gtgctcgcgc tgcggcacgg gacgttgccg   43740
ccgacgttgc acgtggacgc gcccacgccg catgtggact gggcgtcggg acaggtgcgg   43800
ctgctcaccg agccggtggc gtggccggcg ggggaacggg tgcgtcgggc cgggatctcc   43860
tcgttcgggg tgagcgggac caacgcgcac gtgatcatcg agcaggcgcc ggcggagggc   43920
gcggtcgatg ccgcgccggt cgatgccgcg ccggccgccg cgctcggggg gatcgtgccg   43980
tgggtggtgt ccgcgcgatc ccaggccggg ttgcgggcgc aggcggcgcg gctgcgggac   44040
tgggccgccg tgcatccgga gttgccccg gccgacgtgg ccgcctcgct ggtgcgcggg   44100
cgggcggtgt tcgagcggcg cgcagtggtc cggggtcggg ataccgacga actggtcgcc   44160
gcactcgctg agttggtcga ctcgtcggca acgggcgagg cgccgacggc gatcgggccc   44220
gggccggtgt tcgtcttccc cggccaggga tcgcaatggg tgggcatggc ggcggagttg   44280
ctgacgtgct gcccggtctt cgcggagacc gtcacgcagt gcgccgaggt gatggacccg   44340
ctgctgccgg gctgggcgct gctcgacgtg ctgcgcggca ccgacgacga cacggccgaa   44400
ctgctgcgcc gggtcgaggt ggtgcaaccc gtgctgttcg cggtgatggt gggtctggcc   44460
cgctggtggg agtcgtgcgg ggtgcgaccg gccgcggtga tcgggcactc ccagggcgag   44520
atcgccgccg cgtacatagc cggccacctg accctgccgg acgccgcccg gatcgccgcg   44580
ctgcggatcc gcgcggtgca ggccgccgac atgatccgcg gcgcgatggt ggctgtcgcg   44640
gtatccgccc tgcgggccga ggagttgatc acccgcaccg gcaccgggga cctggtcaac   44700
gtgggcggga tcaacagccc gaccaacacc gtgttgtccg gcgacaccga cgccttggcc   44760
ctgatcgtgg ccgactgcga gcgcgagggt gtacgggcgc gctggatccc ggccgcgtac   44820
tcctcgcact cgccgcagat ggacgctgta cgcggcgacc tggaacgcct gctcgcgggc   44880 atccaacccca ccccgggcg ggtgccgatg tactccacgg tcaccggcgg ccgactcgcc   44940
gacgacgcgc tgctcgacat cgactactgg ttcgagaaca tgcggcgcac cgtgcggttc   45000
gaggaggcga tcggcgcggc ggcggccgac ggacacaccg tgttcctcga atgcagctcg   45060
caccccggcc tggtggtgcc gctcggcgac acctggact cgctcggcgt gcacggcgcc   45120
accctggaga cgctgcgccg cgcggacggc ggcgccgatc ggctgctcgc cgcgctctcc   45180
gcgatgttcg tgcacggcgg cgcggtggac tgggccgggc tgctaccggg tcgccgggtc   45240
gcgctgccca cgtacgcctt ccagcgtcgg cggcactggg tggagcccgt cggaccggcc   45300 cgaggggcg tcggctgggg gcagttcgcg gtggagcacc cgatcctggg cgccgggtc   45360 gacctggccg acggctcggc gaccgtgttc accgggcgcc tggacaccac cacacacggt   45420
tggctcgccg accacctcgt gctcggcgaa gtcctggtcc cgggcacggt gttcgtggac   45480
ctggcgctgc gcgcgggcgg cgccctcggc tgtgcggtgg tcgaggagtt ggccctgcac   45540
```

```
gagccgctgg tgttgccgga cgcggacggg gtgcggatcc aggtcaccgt cgaggcaccg    45600
gacgacgcgg gtacgcgggc gctgaccata cactcccggc ccgaggacgc gcccgccgcc    45660
gagccgtgga cccgacacgc ctcgggcacg gtggcccccg gcgcgcaccg gccgcagcag    45720
gagtccgggc catggccgcc gatcggggcg acgccgctgg acgtggcgga cgtatatctg    45780
cggttgaccg aactgggcct gggctacggc ccgacgctcg ccggactgcg ggccgcgtgg    45840
cggcgcggcg acgacctgtt cgccgaggtc gcgcgcaccg ccgacggcga acgtggcacc    45900
gcccgcttcg gcctgcaccc ggccctgctc gatgcggccc tgcacgggct tgcccccggc    45960
tcggcacccg gcggcgcacc taccgaggtg cggctggccg gcgcctggcg cggggtgacg    46020
ctgggcggca atgccggtac cgccggccgg attcggctgc ggggcgtcga cggggacggc    46080
gtcgaggtcg aactggccga cgaggcaggt cgatccatgg cccggatcga gtcggtggcg    46140
ctgcggccat ggagcgcggg gcaggtgcgg cggccgggc gggcccgacc gtggttgacc    46200
cgctgggagt gggcccgggt cgagccgacc gacccggcgg cggcaggagg tcgctgggcc    46260
gtgctcggtg cgcgggcttg ggacggggtg ccggcctatg cgaccgccgc cgaactgatc    46320
gcggccgtcg aggtcggcgt cccggttccg gatctggtcg cgctgcccgt gcggatcgac    46380
ccggccggcg ggctcgatcc ggaggcgatc cgggccacga tccgggcggt gcgcgagacc    46440
ctgcggcagt ggcgggccga ccgcggctg gcggcctccc gcctggtcgt ggtgacccac    46500
gacgcggtct cggcgcggcc cgaggaccgg gtcaccgatc cgggcgcggc ggcggtgtgg    46560
ggcgtggtcc gggcggcccg ggcggcggac cccgagcggt tcgtgctcgc cgacgtggac    46620
ggggaggacg ggtcctggcc ggtgctgctg gccgaagcgt ccgccggtcg cgccgagttc    46680
gcgatccgcg cgggcacggt actgctgccg ggcctggccc gggtaccggc gggcgagacc    46740
ggcacggcgg gcttcccgac cgacggcacg gtattggtca ctgtcgcgac cgacccgacc    46800
gacccgaccg acggcaccga cccggtcggc acactgctgg ctcggcacct ggtgaccgcc    46860
cacggagtgc gccggctgat cctggccggc gggcccgccg ccgggatgcc gcttgcccgg    46920
gaactggccg cgcagggcgc ggagatccac gtggtcgtct gcgacgtgac cgaccgcacc    46980
gaactggcga agctgctggc cacgatcccc gagcacagcc cgctgaccgc cgtggtgcac    47040
accgccgggc tcggccggtc gcacaccgag gccatgctgc gggcccgggt ggacgcggcc    47100
gtacacctgc acgaactcac ccgcgacgcc gacctgtccg ccttcgtgct ctgcaccgcc    47160
ctggacggca tactcgccga ccccgggcgc ggcgaacacg cggccggcga cgccttcctg    47220
gacgccctgg cccggcaccg gcacgccgcc gggctgcccg cgctcgcgct ggcctgggca    47280
ccgggggccc aaccggtcgc cgggctgctg ccgttgcccg gcgagcaggc cacggtcctg    47340
ttcgaccggg ccctcgggct gcccgaaccg gccctgatcc cgctcgcgcc ggacacctcg    47400
gcgctgcgcc gggccgaacc gggcgcactg ccggcgctgt tgaccacgct ggtggccgac    47460
ccgaaccacc gcgtcggcgc cgccgccgag gcggcgcccg cactgatcgg ccgactgctc    47520
gacctgccgg acgacgagcg ggaaagcgtc ctggtcgacc tggttcgcgg ctgcgccgcc    47580
gcgatcctcg gtcatgccga tccgaccgcg atcgagacgg gagcggcgtt caaggatctc    47640
ggcttcgact cgctgaccgc cctggagatg cgcaaccgac tgcgcgccgc gctgggcctg    47700
accctgccgg ccacgctgat cttcagccac cccaacgcgg cggccctggg ccggcacctg    47760
cacggcctgc tgcgccgcga gcacggggtc tcgtgggact cggtgctcgg cgagatcgac    47820
cgggtcgagg cgatgctcgc acaactcgac gacgcggacc gcgccagggc gacggagcgg    47880
```

```
ctgcgggacc tgatcggcgg cccggaagcc ccgctcgccg gccgcgagtc gggcgcgaac    47940
ggcgacgcgg ccggcggccg agggttcgac gcggccacgg acgaggagct gttcgacttc    48000
atcgacggcg ggatcgagca ctgattcgac aacggcggga tcgaggaccg acgacagatc    48060
gcggggctgg gactctcccg tcctcctgaa caggcaagga gaagcaccga tggcgaacga    48120
agacaagctc cgcgactatc tgcgccgggc caccaccgaa ctgcaggaga cccgactgcg    48180
gttgcgcgag acagaggaca agtggcacga accgctcgcc atcgtcggca tgcactgccg    48240
ctacccgggc ggggtggcct cgccggacga cctgtgggac ctggtcgacg cgggcaccga    48300
cgcgatcacc ggactgcccc cgggccgggg ctggaggtg gacgaggccg cgaacggcac     48360
gtcgtaccgg ggcggtttcc tgaccgacgc ggccgacttc gacgccgact tcttcggcat    48420
ctcgccgcgc gaggcgctgg ccatggatcc gcagcagcgg gtgctcctgg aggcgtcctg    48480
gacggtcttc gagcacgccg ggatcgatcc gaccacgctg cgcggcagcc gtaccggggt    48540
gttcgtcggg gtgatcgcca gtgactacct gtcgcgcctg gcccgggtgc ccaaggaggt    48600
cgagggccat ctgctgaccg gcagcctggt cagcgtggcg tccggtcgtc tcgcctacca    48660
cttcgggctg gagggcgcgg cggtcaccgt ggacaccgcc tgctcgtcct cgctggtggc    48720
ggtacacctg gccggccagg cgctgcgcgc gggcgagtgc gacctggccc tggtcggcgg    48780
ggccaccgtc ctgccacccc aggcgcgtt cgacgagttc tcccggcagc agggcctggc     48840
cggcgacggt cgttgcaagt ccttcgcggc cggtgcagac ggcaccggct ggagcgaggg    48900
tgtgggcctg ctgttgatgg agcggttgtc cgacgcgcgc cgcaacggac accgggtgct    48960
cgcggtggtg cgcggctcgg cggtcaacca ggacggcgcc tcgaacggac tgaccgcgcc    49020
gaacgacctg gcccaggagc gggtgatccg gcaggcgctg gccaatgccc gactggccgc    49080
gagcgacgtg gacgcggtgg aggcacacgg caccggcacc cgactcggcg acccgatcga    49140
ggcccaggcg ctgctggcga cctacgggca gaaccggccg gccgcacggc cgttgcggct    49200
gggctcgatc aagtcgaaca tcggccacgc ccaggcggcg gccggggtgg cgggcgtgat    49260
caagatggtg caggcgctgc ggcacggtgt gctgccgcgc acgttgcacg tggacgagcc    49320
gacgccgcac gtggactggt ccgccgggcg ggtggcgctg ctcaccgagc cgatggcgtg    49380
gccggcgggt gaacgggtgc gccgcgcggg ggtgtcctcg ttcggggtga gcggaccaa     49440
cgcgcacgtg atcgtggagg aggcgccgcc ggtcgaggaa ccggtcgggg cggccgatcc    49500
ggcgcggccc ctcggcgtag tgacgccgtg ggtggtgtcg gcgcgcaccg aggacggcct    49560
gcgggcccag gtggagaggt tgcgggagtg ggcgatcgag catccggagg ccgatccggc    49620
cgacgtgggc cggtcgttgg cctcggggcg ggcactgtcc ggccaccggg ccgtggtact    49680
cggccgggac gcggcggagt tggtcgaggg gttgtccgtc gtggtggacg cgcagcccga    49740
ggcgatcgtg ggcgaggccc ggcgcggatc gggccgtacc gccgtgttgt tcaccgggca    49800
gggggtgcgc tcgcgcggga tggcgcgcga actcacgcg gcgttcccgg tgttcgcggc     49860
ggcgctggac gaggtgtgtg ccgcgttcga cgcggtgttg ccgttctcgg tacgggacgt    49920
gctgctggca gagggcgagg gcggcggcgc ggacggtgac ggcggcgagg acaccggtgt    49980
ggcgcaaccg gcgttgttcg cctacgaggt ggcgctgtac cggttgtgga cctcgtgggc    50040
ggcggcgccc gacgcggtgg ccgggcactc gctcggcgag gtggtcgcgg cctatgtggc    50100
aggggtgttc tcgctcgccg acgcaaccac gttcgtcgcg gcccgcgcca cgctgatgag    50160
cgcgctgccg cccggtggcg cgatggtcgc ggtgggcacg tcggagagcg cggcggcccg    50220
gttgctcgcc gaccatccgg gagtgggcat cgcggcggtg aacgggccga ccggcgtggt    50280
```

```
gctttccggc gaggcggcgg ccgtggcgga ggttgcccgg gtgtgtgccg agcgcgggct    50340
ccgcatctcc cggctgcggg tgtcgcatgc gttccactcg gcgctgatgg aaccgatgct    50400
ggacgaactg gccgaggtcg tctcgggatt gacgctgcgt ccggcgcgca tggcgatcgg    50460
gtcgaacgtg accggccgga tcgggtcggc ggagcagctg tgcgatccgc gctattgggt    50520
ggaccacgtg cggcgcgcgg tgcgcttcgg cgatgtgctg gacgcgctgc cgccgacgg    50580
ggtgcgtacg ttcgtcgaga tcgggccgga cgccgcgttg accccgatgg ttgccgatgt    50640
cacgccgac gccgacgatg tggtggcggt cgccacccgg cggcgtgacc gcgacccggt    50700
gacgggtgtg gtcgaggcgc tggcccgggt gttcgtgcgc ggcgcggtgg tggactgggc    50760
ggcgttggtg cccggacggt gggtcgagct gcccacgtac gccttcaccc ggcggcgctt    50820
ttggctggac gccggtaccg gcgcgggcga cccgaccggc ctggggcagg ggacggtgga    50880
tcacccgctg ctcggtgcgg tggtcggcct ggccgatgga cacggttcgt tgttcaccgg    50940
gcggttgtcc ctggacaccc atccgtggct ggccgatcac gtcgtcctgg acaccgtcct    51000
gctgcccggg accgcgttcc tggaactggc cctgcacacc gggcgccggg tgggctgcga    51060
tcgggtcgag gaactgtccc tggagacccc gttggcgttc ggcgagcgcg gtggttgcca    51120
ggtgcaggta tggatcgagg cggccggcc cgacgagcgg cggcgggcga tcaccatcca    51180
ctccccggccg gacgacggag acggcgacga ggggtggatc cgcaacgcgg tgggcacggt    51240
cgcgccggtc gaggacaagg cgcccgccga cgccgtggcc gacccgaccc cctggccgcc    51300
gacgggcgcg acacccgtgc cgatcgacga cttctacccc tggctggccg acaacggcgt    51360
ggcctacgga ccgtgcttcc gggcggtgcg cgcggtctgg cgtcgcgggg aggagatctt    51420
cggcgagatt gcgctacccg agcaggtcgg gtacgaggcc gaccggttcg gcgtgcaccc    51480
cgcgctgatg gacgccaccc aacaccttct cggggtggcc gcgttcgcgg accggcgga    51540
gagcgagggc ggcggtttgg cgctgccgtt ctcgtggcgt gaggtacggc tgcacactcc    51600
cggcgcggcc tcggtacggg cgcgggtggt gcggaccggg ccggagtcgg tgacgctgag    51660
cctgccgac gaggacggcc gacccgtcgc cgaggtcgag tcgttggccg tgcggccgat    51720
ctcggccgaa caactgcgca cctccacggc gggtcgccgc gacccgctgt acacgctgcg    51780
ctggacgcca ctgccccggc cgtcggccgc gcgggcatc ggatccccgg cgatcatcgc    51840
cgattcgggc tcggggggacc cgttcgcggg ccggctcggc ggcaccgtac atcccgatct    51900
gaccgcgctc gccgacgcgg tggacgccgg gctgccgacg cccgaggtcg tcgtcctcgc    51960
gtggcccacg atcccggccg gaccgctcgg cgacgtgccg gacccggacg acgtacacgc    52020
cgccgtacac cggcgttgg ccaccgtgca gacctggctc ggggacgaac gcttcaccgg    52080
cgcccgcctc gtcgtggtca cccgggggcgc ggtcgccgtc gcggacgagg aggtgcggga    52140
tccgccgcc gccgccgtcg gcggcctggt gcggtcggcc cagtccgagc acccggaccg    52200
gctcgtcctc gtcgacctgg acgaggacgc ggcctcgccc ggggcgctgc cggccgcgat    52260
cggcgcggga gagccgcaac tcgcggtacg ggcgggggtg gcgtacctgc ccaggctcac    52320
ccggacaccc gcgatcgagc cgagcacgcc actgttcgcg cccgacggta cgaccctggt    52380
caccggcgg accggtgcgc tcggcgccct ggtcgcccgg cacctggtgg tcgcgcacgg    52440
ggtgcgccgg ctgctcctgg tcagccggcg cgggatcgcg caccgggcg ccgggtcgct    52500
cgccgccgaa ctcaccggcc tgggcgcgac ggtcgacgtg gtggcctgcg acgtgtcgga    52560
ccgggccgac ctgccaaga agctggccgc gatcccgtcc gcacacccac tgtccgccgt    52620
```

```
cgtgcacgtc gcgggagtgg tcgacgacgg ggtgatcggc gcactgacgc ccgagcgggt   52680
cgaccgggtg ttgcggccca aggtcgacgc ggcgctgcac ctgcacgagt tgacccggga   52740
cgcggacctg accgcgttcg tgctgttctc ctcggtggcc ggggtgatcg gcagcctcgg   52800
acaggcgaac tacgcagccg gcaacgcctt cctggacgcc ttcgcacagc ggcgacgtgc   52860
cctcgggctg cccgcggtgt ccatggcctg gggattgtgg gccgaggaaa gcgggctgat   52920
gcgtgaggag ttcgccgaga ccgaccggca acgcatcaac cgcagcggtg tattgccgct   52980
gtccgacgaa cagggcctgg cactgttcga cgcggcgctc gcgcacggcg agccgatcct   53040
ggccccggtc cgcctggacc tgagcgcgct gcgccgcctg gaggacgaac ttcccgccat   53100
cctgggcgga ttggtgccca cctcgcgccg cgacggcgcc cgccccggcg cggcggacac   53160
ccgccgactg gcccagcggc tcgccggccg ctccgagccg gagcagctgc gcctgctcac   53220
cgaactgacc cgcgcccagg ccgccgtggt gctcgggcac gcgggcgccg acgcggtcgc   53280
cgccgaccgc gcgttcaccg aactgggctt cgactcgctc accgcgctgg agatgcgcaa   53340
ccggctcaac acggtcaccg gcctgcggct gcccgccacg gtgctgttcg actatcccaa   53400
cgccgccgcg ctgccccgct tcctgcgcgc cgagacgctg cgcgtaccgc agtacaccca   53460
ggcggcggcg aacactgccg ccaaggcccg gacttcggac gaaccgatcg cgatcgtggc   53520
gatgagctgt cgctacccgg gcggcatcga caccccgag gagttgtggc gctgcgtcgc   53580
cggcggagtg gacctgacct cgccgttccc gaccgaccgc ggctgggacc tgggcgcgct   53640
gtacgacccg gacccggacc gctccggcg ctgctacacc cgcgagggct cgttcatgcg   53700
cgacatcgac cgcttcgacg ccgaactgtt cgggatctcc ccgcgcgagg cgctggccat   53760
ggacccgcaa cagcggctgc tcctggagac ctcctgggag gcgttcgaac gcgcgggcat   53820
cgacccgtcc tcgctgcgcg ggagcaatac ggcggtcttc gcgggcctga tgtacgcgga   53880
ctacgccgcg ggtcgagtgg gtgacgtcgg cgacgagttg gaggcgtaca tcggcaacgg   53940
caactcgttc ggcgtcgcct ccggtcgggt cgcctacacg ctgggactgg agggcccggc   54000
ggtgaccgtg gactcggcct gctcgtcctc gctggtcgcg ctgcactggg cggcgcacgc   54060
gctgcgcagc ggggaatgtg atctcgcgct ggcgggcggg gcgacggtga tgtccacgcc   54120
cagtgtcttc gtggagttcg cccggcagcg cggcctggca cccgacgcc ggtgcaagtc   54180 gttcgccgcg gcggccgacg gcacggcgtg gggcgagggc atcggcatgt tgctggtgga   54240
gcggctggcc gatgcgcgcc gcaacgggca tccggtcctc gcggtgctgc ggggttcggc   54300
gatcaaccag gacggcgcct ccaacggcct caccgcgccc aacggcccgt cgcaacagcg   54360
ggtgatccgg caggcgctgg cgaacgccgg gctggccacg gccgatgtgg acgcggtcga   54420
ggcgcacggc accgggacgg tactcggcga cccgatcgag gcccaggcgc tgctggccac   54480
ctacggtcgg gaccggccgg cggaacggcc gctgtggttg ggatcgatca agtcgaactt   54540
cggccacacc caggcggcgg ccggggtggc cggggtgatc aagatggtga tggcgatgcg   54600
gcacgggatg ttgccgccga cgctgcacgt ggacgaaccc tcgccgcatg tggactggtc   54660
gaccgggcgg gtcgaactgc tcgccgaggg gcggccgtgg cccgaggtgg ggcgggcccg   54720
tcgggtggcg gtgtcctcgt tcgggatcag cgggaccaac gcgcacgtca tcctcgaaca   54780
ggccgacgag gagccggaac ccgccgcccg aaccacgtcc ggcaccggca tcggcggggt   54840
gctgccgtgg gtgctctcgg cccggaccga ggcgggcgtg cgggcccagg cggcccggct   54900
gagggactgg gccggggccc ggcccgaggt cgatccggcc gacgtgggct ggtcgttggc   54960
gtcgggacgg tccgtattcg agcggcgcgc ggtggtgtgg ggccgggacg gcgcggagtt   55020
```

```
gacggcgggc ctggacgcgc tggcggccgg gcgggatgcg ggagcacgtg ccgtgcttgc    55080
cggcggcacc ggcgtgtcgg gcgaggcggc cgtcgggccg gtgttcgtgt ttcccggtca    55140
gggctcgcag tgggtcggga tggcggcgga actgctgacc tgctgcccgg tgttcgccga    55200
gtcggtggcg gagtgcgcgg cggcgatgga tccgctgctg gccgactggg cactgctcga    55260
cgtgctccgg gacgcgtccg ccgcgctgtt ggagcgggtg gatgtgatcc agcccgtgct    55320
gttcgccgtg atggtcggcc tggcccggtg gtgggagtcg tgcggggtgc gaccgagcgc    55380
ggtgatcggg cattcccagg gggagatcgc cgccgcgcat gtggcgggct tcctgtccct    55440
ggaggacgcg gtccggatcg tggtgctgcg cagccgggca ctgcgggggc tcgcggccga    55500
cggtgacggg atgttgtcgg tgggcgtgtc cgccgagcgt ggccgcgaac tcgtggcacg    55560
cgtgcaggga ttgtccctgg cggcggtcaa cgggcccgac agcgtggtgc tttccgggcc    55620
ggtcgagggt ctgacgccaa tcgccgccgc gtgcgagcgc gacggggttc gggcgcgatg    55680
gatcccggtg gactacgcct cgcactcggc gcggatggac gacgtacgcg aggtgctggc    55740
cgagtcgctg gccggggtcg agccggggat cgggcgggtg ccgatgtact cgaccgtgag    55800
cgggctgaag gtcaccgatg cggcggatct gggcggggag tactggttcg agaacttgcg    55860
tcgcaccgtg cagttggcca cggcggtcgg ggcggcggcg gccgacgggc acagcgtgtt    55920
cgtcgaatgc agcccgcacc ccggtctggt ggtgccgctc ggcgacaccc tcgacgccct    55980
cgggagcacg tccggcacgg tcctggagac gctgcgccgg ggcgagggcg gccccgaacg    56040
cctggtcgcg gcactggcag cggccttcgt gagcggcctg ccggtcgact gggccgggct    56100
gctgcaccac gacggggtcc ggcgagtaca gctgccgaca tacgccttcc agggccgccg    56160
cttctggctc gaaccggaca tgggcacggc gctgcccggc cggacgacac cgacgccggt    56220
ggtgggcgac accgaggaca gcaggttgtg ggaggcgctg gaggcggcgg gcgccgagga    56280 cttgccgcc gaactggagg tggcggcgga cgcgccgctg agcgacgtgt tgccggcgct    56340
gacgtcctgg cgggcgcggc ggcgggcgga cgcgacggtg cggtcctggc ggtacggagt    56400
gcggtgggag ccgtgggcgg cgccggccgc ctccgccgac aggatggggc gtctgctgct    56460
cgtcgctccg gacggggaga tcggggacgt gctcgcgggc gcgctggccg agtgtggtgc    56520
cgaggtggtg gtgctgtccg cggagggggga acggaccgcg ttggcgcggc ggctcgcggc    56580
aatcggcgag gagggtgtgc cggccggggt ggtgtcgttg tcggcggtgg gttgcgccgc    56640
cgacgcggat cccgtgcccg cgctcgcgcc ggtgctcacg ctggtgcagg cgctgggcga    56700
cgccgggatg gaggcaccgt tgtgggtgct gacgcgcggc gcggtgtcgg tgctgggcga    56760
ggagccgacc ggcccggcgg gtgcggccgt gcagggctc gggcggtgg tcgggctgga    56820 acatcccggg cggtggggtg ggctgatcga tctgccgcag gtggtggacg ccgggtggc    56880 ggagacgctg gcggggatcc tggcggccgg cgcgggcggc accggctcgg gtgaggacga    56940
gatcgcgatc cggccgctgg gagtgttcgt ccggcggttg gcgcggatgg ccgggccgga    57000
gggcagcggc acgagccggt ggcgcccgg tggtacggcg ttggtcaccg gcggtaccgg    57060
tgcgctgggc gggcgggtcg cgcggtgct ggtccggag ggcgtcgagc gggtggtgtt    57120
ggccgggcgg cgtgggcccg acgcgccggg cgcggaccga ctgcgcgagg aactggcggc    57180
ggccggggcc gaggtggcgg tgctcgcctg tgacctgggc gatcgcgacg cggtggccgc    57240
gctgttggcg gaggtgcggg ccggcggccg gcggatcgac accgtcgtac acgcggccgg    57300
cgcggtggtg gtcggcccgc tggcggacag caccgtcgcg gatctcgccg acgcctcggc    57360
```

```
ggccaaggtc ggcggcgcgc tgctcctgga cgagttgttg cgggccgacg agcccgacac    57420
cgtggtgctg ttctcctccg ccgccggggt gtggggcggc gcggggcagg gggcgtacgc    57480
ggcggccaat gcctgcctcg acacgatcgc cgagcggcgc cgggcgcgcg ggctgcgtac    57540
cgtctcgatc gcttgggggc agtgggccgg tggcgggatg gccgacggcg cggccggcgc    57600
gcacctcgac cggatcgggg tcccggcgat ggacccggat cgggccctgg aggcactgcg    57660
gcaggccctg gacgaggacc tgacctgcgt caccgtggcc gacgtggact ggccgaggtt    57720
cgccgccggg tacacggcgg cccgccgcg accgctgatc gcggacctgg tggcggcgga    57780
ggtcgcggcg gcgccggtca ccgaagcgcg cggggcgggc gagccggacg gtccgagtgt    57840
gtggcgggcc cgactggccg aactgggcgc ggcggatcgg gaggcggaac tgctcgcgct    57900
ggtccgcacc gaggtcgccg cgcagttggg ccacgccgac ccggccgcga tcgaacccga    57960
acggccgttc cgcgatctcg ggttcgactc gctcgcggcg gtgggcctgc gcaaccgact    58020
gaccgagacc atcggtctgc ggctgcccag cacgctggtc ttcgaccacc cgacggccgt    58080
cgcactggcc gcgcacatcg acggcgaact cttcgccgag accgtcggga cggtctccgt    58140
cttcgccgaa ctggaccgcc tggaagcggc gctcggcgaa ctgggcggcg acttcgccga    58200
acggggcagg gtcggtgccc ggttggccga actcgccggg aaatggcggg agatcgaggc    58260
cgcgagccaa aaggccgagc ccgagggagc cgacttcgcg gcagcggagg acgaggagat    58320
gttcgacatg ctcggaaagg agttcggcat ctcctgagcg gggccggcga cgaccgccgg    58380
tcacgggtcc cgacggcaca cggctcgatc aggttcgacc aggcagagga cggacgtacg    58440
gacatgtcga acgaagaacg gctgcggcac ttcctccggg agaccgccac ggatctgcgc    58500
cgcaccaagc agcggctgca cgaggtggag tcggccgccc gcgagccggt ggcgatcgtg    58560
gcgatcgggt gccgactgcc gggcggcgtg cgctccgccg aggacctgtg ggagctggtg    58620
cggaccggga cggacgcgat cgccggcttc ccgtccgacc ggggttggga tccggcgaac    58680
gtctacgcgg acctgccggg cggcgagggc gtctcgggcg gttcggccgg atccggcggg    58740
tcgaccaccc ggcagggcgg attcgtctac gacgcggctg cgttcgacgc cgagttcttc    58800
ggcgtctcgc cgcacgaggc gttggcgatg gacccgcagc agcggctgct cctggagacc    58860
gcgtgggaga ccttcgagcg ggccggcatc gatccgctgt cgatgcggcg cagccggacc    58920
ggcgtgttcg tcggcgccgg tgcgctcggc tacgcggcg ggatgcgggc ggacaacgcc    58980
gagatccagg cccatcgggt caccggcggc tcgatgtccg tggtgtcggg gcggatcgcc    59040
tacacgctcg gtctggaggg cccggcggtc accctcgaca cggcgtgttc gtcgtcgctg    59100
gtggcgctgc acctggcggc caacgcgctg cgctcggggg agtgcgacct ggccctggcc    59160
gggggcgtca cggtgatggc ccggccgacc gccttcgtgg agttctcccg gcagggcgga    59220
ttggcctcgg acggccgctg ccggtcgttc gcggcggcgg cggacggcac cgggtggggt    59280
gagggtgtcg ggctgctgct ggtggagcgg ttgtcggatg cgcggcgcaa cggccatccc    59340
gtactggcgg tgctgcgcgg ctcggcggtg aaccaggacg gcgcgtcgaa cgggttgacc    59400
gcgccgaacg ggccgtcgca acagcgggtg attcgacagg cgttggcggc ggcgggcttg    59460
tcggccgccg atgtggacgc ggtggaggcg catgggaccg ggacggtgct cggcgacccg    59520
atcgaggcgc acgcgctgtt ggccacctac gggcgggatc ggcccgcgga tcggccgttg    59580
tggctggggt cggtcaagtc caacatcggg cacacccagt ccgcggccgg ggtcgccggg    59640
gtgatcaaga tggtgatggc cctgcggcac gggctgctgc cgcgcaccct gcatgtggac    59700
cggccgtcgc cgcacgtgga ctgggcctcg ggacgggtcg agctgctgac cgacgaggtg    59760
```

-continued

```
ccgtggcccg cgggcggtcg ggtgcgtcgg gcgggtgtgt cgtcgttcgg gatcagcggg    59820
acgaacgcgc acgtggtcct ggaggaggcg ccggccgtcg agggggcctc gggggagggg    59880
gccgaacccg cgccggtgt cggtgggttg attccgtggg tggtatcggc gcgctccccg     59940
gaggcgttgc gcgcgcaggc ggcgcggttg cgggagccgg cggtcgcgga tccggcggat    60000
gtcggtcggt ccttggtgac gggacgggcg ttgctcgacc atcgggcggt ggtgctgggt    60060
cgggacgccg ccgagttggg ccgtggactg gccgcgttgg cggccgggtc tccgggtgcg    60120
gtcgagccgt cggagggggg aactccggtc gtggtgaccg ggaatgtgcc ccgagcgggt    60180
ggtgcgggtg gtcgggtcgc cgggcgggc gcggtggtgt tcaccgggca ggggggtcgg     60240
ttgcccggga tcgggcggga actgtacgcg ggtttccgg tgttcgctcg cgcgctggac     60300
gaggtgggtg cggcgttcga cgcggtggtg ccgttctcgg tccgggacgt gttgctcggc    60360
gtggagggca cggtcggcgt cgatgccgac gacaccggcg tggctcagcc ggtgttgttc    60420
gcgttcgagg tggcgctgta ccggctgtgg agttcgctgg ggtcggtccc ggatttcgtg    60480
gtcggacact cgttgggtgg gatcgtcgcg gcgcatgtgg cggggtgtt ctcgctcgcg     60540 gacgcggtgg cgttcgtcgc ggcgcgcgcc cggttgatga gcgcgttgcc gggcggggc     60600 gcgatgctcg cggtggggc gagcgaggcg caggtcaccg cgctgtcgga tgggctgccg     60660
gtgtcgatcg cggcggtcaa cggaccggcg agtgtggtgg tttcgggcgc ggtggcggcg    60720
gtggacgagg tggcggcgcg cgtgtgcggcg cgcagttggc gcagttcgcg gttgcgggtc    60780
tcgcacgcct tccattcggt gctgatggag ccgatgttgg ccgaactacg ggacgtgctg    60840
cgccggttgt cgttcggggc gccggagatc gggttggtgt cggataccac cgggcgggtc    60900 gttacgccg aggaggtggg tgatcccgag tactgggtgc ggcatgtgcg cgacgcggtg     60960
cggttcgcgg atgcggtcgg cacgttgcgt gagcggggtg tggccacctt cgtggaactg    61020
ggtccggacg cggcgttgac cgcgatggtg gccgagtgca cggcgggtgt gggcgaggtg    61080 ctggggggtgc cggcccagcg gcgtggccga ccggccgtgg cgacgctggc cggcgcgctg    61140
gccacggcgt tcgtgcgggg gctgccggtg gactgggtcg gggctctcgg cggcccgggc    61200
gggcggcggg tggagctgcc gacctacgcg ttccaggggc ggcgctattg gctggagccg    61260
gggaaggctt cggtgacgcc ggccgggccg gattcggtgg acggtccgct gtgggacgcg    61320
gtcgagcggg ccggggcggg cgaactggcg gcgatcctgg cggtgtccga ggacgcgacg    61380
ctgcgcgagg tggtgccggc gctgtcgtcc tggcgagccc gacgacgggt ggacgcgacg    61440
gccgcgtcgt ggcgctacgc ggtgcggtgg gagccgtggg cgggtggttc gtccgacgcg    61500
gccgcgttgt ccgggcgttg gctgctcgtg caccccggcg cgagcgagct ggcggatgcg    61560
gtggcccggg agctgaccga gcgtggcgcg gaggtggtgc gggtcggggg cgagggcatc    61620
gggtcgcacg tcggtgccga acccgtcgcc ggggtggtgt cgttgatcgg ctccggttcg    61680
ggctccggct ccacttcggg ttcgggctcg ggctccggtt ccgcttcggg ctcgggctcc    61740
gggtccggtt cgggctccgg ctccggctct ggttcgagtt gcggctccgg ttcggtgccg    61800
ggcttgggtt cgtgcgcggg cgacgactgc gccgacctcg tggccgccgt ggtggcgatg    61860
ggcgaactgc tcgcggagct gcgccggttc gaggtcgccg ccccgctctg gtgtgtgacc    61920
cgggcggcgc tgtcggttct gggcgaggac ctggccaatc ccgtgggcgc cggcctgtgg    61980
ggcaggggcc tggtgcgag cctggagcaa cccgggtgct ggggcggcct ggtcgacctg     62040
ccggccgtcg cggatacccg cgcgctgggg gtgctggcca cgatcctggc cgggacttcg    62100
```

```
gacgaggacc agttcgccat ccgcccgctg ggcgtgttca cccggcggct gacccgctg   62160
ccggccgagg gatcgggccg ggtggtgcgt accgcgaag cggcgctgat caccggcggc   62220
accggcgtgt tgggcgcgca cgccgcccgc tggctggtcg cgcacggcac cgagcgggtg   62280
atcctgctgg gccgacgcgg cgctcgggcg cccggattcg atgcgctgcg ggccgacctc   62340
gaggcggccg cgccgaggt ggtggcgatc gcctgcgacc tgaccgcgcc cgacgcggcg   62400
gagcggctgc gggccgcgtt gcccgcgacg ggtgcgccga tccgtaccgt cgtgcacgcg   62460
gcgggcgtgc ccggatcgcc caccgcgacc ggcgccgacg ccgtcgcgga caccgtcacc   62520
gccaaggtcg ccggcgcgct ggccctggac acgcttttg gggcggaccg ggccctggac   62580
gcgttcgtgc tctactcctc cggcgcgggg gtgtggggcg cgccggaca gggcgcctac   62640
gcggcggcca acgccttcct ggacgcgctc gccgtacgcc gtcggcaacg cggcctgccc   62700
gccacggcga tcgcgtgggg gccgtgggcg gccggcggga tggcggacgg cgagggggaa   62760
cggctgctgg cccgggtcgg tgtacgggcg atggacccgg ccgcggcgct ggccgcactg   62820
ggccgggccc tggtcgagga cctcacctgc gtgacggtgg ccgacctgga ccggccccga   62880
ttcgcggcgg gctacacctc cgcccgtccc cggccgctga tcgccgacct gatcgacgcg   62940
gagccgccga ccgcgaccgc cccgccgacc cggcccggcg gggtgtggga cccggcggtg   63000
acccgctcgc cggcccggct cgcggccgaa ctgctcgacc tggtccgcgc cgaggtcgcc   63060
gcgcaactcg gccacgcggg cgtcgaggcg atcgaacccg accggccgtt ccgcgacctc   63120
ggcttcgact cgctgccgc cgtcggactg cgcaaccgga tcgccgaggc caccgggta   63180
cacctggccg gcaccctgat ctacgaccac gagacacccg cggccctggc cgcacacctg   63240
gccgacgccc tgcgcgaggg tgtgcccgag accgcccgg cgccgacggc accggcggc   63300
gccgaggact cgaacgacat gctcggcacg gtctaccgca aactggccct gctcggccgg   63360
atggacgacg cggaatcgct cctggtcggc gctgccggcc tgcggcagac cttcgaggac   63420
ccgaaccggc tcccgaagac acccggcttc accggctcg cgcgcggacc ggcccggccc   63480
cgggtgatct gcttcccgcc gttcgcgccg gtcgagggcg ccatccagtt cggccggctg   63540
gcgggcacgt tcgagggccg gcacgacacg gcggtggtga ccgtaccggg ctttcggccc   63600
ggcgagccgc tggccgcctc gctggacgtg ctgctcgacc tgctggccga cgcgacgctg   63660
cggtgcgccg gagacgaccc gttcgccgtg ctcggctact cctccagcgg ctggctcgcc   63720
caggggggtgg ccggccgcct ggaggcgacc ggccgtacgc ccgccggggt cgtactgctc   63780
gacacctacc tgcccgccac gatgtcgcgg cgcatgcgca aggcgatgaa ctacgaggtg   63840
atcgtgcgcc ggcaggcgtt caccgcgctc gactacatcg ggctgaccgc gatcggcacc   63900
taccgccgga tgttccgggg ctgggagccc aagcccggct ccgcgccgac gctcgtggtg   63960
cggccctcgc gctgcgtccc gggctcgccg gaggagccga tgaccggcga ggactggcgt   64020
tccacctggc cgtacgagca caccgccgcc gaggtggagg cgaccactg cacgatgatc   64080
ggcgaacacg cggagcagac cggtgcggtg gtgcgcgcgt ggctggccgg tgacaggacg   64140
gtttcgatcg acacgaggga aggcacggca tgaccgaccc gcgctatccg cgataccgcc   64200
aacccggctc cgtcgaccat ctcgacgcgg agttcctggt ccaccgggcc gcgatccagg   64260
atctcgtcgc cgcgtacagc ctgctctacg acgggcga ctacgacggg ctcggcgacc   64320
tgttcaccga ggacgcgacg tacgcgttca ctcccgcccc cgagggattt ccgccctcgg   64380
tgtccggccg ggacaagatc gtcgcggcga tggccgcgct gcgcgagcac aacctgcgca   64440
cccgggccgc ccaccagcgg cacttcgtga ccaacacggt gatcacccgc ctcgacggcg   64500
```

```
acaccgccga ggcgcggtcg ctgatggcgg tggcgttcgc ccatccgggg gacggccgcc    64560
aagagttcac ccgcagtggg gtgtacgccg acgtgctggc ccgacaggga agccggtggc    64620
gcatcgccga ccggcacctg tggttggccg agttgccggc gccgcgtccc ggcgacacat    64680
ccgctcccga ggagagtcgg ccatgattcc cgtgctcgaa ctggtccaga tctccacact    64740
ccccgacgcc gaacgggaac tggagcaact ggcccggcga tacccgatca tccgcacccg    64800
acaggtcggc ggcatcgagg cgtggaccgt gctcggcgcc gggctgaccc ggcaactcct    64860
cggcgaccca aggctgtcca acgacctgca cacgcacgcg ccgcacgcgg cccagtccgc    64920
cgacggtccg accgtgctgt tcgagcagga caatccggac cacgcccgct accgccgcct    64980
ggtcagcgcc gcgttcgcgt cgcgggccgt gcgcaacctc gaaccgcgga tcgtcgacat    65040
cgcgcgcgca ctgctcgacc ggctgccggc cgaaggcggc acggtggaca tcgtcgaggc    65100
gttcgccaac cccttcccgc tggaggtgat ctgcgaactg ctcggggtac cgatggcgga    65160
ccgcgaggtg ttccgcaccc gggtggagaa catggactcg ccctcgacgg cggtacgccg    65220
ggcggcgatg gacgcgttcg tcgcctactg cgccaacctc gtcgacgcca gcgcaccga    65280 accgaccgag gacctgctga gcgagctggt acaggccgaa ctcgacgacg gatcacggct    65340
gtcggccaat gaactgatcg gcttcggctc cgtgctgctg ttcgcggggc acgtcaccac    65400
ggcctacctg atcgccgccg cgctgtacga actcatcacc cacaacgacc agttggccgc    65460
actccgggcc gatcccacgc tcgtcgaggg caccgtcgag gaggcgctgc gctttcgcgg    65520
ctcgttgttg tccaccacga accgggtggc gctgaccgac ctggagatcg gcggcgtgct    65580
cgtgcgccgt ggcgacctgg tgcgcttcct gctctccgcc gccaaccgcg acccggcgat    65640
ccgcgaggac ccgcacacct tcgacatcac ccggtccacc accgcccacc tgggcttcgg    65700
ccacggcccc cacttctgcc tcggccaacg cctggcccgc caggagatca aggtcgccct    65760
caccgagatc gtcacccgct tcccgaccct cgaactggcg gtcccggcgg aaaagctgcg    65820
ctggcgcgcc tcggacttcc tgcgcggcct tgccgaacta cccctgacgt acgccccgtg    65880
accaccgacg aggacaggcg gcccggaccc gggccgcccg ggctccgcgg cggtccgcgc    65940
cggtgtccgg cgagtgtgac gcgccgtcga acagtcgatg tcggctgcgc ggcgtccgtc    66000
gcggatcccg gacccgtcgt ggttgcgtag catctccggg ggtcggcggg cgacgccggg    66060
ccacgaacgg caggggcgcg cgccatggac cggaccggcg gggagccgaa ggcacccacg    66120
ggcctgcgcg agcgcaagaa ggcccgcacc cggcaggtga tctccacggt cgcgttcgac    66180
ctgttcgagg aacagggctt cgaacagacc accgtcgaca tgatctgccg ccgccacgcg    66240
atgacggtca gccacggcaa cctcgaagac cacgccgaac aaaccgcccg ccgacacgcg    66300
ctgcgccgcc gcttcctggg cgtgcgctcg gtccacgacc acggcgtggc cctgatcgac    66360
acggtcgccc accgcatcgt caccaccgcc gccgcccgcc tcggggtcga cccggccgtg    66420
gacctgcgcc cccacgccct cggcgccctg gtcgcggcga tgacccgccg cgtggtgatc    66480
gacgacatcg ccccgggccc gatcaacgag tgggcggagg ccttccgcac cctgctcccg    66540
acgccggccg cacacaccga ctgacacacc gcccgggcgc cgacccggaa accgccgggt    66600
tccttcgcac cgcagggtga tcaccggtct tcgtccgtgc ggacacatct tcggcccgcc    66660
gctcgtgtac ggatccgagg ctcccggccc ggccgcgggc gatactcggg aaacgtcggg    66720
gcccggggag gcggcgggtt ccccataccc gagaggttcc acatgcagcc cgacccgcgg    66780
ttcgacccgc aacccgacac ggccgtcgaa acacccgtgg acgagcacgc cgccggcgcg    66840
```

-continued

```
cccgccgatc ggctcgtcga cctcgtcgtc cgggccggtt ccctcgtcga cggcagcgga    66900
tcccccgcgt acgacggcga cctcgcgatc gacggcgggc ggatcgtcgc gctcggcgac    66960
atcggcgcca tcacggggcg tgacgagatc gacgcacagg gctgcgtggt gtgtccgggc    67020
ttcgtcaacg tgctgagcca cgcctacttc accctccagc aggaccccg tggcctgtcc     67080 gacctgtacc agggcgtgac cacccagatc ttcggcgagg gcgtctcgct cggcccggtg    67140
accggggcga tgaccgagtc catgatc                                        67167
```

<210> SEQ ID NO 4
<211> LENGTH: 8438
<212> TYPE: PRT
<213> ORGANISM: Streptomyces sp. ATCC 39366

<400> SEQUENCE: 4

```
Met Gln Val Met Glu Arg Gly Met Thr Glu Phe Asn Ala Asp Ala His
  1               5                  10                  15

Arg Ala His Pro Ala Pro Glu Asp Ala Val Ala Ile Val Gly Leu Ala
             20                  25                  30

Cys Arg Leu Pro Gly Ala Asp Gly Pro Asp Glu Phe Trp Asp Leu Leu
         35                  40                  45

Ser Asn Gly Arg Asp Thr Ile Thr Glu Val Pro Arg His Arg Arg Asp
     50                  55                  60

Ala Arg Ala Ala Asp Asp Thr Asn Arg Thr Ala Gly Gly Ser Pro His
 65                  70                  75                  80

Pro Ala Ala Asn Arg Pro Arg Arg Gly Gly Phe Leu Asp Ala Val Asp
             85                  90                  95

Arg Phe Asp Ala Ala Phe Phe Gly Ile Thr Pro Gly Glu Ala Ala Leu
            100                 105                 110

Ile Asp Pro Gln Gln Arg Leu Met Leu Glu Leu Cys Trp Glu Ala Leu
        115                 120                 125

Glu His Ala Gly Ile Pro Pro Thr Arg Ile Arg Gly Ser Ala Thr Gly
    130                 135                 140

Val Phe Ala Gly Ala Ile Trp Asp Asp Tyr Ala Thr Leu Leu Arg Arg
145                 150                 155                 160

Ala Gly Val Glu Pro Gly Pro Arg His Ala Thr Gly Leu His Arg Ser
                165                 170                 175

Met Ile Ala Asn Arg Val Ser Tyr Thr Leu Gly Leu Arg Gly Pro Ser
            180                 185                 190

Met Thr Val Asp Ala Ala Gln Ser Ser Leu Val Ala Val His Leu
        195                 200                 205

Ala Gly Glu Ser Leu Arg Arg Gly Glu Ser Thr Leu Ala Leu Val Gly
    210                 215                 220

Gly Val Asn Leu Asp Leu Val Pro Asp His Asp Gly Asp Ala Ala Lys
225                 230                 235                 240

Phe Gly Gly Leu Ser Pro Gln Gly Arg Cys Phe Thr Phe Asp Ala Arg
                245                 250                 255

Ala Asp Gly Tyr Val Arg Gly Glu Gly Gly Ala Val Val Leu Lys
            260                 265                 270

Pro Leu Ser Arg Ala Leu Ala Asp Gly Asp Val Val His Gly Val Ile
        275                 280                 285

Arg Gly Ser Ala Met Asn Asn Asp Gly Gly Asp Ala Leu Thr Ala
    290                 295                 300

Pro Asp Pro Arg Ala Gln Ala Glu Val Ile Arg Leu Ala Arg Arg
305                 310                 315                 320
```

-continued

Ala Gly Val Ala Ala Ser Ala Val Gln Tyr Val Glu Leu His Gly Thr
            325                 330                 335

Gly Thr Pro Val Gly Asp Pro Ile Glu Ala Ala Leu Gly Ala Ala
            340                 345                 350

Leu Gly Thr Glu Arg Ala Asn Arg Pro Leu Ala Val Gly Ser Val
            355                 360                 365

Lys Thr Asn Val Gly His Leu Glu Gly Ala Ala Gly Ile Val Gly Leu
            370                 375                 380

Val Lys Thr Val Leu Ala Ile Arg His Arg Leu Pro Ala Ser Leu
385                 390                 395                 400

Asn Phe Ala Glu Pro His Pro Arg Ile Pro Leu Gly Glu Leu Gly Leu
                    405                 410                 415

Arg Val Gln Thr Ala Glu Gly Asp Trp Pro Cys Pro Asp Glu Thr Leu
                    420                 425                 430

Ile Ala Gly Val Ser Ser Phe Gly Met Gly Gly Thr Asn Cys His Val
                    435                 440                 445

Val Leu Ala Glu Ala Glu Pro Ala Asp Gly Val Gly Pro Ser Val Ala
450                 455                 460

Ser Ala Pro Ser Gly Gly Ser Asp Pro Gly Met Glu Ser Ala Thr Gly
465                 470                 475                 480

Pro Val Pro Ser Asp Ala Val Ala Val Pro Ile Ser Gly Val Asp Ala
                    485                 490                 495

Asp Gly Leu Arg Ala Gln Ala Gly Arg Trp His Gly His Val Arg Glu
                    500                 505                 510

His Pro Asp Val Ala Pro Ala Asp Leu Gly Tyr Ser Ala Ala Thr Thr
                    515                 520                 525

Arg Thr Ala Phe Ala Ala Arg Ala Val Val Leu Ala Arg Asp His Ala
                    530                 535                 540

Glu Leu Leu Ala Gly Leu Asp Ala Leu Arg Gly Ala Gly Ala Asp Pro
545                 550                 555                 560

His Leu Val Arg Ala Asp Ala Gln Pro Gly Arg Thr Ala Phe Leu Phe
                    565                 570                 575

Thr Gly Gln Gly Ser Gln Arg Pro Ala Met Ala Gln Glu Ser Tyr Ala
                    580                 585                 590

Arg His Ala Val Phe Ala Ala Phe Asp Ala Ala Cys Ala His Leu
                    595                 600                 605

Asp Pro His Leu Pro Arg Pro Leu Arg Glu Val Leu Phe Ala Ser Pro
                    610                 615                 620

Asp Ser Pro Asp Ala Ala Leu Val His Arg Thr Glu Tyr Thr Gln Pro
625                 630                 635                 640

Ala Leu Phe Ala Val Glu Val Ala Leu Tyr Arg Leu Phe Glu His Trp
                    645                 650                 655

Gly Val Thr Pro Asp Leu Leu Leu Gly His Ser Ile Gly Glu Leu Cys
                    660                 665                 670

Ala Ala His Val Ala Gly Val Trp Ser Leu Pro Asp Ala Cys Ala Leu
                    675                 680                 685

Val Ala Ala Arg Gly Arg Leu Met Gln Glu Leu Pro Asp Gly Gly Ala
                    690                 695                 700

Met Val Ser Leu Arg Val Ala Glu Asp Asp Val Leu Ala Ser Leu Glu
705                 710                 715                 720

Pro Val Arg Asp Arg Val Ser Ile Ala Ala Val Asn Gly Pro Leu Ala
                    725                 730                 735

```
Thr Val Ile Ser Gly Asp Arg Asp Ala Val Leu Asp Val Ala Ala Gly
                740                 745                 750

Trp Arg Ala Gln Gly His Lys Thr Thr Arg Leu Arg Val Ala His Ala
                755                 760                 765

Phe His Ser Pro Arg Met Asp Ala Met Thr Asp Ala Phe Ala Glu Val
                770                 775                 780

Ala Ala Gly Leu Thr Ala Arg Ala Pro Thr Leu Pro Val Val Ser Asn
785                 790                 795                 800

Leu Thr Gly Leu Pro Leu Thr Ala Glu Gln Ala Cys Ser Pro Asp Tyr
                805                 810                 815

Trp Val Arg His Val Arg His Thr Val Arg Phe His Asp Gly Val Arg
                820                 825                 830

Arg Leu Arg Ala Glu Gly Ala Thr Ile Leu Leu Glu Leu Gly Pro Asp
                835                 840                 845

Gly Ser Leu Ser Ala Ala Arg Thr Cys Leu Leu Asp Gly Glu Arg
                850                 855                 860

Asp Thr Val Ala Thr Ile Pro Thr Leu Arg Arg Asn Arg Pro Glu Thr
865                 870                 875                 880

Asp Ala Leu Thr Thr Ala Val Ala Arg Leu Tyr Ala Asn Gly Val Asp
                885                 890                 895

Pro Asp Trp Glu Arg Val Phe Ala Gly Arg Gly Ala Arg Val Ala
                900                 905                 910

Leu Pro Thr Tyr Ala Phe Arg Arg Ala Arg His Trp Pro Gly Ala Ser
                915                 920                 925

Ala Glu Ala Ala Asp Thr Ala Val Pro Asp Glu Ser Leu Ala Val Val
                930                 935                 940

Pro Thr Leu Ala Glu Arg Leu Ala Leu Ser Ala Val Glu Gln His
945                 950                 955                 960

Arg Ile Leu Leu Asp Leu Ile Arg Ala His Ala Thr Ala Val Leu Gly
                965                 970                 975

Pro Gly Ala Thr Thr Thr Val Glu Pro Asp Arg Thr Tyr Arg Glu Ser
                980                 985                 990

Gly Leu Asp Ser Leu Gly Thr Val Glu Leu Ile Thr Arg Leu Ala Arg
                995                 1000                1005

Asp Thr Gly Leu Asp Leu Pro Pro Thr Thr Val Phe Asp His Pro Thr
        1010                1015                1020

Pro Thr Ala Leu Ala His His Leu Arg Thr Arg Ala Leu Asp Leu Pro
1025                1030                1035                1040

Val Pro Thr Arg Pro Arg Pro Thr Pro Gly Pro Ala Arg Ala Asp Glu
                1045                1050                1055

Pro Ile Ala Ile Val Ala Met Gly Cys Arg Leu Pro Gly Ala Val Arg
        1060                1065                1070

Thr Pro Glu Asp Leu Trp Arg Leu Val Ala Asp Gly Val Asp Ala Ile
        1075                1080                1085

Thr Ala Phe Pro Thr Asp Arg Gly Trp Asp Leu Asp Arg Leu His His
        1090                1095                1100

Asp Asp Pro Asp Arg Pro Gly Thr Ser Tyr Val Arg Ser Gly Gly Phe
1105                1110                1115                1120

Leu Asp Arg Ala Gly Asp Phe Asp Ala Glu Phe Phe Gly Ile Gly Pro
        1125                1130                1135

Arg Glu Ala Leu Ala Met Asp Pro Gln Gln Arg Leu Leu Glu Thr
        1140                1145                1150

Ser Trp Glu Ala Ile Glu Arg Ala Gly Leu Asp Pro Ser Thr Leu Arg
```

-continued

```
           1155                1160                1165
Gly Glu Arg Val Gly Val Phe Val Gly Ala Thr Ala Gln Glu Tyr Gly
    1170                1175                1180
Pro Arg Met His Glu Ser Thr Asp Ala Leu Ala Gly Phe Leu Leu Thr
1185                1190                1195                1200
Gly Thr Thr Pro Ser Val Ala Ser Gly Arg Ile Ala Tyr Thr Leu Gly
                1205                1210                1215
Leu Ser Gly Pro Ala Leu Thr Val Asp Thr Ala Cys Ser Ser Ser Leu
            1220                1225                1230
Val Ala Val His Leu Ala Ala Arg Ser Leu Ala Ser Gly Glu Cys Ala
            1235                1240                1245
Leu Ala Leu Ala Gly Gly Ala Thr Val Met Ala Gly Pro Gly Met Phe
            1250                1255                1260
Val Glu Phe Ala Arg Gln Arg Gly Leu Ala Pro Asp Gly Arg Cys Lys
1265                1270                1275                1280
Pro Phe Ser Ala Asp Ala Asp Gly Thr Ala Trp Ala Glu Gly Val Gly
                1285                1290                1295
Val Leu Leu Leu Glu Arg Leu Ser Asp Ala Arg Arg Asn Gly His Pro
            1300                1305                1310
Val Leu Ala Val Leu Arg Gly Ser Ala Ile Asn Gln Asp Gly Ala Ser
            1315                1320                1325
Asn Gly Leu Ser Ala Pro Asn Gly Thr Ala Gln Gln Arg Val Ile Arg
            1330                1335                1340
Asp Ala Leu Ala Ala Ala Gly Leu Asp Pro Gln Asp Val Asp Leu Val
1345                1350                1355                1360
Glu Ala His Gly Thr Gly Thr Pro Leu Gly Asp Pro Ile Glu Ala Gln
                1365                1370                1375
Ala Leu Leu Ala Thr Tyr Gly Arg Asp Arg Ala Ala Asp Arg Pro Leu
            1380                1385                1390
Leu Leu Gly Ser Val Lys Ser Asn Ile Gly His Thr Gln Ala Ala Ala
            1395                1400                1405
Gly Val Ala Gly Leu Ile Lys Thr Val Leu Ala Leu Arg His Gly Ala
            1410                1415                1420
Ile Pro Gly Thr Leu His Leu Arg Glu Pro Ser Pro His Val Arg Trp
1425                1430                1435                1440
Ser Asp Gly Ala Ile Thr Leu Pro Thr Thr Thr Asp Trp Pro Ala
                1445                1450                1455
Tyr Asp Arg Pro Arg Arg Ala Ala Val Ser Ser Phe Gly Ile Ser Gly
            1460                1465                1470
Thr Asn Ala His Val Ile Val Glu Glu Ala Gly Gly Ala Glu Ile
            1475                1480                1485
Pro Gly Pro Ala Pro Ala Arg Gly Leu Ala Ser Ala Gly Val Ala Asp
            1490                1495                1500
Pro Val Pro Leu Val Val Ser Ala Arg Ser Glu Ala Ala Leu Arg Gly
1505                1510                1515                1520
Gln Ala Glu Gln Leu Ala Gly Leu Leu Arg Ala Asp Ala Pro Ala
                1525                1530                1535
Leu Ala Asp Val Gly Tyr Ser Leu Leu Arg Gly Arg Ala Gly Phe Glu
            1540                1545                1550
Tyr Thr Ala Val Ile Pro Ala Arg Thr His Ala Glu Ala Leu His Gly
            1555                1560                1565
Leu Thr Ala Leu Ala Ala Asp Arg Pro Ala Asp Arg Leu Ile Arg Gly
            1570                1575                1580
```

```
Gly Ala Ala Ala Arg Gly Gly Thr Val Phe Val Phe Pro Gly Gln
1585                1590                1595                1600

Gly Thr Gln Trp Ser Gly Met Ala Leu Glu Leu Leu Asp Thr Ser Glu
            1605                1610                1615

Pro Phe Ala Ala Ser Met Arg Ala Cys Thr Asp Ala Leu Asp Pro Tyr
        1620                1625                1630

Ala Val Asp Trp Ser Leu Leu Asp Val Leu Arg Glu Pro Gly Thr Pro
            1635                1640                1645

Gly Leu Thr Arg Val Asp Val Val Gln Pro Ala Leu Phe Ala Val Met
        1650                1655                1660

Val Ser Leu Ala Ala Leu Trp Arg Ser Ile Gly Ile Glu Pro Gln Ala
1665                1670                1675                1680

Val Val Gly His Ser Gln Gly Glu Ile Ala Ala Ala Tyr Val Ala Gly
            1685                1690                1695

Ala Leu Ser Leu Ala Asp Ala Ala Lys Val Val Ala Leu Arg Ser Arg
        1700                1705                1710

Ala Leu Val Ala Ala Ala Gly Ser Gly Gly Met Ala Ser Val Ser Leu
            1715                1720                1725

Pro Ala Glu Gln Val Ala Ala Leu Leu Glu Pro Trp Ala Gly Arg Leu
        1730                1735                1740

Gly Val Ala Ala Val Asn Gly Pro Ser Ala Thr Val Val Ser Gly Asp
1745                1750                1755                1760

Thr Ala Ala Leu Asp Thr Phe Leu Asp Arg Cys Ala Ala Asp Asp Leu
            1765                1770                1775

Arg Ala Arg Arg Ile Pro Val Asp Tyr Ala Ser His Ser Val His Met
        1780                1785                1790

Glu Glu Ile Arg Asp Arg Leu Leu Thr Asp Leu Ala Asp Val Thr Pro
            1795                1800                1805

Arg Ala Ala Ser Thr Ala Phe Tyr Ser Thr Leu Thr Gly Gly Arg Met
        1810                1815                1820

Ala Asp Thr Ser Gly Leu Asp Ala Asp Tyr Trp Tyr Arg Asn Leu Arg
1825                1830                1835                1840

Arg Thr Val Arg Tyr Glu Thr Ala Val Arg Ala Leu Ser Glu Asp Gly
            1845                1850                1855

His Arg Leu Phe Val Glu Val Gly Pro His Pro Val Leu Thr Leu Gly
        1860                1865                1870

Thr Gln Glu Thr Leu Asp Ala Cys Gly Ser Gly Gly Thr Thr Ile Gly
        1875                1880                1885

Thr Leu Ser Arg Asp Asp Gly Gly Arg Ala Arg Phe Leu Val Ala Val
        1890                1895                1900

Ala Glu Ala Val Ala His Gly Ala Arg Pro Asp Ala Glu Ala Leu Phe
1905                1910                1915                1920

Asp Pro Pro Gly Thr Gly Val Arg Ala Val Ala Leu Pro Thr Tyr Ala
            1925                1930                1935

Phe Gln His Arg Arg Tyr Trp Leu Thr Pro Arg Glu Ala Ala Pro Glu
        1940                1945                1950

Gly Thr Ala Ala Leu Gly Leu Thr Pro Ile Ser His Pro Leu Leu Gly
        1955                1960                1965

Ala Leu Gly Ala Leu Gly Val Glu Pro Asp Gly Thr Val Ile Ala Thr
        1970                1975                1980

Gly Arg Ile Ser Leu Arg Glu Leu Pro Trp Leu Ala Asp His Ala Val
1985                1990                1995                2000
```

-continued

```
Ala Asp Thr Val Val Leu Pro Gly Thr Ala Phe Leu Glu Leu Ala Leu
            2005                2010                2015
Cys Val Gly Glu Ser Val Gly Ala Pro Gln Val Glu Leu Thr Leu
        2020                2025                2030
Glu Ser Pro Leu Leu Pro Glu Thr Gly Asp Val Tyr Leu Arg Val
        2035                2040                2045
Ala Val Ala Pro Ala Asp Glu Ala Arg Arg Ala Val Thr Ile His
        2050                2055                2060
Ser Arg Arg Ala Gly Gly Gly Ala Asp Ala Glu Arg Glu Ser Trp
2065            2070                2075                2080
Val Arg His Ala Gly Gly Leu Leu Val Asp Ser Val Arg Glu Val Asp
                2085                2090                2095
Asp Gly Gly Ser Gly Gly Leu Thr Gln Trp Pro Pro Gly Ala Asp
            2100                2105                2110
Val Leu Asp Leu Ala Asp Ala Tyr Pro Val Leu Ala Gly Leu Gly Tyr
                2115                2120                2125
Gly Tyr Gly Pro Ala Phe Arg Gly Leu Arg Ala Ala Trp Arg Gly Ala
            2130                2135                2140
Gly Gly Glu Leu Phe Ala Glu Val Arg Leu Pro Asp Glu Leu Arg Glu
2145            2150                2155                2160
Ser Glu Ser Gly Val Val Gly Pro Glu Phe Gly Ile His Pro Ala Leu
            2165                2170                2175
Leu Asp Ala Ala Leu His Pro Leu Leu Ser Ser Leu Ser Leu Thr Ser
            2180                2185                2190
Leu Ser Ser Thr Arg Asp Gly Pro Ala Gly Ala Pro Pro Arg Ile Pro
            2195                2200                2205
Phe Ser Leu Ala Asp Val Arg Leu Tyr Ala Thr Gly Ala Asp Met Leu
            2210                2215                2220
Arg Val Arg Leu Arg Arg Ala Asp Gly Gly Ala Ala Ala Leu Thr Val
2225            2230                2235                2240
Ala Asp Gly Val Gly Ala Pro Val Leu Ser Ile Gly Ala Leu Thr Leu
                2245                2250                2255
Arg Glu Leu Pro Ala Asp Gly Leu Ile Ala Ala Glu Pro Gly Pro Gly
            2260                2265                2270
Glu Ala Met Phe Asp Leu Arg Trp Ile Ala Gly Ser Ile Pro Ala Glu
            2275                2280                2285
Pro Thr Gly Leu Gly Tyr Ala Phe Ile Gly Asp Asp Leu Gly Leu Gly
            2290                2295                2300
Asp Gly Glu Val Tyr Pro Ser Leu Ala Asp Leu Asp Ala Arg Leu Leu
2305            2310                2315                2320
Ala Thr Gly Glu Pro Thr Pro Asp Val Val Phe Ala Ala Ala Pro Val
                2325                2330                2335
Gly Val Asp Asp Asp Val Pro Gly Ala Ala His Asp Ser Ala Arg Trp
            2340                2345                2350
Ala Leu Asp Leu Val Gly Gly Trp Leu Ala Gly Glu Arg Ser Ser Ala
            2355                2360                2365
Ala Arg Leu Val Val Val Thr Arg Gly Ala Val Ala Ala Arg Thr Gly
            2370                2375                2380
Asp Ala Leu Ser Gly Leu Pro Ala Ala Pro Val Trp Gly Leu Leu Arg
2385            2390                2395                2400
Thr Ala Gln Ser Glu His Pro Asp Arg Phe Val Leu Ile Asp Leu Asp
                2405                2410                2415
Asp Ala Val Arg Ser Pro Ser Ala Leu Leu Gly Ala Ala Val Ala Gly
```

-continued

```
                2420                2425                2430
Glu Pro Gln Leu Ala Leu Arg Asp Gly Val Val His Leu Pro Arg Met
        2435                2440                2445
Val Ala Val Asp Ser Ala Asp Ala Gln Val Thr Arg Arg Pro Asp
    2450                2455                2460
Pro Asn Gly Thr Ala Leu Ile Thr Gly Gly Thr Gly Thr Leu Gly Ala
2465                2470                2475                2480
Leu Ile Ala Arg Arg Leu Ala Ala Glu His Gly Ile Arg His Leu Leu
            2485                2490                2495
Leu Leu Gly Arg Ala Gly Arg Glu Ala Pro Gly Ala Glu Glu Leu Ile
        2500                2505                2510
Ala Glu Leu Gly Ala Leu Gly Ala Arg Val Thr Val Ala Ala Cys Asp
        2515                2520                2525
Val Ala Asp Arg Ala Ala Leu Arg Arg Val Ile Glu Asp Ile Pro Ala
    2530                2535                2540
Glu His Pro Pro Thr Ile Val Val His Ala Ala Gly Val Leu Asp Asp
2545                2550                2555                2560
Ala Thr Leu Leu Ser Leu Thr Pro Asp Arg Leu Asp Ala Val Leu Arg
            2565                2570                2575
Pro Lys Val Asp Ala Ala Trp His Leu His Glu Leu Thr Arg Ala Ala
        2580                2585                2590
Asn Pro Ala Ala Phe Val Leu Phe Ser Ser Ile Thr Ala Ile Thr Gly
        2595                2600                2605
Asn Ala Gly Gln Gly Ala Tyr Thr Ala Ala Asn Thr Phe Leu Asp Ala
    2610                2615                2620
Leu Ala Glu His Arg Arg Ala Ala Gly Leu Pro Ala Asn Ala Leu Ala
2625                2630                2635                2640
Trp Gly Leu Trp Ala Glu Gly Ser Gly Met Thr Arg His Leu Asp His
            2645                2650                2655
Thr Asp Arg Ala Arg Met Ser Arg Gly Gly Ile Ala Ala Leu Pro Thr
        2660                2665                2670
Glu Thr Gly Leu Ala Leu Phe Asp Ala Ala Leu His Arg Asp Arg Pro
        2675                2680                2685
Tyr Thr Ile Pro Ala Arg Leu Asp Arg Gly Ala Leu Arg Ala Leu Ala
        2690                2695                2700
Ala Ser Gly Val Leu Pro Ala Val Leu Arg Ser Leu Val Arg Val Pro
2705                2710                2715                2720
Pro Pro Arg Ala Ala Ala Ser Gly Asp Gly Thr Asp Ala Ser Ser Trp
            2725                2730                2735
Pro Arg Arg Ile Arg Glu Leu Pro Gly Glu Gln Arg Glu Arg Ala Ile
            2740                2745                2750
Thr Asp Leu Val Arg Gly Gln Leu Ala Ala Val Leu Gly His Asp Ala
        2755                2760                2765
Pro Glu Arg Leu Asp Leu Asp Arg Ala Phe Arg Glu Leu Gly Val Asp
        2770                2775                2780
Ser Leu Thr Ala Leu Glu Leu Arg Asn Arg Ile Asn Ala Phe Thr Gly
2785                2790                2795                2800
Leu Arg Leu Pro Ala Thr Val Val Phe Asp His Pro Ser Gly Thr Ala
                2805                2810                2815
Leu Val Ala Arg Met Met Arg Glu Leu Val Gly Ala Val Pro Ser Glu
            2820                2825                2830
Pro Thr Thr Pro Val Val Ala Pro Thr Val Thr Val Asp Glu Pro Ile
        2835                2840                2845
```

```
Ala Val Val Gly Ile Gly Cys Arg Tyr Pro Gly Gly Val Ala Gly Pro
    2850                2855                2860

Glu Asp Leu Trp Arg Leu Val Ala Ala Gly Thr Asp Ala Val Gly Asp
2865                2870                2875                2880

Phe Pro Glu Asp Arg Gly Trp Asp Leu Ala Lys Leu Tyr Asp Pro Asp
                2885                2890                2895

Pro Asp Lys Val Gly Lys Val Tyr Thr Arg Arg Gly Gly Phe Leu Tyr
            2900                2905                2910

Glu Ser Gly Glu Phe Asp Ala Glu Phe Phe Gly Ile Ser Pro Arg Glu
        2915                2920                2925

Ala Ala Ala Met Asp Pro Gln Gln Arg Leu Leu Leu Glu Thr Ala Trp
    2930                2935                2940

Glu Ala Phe Glu His Ala Gly Leu Asp Pro Arg Thr Leu Arg Gly Ser
2945                2950                2955                2960

Asn Thr Gly Val Phe Ala Gly Val Met Tyr Asn Asp Tyr Ala Ser Arg
                2965                2970                2975

Leu His Arg Ala Pro Asp Gly Phe Glu Gly Met Leu Leu Ala Gly Asn
            2980                2985                2990

Val Gly Ser Val Val Thr Gly Arg Val Ser Tyr Ala Leu Gly Leu Glu
        2995                3000                3005

Gly Pro Ala Val Ser Val Asp Thr Ala Cys Ser Ser Leu Val Ala
    3010                3015                3020

Leu His Leu Ala Ala Asn Ala Leu Arg Ser Gly Glu Cys Asp Leu Ala
3025                3030                3035                3040

Leu Ala Gly Gly Val Thr Val Met Ser Thr Pro Asn Val Phe Val Glu
                3045                3050                3055

Phe Ser Arg Gln Arg Gly Leu Ser Ala Asp Gly Arg Cys Arg Ser Phe
            3060                3065                3070

Ala Ala Gly Ala Asp Gly Thr Gly Trp Gly Glu Gly Val Gly Leu Leu
        3075                3080                3085

Val Val Glu Arg Leu Ser Asp Ala Arg Arg Asn Gly His Pro Val Leu
    3090                3095                3100

Ala Leu Leu Arg Gly Ser Ala Val Asn Gln Asp Gly Ala Ser Asn Gly
3105                3110                3115                3120

Leu Thr Ala Pro Asn Gly Pro Ser Gln Glu Arg Val Ile Arg Ala Ala
                3125                3130                3135

Leu Ala Gly Ala Gly Leu Ser Thr Asp Val Asp Ala Val Glu Ala
            3140                3145                3150

His Gly Thr Gly Thr Thr Leu Gly Asp Pro Ile Glu Ala Gln Ala Leu
        3155                3160                3165

Leu Ala Thr Tyr Gly Arg Asp Arg Pro Ala Asp Arg Pro Leu Trp Leu
    3170                3175                3180

Gly Ser Ile Lys Ser Asn Ile Gly His Thr Gln Ala Ala Ala Gly Ala
3185                3190                3195                3200

Ala Gly Leu Ile Lys Met Ile Met Ala Met Arg His Gly Val Leu Pro
                3205                3210                3215

Glu Thr Leu His Val Asp Ala Pro Ser Pro His Val Asp Trp Ser Thr
            3220                3225                3230

Gly His Val Glu Leu Leu Ala Glu Arg Pro Trp Pro Glu Val Asp
        3235                3240                3245

Arg Ala Arg Arg Ala Ala Val Ser Ser Phe Gly Ile Ser Gly Thr Asn
    3250                3255                3260
```

```
Ala His Val Ile Val Glu Gln Ala Pro Ala Glu Ala Val Val Ser
3265                3270                3275                3280

Arg Asp Glu Pro Val Gly Val Ala Gly Leu Val Pro Trp Val Leu Ser
                3285                3290                3295

Ala Arg Thr Ala Asp Gly Leu Arg Ala Gln Ala Ala Arg Leu Arg Glu
    3300                3305                3310

Trp Ser Ala Arg His Pro Glu Ala Asp Pro Val Asp Val Gly Trp Ser
    3315                3320                3325

Leu Val Arg Glu Arg Ser Val Phe Asp Arg Ala Val Val Gly Gly
        3330                3335                3340

Arg Asp Pro Gly Glu Leu Gly Ala Gly Leu Asp Arg Leu Ala Ala Gly
3345                3350                3355                3360

Gly Gly Ile Ala Asp Gly Arg Pro Met Phe Ser Gly Pro Gly Pro Val
            3365                3370                3375

Phe Val Phe Pro Gly Gln Gly Ser Gln Trp Val Gly Met Ala Ala Gly
                3380                3385                3390

Leu Leu Glu Cys Ser Pro Val Phe Ala Glu Ala Val Thr Glu Cys Ala
        3395                3400                3405

Ala Val Met Asp Pro Leu Val Ala Asp Trp Ser Leu Leu Asp Val Leu
    3410                3415                3420

Arg Gly Gly Ser Ala Gly Glu Leu Glu Arg Val Asp Val Val Gln Pro
3425                3430                3435                3440

Val Leu Phe Ala Val Met Val Gly Leu Ala Arg Trp Trp Glu Ser Cys
            3445                3450                3455

Gly Val Lys Pro Gly Ala Val Ile Gly His Ser Gln Gly Glu Ile Ala
            3460                3465                3470

Ala Ala His Val Ala Gly Tyr Leu Ser Leu Ala Asp Ala Val Trp Val
        3475                3480                3485

Val Val Leu Arg Ser Arg Ala Leu Leu Gly Val Ala Ser Ala Gly Gly
            3490                3495                3500

Gly Met Val Ser Val Gly Val Ser Ala Glu Arg Ala Arg Glu Leu Val
3505                3510                3515                3520

Ala Gly Asp Asp Arg Leu Ser Leu Ala Ala Val Asn Gly Pro Thr Ser
            3525                3530                3535

Val Val Leu Ser Gly Asp Val Glu Ala Leu Ser Val Val Glu Ala
        3540                3545                3550

Cys Glu Arg Asp Gly Val Arg Ala Arg Trp Ile Pro Val Asp Tyr Ala
        3555                3560                3565

Ser His Ser Ala Arg Met Glu Ala Val Arg Asp Glu Val Glu Arg Leu
    3570                3575                3580

Leu Ala Asp Val Thr Pro Gln Val Gly Arg Val Pro Met Tyr Ser Thr
3585                3590                3595                3600

Val Ser Gly Glu Val Val Asp Pro Ala Glu Leu Gly Gly Ala Tyr
        3605                3610                3615

Trp Phe Glu Asn Leu Arg Arg Thr Val Glu Leu Glu Arg Ala Val Gly
            3620                3625                3630

Ala Ala Val Ala Asp Gly His Gly Ala Phe Val Glu Cys Ser Pro His
        3635                3640                3645

Pro Gly Leu Val Val Pro Met Gly Asp Thr Leu Glu Ala Ala Gly Val
    3650                3655                3660

Asp Gly Val Val Leu Glu Thr Leu Arg Arg Gly Glu Gly Gly Pro Asp
3665                3670                3675                3680

Arg Leu Val Ala Ala Leu Ser Ala Ala Phe Val Ala Gly Val Ala Val
```

-continued

```
                    3685                3690                3695
Asp Trp Ala Gly Met Leu Pro Gly Arg His Val Glu Leu Pro Thr Tyr
                3700                3705                3710

Ala Phe Gln Arg Arg Arg Tyr Trp Leu Thr Gly Gly Glu Arg Ala Gly
            3715                3720                3725

Asp Pro Ala Gly Leu Gly Leu Val Ala Ala Asp His Pro Leu Leu Gly
        3730                3735                3740

Ala Val Val Gly Ser Val Arg Asp Gly Glu Leu Leu Tyr Thr Gly Arg
3745                3750                3755                3760

Leu Ser Ala Ala Thr His Gly Trp Leu Ala Asp His Ala Val Phe Gly
            3765                3770                3775

Ser Val Val Val Pro Gly Thr Ala Phe Val Glu Leu Ala Ser Trp Val
        3780                3785                3790

Gly Val Glu Ala Gly Cys Pro Val Val Asp Glu Leu Thr Leu His Ala
    3795                3800                3805

Pro Leu Val Leu Pro Asp Gly Val Gly Ile Arg Leu Arg Val Ala Val
        3810                3815                3820

Gly Ala Ala Asp Ser Ala Gly Arg Arg Val Val Glu Phe His Ser Arg
3825                3830                3835                3840

Pro Glu Asp Ala Pro Asp Glu Gln Ser Trp Thr Arg His Ala Thr Gly
            3845                3850                3855

Thr Leu Gly Ala Ala Ser Val Pro Gly Ser Ala Ser Ala Gly Ala Ala
        3860                3865                3870

Ala Trp Ala Val Trp Pro Pro Ala Asp Ala Glu Val Val Asp Pro Glu
    3875                3880                3885

Ala Val Tyr Glu Arg Leu Ala Glu His Gly Tyr Glu Tyr Gly Pro Ile
    3890                3895                3900

Phe Arg Gly Leu Arg Ala Ala Trp Arg Arg Gly Asp Asp Phe Phe Ala
3905                3910                3915                3920

Glu Val Ala Leu Pro Glu Ala Ala Gly Arg Asp Ala His Gly Tyr Asp
            3925                3930                3935

Leu His Pro Ala Val Leu Asp Ala Ala Leu His Val Ala Ala Ala Glu
        3940                3945                3950

Ala Val Ala Glu Ser Gly Ala Thr Leu Leu Pro Phe Ala Trp Thr Gly
    3955                3960                3965

Val Ala Leu His Gly Pro Gly Ala Ser Val Leu Arg Val Met Leu Arg
    3970                3975                3980

Arg Thr Gly Arg Glu Thr Leu Ala Val Asp Val Ala Asp Glu Arg Gly
3985                3990                3995                4000

Val Pro Val Ala Ser Val Ala Ser Leu Thr Leu Arg Pro Val Ala Ala
            4005                4010                4015

Glu Gln Leu Val Ala Ala Glu Glu Ala Gly Arg Glu Trp Leu Tyr Arg
        4020                4025                4030

Met Val Trp Glu Ile Ala Asp Ala Pro Val Ala Glu His Val Glu Gly
    4035                4040                4045

Glu Leu Leu Gly Ser Asp Glu Glu Ser Asp Ala Ser Ala Glu Leu Val
    4050                4055                4060

Ala Gly Gly Ile Arg Val Val Thr Pro Ala Gly Ala Glu Gln Val Ser
4065                4070                4075                4080

Glu Val Gly Leu Phe Asp Cys Pro Pro Val Val Gly Glu Ala Pro Glu
            4085                4090                4095

Glu Val Ala Gly Ala Val His Ala Val Leu Ala Ala Val Arg Ala Trp
        4100                4105                4110
```

-continued

```
Val Ala Asp Glu Arg Phe Ala Gly Ala Arg Leu Val Val Arg Thr Arg
        4115                4120                4125

Gly Ala Val Ala Thr Asp Ala Gln Asp Arg Val Gly Ser Pro Ala His
        4130                4135                4140

Ala Ala Ile Trp Gly Leu Val Arg Val Ala Gln Ser Glu His Pro Gly
4145                4150                4155                4160

Arg Phe Val Leu Val Asp Gly Asp Val Asp Ser Gly Ala Ala Leu
                4165                4170                4175

Arg Ala Ala Val Ala Cys Gly Leu Pro Gln Val Ala Ile Arg Glu Gly
                4180                4185                4190

Val Val Leu Ala Pro Arg Leu Val Gly Ala Val His Asp Thr Ala Leu
        4195                4200                4205

Val Pro Pro Ala Pro Gly Ala Asp Gln Ala Trp Arg Ile Glu Ser Gly
        4210                4215                4220

Thr Ala Gly Thr Pro Asp Asp Leu Val Val Thr Ala His Pro Ala Ala
4225                4230                4235                4240

Ser Ala Pro Leu Ala Ala Gly Gln Val Arg Val Ala Val Arg Ala Ala
                4245                4250                4255

Gly Val Asn Phe Arg Asp Val Leu Ile Thr Leu Gly Met Tyr Pro Gly
                4260                4265                4270

Arg Ala Val Val Gly Ala Glu Ala Ala Gly Val Val Glu Val Gly
        4275                4280                4285

Pro Gly Val Ser Glu Pro Ala Val Gly Asp Arg Val Met Gly Leu Phe
        4290                4295                4300

Glu Gly Ala Phe Gly Pro Leu Ala Val Ala Asp Arg Arg Leu Leu Ala
4305                4310                4315                4320

Arg Val Pro Ala Gly Trp Ser Phe Ala Gln Ala Ala Ser Val Pro Val
                4325                4330                4335

Val Phe Leu Thr Ala Leu Tyr Gly Leu His Asp Leu Ala Gly Leu Arg
                4340                4345                4350

Ser Gly Glu Ser Val Leu Val His Ala Ala Thr Gly Gly Val Gly Met
        4355                4360                4365

Ala Ala Thr Gln Leu Ala Arg His Arg Gly Ala Glu Val Tyr Ala Thr
        4370                4375                4380

Ala Ser Ala Thr Lys Trp Ala Thr Val Arg Gly Leu Gly Val Pro Asp
4385                4390                4395                4400

Glu Arg Ile Ala Ser Ser Arg Asp Leu Ser Phe Glu Gln Arg Phe Ala
                4405                4410                4415

Arg Ala Thr Asp Gly Arg Gly Ile Asp Val Val Leu Asn Ser Leu Ala
                4420                4425                4430

Gly Glu Phe Thr Asp Ala Ser Leu Arg Leu Leu Ala Glu Gly Gly Arg
        4435                4440                4445

Phe Val Glu Met Gly Lys Thr Asp Val Arg Thr Glu Gly Leu Pro Ala
        4450                4455                4460

Gly Val Arg Tyr Arg Ala Phe Asp Leu Ile Glu Ala Gly Pro Asp Arg
4465                4470                4475                4480

Ile Ala Glu Met Phe Ala Glu Leu Val Asp Leu Phe Glu Arg Gly Val
                4485                4490                4495

Leu Gln Pro Leu Pro Ile Arg Thr Trp Asp Ile Arg Arg Ala Arg Glu
                4500                4505                4510

Ala Leu Arg Phe Leu Gly Gln Ala Arg His Val Gly Lys Val Val Leu
        4515                4520                4525
```

-continued

```
Thr Val Pro Gln Pro Leu Ala Ala Asp Gly Thr Val Leu Ile Thr Gly
    4530                4535                4540

Gly Thr Gly Thr Leu Gly Arg Ser Leu Ala Arg His Leu Val Thr Arg
4545                4550                4555                4560

Trp Gly Val Arg Arg Leu Val Leu Thr Gly Arg Ala Gly Pro Ala Ala
                4565                4570                4575

Pro Gly Ala Ala Glu Leu Val Ala Glu Leu Ala Glu Ser Gly Ala Asp
            4580                4585                4590

Thr Thr Ile Val Ala Cys Asp Ala Ala Asp Arg Ala Ala Met Ala Glu
        4595                4600                4605

Val Leu Ala Ala Ile Pro Ala Glu His Pro Leu Thr Ala Val Val His
    4610                4615                4620

Ala Ala Gly Thr Leu Asp Asp Ala Pro Ile Glu Ala Leu Thr Pro Glu
4625                4630                4635                4640

Arg Val Asp His Val Leu Arg Pro Lys Val Asp Ala Ala Leu Val Leu
                4645                4650                4655

Asp Glu Leu Thr Arg Asp Ala Asp Leu Ala Ala Phe Val Leu Phe Ser
            4660                4665                4670

Ser Val Ala Gly Val Leu Gly Val Ala Gly Gln Gly Gly Tyr Ala Ala
        4675                4680                4685

Gly Asn Ala Phe Leu Asp Gly Leu Ala Gly Arg Arg Arg Glu Arg Gly
    4690                4695                4700

Leu Pro Ala Thr Ala Leu Ala Trp Gly Leu Trp Ala Glu Arg Ser Ala
4705                4710                4715                4720

Met Thr Ala Gln Leu Gly Val Gly Asp Leu Lys Arg Leu Ala Arg Gly
                4725                4730                4735

Gly Leu Val Pro Ile Ser Thr Ala Gln Gly Leu Ala Leu Phe Asp Ala
            4740                4745                4750

Ala Trp Gln Ala Asp Glu Ala Ala Leu Ile Pro Ala Arg Leu Asp Leu
        4755                4760                4765

Ala Ala Leu Arg Ala Gln Ala Ala Thr Gln Pro Val His Pro Leu Leu
    4770                4775                4780

Arg Gly Leu Val Gly Thr Thr Pro Thr Arg Arg Asn Gly Thr Pro Ser
4785                4790                4795                4800

Glu Ala Pro Trp Ala Arg Arg Leu Ala Ser Ala Ala Pro Ala Glu Arg
                4805                4810                4815

Val Asp Val Ala Leu Arg Leu Val Arg Ala Glu Ala Ala Val Val Leu
            4820                4825                4830

Gly His Glu Ser Ile Asp Gly Val Arg Pro Glu Val Thr Phe Arg Asp
        4835                4840                4845

Leu Gly Phe Asp Ser Leu Thr Gly Val Glu Leu Arg Asn Arg Leu Ser
    4850                4855                4860

Gly Ala Thr Gly Leu Arg Leu Pro Ser Thr Leu Val Phe Asp Phe Pro
4865                4870                4875                4880

Thr Pro Leu Gly Leu Ala Gly Phe Leu Val Ala Glu Ser Val Gly Glu
                4885                4890                4895

Met Asp Thr Ala Pro Thr Gly Pro Val Ala Gly Ala Val Val Ala
            4900                4905                4910

Ala Asp Pro Val Val Ile Val Gly Met Gly Cys Arg Phe Pro Gly Gly
        4915                4920                4925

Val Asp Ser Ala Ala Gly Leu Trp Asp Leu Val Ala Ala Gly Gly Asp
    4930                4935                4940

Ala Ile Gly Pro Phe Pro Thr Asp Arg Gly Trp Asp Val Asp Ala Leu
```

-continued

```
            4945                4950                4955                4960
Phe Asp Pro Asp Pro Glu Arg Val Gly Lys Ser Tyr Val Arg Thr Gly
                    4965                4970                4975
Gly Phe Leu Ser Gly Ala Ala Glu Phe Asp Ala Glu Phe Phe Gly Val
                    4980                4985                4990
Ser Pro Arg Glu Ala Leu Ala Met Asp Pro Gln Gln Arg Leu Leu Leu
                    4995                5000                5005
Glu Thr Ala Trp Glu Thr Phe Glu Gln Ala Gly Ile Asp Pro Thr Ser
            5010                5015                5020
Leu Arg Gly Ser Arg Thr Gly Val Phe Ala Gly Met Ala Gly His Asp
5025                5030                5035                5040
Tyr Ala Thr Gly Gly Ala Arg Ser Gln Ala Gly Leu Glu Gly His Leu
                    5045                5050                5055
Leu Thr Gly Asn Ala Ala Ser Val Ala Ser Gly Arg Val Ala Tyr Thr
                    5060                5065                5070
Phe Gly Leu Glu Gly Pro Ala Val Thr Val Asp Thr Ala Cys Ser Ser
            5075                5080                5085
Ser Leu Val Ala Leu His Leu Ala Ala Asn Ala Leu Arg Ala Gly Glu
            5090                5095                5100
Cys Asp Leu Ala Leu Ala Gly Gly Val Thr Ala Met Ser Thr Pro Asp
5105                5110                5115                5120
Phe Phe Leu Glu Phe Ser Arg Gln Arg Gly Leu Ser Val Asp Gly Arg
                    5125                5130                5135
Cys Lys Ala Phe Ala Ala Thr Ala Asp Gly Met Gly Ala Ala Glu Gly
                    5140                5145                5150
Val Gly Leu Leu Leu Val Glu Arg Leu Ser Asp Ala Arg Arg Asn Gly
                    5155                5160                5165
His Ser Val Leu Ala Val Val Arg Gly Ser Ala Val Asn Gln Asp Gly
            5170                5175                5180
Ala Ser Asn Gly Leu Thr Ala Pro Asn Gly Pro Ser Gln Gln Arg Val
5185                5190                5195                5200
Ile Arg Ala Ala Leu Ala Asp Ala Gly Leu Ser Ala Ala Asp Val Asp
                    5205                5210                5215
Ala Val Glu Ala His Gly Thr Gly Thr Thr Leu Gly Asp Pro Ile Glu
                    5220                5225                5230
Ala Gln Ala Leu Leu Ala Thr Tyr Gly Arg Asp Arg Ala Pro Asp Arg
                    5235                5240                5245
Pro Leu Trp Leu Gly Ser Val Lys Ser Asn Ile Gly His Thr Gln Ala
            5250                5255                5260
Ala Ala Gly Val Ala Gly Val Ile Lys Met Val Ser Ala Leu Arg His
5265                5270                5275                5280
Gly Met Leu Pro Arg Thr Leu His Val Asp Glu Pro Thr Pro His Val
                    5285                5290                5295
Asp Trp Ser Ala Gly Gly Val Glu Leu Leu Thr Ser Ala Arg Ala Trp
            5300                5305                5310
Pro Glu Ala Gly Arg Val Arg Arg Ala Gly Val Ser Ser Phe Gly Ile
            5315                5320                5325
Ser Gly Thr Asn Ala His Val Ile Leu Glu Gln Ala Glu Glu Ser Pro
            5330                5335                5340
Ala Gly Ser Val Pro Ser Ala Thr Pro Pro Val Ala Gly Thr Pro Val
5345                5350                5355                5360
Trp Gly Gly Arg Val Pro Trp Val Leu Ser Ala Arg Ser Glu Pro Ala
                    5365                5370                5375
```

```
Leu Arg Ala Gln Ala Ala Arg Leu Arg Asp Trp Leu Ala Val His Pro
        5380                5385                5390

Asp Ala Asp Pro Leu Asp Val Gly Arg Ser Leu Ala Thr Gly Arg Ala
        5395                5400                5405

Ala Leu Asp His Arg Ala Val His Gly Arg Asp Leu Ala Glu Leu
        5410                5415                5420

Arg Leu Ala Val Ala Lys Leu Ala Asp Ser Gly Pro Gly Asp Glu Ala
5425                5430                5435                5440

Ser Ile Val Gly Ser Val Ser Ala Ala Gly Pro Val Phe Val Phe Pro
                5445                5450                5455

Gly Gln Gly Ser Gln Trp Val Gly Met Ala Ala Gly Leu Leu Glu Cys
                5460                5465                5470

Ser Pro Val Phe Ala Gly Val Ala Glu Cys Ala Ala Val Met Asp
        5475                5480                5485

Pro Leu Val Ala Asp Trp Ser Leu Leu Asp Val Leu Arg Gly Gly Ser
        5490                5495                5500

Ala Gly Gly Glu Ala Leu Ala Glu Arg Val Asp Val Val Gln Pro Ala
5505                5510                5515                5520

Leu Phe Val Val Met Val Gly Leu Ala Arg Trp Trp Glu Ser Cys Gly
                5525                5530                5535

Val Lys Pro Gly Ala Val Ile Gly His Ser Gln Gly Glu Ile Ala Ala
                5540                5545                5550

Ala His Val Ala Gly Tyr Leu Ser Leu Ala Asp Ala Val Arg Val Val
        5555                5560                5565

Val Leu Arg Ser Arg Ala Leu Leu Gly Val Ala Ser Ser Gly Gly Gly
        5570                5575                5580

Met Val Ser Val Gly Val Ser Ala Asp Arg Ala Arg Glu Leu Val Ala
5585                5590                5595                5600

Glu Asp Asp Arg Leu Ser Leu Ala Ala Val Asn Gly Pro Thr Ser Val
                5605                5610                5615

Val Leu Ser Gly Asp Val Glu Ala Leu Ala Val Val Asp Gly Cys
        5620                5625                5630

Glu Arg Asp Gly Val Arg Ala Arg Trp Ile Pro Val Asp Tyr Ala Ser
        5635                5640                5645

His Ser Ala Arg Met Glu Ala Val Arg Asp Val Glu Arg Leu Leu
        5650                5655                5660

Ala Asp Val Thr Pro Gln Ala Gly Arg Val Pro Met Tyr Ser Thr Val
5665                5670                5675                5680

Ser Gly Gly His Val Thr Asp Pro Ser Val Leu Gly Gly Ser Tyr Trp
                5685                5690                5695

Phe Asp Asn Leu Arg Arg Thr Val Glu Leu Glu Arg Ala Val Gly Ala
        5700                5705                5710

Ala Val Val Asp Gly His Ser Val Phe Val Glu Cys Ser Pro His Pro
        5715                5720                5725

Gly Leu Val Val Pro Leu Gly Asp Thr Leu Glu Ala Ala Gly Val Asp
        5730                5735                5740

Gly Val Val Leu Glu Thr Leu Arg Arg Gly Glu Gly Gly Pro Asp Arg
5745                5750                5755                5760

Leu Val Gly Ala Leu Ser Ala Ala Phe Arg Ser Gly Leu Ala Val Asp
                5765                5770                5775

Trp Ala Gly Ser Gly Met Val Pro Gly Arg Arg Val Glu Leu Pro Thr
                5780                5785                5790
```

-continued

Tyr Ala Phe Gln Arg Arg Tyr Trp Val Glu Pro Gly Glu Arg Ala
            5795                5800                5805

Gly Gly Val Gly Trp Gly Gln Phe Thr Val Glu His Pro Val Leu Gly
            5810                5815            5820

Ala Gly Val Asp Leu Ala Asp Gly Ala Gly Thr Val Phe Thr Gly Arg
5825                5830                5835                5840

Leu Ser Ala Ala Ser His Gly Trp Leu Ala Glu His Val Val Leu Gly
                5845                5850                5855

Thr Val Ile Ala Pro Gly Thr Ala Phe Val Asp Leu Ala Leu Arg Ala
            5860                5865            5870

Gly Ala Thr Val Gly Arg Ala Thr Val Glu Glu Leu Thr Leu His Ala
            5875                5880            5885

Pro Leu Ile Leu Pro Asp Ala Gly Gly Val Arg Ile Gln Val Arg Val
            5890                5895            5900

Gly Ala Pro Asp Ala Ala Gly Val Gly Ser Val Glu Ile His Ser Arg
5905                5910                5915                5920

Pro Glu Asp Ala Ala Gly Asp Glu Pro Trp Thr Arg His Ala Ser Gly
            5925                5930            5935

Thr Leu Thr Ala Thr Asp Leu Asp Pro Ala Asp Val Ala Thr Glu Ala
            5940                5945            5950

Ala Ile Trp Pro Pro Ala Gly Ser Thr Pro Val Asp Leu Asp Gly Ala
            5955                5960            5965

Tyr Glu Arg Leu Ala Thr Ala Gly Phe Glu Tyr Gly Pro Ala Phe Gln
            5970                5975            5980

Gly Leu Arg Ala Leu Trp Arg Arg Gly Ala Glu Ser Phe Ala Glu Ile
5985                5990                5995                6000

Glu Leu Ala Asp Asp Ala Arg Gln Glu Ala Glu Arg Tyr Glu Val His
            6005                6010            6015

Pro Ala Leu Leu Asp Ala Ala Val His Ala Leu Gly Met Glu Pro Thr
            6020                6025            6030

Ala Glu Val Ala Pro Asp Glu Ala Arg Ile Ala Phe Ser Trp Arg Gly
            6035                6040            6045

Val Arg Leu Val Ala Ala Gly Ala Gly Arg Leu Arg Val Arg Leu Ala
            6050                6055            6060

Pro Val Gly Ser Asp Ala Val Ser Leu Trp Leu Ser Asp Met Asp Gly
6065                6070                6075                6080

Glu Pro Val Gly Ser Val Arg Ala Leu Thr Val Arg Pro Val Ala Ala
            6085                6090            6095

Glu Arg Leu Arg Pro Ala Gly Ala Pro Pro Arg Asp Ser Met Phe Arg
            6100                6105            6110

Val Glu Trp Arg Pro Val Ser Gly Asp Glu Ser Gly Val Ala Val Arg
            6115                6120            6125

Trp Ala Val Val Gly Ala Ala Asp Ser Gly Pro Leu Ala Arg Leu Val
            6130                6135            6140

Ala Ala Tyr Pro Asp Val Pro Val Tyr Arg Ser Val Val Glu Ala Ala
6145                6150                6155                6160

Gly Asp Val Ala Ala Gly Pro Pro Asp Val Val Val Gly Val Gly
            6165                6170                6175

Glu Ala Asp Cys Ser Glu Gly Ser Val Glu Arg Thr Arg Arg Val Leu
            6180                6185            6190

Ala Asp Val Leu Ala Trp Met Gln Asp Trp Leu Ala Asp Ser Arg Phe
            6195                6200            6205

Ala Ala Thr Arg Leu Val Val Val Thr Ser Gly Ala Val Ala Ala Asp

-continued

```
          6210                6215                6220
Val Asp Ala Asp Pro Asp Glu Arg Val Ala Asp Leu Ala Gly Ala Ala
6225                6230                6235                6240
Val Trp Gly Leu Leu Arg Ser Ala Gln Ser Glu His Pro Asp Arg Cys
                    6245                6250                6255
Thr Leu Val Asp Leu Asp Glu Asp Ala Ala Ser Ile Asp Ala Trp Pro
                    6260                6265                6270
Ala Ile Leu Ala Ser Ala Glu Pro Gln Leu Ala Val Arg Met Gly Arg
            6275                6280                6285
Phe Arg Val Pro Arg Leu Ala Arg Val Thr Ala Gly Gly Glu Pro
6290                6295                6300
Val Ala Phe Ala Pro Asp Gly Thr Val Leu Val Thr Gly Ala Thr Gly
6305                6310                6315                6320
Gly Leu Gly Ala Leu Val Ala Arg His Leu Val Thr Ala His Gly Val
                    6325                6330                6335
Arg Arg Leu Leu Leu Ser Arg Arg Gly Ala Ala Ala Pro Gly Ala
            6340                6345                6350
Ala Glu Leu Val Glu Asp Leu Thr Ala Gln Gly Ala Glu Val Thr Leu
            6355                6360                6365
Ala Ala Cys Asp Leu Ala Asp Arg Ala Ala Leu Ala Ala Glu Leu Ala
            6370                6375                6380
Arg Ile Pro Ala Glu His Ala Leu Thr Gly Val Ile His Thr Ala Gly
6385                6390                6395                6400
Val Val Asp Asp Ala Thr Ile Ala Asn Leu Thr Asp Ala His Met Glu
                    6405                6410                6415
His Ala Leu Arg Pro Lys Ala Asp Ala Ala Phe His Leu Asp Glu Leu
                    6420                6425                6430
Thr Arg Asp Val Asn Pro Ala Ala Phe Val Leu Phe Ser Ser Gly Ala
            6435                6440                6445
Thr Thr Phe Gly Gly Pro Gly Gln Gly Asn Tyr Ala Ala Ala Asn Ala
            6450                6455                6460
Phe Leu Asp Gly Leu Ala Arg Gln Arg Asp Arg Gly Leu Pro Gly
6465                6470                6475                6480
Ile Ser Leu Ala Trp Gly Leu Trp Ala Gly Ala Gln Gly Met Gly Gly
                    6485                6490                6495
Arg Leu Ser Glu Ala Asp Leu Ala Arg Trp Ala Arg Thr Gly Ala Val
            6500                6505                6510
Ala Met Pro Ala Ala Glu Ala Leu Arg Leu Phe Asp Ile Ala Leu Gly
            6515                6520                6525
Arg Pro Glu Ala Ala Leu Val Pro Ala His Leu Asp Leu Pro Ala Met
            6530                6535                6540
Arg Ala Asp Ala Gly Ala Arg Pro Ala Leu Phe Arg Glu Leu Leu Gly
6545                6550                6555                6560
Ile Gly Thr Arg Arg Ala Ala Val Gly Ala Gly Gly Ser Ala Leu Thr
                    6565                6570                6575
Arg Arg Leu Ala Gly Met Ser Pro Ala Glu Arg Glu Gln Ala Val Leu
            6580                6585                6590
Asp Val Val Arg Thr Glu Ala Ala Asn Thr Leu Gly His Glu Ser Ala
            6595                6600                6605
Gly Ala Val Ser Ala Gly Arg Ala Phe Lys Glu Leu Gly Phe Asp Ser
6610                6615                6620
Leu Thr Gly Val Glu Leu Arg Asn Arg Leu Asn Thr Ala Thr Gly Leu
6625                6630                6635                6640
```

-continued

Arg Leu Pro Ser Thr Leu Val Phe Asp Tyr Pro Thr Pro Ala Gly Leu
              6645                6650                6655

Ala Ala Phe Leu Val Ala Glu Leu Val Gly Arg Ser Val Gln Ala Val
              6660                6665                6670

Pro Val Pro Pro Val Gly Gly Arg His Gly Asp Ala Asp Ala Ile
              6675                6680                6685

Val Ile Val Gly Met Gly Cys Arg Phe Pro Gly Gly Val Ala Ser Pro
6690                6695                6700

Glu Asp Leu Trp Asn Leu Leu Ala Ser Gly Gly Asp Ala Ile Gly Pro
6705                6710                6715                6720

Phe Pro Thr Asp Arg Gly Trp Asp Leu Ala Gly Leu Phe Asp Pro Asp
              6725                6730                6735

Pro Glu Arg Ala Gly Lys Ser Tyr Val Glu Ser Gly Gly Phe Leu Tyr
              6740                6745                6750

Gly Ile Gly Glu Phe Asp Ala Glu Phe Phe Gly Ile Ser Pro Arg Glu
              6755                6760                6765

Ala Leu Ala Met Asp Pro Gln Gln Arg Leu Leu Leu Glu Thr Ala Trp
              6770                6775                6780

Glu Thr Phe Glu Arg Ala Gly Ile Asp Pro Thr Ser Leu Arg Gly Ser
6785                6790                6795                6800

Arg Thr Gly Val Phe Ala Gly Val Ile Asp Asn Asp Tyr Gly Ala Arg
              6805                6810                6815

Val Asn Gln Val Pro Asp Glu Val Glu Gly Tyr Leu Gly Tyr Gly Ser
              6820                6825                6830

Ser Ala Ser Ile Ala Ser Gly Arg Val Ser Tyr Val Leu Gly Leu Glu
              6835                6840                6845

Gly Pro Ala Val Ser Ile Asp Thr Ala Cys Ser Ser Ser Leu Val Ala
              6850                6855                6860

Leu His Leu Ala Val Asn Ala Val Arg Ser Gly Glu Cys Glu Leu Ala
6865                6870                6875                6880

Leu Ala Gly Gly Val Thr Ala Met Ala Thr Thr Glu Phe Phe Val Glu
              6885                6890                6895

Phe Ser Arg Gln Arg Gly Leu Ser Pro Asp Gly Arg Cys Lys Ala Phe
              6900                6905                6910

Ala Ala Ala Ala Asp Gly Met Gly Ala Ala Glu Gly Ile Gly Leu Val
              6915                6920                6925

Leu Val Glu Arg Leu Ser Asp Ala Arg Arg His Gly His Ser Val Leu
              6930                6935                6940

Ala Val Val Arg Gly Ser Ala Val Asn Gln Asp Gly Ala Ser Asn Gly
6945                6950                6955                6960

Leu Thr Ala Pro Asn Gly Pro Ser Gln Gln Arg Val Ile Arg Gln Ala
              6965                6970                6975

Leu Gly Ala Ala Gly Leu Ser Ala Ala Asp Val Asp Ala Val Glu Ala
              6980                6985                6990

His Gly Thr Gly Thr Thr Leu Gly Asp Pro Ile Glu Ala Gln Ala Leu
              6995                7000                7005

Leu Ala Thr Tyr Gly Gln Asp Arg Pro Gly Arg Pro Leu Trp Leu
              7010                7015                7020

Gly Ser Val Lys Ser Asn Ile Gly His Thr Gln Ala Ala Ala Gly Val
7025                7030                7035                7040

Ala Gly Val Ile Lys Met Val Leu Ala Leu Arg His Gly Val Leu Pro
              7045                7050                7055

```
Arg Thr Leu His Val Asp Glu Pro Thr Pro His Val Asp Trp Ser Ala
            7060                7065                7070
Gly Arg Val Glu Val Leu Ala Asp Glu Val Ala Trp Pro Ala Gly Glu
            7075                7080            7085
Arg Val Arg Arg Ala Gly Val Ser Ser Phe Gly Ile Ser Gly Thr Asn
            7090                7095                7100
Val His Val Val Leu Glu Glu Ala Pro Ala Asp Ala Ala Glu Pro Ala
7105                7110                7115                7120
Pro Ala Ala Pro Glu Val Pro Gly Val Gly Gly Val Leu Pro Trp Val
            7125                7130                7135
Val Ser Ala Arg Thr Glu Ala Gly Leu Arg Ala Gln Ala Ala Arg Leu
            7140                7145                7150
Arg Asp Trp Val Ser Glu His Pro Asp Ala Glu Pro Thr Asp Val Ala
            7155                7160                7165
Arg Ser Leu Val Val Gly Arg Ala Val Leu Asp Val Arg Ala Val Val
7170                7175                7180
Arg Gly Arg Glu Ser Gly Glu Leu Val Ala Gly Leu Asp Glu Leu Ala
7185                7190                7195                7200
Arg Ala Gly Val Gly Asp Pro Gly Ser Leu Val Ser Gly Ser Asp Pro
            7205                7210                7215
Val Phe Val Phe Pro Gly Gln Gly Ser Gln Trp Val Gly Met Ala Ala
            7220                7225                7230
Gly Leu Leu Glu Cys Ser Pro Val Phe Ala Gly Val Val Ala Glu Cys
            7235                7240                7245
Ala Ala Val Met Asp Pro Leu Val Ala Asp Trp Ser Leu Leu Asp Val
            7250                7255                7260
Leu Arg Gly Gly Ser Ala Gly Glu Leu Glu Arg Val Asp Val Val Gln
7265                7270                7275                7280
Pro Val Leu Phe Ala Val Met Val Gly Leu Ala Arg Trp Trp Glu Ser
            7285                7290                7295
Cys Gly Val Lys Pro Gly Ala Val Ile Gly His Ser Gln Gly Glu Ile
            7300                7305                7310
Ala Ala Ala His Ile Ala Gly Tyr Leu Ser Leu Ala Asp Ala Val Arg
            7315                7320                7325
Val Val Val Leu Arg Ser Arg Ala Leu Leu Gly Val Ala Ser Ser Gly
            7330                7335                7340
Gly Gly Met Val Ser Val Gly Val Ser Ala Glu Arg Ala Arg Glu Leu
7345                7350                7355                7360
Val Ala Gly Ala Asp Gly Leu Ser Leu Ala Ala Val Asn Gly Pro Thr
            7365                7370                7375
Ser Val Val Leu Ser Gly Asp Val Glu Ala Leu Ser Val Val Val Glu
            7380                7385                7390
Ala Cys Glu Arg Asp Gly Val Arg Ala Arg Trp Ile Pro Val Asp Tyr
            7395                7400                7405
Ala Ser His Ser Ala Arg Met Glu Ala Val Arg Asp Glu Val Glu Arg
            7410                7415                7420
Leu Leu Ala Asp Val Thr Pro Gln Val Gly Cys Val Pro Met Tyr Ser
7425                7430                7435                7440
Thr Leu Thr Gly Ala Pro Ile Ala Asp Pro Ala Glu Leu Gly Gly Ala
            7445                7450                7455
Tyr Trp Phe Glu Asn Leu Arg Arg Thr Val Glu Leu Glu Arg Ala Val
            7460                7465                7470
Gly Ala Ala Val Ala Asp Gly Arg Thr Val Phe Val Glu Cys Ser Pro
```

-continued

```
                7475                7480                7485
His Pro Gly Leu Val Val Pro Leu Gly Asp Thr Leu Glu Ala Ala Gly
        7490                7495                7500
Val Asp Gly Ala Val Leu Glu Thr Leu Arg Arg Gly Glu Gly Gly Pro
7505                7510                7515                7520
Asp Arg Leu Val Ala Ala Leu Ser Ala Ala Phe Val Arg Gly Leu Ala
            7525                7530                7535
Val Asp Trp Ala Gly Leu Ile Val Gly Ala Arg Val Glu Leu Pro Thr
        7540                7545                7550
Tyr Ala Phe Gln Arg Arg Tyr Trp Leu Asp Asp Gly Ala Arg Ser
        7555                7560                7565
Gly Asp Pro Gly Gly Leu Gly Leu Ala Ala Val Ala His Pro Leu Leu
        7570                7575                7580
Gly Ala Ala Val Arg Pro Ala Gln Gly Ala Gly Leu Leu Phe Thr Gly
7585                7590                7595                7600
Arg Leu Ser Thr Ala Thr His Pro Trp Leu Ala Asp His Val Val Leu
            7605                7610                7615
Gly Ser Thr Ile Val Pro Gly Thr Val Phe Val Asp Leu Ala Leu Trp
        7620                7625                7630
Ala Gly Ala Glu Ala Glu Cys Pro Val Val Asp Glu Leu Thr Leu His
        7635                7640                7645
Thr Pro Leu Val Leu Pro Glu His Gly Gly Val His Val Gln Val Thr
        7650                7655                7660
Val Asp Gly Pro Asp Ala Ala Gly Ala Arg Ala Val Ala Val Tyr Ser
7665                7670                7675                7680
Arg Pro Glu Asp Ala Pro Gly Glu Glu Pro Trp Thr Arg His Ala Val
            7685                7690                7695
Gly Ala Leu Val Ala Asp Ala Asp Thr Gly Ala Ala Pro Asp Ala Ala
        7700                7705                7710
Ala Glu Ala Trp Pro Pro Val Gly Ala Lys Pro Ile Glu Val Ala Asp
            7715                7720                7725
Phe Tyr Ala Arg Leu Val Glu Ser Gly Val Asp Tyr Gly Pro Ala Phe
        7730                7735                7740
Arg Gly Met Arg Ala Ala Trp Arg Arg Gly Asp Glu Leu Phe Ala Asp
7745                7750                7755                7760
Val Ala Leu Pro Ala Glu Glu Arg Asp Ala His Arg Phe Gly Val
            7765                7770                7775
His Pro Ala Leu Leu Asp Ala Gly Val Gln Thr Leu Arg Val Asp Pro
        7780                7785                7790
Gly Gln Val Asp Glu Asp Ile Arg Val Ala Phe Ser Trp His Gly
        7795                7800                7805
Val Arg Leu Phe Ala Ala Gly Val Thr Arg Leu Arg Val Ser Cys Val
        7810                7815                7820
Pro Ser Gly Glu Gly Ala Val Ser Leu Arg Ile Thr Asp Glu Thr Gly
7825                7830                7835                7840
Arg Ala Val Ala Ala Ile Glu Ala Leu Thr Val Arg Ala Ile Ser Ala
            7845                7850                7855
Asp Gln Leu Arg Arg Ala Gly Gly Arg Asp Val Leu Tyr Arg Leu
        7860                7865                7870
Ala Trp Arg Ala Ser Ala Val Pro Val Pro Val Ala Thr Pro Arg Val
            7875                7880                7885
Ala Val Val Gly Gly Trp Asp Leu Pro Gly Leu Gly Gly Leu Val Asp
        7890                7895                7900
```

-continued

```
Arg Tyr Pro Gly Phe Ala Glu Leu Ala Ser Cys Asp Pro Pro Leu Pro
7905                7910                7915                7920

Asp Leu Val Leu Leu Pro Val Gly Asp Pro Asp Ala Asp Val Pro Phe
                7925                7930                7935

Ser Glu Arg Arg Met Arg Glu Val Thr Ala Glu Leu Ile Gly Arg Leu
                7940                7945                7950

Glu Ala Phe Leu Gly Asp Glu Arg Phe Ala Ala Arg Val Val Val
            7955                7960                7965

Val Thr Arg Ser Ala Val Leu Val Asp Gly Asp Ala Gly Leu Gly Asp
            7970                7975                7980

Pro Ala Ser Ala Ser Val Trp Gly Val Val Arg Ala Ala Gln Ala Gly
7985                7990                7995                8000

His Pro Gly Arg Ile Val Leu Val Asp Leu Asp Asp Glu Pro Ala Ser
                8005                8010                8015

Ala Ala Ala Leu Ala Ala Val Ala Ser Ala Gly Gly Glu Pro Gln Phe
            8020                8025                8030

Ala Val Arg Gly Gly Arg Val Ser Val Pro Arg Leu Glu Arg Ile Pro
            8035                8040                8045

Ala Ser Gly Gly Ala Arg Ser Ala Val Gly Thr Gly Thr Val Leu Ile
    8050                8055                8060

Ala Gly Ala Asp Arg Ala Val Gly Ala Gly Val Ala Glu His Leu Ala
8065                8070                8075                8080

Gly Ala Tyr Gly Val Gly Arg Phe Val Leu Leu Ser Val Asp Pro Ser
            8085                8090                8095

Gly Ala Gly Pro Thr Glu Leu Ala Ala Arg Leu Gly Glu Ala Gly Ala
            8100                8105                8110

Glu Val Val Ser Ala Ala Trp Asp Gly His Asp Pro Gly Val Leu Ala
            8115                8120                8125

Ala Leu Val Thr Glu His Arg Pro Ala Gly Val Val Asp Ala Ser Gly
            8130                8135                8140

Glu Ser Asp Ala Ala Trp Ala Leu His Glu Leu Thr Ala Asp Val Asp
8145                8150                8155                8160

Pro Ala Phe Phe Val Leu Phe Ser Ser Ala Ala Ser Leu Leu Gly Ser
            8165                8170                8175

Ser Ala His Ala Ala Thr Ala Gly Val Asp Ala Phe His Asp Ala Leu
            8180                8185                8190

Ala Ala His Arg Arg Ala Ser Gly Leu Pro Gly Val Ser Leu Ala Cys
            8195                8200                8205

Gly Thr Asp Pro Leu Pro Gly Leu Pro Asp Leu Phe Asp Glu Ala Ile
    8210                8215                8220

Arg Arg Glu Asp Ala Val Leu Val Ser Ala Ser Thr Asp Leu Thr Gly
8225                8230                8235                8240

Pro Ala Ser Thr Ser Pro Leu Leu Pro Ser Arg Asn Gly Arg Gly Ala
                8245                8250                8255

Thr Asn Ser Ala Glu Thr Ser Ile Glu Ala Asp Gly Glu Ala Leu Ala
            8260                8265                8270

Arg Arg Leu Ala Ala Leu Ser Glu Glu Glu Arg Glu Arg Glu Leu Val
        8275                8280                8285

Gly Leu Val Arg Ala Gln Ala Ala Val Leu Gly His Ala Gly Ile
            8290                8295                8300

Gly Glu Ile Gly Pro Glu Arg Ala Phe Lys Glu Val Gly Phe Asp Ser
8305                8310                8315                8320
```

```
Leu Thr Ala Val Glu Leu Arg Asn Arg Leu Ile Arg Gly Thr Gly Val
            8325                8330                8335

Gly Leu Arg Ser Thr Leu Val Phe Asp Phe Pro Thr Pro Arg Ile Leu
            8340                8345                8350

Ala Arg His Leu Ser Gly Arg Leu Val Glu Ala Ala Ser Pro Ile Gly
            8355                8360                8365

Ala Leu Leu Ala Asp Leu Asp Arg Phe Glu Gly Glu Leu His Ala Val
            8370                8375                8380

Leu Gly Glu Ala Glu Ala Arg Asp Arg Leu Ala Glu Arg Leu Arg Arg
8385                8390                8395                8400

Leu Leu Ala Asp Cys Thr Ala Pro Asp Glu Ser Ala Pro Ala Ala Asp
            8405                8410                8415

Asp Val Ser Asp Val Gln Ser Ala Thr Asp Asp Glu Leu Phe Ser Leu
            8420                8425                8430

Val Asp Gln Gly Phe Glu
            8435

<210> SEQ ID NO 5
<211> LENGTH: 7429
<212> TYPE: PRT
<213> ORGANISM: Streptomyces sp. ATCC 39366

<400> SEQUENCE: 5

Met Ala Glu Ser Glu Glu Lys Leu Arg Ser Tyr Leu Arg Lys Ala Ile
1               5                   10                  15

Thr Asp Ala Arg Asp Ala His Arg Arg Val Arg Glu Leu Glu Asp Arg
            20                  25                  30

Gln Arg Glu Pro Ile Ala Ile Val Gly Met Ala Cys Arg Phe Pro Gly
        35                  40                  45

Gly Leu Gly Thr Pro Glu Asp Leu Trp Arg Phe Val Glu Gly Gly
    50                  55                  60

Asp Ala Ile Gly Glu Phe Pro Thr Asp Arg Gly Trp Asp Leu Asp Gly
65                  70                  75                  80

Leu Tyr Asp Pro Asp Pro Asp Arg Pro Gly Thr Ser Tyr Val Arg Glu
                85                  90                  95

Gly Gly Phe Leu Tyr Asp Val Ala Asp Phe Asp Ala Glu Phe Phe Gly
            100                 105                 110

Ile Ser Pro Arg Glu Ala Ala Ala Met Asp Pro Gln Gln Arg Leu Leu
        115                 120                 125

Leu Glu Thr Ser Trp Glu Ala Val Glu Arg Ala Gly Ile Asp Pro Thr
    130                 135                 140

Ser Leu Arg His Ser Arg Thr Gly Ile Tyr Thr Gly Ile Asn Gly Leu
145                 150                 155                 160

Asp Tyr Thr Thr Val Leu Ala Arg Thr Ala Lys Gly Arg Asp Gly Thr
                165                 170                 175

Leu Gly Met Ala Asn Gly Ala Ser Leu Leu Ala Gly Arg Val Ala Tyr
            180                 185                 190

Ile Leu Gly Leu Glu Gly Pro Ala Val Thr Val Asp Thr Ala Cys Ser
        195                 200                 205

Ser Ser Leu Val Ala Leu His Leu Ala Ser Asn Ala Leu Arg Ser Gly
    210                 215                 220

Glu Cys Asp Leu Ala Leu Ala Gly Gly Ala Thr Val Met Cys Thr Pro
225                 230                 235                 240

Glu Ile Phe Val Asn Phe Ser Arg Gln Arg Gly Leu Ala Arg Asp Gly
                245                 250                 255
```

```
Arg Cys Lys Pro Phe Ser Ala Ala Asp Gly Phe Ile Leu Ser Asp
            260                 265                 270

Gly Ala Gly Leu Phe Leu Ile Glu Arg Leu Ser Asp Ala Arg Arg Asn
        275                 280                 285

Gly His Pro Val Leu Ala Val Leu Arg Gly Ser Ala Ile Asn Gln Asp
        290                 295                 300

Gly Ala Ser Asn Gly Leu Thr Ala Pro Asn Gly Pro Ala Gln Glu Arg
305                 310                 315                 320

Val Ile Arg Gln Ala Leu Gln Ser Ala Gly Leu Val Thr Gly Asp Val
                325                 330                 335

Asp Ala Val Glu Ala His Gly Thr Gly Thr Thr Leu Gly Asp Pro Ile
            340                 345                 350

Glu Ala His Ala Leu Leu Ala Thr Tyr Gly Gln Asp Arg Pro Ala Asp
            355                 360                 365

Arg Pro Leu Arg Leu Gly Ser Ile Lys Ser Asn Ile Gly His Thr Gln
        370                 375                 380

Ala Ala Ala Gly Val Ala Gly Met Ile Lys Met Val Leu Ala Leu Arg
385                 390                 395                 400

His Gly Val Leu Pro Arg Thr Leu His Val Asp Ala Pro Ser Pro His
                405                 410                 415

Ile Asp Trp Ser Ala Gly Arg Val Glu Leu Leu Thr Glu Pro Val Pro
            420                 425                 430

Trp Pro Arg Ser Asp Arg Pro Arg Arg Ala Gly Val Ser Ser Phe Gly
        435                 440                 445

Ala Ser Gly Thr Asn Ala His Val Val Val Glu Glu Ala Pro Ser Asp
        450                 455                 460

Gly Asp Asp Gly Val Val Glu Val Pro Ala Pro Thr Gly Ile Gly Ser
465                 470                 475                 480

Val Leu Pro Trp Val Leu Ser Ala Arg Ser Glu Ala Ala Leu Arg Ala
                485                 490                 495

Gln Ala Gly Arg Leu Arg Asp Trp Leu Ala Glu His Pro Glu Ala Asp
            500                 505                 510

Pro Val Asp Val Gly Arg Ser Leu Ala Val Gly Arg Ala Val Leu Glu
        515                 520                 525

Arg Arg Ala Val Val Arg Gly Arg Asp Val Ala Glu Leu Ala Val Gly
        530                 535                 540

Ile Gly Glu Val Ala Asp Arg Gly Glu Leu Ala Gly Gly Arg Pro Met
545                 550                 555                 560

Phe Ala Gly Pro Gly Pro Val Phe Val Phe Pro Gly Gln Gly Ser Gln
                565                 570                 575

Trp Val Gly Met Ala Ala Gly Leu Leu Glu Cys Ser Pro Val Phe Ala
            580                 585                 590

Gly Val Val Ala Glu Cys Ala Ala Val Met Asp Pro Leu Val Ala Asp
        595                 600                 605

Trp Ser Leu Leu Asp Val Leu Arg Gly Gly Ser Ala Gly Gly Glu Ala
        610                 615                 620

Leu Ala Glu Arg Val Asp Val Val Gln Pro Ala Leu Phe Ala Val Met
625                 630                 635                 640

Val Gly Leu Ala Arg Trp Trp Glu Ser Cys Gly Val Lys Pro Gly Ala
                645                 650                 655

Val Ile Gly His Ser Gln Gly Glu Ile Ala Ala His Val Ala Gly
            660                 665                 670
```

```
Tyr Leu Ser Leu Ala Asp Ala Val Arg Ile Val Val Phe Arg Ser Arg
            675                 680                 685

Ala Leu Arg Gly Ile Ala Ala Gly Gly Gly Met Val Ser Val Gly
            690                 695                 700

Val Ser Val Glu Arg Ala Glu Glu Leu Val Ala Gly Ser Ala Gly Leu
705                 710                 715                 720

Ser Leu Ala Ala Val Asn Gly Pro Gln Ser Val Val Leu Ser Gly Asp
                725                 730                 735

Arg Glu Ala Leu Ala Ala Val Val Asp Ala Cys Glu Arg Glu Gly Ala
            740                 745                 750

Arg Ala Arg Trp Ile Pro Val Asp Tyr Ala Ser His Ser Ala His Met
            755                 760                 765

Glu Val Val Arg Asp Glu Val Glu Arg Leu Ser Ala Glu Val Thr Pro
770                 775                 780

Arg Ala Gly Arg Val Pro Met Tyr Ser Thr Leu Thr Gly Glu Val Val
785                 790                 795                 800

Thr Asp Pro Ala Glu Leu Gly Ala Gly Tyr Trp Phe Glu Asn Leu Arg
                805                 810                 815

Gly Thr Val Arg Leu Thr Thr Ala Val Gly Ala Ala Val Ala Asp Gly
            820                 825                 830

His Val Ala Phe Val Glu Cys Ser Pro His Pro Gly Leu Val Val Pro
            835                 840                 845

Leu Ala Asp Thr Leu Asp Glu Leu Gly Val Asp Gly Thr Val Leu
850                 855                 860

Glu Thr Leu Arg Arg Asp Asp Gly Gly Pro Asp Arg Leu Val Ala Ala
865                 870                 875                 880

Leu Ser Ala Ala Phe Val Ala Gly Val Pro Val Asp Trp Ala Ala Leu
                885                 890                 895

Phe Pro Gly Glu Gly Arg Ala Asp Leu Pro Thr Tyr Ala Phe Gln His
            900                 905                 910

Arg Arg Tyr Trp Ala Glu Ala Glu Ser Pro Ala Gly Gly Val Ala
            915                 920                 925

Trp Gly Gln Arg Ala Val Thr His Pro Val Leu Gly Ala Ala Val Asp
930                 935                 940

Leu Ala Gly Asp Ala Gly Thr Val Phe Thr Gly Arg Leu Ser Thr Thr
945                 950                 955                 960

Ala Gln Pro Trp Leu Ala Asp His Ala Val Leu Gly Thr Val Ile Val
                965                 970                 975

Pro Gly Thr Ala Phe Leu Asp Leu Val Leu Arg Ala Gly Ala Glu Val
            980                 985                 990

Gly Tyr Pro Ala Ile Glu Glu Leu Thr Leu His Thr Pro Leu Val Leu
            995                 1000                1005

Pro Asp Ala Ser Gly Val Leu Val Gln Val Val Gly Ala Ala Asp
            1010                1015                1020

Gly Asp Gly Gly Asp Gly Gly Asp Gly Ala Arg Thr Val Asp Val His
1025                1030                1035                1040

Ser Arg Ala Glu Asp Ala Pro Asp His Pro Trp Thr Arg His Ala
            1045                1050                1055

Ser Gly Val Leu Val Ala Gly Glu Glu Arg Ala Glu Asp Ala Pro
            1060                1065                1070

Ala Gly Arg Trp Pro Pro Thr Gly Ala Glu Val Val Gly Val Asp Asp
            1075                1080                1085

Ala Tyr Glu Arg Leu Ala Val Ala Gly Phe Asp Tyr Gly Pro Val Phe
```

-continued

```
             1090                 1095                 1100
Gln Gly Leu Arg Ser Val Arg Ala Arg Gly Asp Glu Leu Phe Ala Glu
1105                1110                1115                1120
Val Glu Leu Pro Glu Glu Gly His Ala Asp Ala Asp Arg Phe Ala Val
                1125                1130                1135
His Pro Ala Leu Leu Asp Ala Ala Leu His Pro Leu Val Ala Ala
            1140                1145                1150
Gly Ala Asp Ala Pro Val Val Ala Gly Leu Pro Phe Val Trp His Gly
            1155                1160                1165
Ile Arg Ala Gly Val Pro Gly Ala Arg Arg Leu Arg Val Arg Leu Val
1170                1175                1180
Arg Ser Ala Ser Gly Ser Ala Ser Gly Ser Ala Ala Gly Ser Asp Ser
1185                1190                1195                1200
Ala Ser Gly Glu Val Ser Val Arg Ala Trp Asp Glu Gly Gly Arg Glu
                1205                1210                1215
Val Val Ala Ile Glu Ser Leu Thr Ile Arg Pro Val Ser Ala Asp Gly
            1220                1225                1230
Leu Arg Thr Pro Asp Ala Leu Val Arg Asp Ser Leu Phe Thr Leu Ala
            1235                1240                1245
Trp Thr Ala Leu Glu Leu Pro Asp Val Asp Asp Val Pro Asn Ala
            1250                1255                1260
Thr Leu Leu Gly Gly Asp Gly Ala Ala Asp Leu Ala Ala Leu Val Ala
1265                1270                1275                1280
Ala Met Asp Thr Gly Thr Asp Val Pro Ala Leu Val Ala Leu Pro Val
                1285                1290                1295
Ser Val Asp Asp Ala Asp Pro Val Ala Ala His Thr Ala Gly Arg
                1300                1305                1310
Gln Val Leu Ala Val Leu Arg Asp Trp Leu Ala Asp Glu Arg Phe Ala
            1315                1320                1325
Asp Ser Arg Leu Val Phe Val Thr Ser Gly Ala Val Ala Val Ala Asp
            1330                1335                1340
Glu Gln Val Arg Pro Ala Ser Ala Ala Val Trp Gly Leu Val Arg Ser
1345                1350                1355                1360
Ala Gln Ser Glu His Pro Gly Arg Phe Val Leu Val Asp Ala Asp Ser
                1365                1370                1375
Val Ala Asp Pro Gly Pro Glu Phe Asp Arg Ala Leu Arg Thr Gly Ala
            1380                1385                1390
Asp Gln Leu Ile Leu Arg Asp Gly Thr Ala Leu Ile Pro Arg Leu Val
            1395                1400                1405
Arg Ala Pro Ala Asp Gly Gly Ser Gly Gly Phe Val Pro Ala Ala Asp
            1410                1415                1420
Gly Thr Val Leu Ile Thr Gly Gly Thr Gly Thr Leu Gly Thr Leu Leu
1425                1430                1435                1440
Ala Arg His Leu Val Thr Glu His Gly Val Arg Arg Leu Leu Leu Leu
                1445                1450                1455
Ser Arg Arg Gly Gly Thr Ala Ala Gly Ala Thr Asp Leu Val Ala Glu
            1460                1465                1470
Leu Ala Ala Phe Gly Ala Glu Val Thr Cys Val Ala Gly Asp Ala Ala
            1475                1480                1485
Asp Arg Ala Thr Leu Glu Arg Val Leu Ala Asp Ile Pro Ala Glu His
            1490                1495                1500
Pro Leu Thr Ala Val Ile His Ala Ala Gly Val Val Asp Asp Gly Val
1505                1510                1515                1520
```

-continued

```
Val Gln Ser Leu Thr Ala Asp Arg Leu Asp Ala Val Leu Arg Pro Lys
            1525                1530                1535

Val Asp Ala Ala Trp Asn Leu His Glu Ala Thr Arg His Leu Asp Leu
            1540                1545                1550

Thr Ala Phe Val Leu Phe Ser Ser Ala Ala Gly Val Leu Gly Asn Pro
            1555                1560                1565

Gly Gln Gly Asn Tyr Ala Ala Asn Ala Phe Leu Asp Ala Leu Ala
            1570                1575            1580

Arg Arg Arg Arg Glu Gly Leu Pro Gly Ser Ser Leu Ala Trp Gly
1585                1590                1595                1600

Trp Trp Ala Pro Thr Ser Glu Met Thr Ala Gly Leu Gly Asp Ala Asp
            1605                1610                1615

Arg Gln Arg Met Ala Arg Leu Gly Val Leu Pro Leu Ala Pro Glu Gln
            1620                1625                1630

Gly Leu Ala Leu Phe Asp Ala Ala Thr Asn His Ala Glu Pro Thr Pro
            1635                1640                1645

Thr Val Val Arg Met Asp Leu Ala Val Leu Arg Thr Ala Gly Ser Val
            1650                1655                1660

Val Pro Thr Leu Leu Arg Gly Leu Ala Arg Val Pro Asn Arg Arg Ala
1665                1670                1675                1680

Ala Thr Ala Gly Ser Val Ala Glu Leu Arg Arg Pro Ala Gly Val
            1685                1690                1695

Ser Ala Phe Asp Trp Glu Gln Thr Leu Ile Arg Ala Val Cys Val His
            1700                1705                1710

Ala Ala Ala Val Ile Gly His Ala Asp Ala Thr Glu Ile Asp Glu Thr
            1715                1720                1725

Arg Ala Phe Arg Asp Leu Gly Phe Asp Ser Leu Thr Gly Leu Glu Leu
            1730                1735                1740

Arg Asn Arg Leu Asn Thr Ala Thr Gly Leu Arg Leu Pro Ala Thr Leu
1745                1750                1755                1760

Val Phe Asp Tyr Pro Ser Pro Val Val Leu Gly Arg Trp Leu Arg Asp
            1765                1770                1775

Arg Leu Ala Glu Glu Asp Ala Gly Gly Pro Val Gly Ser Thr Leu Gly
            1780                1785                1790

Ala Gln Val Val Ser Pro Val Gly Ser Asp Ala Gly Glu Asp Ser Ile
            1795                1800                1805

Val Ile Val Gly Met Gly Cys Arg Phe Pro Gly Gly Ile Thr Ala Pro
            1810                1815                1820

Glu His Leu Trp Asp Val Val Ala Gly Gly Val Asp Thr Leu Thr Asp
1825                1830                1835                1840

Phe Pro Thr Asp Arg Gly Trp Asp Val Glu Arg Ile Phe Asp Pro Asp
            1845                1850                1855

Pro Asp Arg Pro Gly Ser Thr Tyr Val Arg Thr Gly Gly Phe Val Asp
            1860                1865                1870

Ser Ala Ala Asp Phe Asp Pro Asp Leu Phe Gly Ile Ser Pro Arg Glu
            1875                1880                1885

Ala Leu Ala Met Asp Pro Gln Gln Arg Leu Leu Leu Glu Thr Ala Trp
            1890                1895                1900

Glu Thr Phe Glu Arg Ala Gly Ile Asp Pro Thr Ser Leu Arg Gly Ser
1905                1910                1915                1920

Arg Thr Gly Val Phe Ala Gly Ala Ile Tyr Tyr Asp Tyr Ala Gly Gly
            1925                1930                1935
```

```
Arg Leu Arg Lys Val Pro Asp Glu Leu Glu Gly Tyr Ile Gly Asn Gly
            1940                1945                1950

Asn Val Gly Ser Val Ala Ser Gly Arg Val Ala Tyr Thr Phe Gly Leu
            1955                1960                1965

Glu Gly Pro Ala Val Thr Val Asp Thr Ala Cys Ser Ser Ser Leu Val
            1970                1975                1980

Ala Leu His Leu Ala Val Asn Ala Val Arg Ser Gly Glu Cys Glu Leu
1985                1990                1995                2000

Ala Leu Ala Gly Gly Val Thr Val Met Ser Thr Pro Ser Val Phe Leu
            2005                2010                2015

Asp Phe Ser Arg Gln Arg Gly Leu Ser Ser Asp Gly Arg Cys Arg Ser
            2020                2025                2030

Phe Ala Ala Ala Ala Asp Gly Thr Gly Trp Gly Glu Gly Val Gly Leu
            2035                2040                2045

Val Leu Val Glu Arg Leu Ser Asp Ala Arg Arg Asn Gly His Pro Val
            2050                2055                2060

Leu Ala Val Val Arg Gly Ser Ala Val Asn Gln Asp Gly Ala Ser Asn
2065                2070                2075                2080

Gly Leu Thr Ala Pro Asn Gly Pro Ser Gln Gln Arg Val Ile Arg Gln
            2085                2090                2095

Ala Leu Gly Ser Ala Gly Leu Ser Pro Ala Asp Val Asp Ala Val Glu
            2100                2105                2110

Ala His Gly Thr Gly Thr Thr Leu Gly Asp Pro Ile Glu Ala Gln Ala
            2115                2120                2125

Leu Leu Ala Thr Tyr Gly Gln Asp Arg Pro Gly Asp Arg Pro Leu Trp
            2130                2135                2140

Leu Gly Ser Val Lys Ser Asn Leu Gly His Thr Gln Ala Ala Ala Gly
2145                2150                2155                2160

Val Ala Gly Val Ile Lys Met Val Leu Ala Leu Arg His Gly Val Leu
            2165                2170                2175

Pro Arg Thr Leu His Val Asp Glu Pro Thr Pro His Val Asp Trp Ser
            2180                2185                2190

Ala Gly Arg Val Glu Val Leu Ala Asp Glu Val Ala Trp Pro Ala Gly
            2195                2200                2205

Glu Arg Val Arg Arg Ala Gly Val Ser Ser Phe Gly Ile Ser Gly Thr
            2210                2215                2220

Asn Ala His Val Val Leu Glu Glu Pro Pro Val Thr Glu Val Pro
2225                2230                2235                2240

Asp Val Ala Val Glu Ser Gly Leu Gly Gly Arg His Thr Trp Val Val
            2245                2250                2255

Ser Ala Arg Ser Glu Ala Ala Val Arg Glu Gln Ala Ala Arg Leu Arg
            2260                2265                2270

Asp Trp Val Thr Ala Arg Pro Asp Leu Asp Pro Ala His Val Ala Arg
            2275                2280                2285

Ser Leu Val Cys Glu Arg Ala Leu Phe Gly His Arg Ala Val Val Ser
            2290                2295                2300

Gly Ala Asp Leu Ala Glu Leu Ala Asp Gly Leu Ser Ala Val Ala Ala
2305                2310                2315                2320

Gly Ala Glu Gly Ala Val Val Gly Ala Val Gly Arg Gly Pro Gly Lys
            2325                2330                2335

Thr Ala Val Leu Cys Thr Gly Gln Gly Val Arg Ala Leu Gly Ile Gly
            2340                2345                2350

Arg Glu Leu His Ala Ala Phe Pro Val Phe Ala Gly Ala Leu Asp Glu
```

-continued

```
                2355                2360                2365
Val Cys Ala Ala Phe Asp Asp Val Val Pro Phe Ser Val Arg Asp Val
    2370                2375                2380
Val Leu Gly Ala Glu Gly Val Ser Asp Ala Asp Ala Gln Asp Thr Gly
2385                2390                2395                2400
Val Ala Gln Pro Ala Leu Phe Ala Phe Glu Val Ala Leu Tyr Arg Leu
        2405                2410                2415
Trp Ala Ser Trp Gly Gln Ala Pro Asp Phe Val Val Gly His Ser Leu
            2420                2425                2430
Gly Glu Ile Val Ala Ala His Val Ala Gly Val Phe Ser Leu Ala Asp
        2435                2440                2445
Ala Val Val Phe Val Ala Ala Arg Ala Arg Leu Met Ser Ala Leu Pro
    2450                2455                2460
Ser Gly Gly Ala Met Leu Ala Val Gly Ala Ser Glu Ala Glu Val Ala
2465                2470                2475                2480
Ala Ser Cys Pro Ala Glu Val Thr Ile Ala Ala Val Asn Gly Pro Ala
            2485                2490                2495
Ser Val Val Val Ser Gly Pro Ala Glu Ala Val Ala Ala Leu Glu Pro
        2500                2505                2510
Asp Cys Val Met Arg Gly Trp Arg Ile Ser Arg Leu Ser Val Ser His
    2515                2520                2525
Ala Phe His Ser Ala Leu Met Gln Pro Met Leu Ala Glu Leu Arg Glu
    2530                2535                2540
Val Leu Thr Gly Leu Thr Tyr Gly Thr Pro Glu Ile Ala Val Val Ser
2545                2550                2555                2560
Asp Thr Thr Gly Arg Val Ala Gly Ala Glu Glu Leu Ala Asp Pro Glu
            2565                2570                2575
Tyr Trp Val Arg His Val Arg Arg Ala Val Arg Phe Gly Asp Ala Ile
        2580                2585                2590
Ala Thr Leu Arg Ala Glu Gly Val Arg Thr Phe Val Glu Ile Gly Pro
        2595                2600                2605
Glu Ala Ala Leu Thr Ala Met Val Val Glu Gly Thr Ala Gly Ala Glu
    2610                2615                2620
Asp Val Ala Ala Val Ala Thr Arg Arg Gly Arg Ala Ala Val Ser
2625                2630                2635                2640
Ser Val Val Glu Ala Leu Ala Arg Val Phe Val His Gly Ala Thr Val
            2645                2650                2655
Asp Trp Ala Ala Leu Ser Thr Gly Ser Gly Pro Gly Gly Arg Val Asp
        2660                2665                2670
Leu Pro Thr Tyr Ala Phe Glu Arg Arg Arg Phe Trp Leu His Ala Gly
        2675                2680                2685
Val Asp Ala Gly Asp Ala Val Gly Leu Gly Gln Gly Val Val Asp His
    2690                2695                2700
Pro Leu Leu Gly Ala Val Val Gly Leu Ala Asp Asp Gln Gly Val Leu
2705                2710                2715                2720
Phe Thr Gly Arg Leu Ala Leu Asp Thr His Pro Trp Leu Ala Glu His
            2725                2730                2735
Thr Val Leu Gly Thr Val Leu Pro Gly Thr Ala Phe Leu Glu Leu
        2740                2745                2750
Ala Leu His Val Gly Arg Leu Leu Asp Cys Ala Arg Val Asp Glu Leu
    2755                2760                2765
Thr Leu Ser Ala Pro Leu Ala Leu Pro Ser Thr Gly Gly Val Gln Val
    2770                2775                2780
```

```
Gln Val Arg Val Gly Val Pro Glu Ser Gly Thr Arg Thr Ile Thr
2785                2790                2795                2800

Val His Ala Arg Pro Asp Ser Ala Glu Glu Ala Pro Trp Thr Leu His
                2805                2810                2815

Ala Ala Gly Ala Leu Gly Pro Ser Ala Glu Val Asp Ala Pro Ser Asp
                2820                2825                2830

Ala Ala Ser Trp Pro Pro Ala Asp Ala Thr Ala Met Asp Ser Ala Gly
                2835                2840                2845

Leu Tyr Pro Trp Phe Ala Glu Thr Gly Val Asp Tyr Gly Pro Ser Phe
                2850                2855                2860

Arg Gly Val Gln Ala Thr Trp Arg Arg Asp Asp Glu Val Phe Ala Glu
2865                2870                2875                2880

Ile Val Leu Ala Ala Asp Asp Pro Ala Ala Asp Gly Arg Phe Glu Leu
                2885                2890                2895

His Pro Ala Leu Phe Asp Ala Ala Leu His Pro Leu Gly Leu Thr Leu
                2900                2905                2910

Leu Asp Ala Ala Glu Pro Arg Leu Arg Leu Pro Phe Ser Trp Arg Gly
                2915                2920                2925

Val Ala Leu His Thr Ser Gly Ala Arg Thr Leu Arg Val Arg Leu Arg
                2930                2935                2940

Pro Thr Gly Pro Asp Thr Ile Ala Val Thr Ala Thr Asp Glu Thr Gly
2945                2950                2955                2960

Arg Pro Val Val Ala Val Glu Ala Leu Ala Val Arg Glu Pro Ser Arg
                2965                2970                2975

Asp Arg Leu Pro Arg Pro Asp Ala Asn Ala Gly Glu Leu Phe Glu Pro
                2980                2985                2990

Gln Trp Thr Pro Leu Ser Pro Ala Asp Thr Ala Asp Met Ala Asp Thr
                2995                3000                3005

Leu Gly Ala Val Val Gly Gly Pro Glu Leu Ala Ser Thr Ala Thr Arg
                3010                3015                3020

Phe Gly Ala Thr His His Pro Asp Leu Ala Ala Leu Ala Glu Ser Ala
3025                3030                3035                3040

Ile Pro Glu Thr Val Leu Tyr Asp Leu Val Thr Ala Val Pro Gly Val
                3045                3050                3055

Ser Ala Glu Ala Val His Gln Ala Ala Gln Ala Leu Asp Leu Ala
                3060                3065                3070

Arg Ser Trp Leu Ala Asp Glu Arg Phe Glu Ser Ala Arg Leu Ile Val
                3075                3080                3085

Arg Thr Arg His Ala Val Ala Ala Glu Gly Asp Ala Pro Asp Pro
                3090                3095                3100

Ala Ala Ala Ala Thr His Gly Leu Phe Arg Thr Ala Cys Ser Glu His
3105                3110                3115                3120

Pro Glu Arg Phe Ala Leu Val Asp Ala Asp Leu Asp Glu Val Ser
                3125                3130                3135

Pro Glu Ala Ile Ala Ala Val Val Glu Pro Glu Ala Ala Val Arg
                3140                3145                3150

Ala Gly Arg Val Leu Val Pro Arg Leu Arg Arg Ala Ala Val Ala Pro
                3155                3160                3165

Lys Ala Asp Phe Gly Phe Ala Ala Glu Gly Thr Val Leu Ile Thr Gly
                3170                3175                3180

Gly Thr Gly Ala Leu Gly Arg Gln Val Ala Arg His Leu Val Arg Val
3185                3190                3195                3200
```

-continued

```
His Gly Val Arg Arg Leu Leu Leu Ser Arg Arg Gly Asp Glu Ala
            3205                3210                3215

Pro Glu Ala Ala Glu Leu Arg Ala Glu Leu Ile Glu Ala Gly Ala His
            3220                3225                3230

Val Thr Phe Ala Ala Gly Asp Ala Ala Glu Arg Gly Val Leu Ala Asp
            3235                3240                3245

Val Leu Ala Ala Ile Pro Ala Ala His Pro Leu Thr Gly Val Val His
            3250                3255                3260

Leu Ala Gly Val Thr Asp Asp Gly Leu Val Gly Thr Leu Thr Pro Glu
3265                3270                3275                3280

Arg Leu Ala Ala Val Leu Arg Pro Lys Ile Asp Ala Ala Leu His Leu
            3285                3290                3295

Asp Glu Leu Thr Ala Asp Ala Asp Leu Ser Ala Phe Val Leu Phe Ser
            3300                3305                3310

Ser Ala Ala Gly Pro Val Gly Asn Pro Gly Gln Ala Asn Tyr Ala Ala
            3315                3320                3325

Ala Asn Val Ala Leu Asp Ala Leu Ala Arg Arg Arg Ala Arg Gly
            3330                3335                3340

Arg Pro Ala Val Ser Leu Gln Trp Gly Leu Trp Ala Glu Arg Ser Ala
3345                3350                3355                3360

Leu Thr Ala Thr Met Ser Ala Thr Asp Arg Arg Arg Ala Ala Gly Ala
            3365                3370                3375

Gly Val Arg Ala Leu Ser Val Glu Gln Gly Leu Ala Leu Leu Asp Ala
            3380                3385                3390

Ala Ala Gly Arg Pro Glu Ala Val Leu Thr Pro Leu Arg Leu Asp Pro
            3395                3400                3405

Ala Ile Leu Arg Gly Pro Glu Glu Arg Val Ala Pro Val Leu Arg Gly
            3410                3415                3420

Leu Val Pro Thr Arg Ala Arg Arg Ala Pro Ala Arg Thr Ser Asp Thr
3425                3430                3435                3440

Ala Arg Ser Leu Val Arg Arg Leu Ala Ala Leu Pro Glu Ala Glu Gln
            3445                3450                3455

Asp Arg Leu Leu Val Asp Leu Val Arg Thr His Ala Ala Gly Val Leu
            3460                3465                3470

Gly His Ala Asp Ala Arg Thr Ile Asp Pro Asp Arg Ala Phe Gly Glu
            3475                3480                3485

Leu Gly Leu Asp Ser Leu Ala Ala Leu Glu Leu Arg Thr Arg Leu Ser
            3490                3495                3500

Thr Ala Val Gly Leu Arg Leu Pro Ala Thr Met Leu Phe Asp His Pro
3505                3510                3515                3520

Cys Ala Arg Ala Val Gly Val His Leu Arg Ala Gln Leu Leu Asp Ala
            3525                3530                3535

Pro Thr Pro Gly Arg Ala Ala Gly Val Ala Arg Pro Val Ser Asp Glu
            3540                3545                3550

Pro Val Ala Val Val Ala Ile Ser Cys Arg Phe Pro Gly Gly Val Ala
            3555                3560                3565

Ser Pro Glu Asp Leu Trp Arg Leu Val Ser Glu His Thr Asp Ala Ile
            3570                3575                3580

Ser Glu Phe Pro Gln Asp Arg Gly Trp Asp Leu Ala Glu Leu Phe His
3585                3590                3595                3600

Pro Asp Pro Glu His Ala Gly Thr Ser Tyr Val Ser Glu Gly Gly Phe
            3605                3610                3615

Leu Tyr Glu Ala Thr Glu Phe Asp Pro Glu Phe Phe Gly Ile Ser Pro
```

-continued

```
              3620                3625                3630
Arg Glu Ala Leu Ala Met Asp Pro Gln Gln Arg Leu Leu Leu Glu Ala
              3635                3640                3645
Ser Trp Glu Ala Ile Glu Arg Ala Gly Val Asp Pro Arg Ser Leu Arg
              3650                3655                3660
Gly Ser Arg Thr Gly Val Tyr Ala Gly Leu Met Tyr Ala Asp Tyr Ala
3665              3670                3675                3680
Ser Arg Leu Gly Ser Ala Pro Glu Gly Val Asp Gly Tyr Leu Gly Asn
              3685                3690                3695
Gly Ser Ala Gly Ser Ile Ala Ser Gly Arg Val Ala Tyr Thr Leu Gly
              3700                3705                3710
Leu Glu Gly Pro Ala Val Thr Val Asp Thr Ala Cys Ser Ser Ser Leu
              3715                3720                3725
Val Ala Leu His Leu Ala Ala Asn Ala Leu Arg Gln Gly Glu Cys Asp
              3730                3735                3740
Leu Ala Leu Ala Gly Gly Val Thr Val Met Ser Ser Pro Ala Thr Phe
3745              3750                3755                3760
Val Glu Phe Ser Arg Gln Arg Gly Leu Ala Pro Asp Ala Arg Cys Lys
              3765                3770                3775
Ser Phe Ala Ala Gly Ala Asp Gly Thr Ser Trp Ser Glu Gly Ile Gly
              3780                3785                3790
Leu Leu Leu Val Glu Arg Leu Ser Asp Ala Arg Arg Leu Gly His Pro
              3795                3800                3805
Val Leu Ala Val Val Arg Gly Ser Ala Ile Asn Gln Asp Gly Ala Ser
              3810                3815                3820
Asn Gly Leu Ala Ala Pro Asn Gly Leu Ala Gln Glu Arg Val Ile Arg
3825              3830                3835                3840
Asp Ala Leu Ala His Ala Glu Leu Arg Pro Ser Asp Val Asp Ala Val
              3845                3850                3855
Glu Ala His Gly Thr Gly Thr Pro Leu Gly Asp Pro Ile Glu Ala Arg
              3860                3865                3870
Ala Leu Leu Ala Thr Tyr Gly Gln Asp Arg Pro Ala Asp Arg Pro Leu
              3875                3880                3885
Trp Leu Gly Ser Val Lys Ser Asn Leu Gly His Thr Gln Ala Ala Ala
              3890                3895                3900
Gly Val Ala Gly Val Ile Lys Met Ile Met Ala Met Arg His Ala Glu
3905              3910                3915                3920
Leu Pro Gly Thr Leu His Val Asp Ala Pro Ser Pro His Val Asp Trp
              3925                3930                3935
Ser Ala Gly Ala Val Ser Leu Leu Thr Ala Thr Pro Trp Pro Gln
              3940                3945                3950
Thr Gly Arg Pro Arg Arg Ala Gly Val Ser Ser Phe Gly Ile Ser Gly
              3955                3960                3965
Thr Asn Ala His Val Ile Leu Glu Gln Gly Asp Pro Ala Pro Thr Ala
              3970                3975                3980
Pro Ala Glu Pro Ala Pro Ala Ser Ala Pro Leu Ala Ala Leu Ala Trp
3985              3990                3995                4000
Pro Leu Ser Gly Ala Ser Ala Val Ala Leu Arg Gly Gln Ala Glu Arg
              4005                4010                4015
Leu Arg Ala His Leu Asp Ala His Pro Glu Tyr Gly Pro Val Asp Ile
              4020                4025                4030
Ala His Ala Leu Val Gly Gly Arg Ser Arg Phe Glu His Arg Ala Val
              4035                4040                4045
```

```
Val Val Ala Glu Asp Ala Ala Gly Leu Arg Ala Gly Leu Asp Ala Leu
    4050                4055                4060

Ser Ala Asp Arg Pro Asp Ala Ala Val Pro Val Gly Val Ala Gly Glu
4065                4070                4075                4080

Pro Gly Arg Ile Ala Phe Val Phe Gly Gly Gln Gly Ser Gln Trp Pro
                4085                4090                4095

Gly Met Gly Ala Arg Leu Leu Thr Glu Ser Pro Val Phe Ala Ala Arg
        4100                4105                4110

Ile Arg Asp Cys Asp Ala Ala Leu Ala Pro His Thr Asp Trp Ser Leu
            4115                4120                4125

Leu Ala Val Leu Arg Gly Glu Pro Asp Ala Pro Leu Asp Arg Val
        4130                4135                4140

Asp Val Val Gln Pro Val Leu Phe Ala Val Met Val Ala Leu Ala Glu
4145                4150                4155                4160

Leu Trp Arg Ser Leu Gly Val Arg Pro Ala Ser Val Val Gly His Ser
                4165                4170                4175

Gln Gly Glu Ile Ala Ala Ala His Ile Ala Gly Ala Leu Thr Leu Asp
        4180                4185                4190

Asp Ala Ala Arg Ile Val Ala Leu Arg Ser Arg Ala Leu Arg Gly Leu
            4195                4200                4205

Ser Gly Asp Gly Gly Met Met Ser Val Ala Ala Gly Pro Glu Gln Ile
    4210                4215                4220

Ala Arg Leu Leu Asp Gly Phe Ala Asp Arg Leu Gly Ile Ala Ala Val
4225                4230                4235                4240

Asn Gly Pro Ala Ala Val Val Ile Ser Gly Ala Ala Asp Ala Leu Ala
                4245                4250                4255

Glu Leu His Ala His Cys Glu Ala Asp Gly Ile Arg Ala Arg Val Leu
        4260                4265                4270

Pro Val Asp Tyr Ala Ser His Ser Ala Gln Val Glu Gln Val Arg Glu
            4275                4280                4285

Glu Leu Leu Ala Ala Leu Gly Glu Ile Val Pro Thr Pro Thr Thr Asp
    4290                4295                4300

Ala Val Phe Tyr Ser Ser Val Thr Gly Glu Pro Val Glu Gly Thr Ala
4305                4310                4315                4320

Leu Asp Ala Glu Tyr Trp Tyr Arg Asn Leu Arg Ala Thr Val Ala Phe
                4325                4330                4335

Asp Arg Ala Thr Asp Ala Leu Leu Arg Asp Gly His Thr Val Phe Val
        4340                4345                4350

Glu Thr Ser Pro His Pro Val Leu Ala Pro Ala Val Glu Asp Ser Ala
            4355                4360                4365

Gln Arg Ala Gly Thr Asp Val Thr Val Gly Ser Leu Gln Arg Asp
    4370                4375                4380

Thr Asp Thr Leu Ala Arg Phe Leu Thr Ala Ala Gly Leu His Val
4385                4390                4395                4400

His Gly Val Pro Val Asp Trp Ser Ala Thr His Ala Gly His Arg Pro
                4405                4410                4415

Arg Pro Val Asp Leu Pro Thr Tyr Ala Phe Gln Arg Glu Arg Tyr Trp
        4420                4425                4430

Leu Glu Ala Gly Lys Thr Pro Thr Asp Ala Ala Gly Leu Gly Leu His
            4435                4440                4445

Pro Ala Ala His Pro Leu Leu Gly Ala Ala Val Val Pro Ala Glu Gly
    4450                4455                4460
```

-continued

```
Asp Arg His Ile Leu Thr Gly Arg Ile Ser Leu Arg Thr His Pro Trp
4465                4470                4475                4480

Leu Ala Asp His Thr Ile Leu Asp Thr Val Leu Leu Pro Gly Thr Ala
            4485                4490                4495

Phe Val Glu Leu Ala Leu Gln Ala Gly Asp Arg Ala Asp Cys Asp Leu
        4500                4505                4510

Ile Glu Glu Leu Thr Val Glu Ala Pro Leu Arg Leu Thr Asp Thr Gly
    4515                4520                4525

Ala Val His Leu Gln Val Leu Leu Asp Glu Pro Asp Glu Gln Gly Arg
4530                4535                4540

Arg Ala Leu Thr Ile His Ser Arg Ala Asp Asp Ala Pro Ala Glu Gln
4545                4550                4555                4560

Thr Trp Thr Arg His Ala Ser Gly Val Leu Ala Pro Val Ala Asp Gly
            4565                4570                4575

Leu Asp Ala Val Pro Ala Thr Asp Ala Ala Trp Pro Pro Ala Gly Ala
        4580                4585                4590

Val Ala Leu Asp Val Asp Gly Leu Tyr Glu Arg Leu Ala Gly Gln Gly
    4595                4600                4605

Tyr Arg Tyr Gly Pro Ala Phe Arg Ala Val Arg Ala Ala Trp Arg Leu
4610                4615                4620

Gly Asp Thr Val Leu Ala Glu Val Ala Pro Gly Asp Glu Ala His Gly
4625                4630                4635                4640

Ala Arg Asp Phe Ala Leu His Pro Ala Leu Leu Asp Ala Ala Leu His
            4645                4650                4655

Ala Ala Gly Ala Ala Asp Ser Gly Thr Ser Gly Gly Asp Gly Ala Ile
        4660                4665                4670

Gly Leu Pro Phe Ala Trp Thr Asp Val Arg Leu His Ala Val Gly Ala
    4675                4680                4685

Ala Ala Leu Arg Val Arg Leu Glu Arg Arg Gly Pro Asp Thr Val Gly
4690                4695                4700

Leu Glu Leu Thr Asp His Thr Gly Ala Leu Val Ala Thr Val Gly Ala
4705                4710                4715                4720

Leu Val Gly Arg Pro Ala Thr Ala Asp Arg Leu Ala Pro Ala Ala Asp
            4725                4730                4735

Pro Ala His Arg Asp Leu His His Val Asp Trp Ser Pro Leu Pro Thr
        4740                4745                4750

Pro Thr Glu Pro Ser Thr Ala Arg Trp Ser Leu Leu Gly Pro Asp Glu
    4755                4760                4765

Leu Glu Ala Val Ala Gly Leu Arg Ala Ala Gly Ala Glu Val His Ala
    4770                4775                4780

Asp Gly Asp Pro Asp Pro Ala Asp Val Leu Leu Ile Thr Cys Ala Gly
4785                4790                4795                4800

Arg Thr Gly Asp Asp Val Pro Glu Ala Ala Arg Ala Ala Thr His Arg
            4805                4810                4815

Val Leu Asp Leu Leu Gln Arg Ala Leu Thr Asp Pro Arg Leu Thr Ala
        4820                4825                4830

Cys Thr Leu Val Val Leu Thr Arg Gly Ala Val Pro Gly His His Gly
    4835                4840                4845

Glu Asp Val Cys Asp Leu Val Ala Ala Pro Ile Val Gly Leu Val Arg
    4850                4855                4860

Ser Ala Gln Thr Glu His Pro Gly Arg Ile Val Leu Val Asp Leu Asp
4865                4870                4875                4880

Asp His Ala Asp Ser Phe Ala Ala Leu Arg Ala Ala Val Val Thr Asp
```

-continued

```
                        4885                4890                4895
Val Gly Glu Pro Gln Leu Ala Ile Arg Thr Gly Thr Val Ser Ala Pro
            4900                4905                4910

Arg Leu Ile Arg Thr Gly Thr Glu Pro Arg Leu Ser Pro Pro Ala Gly
            4915                4920                4925

Ala Pro Ala Trp Arg Leu Asp Leu Gly Gly Gly Thr Leu Asp Arg
            4930                4935                4940

Leu Ala Leu Leu Pro Asn Ala Asp Ala Ala Val Pro Leu Ala Pro Gly
4945                4950                4955                4960

Gln Val Arg Ile Ala Val Arg Ala Ala Gly Leu Asn Phe Arg Asp Val
            4965                4970                4975

Val Val Ala Leu Gly Met Val Thr Asp Thr Arg Pro Pro Gly Gly Glu
            4980                4985                4990

Gly Ala Gly Ile Val Val Glu Val Gly Pro Asp Val Pro Glu Leu Val
            4995                5000                5005

Pro Gly Asp Arg Val Met Gly Leu Phe Gly Gly Thr Gly Pro Ile
    5010                5015                5020

Thr Val Ala Asp His Arg Leu Leu Ala Pro Ile Pro Thr Gly Trp Thr
5025                5030                5035                5040

Tyr Ala Gln Ala Ala Ala Val Pro Val Val Phe Leu Thr Ala Tyr Tyr
            5045                5050                5055

Gly Leu Ala Asp Leu Gly Gly Leu Arg Ala Gly Glu Ser Leu Leu Val
            5060                5065                5070

His Ala Ala Thr Gly Gly Val Gly Met Ala Ala Val Gln Leu Ala Arg
            5075                5080                5085

His Trp Asn Val Glu Val Phe Gly Thr Ala Ser Pro Gly Lys Trp Ala
            5090                5095                5100

Thr Leu Arg Gly Gln Gly Val Asp Asp Ala His Leu Ala Ser Ser Arg
5105                5110                5115                5120

Asp Leu Asp Phe Ala His Arg Phe Gly Glu Val Asp Val Val Leu Asn
            5125                5130                5135

Ser Leu Ala His Glu Phe Val Asp Ala Ser Leu Arg Leu Leu Ala Pro
            5140                5145                5150

Gly Gly Arg Phe Leu Glu Met Gly Lys Thr Asp Ile Arg Asp Arg Asp
            5155                5160                5165

Glu Val Leu Ala Ala His Pro Gly Arg Asp Tyr Arg Ala Phe Asp Leu
5170                5175                5180

Met Asp Ala Gly Pro Glu Arg Ile Arg Glu Met Leu Ala Asp Leu Tyr
5185                5190                5195                5200

Arg Leu Phe Glu Thr Gly Val Leu His Pro Leu Pro Val Thr Pro Trp
            5205                5210                5215

Asp Val Arg Gly Ala Val Gly Ala Phe Arg His Leu Ser Gln Ala Arg
            5220                5225                5230

His Thr Gly Lys Ile Val Leu Thr Leu Pro Pro Thr Leu Gly Ala Ala
            5235                5240                5245

Pro Asp Pro Glu Gly Thr Val Leu Ile Thr Gly Gly Thr Gly Thr Leu
    5250                5255                5260

Gly Gly Leu Leu Ala Arg His Leu Val Arg Thr Ala Gly Val Arg His
5265                5270                5275                5280

Leu Leu Leu Ile Gly Arg Arg Gly Pro Ala Ala Asp Gly Ala Ala Glu
            5285                5290                5295

Leu Ser Ala Glu Leu Thr Ala Leu Gly Ala Arg Val Thr Ile Ala Ala
            5300                5305                5310
```

```
Cys Asp Ala Ala Asp Arg Ala Ala Leu Ala Ala Leu Leu Ala Asp Ile
    5315                5320                5325

Pro Ala Glu His Ala Leu Thr Ser Val Ile His Ala Ala Gly Val Ile
    5330                5335                5340

Asp Asp Ala Ala Leu Thr Ala Leu Thr Pro Glu Arg Leu Asp Arg Val
5345                5350                5355                5360

Leu Arg Pro Lys Leu His Ala Ala Trp Asn Leu His Glu Leu Thr Arg
                5365                5370                5375

Asp Leu Asp Leu Ala Glu Phe Val Leu Phe Ser Ser Met Ala Gly Thr
            5380                5385                5390

Phe Gly Gly Ala Gly Gln Ala Asn Tyr Ala Ala Ala Asn Ala Phe Leu
        5395                5400                5405

Asp Ala Leu Ala Gln His Arg Arg Ala Arg Gly Leu Ala Ala Thr Ala
    5410                5415                5420

Ala Ala Trp Gly Leu Trp Ala Gln Ala Ser Gly Met Thr Gly His Leu
5425                5430                5435                5440

Gly Ala Glu Asp Leu Asp Arg Ile Ala Arg Thr Gly Val Ala Ala Leu
                5445                5450                5455

Glu Thr Ala His Ala Leu Thr Leu Tyr Asp Ala Leu Arg Ala Ala Asp
            5460                5465                5470

Arg Pro Thr Ile Val Pro Ala Arg Leu Asp Pro Asp Ala Leu Arg Ala
        5475                5480                5485

Ala Ala Pro Thr Val Pro Ala Leu Leu Arg Asp Leu Val Arg Asp Leu
    5490                5495                5500

Val Arg Pro Arg Gly Arg Arg Ala Ala Ala Asp Thr Ala Pro Asp Ala
5505                5510                5515                5520

Ala Ser Leu Ala Glu Arg Leu Ala Arg Leu Pro Glu Glu Arg Arg Arg
                5525                5530                5535

Gln Thr Leu Leu Thr Leu Val Arg Thr Glu Thr Ala Ala Val Leu Gly
            5540                5545                5550

His Ala Thr Pro Asp Ala Val Ala Pro Leu Arg Pro Phe Lys Ala Leu
        5555                5560                5565

Gly Phe Asp Ser Leu Thr Ser Val Glu Leu Arg Asn Arg Ile Gly Ala
    5570                5575                5580

Ala Thr Gly Leu Arg Leu Pro Val Thr Leu Val Phe Asp His Pro Thr
5585                5590                5595                5600

Pro Gln Ala Leu Ala Asp His Val Gly Ala Glu Leu Leu Gly Val Ala
                5605                5610                5615

Pro Val Val Val Glu Pro Glu Arg Pro Ala Ala His Thr Asp Asp Asp
            5620                5625                5630

Pro Ile Val Ile Val Ser Val Gly Cys Arg Tyr Pro Gly Gly Val Ala
        5635                5640                5645

Gly Gln Asp Glu Met Trp Arg Met Leu Ala Glu Gly Thr Asp Thr Ile
    5650                5655                5660

Gly Pro Phe Pro Gln Asp Arg Gly Trp Glu Leu Asp Thr Leu Phe Asp
5665                5670                5675                5680

Pro Asp Pro Asp Arg Val Gly Lys Ser Tyr Val Arg Glu Gly Gly Phe
                5685                5690                5695

Val Ala Asp Ala Val His Phe Asp Ala Glu Phe Phe Gly Ile Ser Pro
            5700                5705                5710

Arg Glu Ala Thr Ser Met Asp Pro Gln Gln Arg Leu Leu Leu Glu Thr
        5715                5720                5725
```

```
Ala Trp Glu Thr Phe Glu Gln Ala Gly Ile Asp Pro Thr Thr Leu Arg
    5730                5735                5740

Gly Ser Gly Thr Gly Val Phe Val Gly Ala Met Ala Gln Asp Tyr His
5745                5750                5755                5760

Gly Thr Ser Gln Ala Met Ala Glu Gly Gln Glu Gly Tyr Leu Leu Thr
            5765                5770                5775

Gly Thr Ala Thr Ser Val Ile Ser Gly Arg Val Ser Tyr Val Leu Gly
                5780                5785                5790

Leu Glu Gly Pro Ala Val Thr Val Asp Thr Ala Cys Ser Ser Ser Leu
        5795                5800                5805

Val Ala Leu His Leu Ala Ala Asn Ala Leu Arg Ala Gly Glu Cys Asp
    5810                5815                5820

Leu Ala Leu Ala Gly Gly Val Ala Val Leu Thr Ser Pro Gln Ala Phe
5825                5830                5835                5840

Ile Glu Phe Ser Arg Gln Arg Gly Leu Ala Ala Asp Gly Arg Cys Lys
            5845                5850                5855

Pro Phe Ala Ala Ala Ala Asn Gly Thr Gly Trp Gly Glu Gly Val Gly
                5860                5865                5870

Leu Val Leu Val Glu Arg Leu Ser Asp Ala Arg Arg Gly His Pro
    5875                5880                5885

Val Leu Ala Val Arg Gly Ser Ala Val Asn Gln Asp Gly Ala Ser
5890                5895                5900

Asn Gly Leu Thr Ala Pro Asn Gly Pro Ser Gln Gln Arg Val Ile Arg
5905                5910                5915                5920

Gln Ala Leu Arg Asn Ala Gly Leu Leu Ala Thr Asp Val Asp Ala Val
            5925                5930                5935

Glu Ala His Gly Thr Gly Thr Thr Leu Gly Asp Pro Ile Glu Ala Gln
                5940                5945                5950

Ala Leu Leu Ala Thr Tyr Gly Gln Asp Arg Pro Ala Gln Arg Pro Leu
        5955                5960                5965

Trp Leu Gly Ser Val Lys Ser Asn Ile Gly His Thr Gln Ala Ala Ala
    5970                5975                5980

Gly Val Ala Gly Val Ile Lys Met Val Leu Ala Leu Arg His Gly Thr
5985                5990                5995                6000

Leu Pro Pro Thr Leu His Val Asp Ala Pro Thr Pro His Val Asp Trp
            6005                6010                6015

Ala Ser Gly Gln Val Arg Leu Leu Thr Glu Pro Val Ala Trp Pro Ala
                6020                6025                6030

Gly Glu Arg Val Arg Arg Ala Gly Ile Ser Ser Phe Gly Val Ser Gly
        6035                6040                6045

Thr Asn Ala His Val Ile Ile Glu Gln Ala Pro Ala Glu Gly Ala Val
    6050                6055                6060

Asp Ala Ala Pro Val Asp Ala Ala Pro Ala Ala Leu Gly Gly Ile
6065                6070                6075                6080

Val Pro Trp Val Val Ser Ala Arg Ser Gln Ala Gly Leu Arg Ala Gln
            6085                6090                6095

Ala Ala Arg Leu Arg Asp Trp Ala Ala Val His Pro Glu Phe Ala Pro
                6100                6105                6110

Ala Asp Val Ala Ala Ser Leu Val Arg Gly Arg Ala Val Phe Glu Arg
        6115                6120                6125

Arg Ala Val Val Arg Gly Arg Asp Thr Asp Glu Leu Val Ala Ala Leu
    6130                6135                6140

Ala Glu Leu Val Asp Ser Ser Ala Thr Gly Glu Ala Pro Thr Ala Ile
```

```
                6145                6150                6155                6160
Gly Pro Gly Pro Val Phe Val Phe Pro Gly Gln Gly Ser Gln Trp Val
                    6165                6170                6175
Gly Met Ala Ala Glu Leu Leu Thr Cys Cys Pro Val Phe Ala Glu Thr
                6180                6185                6190
Val Thr Gln Cys Ala Glu Val Met Asp Pro Leu Leu Pro Gly Trp Ala
                    6195                6200                6205
Leu Leu Asp Val Leu Arg Gly Thr Asp Glu Thr Ala Glu Leu Leu
            6210                6215                6220
Arg Arg Val Glu Val Val Gln Pro Val Leu Phe Ala Val Met Val Gly
6225                6230                6235                6240
Leu Ala Arg Trp Trp Glu Ser Cys Gly Val Arg Pro Ala Ala Val Ile
                6245                6250                6255
Gly His Ser Gln Gly Glu Ile Ala Ala Ala Tyr Ile Ala Gly His Leu
            6260                6265                6270
Thr Leu Pro Asp Ala Ala Arg Ile Ala Ala Leu Arg Ile Arg Ala Val
                6275                6280                6285
Gln Ala Ala Asp Met Ile Arg Gly Ala Met Val Ala Val Ala Val Ser
            6290                6295                6300
Ala Leu Arg Ala Glu Glu Leu Ile Thr Arg Thr Gly Thr Gly Asp Leu
6305                6310                6315                6320
Val Asn Val Gly Gly Ile Asn Ser Pro Thr Asn Thr Val Leu Ser Gly
                6325                6330                6335
Asp Thr Asp Ala Leu Ala Leu Ile Val Ala Asp Cys Glu Arg Glu Gly
            6340                6345                6350
Val Arg Ala Arg Trp Ile Pro Ala Ala Tyr Ser Ser His Ser Pro Gln
            6355                6360                6365
Met Asp Ala Val Arg Gly Asp Leu Glu Arg Leu Leu Ala Gly Ile Gln
        6370                6375                6380
Pro Thr Pro Gly Arg Val Pro Met Tyr Ser Thr Val Thr Gly Gly Arg
6385                6390                6395                6400
Leu Ala Asp Asp Ala Leu Leu Asp Ile Asp Tyr Trp Phe Glu Asn Met
                6405                6410                6415
Arg Arg Thr Val Arg Phe Glu Glu Ala Ile Gly Ala Ala Ala Ala Asp
            6420                6425                6430
Gly His Thr Val Phe Leu Glu Cys Ser Ser His Pro Gly Leu Val Val
                6435                6440                6445
Pro Leu Gly Asp Thr Leu Asp Ser Leu Gly Val His Gly Ala Thr Leu
            6450                6455                6460
Glu Thr Leu Arg Arg Ala Asp Gly Gly Ala Asp Arg Leu Leu Ala Ala
6465                6470                6475                6480
Leu Ser Ala Met Phe Val His Gly Gly Ala Val Asp Trp Ala Gly Leu
                6485                6490                6495
Leu Pro Gly Arg Arg Val Ala Leu Pro Thr Tyr Ala Phe Gln Arg Arg
            6500                6505                6510
Arg His Trp Val Glu Pro Val Gly Pro Ala Arg Gly Gly Val Gly Trp
            6515                6520                6525
Gly Gln Phe Ala Val Glu His Pro Ile Leu Gly Ala Gly Val Asp Leu
            6530                6535                6540
Ala Asp Gly Ser Ala Thr Val Phe Thr Gly Arg Leu Asp Thr Thr Thr
6545                6550                6555                6560
His Gly Trp Leu Ala Asp His Leu Val Leu Gly Glu Val Leu Val Pro
            6565                6570                6575
```

```
Gly Thr Val Phe Val Asp Leu Ala Leu Arg Ala Gly Ala Leu Gly
            6580                6585                6590

Cys Ala Val Val Glu Glu Leu Ala Leu His Glu Pro Leu Val Leu Pro
        6595                6600                6605

Asp Ala Asp Gly Val Arg Ile Gln Val Thr Val Glu Ala Pro Asp Asp
    6610                6615                6620

Ala Gly Thr Arg Ala Leu Thr Ile His Ser Arg Pro Glu Asp Ala Pro
6625                6630                6635                6640

Ala Ala Glu Pro Trp Thr Arg His Ala Ser Gly Thr Val Ala Pro Gly
                6645                6650                6655

Ala His Arg Pro Gln Gln Glu Ser Gly Pro Trp Pro Ile Gly Ala
            6660                6665                6670

Thr Pro Leu Asp Val Ala Asp Val Tyr Leu Arg Leu Thr Glu Leu Gly
        6675                6680                6685

Leu Gly Tyr Gly Pro Thr Leu Ala Gly Leu Arg Ala Ala Trp Arg Arg
    6690                6695                6700

Gly Asp Asp Leu Phe Ala Glu Val Ala Arg Thr Ala Asp Gly Glu Arg
6705                6710                6715                6720

Gly Thr Ala Arg Phe Gly Leu His Pro Ala Leu Leu Asp Ala Ala Leu
                6725                6730                6735

His Gly Leu Ala Pro Gly Ser Ala Pro Gly Gly Ala Pro Thr Glu Val
            6740                6745                6750

Arg Leu Ala Gly Ala Trp Arg Gly Val Thr Leu Gly Gly Asp Ala Gly
        6755                6760                6765

Thr Ala Gly Arg Ile Arg Leu Arg Gly Val Asp Gly Asp Gly Val Glu
    6770                6775                6780

Val Glu Leu Ala Asp Glu Ala Gly Arg Ser Met Ala Arg Ile Glu Ser
6785                6790                6795                6800

Val Ala Leu Arg Pro Trp Ser Ala Gly Gln Val Arg Ala Ala Gly Arg
                6805                6810                6815

Ala Arg Pro Trp Leu Thr Arg Trp Glu Trp Ala Arg Val Glu Pro Thr
            6820                6825                6830

Asp Pro Ala Ala Ala Gly Gly Arg Trp Ala Val Leu Gly Ala Arg Ala
        6835                6840                6845

Trp Asp Gly Val Pro Ala Tyr Ala Thr Ala Ala Glu Leu Ile Ala Ala
    6850                6855                6860

Val Glu Val Gly Val Pro Val Pro Asp Leu Val Ala Leu Pro Val Arg
6865                6870                6875                6880

Ile Asp Pro Ala Gly Gly Leu Asp Pro Glu Ala Ile Arg Ala Thr Ile
                6885                6890                6895

Arg Ala Val Arg Glu Thr Leu Arg Gln Trp Arg Ala Glu Pro Arg Leu
            6900                6905                6910

Ala Ala Ser Arg Leu Val Val Thr His Asp Ala Val Ser Ala Arg
        6915                6920                6925

Pro Glu Asp Arg Val Thr Asp Pro Gly Ala Ala Val Trp Gly Val
    6930                6935                6940

Val Arg Ala Ala Arg Ala Ala Asp Pro Glu Arg Phe Val Leu Ala Asp
6945                6950                6955                6960

Val Asp Gly Glu Asp Gly Ser Trp Pro Val Leu Leu Ala Glu Ala Ser
                6965                6970                6975

Ala Gly Arg Ala Glu Phe Ala Ile Arg Ala Gly Thr Val Leu Leu Pro
            6980                6985                6990
```

```
Gly Leu Ala Arg Val Pro Ala Gly Glu Thr Gly Thr Ala Gly Phe Pro
        6995                7000                7005

Thr Asp Gly Thr Val Leu Val Thr Val Ala Thr Asp Pro Thr Asp Pro
    7010                7015                7020

Thr Asp Gly Thr Asp Pro Val Gly Thr Leu Leu Ala Arg His Leu Val
7025                7030                7035                7040

Thr Ala His Gly Val Arg Arg Leu Ile Leu Ala Gly Gly Pro Ala Ala
            7045                7050                7055

Gly Met Pro Leu Ala Arg Glu Leu Ala Ala Gln Gly Ala Glu Ile His
            7060                7065                7070

Val Val Val Cys Asp Val Thr Asp Arg Thr Glu Leu Ala Lys Leu Leu
        7075                7080                7085

Ala Thr Ile Pro Glu His Ser Pro Leu Thr Ala Val Val His Thr Ala
    7090                7095                7100

Gly Leu Gly Arg Ser His Thr Glu Ala Met Leu Arg Ala Arg Val Asp
7105                7110                7115                7120

Ala Ala Val His Leu His Glu Leu Thr Arg Asp Ala Asp Leu Ser Ala
            7125                7130                7135

Phe Val Leu Cys Thr Ala Leu Asp Gly Val Leu Ala Asp Pro Gly Arg
            7140                7145                7150

Gly Glu His Ala Ala Gly Asp Ala Phe Leu Asp Ala Leu Ala Arg His
            7155                7160                7165

Arg His Ala Ala Gly Leu Pro Ala Leu Ala Leu Ala Trp Ala Pro Gly
    7170                7175                7180

Ala Glu Pro Val Ala Gly Leu Leu Pro Leu Pro Gly Glu Gln Ala Thr
7185                7190                7195                7200

Val Leu Phe Asp Arg Ala Leu Gly Leu Pro Glu Pro Ala Leu Ile Pro
            7205                7210                7215

Leu Ala Pro Asp Thr Ser Ala Leu Arg Arg Ala Glu Pro Gly Ala Leu
            7220                7225                7230

Pro Ala Leu Leu Thr Thr Leu Val Ala Asp Pro Asn His Arg Val Gly
            7235                7240                7245

Ala Ala Ala Glu Ala Ala Pro Ala Leu Ile Gly Arg Leu Leu Asp Leu
            7250                7255                7260

Pro Asp Asp Glu Arg Glu Ser Val Leu Val Asp Leu Val Arg Gly Cys
7265                7270                7275                7280

Ala Ala Ala Ile Leu Gly His Ala Asp Pro Thr Ala Ile Glu Thr Gly
            7285                7290                7295

Ala Ala Phe Lys Asp Leu Gly Phe Asp Ser Leu Thr Ala Leu Glu Met
            7300                7305                7310

Arg Asn Arg Leu Arg Ala Ala Leu Gly Leu Thr Leu Pro Ala Thr Leu
            7315                7320                7325

Ile Phe Ser His Pro Asn Ala Ala Ala Leu Gly Arg His Leu His Gly
            7330                7335                7340

Leu Leu Arg Arg Glu His Gly Val Ser Trp Asp Ser Val Leu Gly Glu
7345                7350                7355                7360

Ile Asp Arg Val Glu Ala Met Leu Ala Gln Leu Asp Asp Ala Asp Arg
                7365                7370                7375

Ala Arg Ala Thr Glu Arg Leu Arg Asp Leu Ile Gly Gly Pro Glu Ala
            7380                7385                7390

Pro Leu Ala Gly Arg Glu Ser Gly Ala Asn Gly Asp Ala Ala Gly Gly
            7395                7400                7405

Arg Gly Phe Asp Ala Ala Thr Asp Glu Glu Leu Phe Asp Phe Ile Asp
```

```
            7410                7415                7420

Gly Gly Ile Glu His
7425

<210> SEQ ID NO 6
<211> LENGTH: 3415
<212> TYPE: PRT
<213> ORGANISM: Streptomyces sp. ATCC 39366

<400> SEQUENCE: 6

Met Ala Asn Glu Asp Lys Leu Arg Asp Tyr Leu Arg Arg Ala Thr Thr
1               5                   10                  15

Glu Leu Gln Glu Thr Arg Leu Arg Leu Arg Glu Thr Glu Asp Lys Trp
            20                  25                  30

His Glu Pro Leu Ala Ile Val Gly Met His Cys Arg Tyr Pro Gly Gly
        35                  40                  45

Val Ala Ser Pro Asp Asp Leu Trp Asp Leu Val Asp Ala Gly Thr Asp
    50                  55                  60

Ala Ile Thr Gly Leu Pro Pro Gly Arg Gly Trp Glu Val Asp Glu Ala
65                  70                  75                  80

Ala Asn Gly Thr Ser Tyr Arg Gly Gly Phe Leu Thr Asp Ala Ala Asp
                85                  90                  95

Phe Asp Ala Asp Phe Phe Gly Ile Ser Pro Arg Glu Ala Leu Ala Met
            100                 105                 110

Asp Pro Gln Gln Arg Val Leu Leu Glu Ala Ser Trp Thr Val Phe Glu
        115                 120                 125

His Ala Gly Ile Asp Pro Thr Thr Leu Arg Gly Ser Arg Thr Gly Val
    130                 135                 140

Phe Val Gly Val Ile Ala Ser Asp Tyr Leu Ser Arg Leu Ala Arg Val
145                 150                 155                 160

Pro Lys Glu Val Glu Gly His Leu Leu Thr Gly Ser Leu Val Ser Val
                165                 170                 175

Ala Ser Gly Arg Leu Ala Tyr His Phe Gly Leu Glu Gly Ala Ala Val
            180                 185                 190

Thr Val Asp Thr Ala Cys Ser Ser Leu Val Ala Val His Leu Ala
        195                 200                 205

Gly Gln Ala Leu Arg Ala Gly Glu Cys Asp Leu Ala Leu Val Gly Gly
    210                 215                 220

Ala Thr Val Leu Ala Thr Pro Gly Ala Phe Asp Glu Phe Ser Arg Gln
225                 230                 235                 240

Gln Gly Leu Ala Gly Asp Gly Arg Cys Lys Ser Phe Ala Ala Gly Ala
                245                 250                 255

Asp Gly Thr Gly Trp Ser Glu Gly Val Gly Leu Leu Leu Met Glu Arg
            260                 265                 270

Leu Ser Asp Ala Arg Arg Asn Gly His Arg Val Leu Ala Val Val Arg
        275                 280                 285

Gly Ser Ala Val Asn Gln Asp Gly Ala Ser Asn Gly Leu Thr Ala Pro
    290                 295                 300

Asn Asp Leu Ala Gln Glu Arg Val Ile Arg Gln Ala Leu Ala Asn Ala
305                 310                 315                 320

Arg Leu Ala Ala Ser Asp Val Asp Ala Val Glu Ala His Gly Thr Gly
                325                 330                 335

Thr Arg Leu Gly Asp Pro Ile Glu Ala Gln Ala Leu Leu Ala Thr Tyr
            340                 345                 350
```

-continued

```
Gly Gln Asn Arg Pro Ala Ala Arg Pro Leu Arg Leu Gly Ser Ile Lys
        355                 360                 365

Ser Asn Ile Gly His Ala Gln Ala Ala Gly Val Ala Gly Val Ile
    370                 375                 380

Lys Met Val Gln Ala Leu Arg His Gly Val Leu Pro Arg Thr Leu His
385                 390                 395                 400

Val Asp Glu Pro Thr Pro His Val Asp Trp Ser Ala Gly Arg Val Ala
                405                 410                 415

Leu Leu Thr Glu Pro Met Ala Trp Pro Ala Gly Glu Arg Val Arg Arg
            420                 425                 430

Ala Gly Val Ser Ser Phe Gly Val Ser Gly Thr Asn Ala His Val Ile
        435                 440                 445

Val Glu Glu Ala Pro Pro Val Glu Pro Val Gly Ala Ala Asp Pro
    450                 455                 460

Ala Arg Pro Leu Gly Val Val Thr Pro Trp Val Val Ser Ala Arg Thr
465                 470                 475                 480

Glu Asp Gly Leu Arg Ala Gln Val Glu Arg Leu Arg Glu Trp Ala Ile
                485                 490                 495

Glu His Pro Glu Ala Asp Pro Ala Asp Val Gly Arg Ser Leu Ala Ser
            500                 505                 510

Gly Arg Ala Leu Ser Gly His Arg Ala Val Leu Gly Arg Asp Ala
        515                 520                 525

Ala Glu Leu Val Glu Gly Leu Ser Val Val Asp Gly Glu Pro Glu
    530                 535                 540

Ala Ile Val Gly Glu Ala Arg Arg Gly Ser Gly Arg Thr Ala Val Leu
545                 550                 555                 560

Phe Thr Gly Gln Gly Val Arg Ser Arg Gly Met Ala Arg Glu Leu His
                565                 570                 575

Ala Ala Phe Pro Val Phe Ala Ala Ala Leu Asp Glu Val Cys Ala Ala
            580                 585                 590

Phe Asp Ala Val Leu Pro Phe Ser Val Arg Asp Val Leu Leu Ala Glu
        595                 600                 605

Gly Glu Gly Gly Gly Ala Asp Gly Asp Gly Glu Asp Thr Gly Val
    610                 615                 620

Ala Gln Pro Ala Leu Phe Ala Tyr Glu Val Ala Leu Tyr Arg Leu Trp
625                 630                 635                 640

Thr Ser Trp Ala Ala Ala Pro Asp Ala Val Ala Gly His Ser Leu Gly
                645                 650                 655

Glu Val Val Ala Ala Tyr Val Ala Gly Val Phe Ser Leu Ala Asp Ala
            660                 665                 670

Thr Thr Phe Val Ala Ala Arg Ala Thr Leu Met Ser Ala Leu Pro Pro
        675                 680                 685

Gly Gly Ala Met Val Ala Val Gly Thr Ser Glu Ser Ala Ala Ala Arg
    690                 695                 700

Leu Leu Ala Asp His Pro Gly Val Gly Ile Ala Ala Val Asn Gly Pro
705                 710                 715                 720

Thr Gly Val Val Leu Ser Gly Glu Ala Ala Val Ala Glu Val Ala
                725                 730                 735

Arg Val Cys Ala Glu Arg Gly Leu Arg Ile Ser Arg Leu Arg Val Ser
            740                 745                 750

His Ala Phe His Ser Ala Leu Met Glu Pro Met Leu Asp Glu Leu Ala
        755                 760                 765

Glu Val Val Ser Gly Leu Thr Leu Arg Pro Ala Arg Met Ala Ile Gly
```

-continued

```
            770             775             780
Ser Asn Val Thr Gly Arg Ile Gly Ser Ala Glu Gln Leu Cys Asp Pro
785             790             795             800

Arg Tyr Trp Val Asp His Val Arg Arg Ala Val Arg Phe Gly Asp Val
                805             810             815

Leu Asp Ala Leu Arg Ala Asp Gly Val Arg Thr Phe Val Glu Ile Gly
            820             825             830

Pro Asp Ala Ala Leu Thr Pro Met Val Ala Asp Val Thr Ala Asp Ala
            835             840             845

Asp Asp Val Val Ala Val Ala Thr Arg Arg Asp Arg Asp Pro Val
850             855             860

Thr Gly Val Val Glu Ala Leu Ala Arg Val Phe Val Arg Gly Ala Val
865             870             875             880

Val Asp Trp Ala Ala Leu Val Pro Gly Arg Trp Val Glu Leu Pro Thr
                885             890             895

Tyr Ala Phe Thr Arg Arg Arg Phe Trp Leu Asp Ala Gly Thr Gly Ala
                900             905             910

Gly Asp Pro Thr Gly Leu Gly Gln Gly Thr Val Asp His Pro Leu Leu
            915             920             925

Gly Ala Val Val Gly Leu Ala Asp Gly His Gly Ser Leu Phe Thr Gly
            930             935             940

Arg Leu Ser Leu Asp Thr His Pro Trp Leu Ala Asp His Val Val Leu
945             950             955             960

Asp Thr Val Leu Leu Pro Gly Thr Ala Phe Leu Glu Leu Ala Leu His
                965             970             975

Thr Gly Arg Arg Val Gly Cys Asp Arg Val Glu Glu Leu Ser Leu Glu
            980             985             990

Thr Pro Leu Ala Phe Gly Glu Arg Gly Gly Cys Gln Val Gln Val Trp
            995             1000            1005

Ile Glu Ala Ala Gly Pro Asp Glu Arg Arg Ala Ile Thr Ile His
            1010            1015            1020

Ser Arg Pro Asp Asp Gly Asp Gly Asp Glu Gly Trp Ile Arg Asn Ala
1025            1030            1035            1040

Val Gly Thr Val Ala Pro Val Glu Asp Lys Ala Pro Ala Asp Ala Val
            1045            1050            1055

Ala Asp Pro Thr Pro Trp Pro Thr Gly Ala Thr Pro Val Pro Ile
            1060            1065            1070

Asp Asp Phe Tyr Pro Trp Leu Ala Asp Asn Gly Val Ala Tyr Gly Pro
            1075            1080            1085

Cys Phe Arg Ala Val Arg Ala Val Trp Arg Arg Gly Glu Glu Ile Phe
            1090            1095            1100

Gly Glu Ile Ala Leu Pro Glu Gln Val Gly Tyr Glu Ala Asp Arg Phe
1105            1110            1115            1120

Gly Val His Pro Ala Leu Met Asp Ala Thr Gln His Leu Leu Gly Val
            1125            1130            1135

Ala Ala Phe Ala Asp Pro Ala Glu Ser Glu Gly Gly Gly Leu Ala Leu
            1140            1145            1150

Pro Phe Ser Trp Arg Glu Val Arg Leu His Thr Pro Gly Ala Ala Ser
            1155            1160            1165

Val Arg Ala Arg Val Val Arg Thr Gly Pro Glu Ser Val Thr Leu Ser
            1170            1175            1180

Leu Ala Asp Glu Asp Gly Arg Pro Val Ala Glu Val Glu Ser Leu Ala
1185            1190            1195            1200
```

```
Val Arg Pro Ile Ser Ala Glu Gln Leu Arg Thr Ser Thr Ala Gly Arg
            1205                1210                1215

Arg Asp Pro Leu Tyr Thr Leu Arg Trp Thr Pro Leu Pro Arg Pro Ser
        1220                1225                1230

Ala Ala Pro Gly Ile Gly Ser Pro Ala Ile Ala Asp Ser Gly Ser
        1235                1240                1245

Gly Asp Pro Phe Ala Gly Arg Leu Gly Gly Thr Val His Pro Asp Leu
        1250                1255                1260

Thr Ala Leu Ala Asp Ala Val Asp Ala Gly Leu Pro Thr Pro Glu Val
1265                1270                1275                1280

Val Val Leu Ala Trp Pro Thr Ile Pro Ala Gly Pro Leu Gly Asp Val
            1285                1290                1295

Pro Asp Pro Asp Asp Val His Ala Ala Val His Arg Ala Leu Ala Thr
        1300                1305                1310

Val Gln Thr Trp Leu Gly Asp Glu Arg Phe Thr Gly Ala Arg Leu Val
        1315                1320                1325

Val Val Thr Arg Gly Ala Val Ala Val Ala Asp Glu Glu Val Arg Asp
        1330                1335                1340

Pro Ala Ala Ala Val Gly Gly Leu Val Arg Ser Ala Gln Ser Glu
1345                1350                1355                1360

His Pro Asp Arg Leu Val Leu Val Asp Leu Asp Glu Asp Ala Ala Ser
            1365                1370                1375

Pro Gly Ala Leu Pro Ala Ala Ile Gly Ala Gly Glu Pro Gln Leu Ala
            1380                1385                1390

Val Arg Ala Gly Val Ala Tyr Leu Pro Arg Leu Thr Arg Thr Pro Ala
            1395                1400                1405

Ile Glu Pro Ser Thr Pro Leu Phe Ala Pro Asp Gly Thr Thr Leu Val
        1410                1415                1420

Thr Gly Gly Thr Gly Ala Leu Gly Ala Leu Val Ala Arg His Leu Val
1425                1430                1435                1440

Val Ala His Gly Val Arg Arg Leu Leu Leu Val Ser Arg Arg Gly Ile
            1445                1450                1455

Ala Ala Pro Gly Ala Gly Ser Leu Ala Ala Glu Leu Thr Gly Leu Gly
            1460                1465                1470

Ala Thr Val Asp Val Val Ala Cys Asp Val Ser Asp Arg Ala Asp Leu
        1475                1480                1485

Ala Lys Lys Leu Ala Ala Ile Pro Ser Ala His Pro Leu Ser Ala Val
        1490                1495                1500

Val His Val Ala Gly Val Val Asp Asp Gly Val Ile Gly Ala Leu Thr
1505                1510                1515                1520

Pro Glu Arg Val Asp Arg Val Leu Arg Pro Lys Val Asp Ala Ala Leu
            1525                1530                1535

His Leu His Glu Leu Thr Arg Asp Ala Asp Leu Thr Ala Phe Val Leu
            1540                1545                1550

Phe Ser Ser Val Ala Gly Val Ile Gly Ser Leu Gly Gln Ala Asn Tyr
            1555                1560                1565

Ala Ala Gly Asn Ala Phe Leu Asp Ala Phe Ala Gln Arg Arg Arg Ala
        1570                1575                1580

Leu Gly Leu Pro Ala Val Ser Met Ala Trp Gly Leu Trp Ala Glu Glu
1585                1590                1595                1600

Ser Gly Leu Met Arg Glu Glu Phe Ala Glu Thr Asp Arg Gln Arg Ile
            1605                1610                1615
```

```
Asn Arg Ser Gly Val Leu Pro Leu Ser Asp Glu Gln Gly Leu Ala Leu
            1620                1625                1630

Phe Asp Ala Ala Leu Ala His Gly Glu Pro Ile Leu Ala Pro Val Arg
        1635                1640                1645

Leu Asp Leu Ser Ala Leu Arg Arg Leu Glu Asp Glu Leu Pro Ala Ile
    1650                1655                1660

Leu Gly Gly Leu Val Pro Thr Ser Arg Arg Asp Gly Ala Arg Pro Gly
1665                1670                1675                1680

Ala Ala Asp Thr Arg Arg Leu Ala Gln Arg Leu Ala Gly Arg Ser Glu
                1685                1690                1695

Pro Glu Gln Leu Arg Leu Leu Thr Glu Leu Thr Arg Ala Gln Ala Ala
            1700                1705                1710

Val Val Leu Gly His Ala Gly Ala Asp Ala Val Ala Ala Asp Arg Ala
        1715                1720                1725

Phe Thr Glu Leu Gly Phe Asp Ser Leu Thr Ala Leu Glu Met Arg Asn
    1730                1735                1740

Arg Leu Asn Thr Val Thr Gly Leu Arg Leu Pro Ala Thr Val Leu Phe
1745                1750                1755                1760

Asp Tyr Pro Asn Ala Ala Ala Leu Ala Arg Phe Leu Arg Ala Glu Thr
                1765                1770                1775

Leu Arg Val Pro Gln Tyr Thr Gln Ala Ala Asn Thr Ala Ala Lys
            1780                1785                1790

Ala Arg Thr Ser Asp Glu Pro Ile Ala Ile Val Ala Met Ser Cys Arg
        1795                1800                1805

Tyr Pro Gly Gly Ile Asp Thr Pro Glu Glu Leu Trp Arg Cys Val Ala
    1810                1815                1820

Gly Gly Val Asp Leu Thr Ser Pro Phe Pro Thr Asp Arg Gly Trp Asp
1825                1830                1835                1840

Leu Gly Ala Leu Tyr Asp Pro Asp Pro Asp Arg Ser Gly Arg Cys Tyr
                1845                1850                1855

Thr Arg Glu Gly Ser Phe Met Arg Asp Ile Asp Arg Phe Asp Ala Glu
            1860                1865                1870

Leu Phe Gly Ile Ser Pro Arg Glu Ala Leu Ala Met Asp Pro Gln Gln
        1875                1880                1885

Arg Leu Leu Leu Glu Thr Ser Trp Glu Ala Phe Glu Arg Ala Gly Ile
    1890                1895                1900

Asp Pro Ser Ser Leu Arg Gly Ser Asn Thr Ala Val Phe Ala Gly Leu
1905                1910                1915                1920

Met Tyr Ala Asp Tyr Ala Ala Gly Arg Val Gly Asp Val Gly Asp Glu
                1925                1930                1935

Leu Glu Ala Tyr Ile Gly Asn Gly Asn Ser Phe Gly Val Ala Ser Gly
            1940                1945                1950

Arg Val Ala Tyr Thr Leu Gly Leu Glu Gly Pro Ala Val Thr Val Asp
        1955                1960                1965

Ser Ala Cys Ser Ser Ser Leu Val Ala Leu His Trp Ala Ala His Ala
    1970                1975                1980

Leu Arg Ser Gly Glu Cys Asp Leu Ala Leu Ala Gly Gly Ala Thr Val
1985                1990                1995                2000

Met Ser Thr Pro Ser Val Phe Val Glu Phe Ala Arg Gln Arg Gly Leu
                2005                2010                2015

Ala Pro Asp Gly Arg Cys Lys Ser Phe Ala Ala Ala Ala Asp Gly Thr
            2020                2025                2030

Ala Trp Gly Glu Gly Ile Gly Met Leu Leu Val Glu Arg Leu Ala Asp
```

2035                2040                2045

Ala Arg Arg Asn Gly His Pro Val Leu Ala Val Leu Arg Gly Ser Ala
    2050                2055                2060

Ile Asn Gln Asp Gly Ala Ser Asn Gly Leu Thr Ala Pro Asn Gly Pro
2065                2070                2075                2080

Ser Gln Gln Arg Val Ile Arg Gln Ala Leu Ala Asn Ala Gly Leu Ala
            2085                2090                2095

Thr Ala Asp Val Asp Ala Val Glu Ala His Gly Thr Gly Thr Val Leu
        2100                2105                2110

Gly Asp Pro Ile Glu Ala Gln Ala Leu Leu Ala Thr Tyr Gly Arg Asp
        2115                2120                2125

Arg Pro Ala Glu Arg Pro Leu Trp Leu Gly Ser Ile Lys Ser Asn Phe
    2130                2135                2140

Gly His Thr Gln Ala Ala Ala Gly Val Ala Gly Val Ile Lys Met Val
2145                2150                2155                2160

Met Ala Met Arg His Gly Met Leu Pro Pro Thr Leu His Val Asp Glu
            2165                2170                2175

Pro Ser Pro His Val Asp Trp Ser Thr Gly Arg Val Glu Leu Leu Ala
            2180                2185                2190

Glu Gly Arg Pro Trp Pro Glu Val Gly Arg Ala Arg Arg Val Ala Val
        2195                2200                2205

Ser Ser Phe Gly Ile Ser Gly Thr Asn Ala His Val Ile Leu Glu Gln
    2210                2215                2220

Ala Asp Glu Glu Pro Glu Pro Ala Ala Arg Thr Thr Ser Gly Thr Gly
2225                2230                2235                2240

Ile Gly Gly Val Leu Pro Trp Val Leu Ser Ala Arg Thr Glu Ala Gly
            2245                2250                2255

Val Arg Ala Gln Ala Ala Arg Leu Arg Asp Trp Ala Gly Ala Arg Pro
        2260                2265                2270

Glu Val Asp Pro Ala Asp Val Gly Trp Ser Leu Ala Ser Gly Arg Ser
    2275                2280                2285

Val Phe Glu Arg Arg Ala Val Trp Gly Arg Asp Gly Ala Glu Leu
    2290                2295                2300

Thr Ala Gly Leu Asp Ala Leu Ala Ala Gly Arg Asp Ala Gly Ala Arg
2305                2310                2315                2320

Ala Val Leu Ala Gly Gly Thr Gly Val Ser Gly Glu Ala Ala Val Gly
            2325                2330                2335

Pro Val Phe Val Phe Pro Gly Gln Gly Ser Gln Trp Val Gly Met Ala
        2340                2345                2350

Ala Glu Leu Leu Thr Cys Cys Pro Val Phe Ala Glu Ser Val Ala Glu
        2355                2360                2365

Cys Ala Ala Ala Met Asp Pro Leu Leu Ala Asp Trp Ala Leu Leu Asp
    2370                2375                2380

Val Leu Arg Asp Ala Ser Ala Ala Leu Leu Glu Arg Val Asp Val Ile
2385                2390                2395                2400

Gln Pro Val Leu Phe Ala Val Met Val Gly Leu Ala Arg Trp Trp Glu
            2405                2410                2415

Ser Cys Gly Val Arg Pro Ser Ala Val Ile Gly His Ser Gln Gly Glu
            2420                2425                2430

Ile Ala Ala Ala His Val Ala Gly Phe Leu Ser Leu Glu Asp Ala Val
        2435                2440                2445

Arg Ile Val Val Leu Arg Ser Arg Ala Leu Arg Gly Leu Ala Ala Asp
    2450                2455                2460

```
Gly Asp Gly Met Leu Ser Val Gly Val Ser Ala Glu Arg Gly Arg Glu
2465                2470                2475                2480

Leu Val Ala Arg Val Gln Gly Leu Ser Leu Ala Ala Val Asn Gly Pro
            2485                2490                2495

Asp Ser Val Val Leu Ser Gly Pro Val Glu Gly Leu Thr Pro Ile Ala
            2500                2505                2510

Ala Ala Cys Glu Arg Asp Gly Val Arg Ala Arg Trp Ile Pro Val Asp
            2515                2520                2525

Tyr Ala Ser His Ser Ala Arg Met Asp Asp Val Arg Glu Val Leu Ala
        2530                2535                2540

Glu Ser Leu Ala Gly Val Glu Pro Gly Ile Gly Arg Val Pro Met Tyr
2545                2550                2555                2560

Ser Thr Val Ser Gly Leu Lys Val Thr Asp Ala Ala Asp Leu Gly Gly
            2565                2570                2575

Glu Tyr Trp Phe Glu Asn Leu Arg Arg Thr Val Gln Leu Ala Thr Ala
            2580                2585                2590

Val Gly Ala Ala Ala Asp Gly His Ser Val Phe Val Glu Cys Ser
        2595                2600                2605

Pro His Pro Gly Leu Val Val Pro Leu Gly Asp Thr Leu Asp Ala Leu
        2610                2615                2620

Gly Ser Thr Ser Gly Thr Val Leu Glu Thr Leu Arg Arg Gly Glu Gly
2625                2630                2635                2640

Gly Pro Glu Arg Leu Val Ala Ala Leu Ala Ala Ala Phe Val Ser Gly
            2645                2650                2655

Leu Pro Val Asp Trp Ala Gly Leu Leu His His Asp Gly Val Arg Arg
            2660                2665                2670

Val Gln Leu Pro Thr Tyr Ala Phe Gln Gly Arg Arg Phe Trp Leu Glu
        2675                2680                2685

Pro Asp Met Gly Thr Ala Leu Pro Gly Arg Thr Thr Pro Thr Pro Val
    2690                2695                2700

Val Gly Asp Thr Glu Asp Ser Arg Leu Trp Glu Ala Leu Glu Ala Ala
2705                2710                2715                2720

Gly Ala Glu Asp Leu Ala Ala Glu Leu Glu Val Ala Ala Asp Ala Pro
            2725                2730                2735

Leu Ser Asp Val Leu Pro Ala Leu Thr Ser Trp Arg Ala Arg Arg Arg
            2740                2745                2750

Ala Asp Ala Thr Val Arg Ser Trp Arg Tyr Gly Val Arg Trp Glu Pro
        2755                2760                2765

Trp Ala Ala Pro Ala Ala Ser Ala Asp Arg Met Gly Arg Leu Leu Leu
    2770                2775                2780

Val Ala Pro Asp Gly Glu Ile Gly Asp Val Leu Ala Gly Ala Leu Ala
2785                2790                2795                2800

Glu Cys Gly Ala Glu Val Val Val Leu Ser Ala Glu Gly Glu Arg Thr
            2805                2810                2815

Ala Leu Ala Arg Arg Leu Ala Ala Ile Gly Glu Glu Gly Val Pro Ala
            2820                2825                2830

Gly Val Val Ser Leu Ser Ala Val Gly Cys Ala Ala Asp Ala Asp Pro
        2835                2840                2845

Val Pro Ala Leu Ala Pro Val Leu Thr Leu Val Gln Ala Leu Gly Asp
        2850                2855                2860

Ala Gly Met Glu Ala Pro Leu Trp Val Leu Thr Arg Gly Ala Val Ser
2865                2870                2875                2880
```

-continued

```
Val Leu Gly Glu Glu Pro Thr Gly Pro Ala Gly Ala Val Gln Gly
            2885                2890                2895
Leu Gly Arg Val Val Gly Leu Glu His Pro Gly Arg Trp Gly Gly Leu
            2900                2905                2910
Ile Asp Leu Pro Gln Val Val Asp Gly Arg Val Ala Glu Thr Leu Ala
            2915                2920                2925
Gly Ile Leu Ala Ala Gly Ala Gly Gly Thr Gly Ser Gly Glu Asp Glu
            2930                2935                2940
Ile Ala Ile Arg Pro Leu Gly Val Phe Val Arg Arg Leu Ala Arg Met
2945                2950                2955                2960
Ala Gly Pro Glu Gly Ser Gly Thr Ser Arg Trp Arg Pro Gly Gly Thr
            2965                2970                2975
Ala Leu Val Thr Gly Gly Thr Gly Ala Leu Gly Gly Arg Val Ala Arg
            2980                2985                2990
Trp Leu Val Arg Glu Gly Val Glu Arg Val Val Leu Ala Gly Arg Arg
            2995                3000                3005
Gly Pro Asp Ala Pro Gly Ala Asp Arg Leu Arg Glu Glu Leu Ala Ala
            3010                3015                3020
Ala Gly Ala Glu Val Ala Val Leu Ala Cys Asp Leu Gly Asp Arg Asp
3025                3030                3035                3040
Ala Val Ala Ala Leu Leu Ala Glu Val Arg Ala Gly Gly Arg Arg Ile
            3045                3050                3055
Asp Thr Val Val His Ala Ala Gly Ala Val Val Gly Pro Leu Ala
            3060                3065                3070
Asp Ser Thr Val Ala Asp Leu Ala Asp Ala Ser Ala Ala Lys Val Gly
            3075                3080                3085
Gly Ala Leu Leu Leu Asp Glu Leu Leu Arg Ala Asp Glu Pro Asp Thr
            3090                3095                3100
Val Val Leu Phe Ser Ser Ala Ala Gly Val Trp Gly Gly Ala Gly Gln
3105                3110                3115                3120
Gly Ala Tyr Ala Ala Ala Asn Ala Cys Leu Asp Thr Ile Ala Glu Arg
            3125                3130                3135
Arg Arg Ala Arg Gly Leu Arg Thr Val Ser Ile Ala Trp Gly Gln Trp
            3140                3145                3150
Ala Gly Gly Gly Met Ala Asp Gly Ala Ala Gly Ala His Leu Asp Arg
            3155                3160                3165
Ile Gly Val Pro Ala Met Asp Pro Asp Arg Ala Leu Glu Ala Leu Arg
            3170                3175                3180
Gln Ala Leu Asp Glu Asp Leu Thr Cys Val Thr Val Ala Asp Val Asp
3185                3190                3195                3200
Trp Pro Arg Phe Ala Ala Gly Tyr Thr Ala Ala Arg Pro Arg Pro Leu
            3205                3210                3215
Ile Ala Asp Leu Val Ala Ala Glu Val Ala Ala Ala Pro Val Thr Glu
            3220                3225                3230
Ala Arg Gly Ala Gly Glu Pro Asp Gly Pro Ser Val Trp Arg Ala Arg
            3235                3240                3245
Leu Ala Glu Leu Gly Ala Ala Asp Arg Glu Ala Glu Leu Leu Ala Leu
            3250                3255                3260
Val Arg Thr Glu Val Ala Ala Gln Leu Gly His Ala Asp Pro Ala Ala
3265                3270                3275                3280
Ile Glu Pro Glu Arg Pro Phe Arg Asp Leu Gly Phe Asp Ser Leu Ala
            3285                3290                3295
Ala Val Gly Leu Arg Asn Arg Leu Thr Glu Thr Ile Gly Leu Arg Leu
```

-continued

```
              3300                3305                3310
Pro Ser Thr Leu Val Phe Asp His Pro Thr Ala Val Ala Leu Ala Ala
    3315                3320                3325

His Ile Asp Gly Glu Leu Phe Ala Glu Thr Val Gly Thr Val Ser Val
    3330                3335                3340

Phe Ala Glu Leu Asp Arg Leu Glu Ala Ala Leu Gly Glu Leu Gly Gly
3345                3350                3355                3360

Asp Phe Ala Glu Arg Gly Arg Val Gly Ala Arg Leu Ala Glu Leu Ala
                3365                3370                3375

Gly Lys Trp Arg Glu Ile Glu Ala Ala Ser Gln Lys Ala Glu Pro Glu
                3380                3385                3390

Gly Ala Asp Phe Ala Ala Ala Glu Asp Glu Glu Met Phe Asp Met Leu
                3395                3400                3405

Gly Lys Glu Phe Gly Ile Ser
                3410                3415

<210> SEQ ID NO 7
<211> LENGTH: 1976
<212> TYPE: PRT
<213> ORGANISM: Streptomyces sp. ATCC 39366

<400> SEQUENCE: 7

Met Ala Gly Asp Arg Gly Arg Glu Pro Lys Gly Arg Ala Arg Gly Ser
1               5                   10                  15

Arg Leu Arg Gly Ser Gly Gly Arg Gly Asp Val Arg His Ala Arg Lys
                20                  25                  30

Gly Val Arg His Leu Leu Ser Gly Ala Gly Asp Asp Arg Arg Ser Arg
                35                  40                  45

Val Pro Thr Ala His Gly Ser Ile Arg Phe Asp Gln Ala Glu Asp Gly
    50                  55                  60

Arg Thr Asp Met Ser Asn Glu Glu Arg Leu Arg His Phe Leu Arg Glu
65                  70                  75                  80

Thr Ala Thr Asp Leu Arg Arg Thr Lys Gln Arg Leu His Glu Val Glu
                85                  90                  95

Ser Ala Ala Arg Glu Pro Val Ala Ile Val Ala Ile Gly Cys Arg Leu
                100                 105                 110

Pro Gly Gly Val Arg Ser Ala Glu Asp Leu Trp Glu Leu Val Arg Thr
                115                 120                 125

Gly Thr Asp Ala Ile Ala Gly Phe Pro Ser Asp Arg Gly Trp Asp Pro
    130                 135                 140

Ala Asn Val Tyr Ala Asp Leu Pro Gly Gly Glu Gly Val Ser Gly Gly
145                 150                 155                 160

Ser Ala Gly Ser Gly Gly Ser Thr Thr Arg Gln Gly Gly Phe Val Tyr
                165                 170                 175

Asp Ala Ala Phe Asp Ala Glu Phe Phe Gly Val Ser Pro His Glu
                180                 185                 190

Ala Leu Ala Met Asp Pro Gln Gln Arg Leu Leu Leu Glu Thr Ala Trp
                195                 200                 205

Glu Thr Phe Glu Arg Ala Gly Ile Asp Pro Leu Ser Met Arg Arg Ser
    210                 215                 220

Arg Thr Gly Val Phe Val Gly Ala Gly Ala Leu Gly Tyr Gly Gly Gly
225                 230                 235                 240

Met Arg Ala Asp Asn Ala Glu Ile Gln Ala His Arg Val Thr Gly Gly
                245                 250                 255
```

```
Ser Met Ser Val Val Ser Gly Arg Ile Ala Tyr Thr Leu Gly Leu Glu
            260                 265                 270

Gly Pro Ala Val Thr Leu Asp Thr Ala Cys Ser Ser Leu Val Ala
        275                 280                 285

Leu His Leu Ala Ala Asn Ala Leu Arg Ser Gly Glu Cys Asp Leu Ala
    290                 295                 300

Leu Ala Gly Gly Val Thr Val Met Ala Arg Pro Thr Ala Phe Val Glu
305                 310                 315                 320

Phe Ser Arg Gln Gly Leu Ala Ser Asp Gly Arg Cys Arg Ser Phe
                325                 330                 335

Ala Ala Ala Ala Asp Gly Thr Gly Trp Gly Glu Gly Val Gly Leu Leu
            340                 345                 350

Leu Val Glu Arg Leu Ser Asp Ala Arg Arg Asn Gly His Pro Val Leu
        355                 360                 365

Ala Val Leu Arg Gly Ser Ala Val Asn Gln Asp Gly Ala Ser Asn Gly
    370                 375                 380

Leu Thr Ala Pro Asn Gly Pro Ser Gln Gln Arg Val Ile Arg Gln Ala
385                 390                 395                 400

Leu Ala Ala Ala Gly Leu Ser Ala Asp Val Asp Ala Val Glu Ala
                405                 410                 415

His Gly Thr Gly Thr Val Leu Gly Asp Pro Ile Glu Ala His Ala Leu
            420                 425                 430

Leu Ala Thr Tyr Gly Arg Asp Arg Pro Ala Asp Arg Pro Leu Trp Leu
        435                 440                 445

Gly Ser Val Lys Ser Asn Ile Gly His Thr Gln Ser Ala Ala Gly Val
    450                 455                 460

Ala Gly Val Ile Lys Met Val Met Ala Leu Arg His Gly Leu Leu Pro
465                 470                 475                 480

Arg Thr Leu His Val Asp Arg Pro Ser Pro His Val Asp Trp Ala Ser
                485                 490                 495

Gly Arg Val Glu Leu Leu Thr Asp Glu Val Pro Trp Pro Ala Gly Gly
            500                 505                 510

Arg Val Arg Arg Ala Gly Val Ser Ser Phe Gly Ile Ser Gly Thr Asn
        515                 520                 525

Ala His Val Val Leu Glu Glu Ala Pro Ala Val Glu Gly Ala Ser Gly
    530                 535                 540

Glu Gly Ala Glu Pro Ala Pro Gly Val Gly Gly Leu Ile Pro Trp Val
545                 550                 555                 560

Val Ser Ala Arg Ser Pro Glu Ala Leu Arg Ala Gln Ala Ala Arg Leu
                565                 570                 575

Arg Glu Pro Ala Val Ala Asp Pro Ala Asp Val Gly Arg Ser Leu Val
            580                 585                 590

Thr Gly Arg Ala Leu Leu Asp His Arg Ala Val Leu Gly Arg Asp
        595                 600                 605

Ala Ala Glu Leu Gly Arg Gly Leu Ala Ala Leu Ala Ala Gly Ser Pro
    610                 615                 620

Gly Ala Val Glu Pro Ser Glu Gly Gly Thr Pro Val Val Val Thr Gly
625                 630                 635                 640

Asn Val Pro Arg Ala Gly Gly Ala Gly Arg Val Ala Gly Arg Gly
                645                 650                 655

Ala Val Val Phe Thr Gly Gln Gly Gly Arg Leu Pro Gly Ile Gly Arg
            660                 665                 670

Glu Leu Tyr Ala Gly Phe Pro Val Phe Ala Arg Ala Leu Asp Glu Val
```

-continued

```
              675                 680                 685
Gly Ala Ala Phe Asp Ala Val Pro Phe Ser Val Arg Asp Val Leu
            690                 695                 700
Leu Gly Val Glu Gly Thr Val Gly Val Asp Ala Asp Thr Gly Val
705                 710                 715                 720
Ala Gln Pro Val Leu Phe Ala Phe Glu Val Ala Leu Tyr Arg Leu Trp
                725                 730                 735
Ser Ser Leu Gly Ser Val Pro Asp Phe Val Val Gly His Ser Leu Gly
                740                 745                 750
Gly Ile Val Ala Ala His Val Ala Gly Val Phe Ser Leu Ala Asp Ala
                755                 760                 765
Val Ala Phe Val Ala Ala Arg Ala Arg Leu Met Ser Ala Leu Pro Gly
770                 775                 780
Gly Gly Ala Met Leu Ala Val Gly Ala Ser Glu Ala Gln Val Thr Ala
785                 790                 795                 800
Leu Ser Asp Gly Leu Pro Val Ser Ile Ala Ala Val Asn Gly Pro Ala
                805                 810                 815
Ser Val Val Val Ser Gly Ala Val Ala Ala Val Asp Glu Val Ala Ala
                820                 825                 830
Arg Cys Ala Ala Arg Ser Trp Arg Ser Ser Arg Leu Arg Val Ser His
            835                 840                 845
Ala Phe His Ser Val Leu Met Glu Pro Met Leu Ala Glu Leu Arg Asp
            850                 855                 860
Val Leu Arg Arg Leu Ser Phe Gly Ala Pro Glu Ile Gly Leu Val Ser
865                 870                 875                 880
Asp Thr Thr Gly Arg Val Val Thr Ala Glu Glu Val Gly Asp Pro Glu
                885                 890                 895
Tyr Trp Val Arg His Val Arg Asp Ala Val Arg Phe Ala Asp Ala Val
                900                 905                 910
Gly Thr Leu Arg Glu Arg Gly Val Ala Thr Phe Val Glu Leu Gly Pro
            915                 920                 925
Asp Ala Ala Leu Thr Ala Met Val Ala Glu Cys Thr Ala Gly Val Gly
            930                 935                 940
Glu Val Leu Gly Val Pro Ala Gln Arg Arg Gly Arg Pro Ala Val Ala
945                 950                 955                 960
Thr Leu Ala Gly Ala Leu Ala Thr Ala Phe Val Arg Gly Leu Pro Val
                965                 970                 975
Asp Trp Val Gly Ala Leu Gly Gly Pro Gly Gly Arg Arg Val Glu Leu
            980                 985                 990
Pro Thr Tyr Ala Phe Gln Gly Arg Arg Tyr Trp Leu Glu Pro Gly Lys
            995                 1000                1005
Ala Ser Val Thr Pro Ala Gly Pro Asp Ser Val Asp Gly Pro Leu Trp
        1010                1015                1020
Asp Ala Val Glu Arg Ala Gly Ala Gly Glu Leu Ala Ala Ile Leu Ala
1025                1030                1035                1040
Val Ser Glu Asp Ala Thr Leu Arg Glu Val Val Pro Ala Leu Ser Ser
                1045                1050                1055
Trp Arg Ala Arg Arg Arg Val Asp Ala Thr Ala Ala Ser Trp Arg Tyr
            1060                1065                1070
Ala Val Arg Trp Glu Pro Trp Ala Gly Gly Ser Ser Asp Ala Ala Ala
        1075                1080                1085
Leu Ser Gly Arg Trp Leu Leu Val His Pro Ala Ala Ser Glu Leu Ala
        1090                1095                1100
```

```
Asp Ala Val Ala Arg Glu Leu Thr Glu Arg Gly Ala Glu Val Val Arg
1105                1110                1115                1120

Val Gly Gly Glu Gly Ile Gly Ser His Val Gly Ala Glu Pro Val Ala
            1125                1130                1135

Gly Val Val Ser Leu Ile Gly Ser Gly Ser Gly Ser Gly Ser Thr Ser
        1140                1145                1150

Gly Ser Gly Ser Gly Ser Gly Ser Ala Ser Gly Ser Gly Ser Gly Ser
    1155                1160                1165

Gly Ser Gly Ser Gly Ser Gly Ser Gly Ser Ser Cys Gly Ser Gly Ser
    1170                1175                1180

Val Pro Gly Leu Gly Ser Cys Ala Gly Asp Asp Cys Ala Asp Leu Val
1185                1190                1195                1200

Ala Ala Val Val Ala Met Gly Glu Leu Leu Ala Glu Leu Arg Arg Phe
                1205                1210                1215

Glu Val Ala Ala Pro Leu Trp Cys Val Thr Arg Ala Ala Val Ser Val
                1220                1225                1230

Leu Gly Glu Asp Leu Ala Asn Pro Val Gly Ala Gly Leu Trp Gly Arg
            1235                1240                1245

Gly Leu Val Ala Ser Leu Glu Gln Pro Gly Cys Trp Gly Gly Leu Val
    1250                1255                1260

Asp Leu Pro Ala Val Ala Asp Thr Arg Ala Leu Gly Val Leu Ala Thr
1265                1270                1275                1280

Ile Leu Ala Gly Thr Ser Asp Glu Asp Gln Phe Ala Ile Arg Pro Leu
                1285                1290                1295

Gly Val Phe Thr Arg Arg Leu Thr Pro Leu Pro Ala Glu Gly Ser Gly
            1300                1305                1310

Arg Val Arg Thr Arg Glu Ala Ala Leu Ile Thr Gly Gly Thr Gly Gly
    1315                1320                1325

Val Leu Gly Ala His Ala Ala Arg Trp Leu Val Ala His Gly Thr Glu
    1330                1335                1340

Arg Val Ile Leu Leu Gly Arg Arg Gly Ala Arg Ala Pro Gly Phe Asp
1345                1350                1355                1360

Ala Leu Arg Ala Asp Leu Glu Ala Ala Gly Ala Glu Val Val Ala Ile
            1365                1370                1375

Ala Cys Asp Leu Thr Ala Pro Asp Ala Ala Glu Arg Leu Arg Ala Ala
        1380                1385                1390

Leu Pro Ala Thr Gly Ala Pro Ile Arg Thr Val Val His Ala Ala Gly
        1395                1400                1405

Val Pro Gly Ser Pro Thr Ala Thr Gly Ala Asp Ala Val Ala Asp Thr
    1410                1415                1420

Val Thr Ala Lys Val Ala Gly Ala Leu Ala Leu Asp Thr Leu Phe Gly
1425                1430                1435                1440

Ala Asp Arg Ala Leu Asp Ala Phe Val Leu Tyr Ser Ser Gly Ala Gly
            1445                1450                1455

Val Trp Gly Gly Ala Gly Gln Gly Ala Tyr Ala Ala Ala Asn Ala Phe
            1460                1465                1470

Leu Asp Ala Leu Ala Val Arg Arg Gln Arg Gly Leu Pro Ala Thr
        1475                1480                1485

Ala Ile Ala Trp Gly Pro Trp Ala Ala Gly Gly Met Ala Asp Gly Glu
    1490                1495                1500

Gly Glu Arg Leu Leu Ala Arg Val Gly Val Arg Ala Met Asp Pro Ala
1505                1510                1515                1520
```

-continued

Ala Ala Leu Ala Ala Leu Gly Arg Ala Leu Val Glu Asp Leu Thr Cys
        1525                1530                1535

Val Thr Val Ala Asp Leu Asp Arg Pro Arg Phe Ala Ala Gly Tyr Thr
    1540                1545                1550

Ser Ala Arg Pro Arg Pro Leu Ile Ala Asp Leu Ile Asp Ala Glu Pro
    1555                1560                1565

Pro Thr Ala Thr Ala Pro Pro Thr Arg Pro Gly Gly Val Trp Asp Pro
    1570                1575                1580

Ala Val Thr Arg Ser Pro Ala Arg Leu Ala Ala Glu Leu Leu Asp Leu
1585                1590                1595                1600

Val Arg Ala Glu Val Ala Ala Gln Leu Gly His Ala Gly Val Glu Ala
            1605                1610                1615

Ile Glu Pro Asp Arg Pro Phe Arg Asp Leu Gly Phe Asp Ser Leu Ala
        1620                1625                1630

Ala Val Gly Leu Arg Asn Arg Ile Ala Glu Ala Thr Gly Val His Leu
    1635                1640                1645

Ala Gly Thr Leu Ile Tyr Asp His Glu Thr Pro Ala Ala Leu Ala Ala
        1650                1655                1660

His Leu Ala Asp Ala Leu Arg Glu Gly Val Pro Glu Thr Arg Pro Ala
1665                1670                1675                1680

Pro Thr Ala Pro Gly Gly Ala Glu Asp Ser Asn Asp Met Leu Gly Thr
            1685                1690                1695

Val Tyr Arg Lys Leu Ala Leu Leu Gly Arg Met Asp Asp Ala Glu Ser
        1700                1705                1710

Leu Leu Val Gly Ala Ala Gly Leu Arg Gln Thr Phe Glu Asp Pro Asn
    1715                1720                1725

Arg Leu Pro Lys Thr Pro Gly Phe Thr Arg Leu Ala Arg Gly Pro Ala
    1730                1735                1740

Arg Pro Arg Val Ile Cys Phe Pro Pro Phe Ala Pro Val Glu Gly Ala
1745                1750                1755                1760

Ile Gln Phe Gly Arg Leu Ala Gly Thr Phe Glu Gly Arg His Asp Thr
            1765                1770                1775

Ala Val Val Thr Val Pro Gly Phe Arg Pro Gly Glu Pro Leu Ala Ala
        1780                1785                1790

Ser Leu Asp Val Leu Asp Leu Leu Ala Asp Ala Thr Leu Arg Cys
        1795                1800                1805

Ala Gly Asp Asp Pro Phe Ala Val Leu Gly Tyr Ser Ser Ser Gly Trp
    1810                1815                1820

Leu Ala Gln Gly Val Ala Gly Arg Leu Glu Ala Thr Gly Arg Thr Pro
1825                1830                1835                1840

Ala Gly Val Val Leu Leu Asp Thr Tyr Leu Pro Ala Thr Met Ser Arg
            1845                1850                1855

Arg Met Arg Lys Ala Met Asn Tyr Glu Val Ile Val Arg Arg Gln Ala
        1860                1865                1870

Phe Thr Ala Leu Asp Tyr Ile Gly Leu Thr Ala Ile Gly Thr Tyr Arg
    1875                1880                1885

Arg Met Phe Arg Gly Trp Glu Pro Lys Pro Gly Ser Ala Pro Thr Leu
    1890                1895                1900

Val Val Arg Pro Ser Arg Cys Val Pro Gly Ser Pro Glu Glu Pro Met
1905                1910                1915                1920

Thr Gly Glu Asp Trp Arg Ser Thr Trp Pro Tyr Glu His Thr Ala Ala
            1925                1930                1935

Glu Val Glu Gly Asp His Cys Thr Met Ile Gly Glu His Ala Glu Gln

```
            1940                1945               1950
Thr Gly Ala Val Val Arg Ala Trp Leu Ala Gly Asp Arg Thr Val Ser
        1955                1960                1965
Ile Asp Thr Arg Glu Gly Thr Ala
        1970            1975

<210> SEQ ID NO 8
<211> LENGTH: 392
<212> TYPE: PRT
<213> ORGANISM: Streptomyces sp. ATCC 39366

<400> SEQUENCE: 8

Met Ile Pro Val Leu Glu Leu Val Gln Ile Ser Thr Leu Pro Asp Ala
 1               5                  10                  15

Glu Arg Glu Leu Glu Gln Leu Ala Arg Arg Tyr Pro Ile Ile Arg Thr
            20                  25                  30

Arg Gln Val Gly Gly Ile Glu Ala Trp Thr Val Leu Gly Ala Gly Leu
        35                  40                  45

Thr Arg Gln Leu Leu Gly Asp Pro Arg Leu Ser Asn Asp Leu His Thr
 50                  55                  60

His Ala Pro His Ala Ala Gln Ser Ala Asp Gly Pro Thr Val Leu Phe
65                   70                  75                  80

Glu Gln Asp Asn Pro Asp His Ala Arg Tyr Arg Leu Val Ser Ala
            85                  90                  95

Ala Phe Ala Ser Arg Ala Val Arg Asn Leu Glu Pro Arg Ile Val Asp
        100                 105                 110

Ile Ala Arg Ala Leu Leu Asp Arg Leu Pro Ala Glu Gly Gly Thr Val
        115                 120                 125

Asp Ile Val Glu Ala Phe Ala Asn Pro Phe Pro Leu Glu Val Ile Cys
        130                 135                 140

Glu Leu Leu Gly Val Pro Met Ala Asp Arg Glu Val Phe Arg Thr Arg
145                 150                 155                 160

Val Glu Asn Met Asp Ser Pro Ser Thr Ala Val Arg Arg Ala Ala Met
            165                 170                 175

Asp Ala Phe Val Ala Tyr Cys Ala Asn Leu Val Asp Ala Lys Arg Thr
        180                 185                 190

Glu Pro Thr Glu Asp Leu Leu Ser Glu Leu Val Gln Ala Glu Leu Asp
        195                 200                 205

Asp Gly Ser Arg Leu Ser Ala Asn Glu Leu Ile Gly Phe Gly Ser Val
        210                 215                 220

Leu Leu Phe Ala Gly His Val Thr Thr Ala Tyr Leu Ile Ala Ala Ala
225                 230                 235                 240

Leu Tyr Glu Leu Ile Thr His Asn Asp Gln Leu Ala Ala Leu Arg Ala
            245                 250                 255

Asp Pro Thr Leu Val Glu Gly Thr Val Glu Glu Ala Leu Arg Phe Arg
        260                 265                 270

Gly Ser Leu Leu Ser Thr Thr Asn Arg Val Ala Leu Thr Asp Leu Glu
        275                 280                 285

Ile Gly Gly Val Leu Val Arg Arg Gly Asp Leu Val Arg Phe Leu Leu
        290                 295                 300

Ser Ala Ala Asn Arg Asp Pro Ala Ile Arg Glu Asp Pro His Thr Phe
305                 310                 315                 320

Asp Ile Thr Arg Ser Thr Thr Ala His Leu Gly Phe Gly His Gly Pro
            325                 330                 335
```

-continued

His Phe Cys Leu Gly Gln Arg Leu Ala Arg Gln Glu Ile Lys Val Ala
            340                 345                 350

Leu Thr Glu Ile Val Thr Arg Phe Pro Thr Leu Glu Leu Ala Val Pro
        355                 360                 365

Ala Glu Lys Leu Arg Trp Arg Ala Ser Asp Phe Leu Arg Gly Leu Ala
370                 375                 380

Glu Leu Pro Leu Thr Tyr Ala Pro
385                 390

<210> SEQ ID NO 9
<211> LENGTH: 146
<212> TYPE: PRT
<213> ORGANISM: Streptomyces sp. ATCC 39366

<400> SEQUENCE: 9

Met Arg Glu Arg Lys Lys Ala Arg Thr Arg Gln Val Ile Ser Thr Val
1               5                   10                  15

Ala Phe Asp Leu Phe Glu Glu Gln Gly Phe Glu Gln Thr Thr Val Asp
            20                  25                  30

Met Ile Cys Arg Arg His Ala Met Thr Val Ser His Gly Asn Leu Glu
        35                  40                  45

Asp His Ala Glu Gln Thr Ala Arg His Ala Leu Arg Arg Phe
    50                  55                  60

Leu Gly Val Arg Ser Val His Asp His Gly Val Ala Leu Ile Asp Thr
65                  70                  75                  80

Val Ala His Arg Ile Val Thr Thr Ala Ala Ala Arg Leu Gly Val Asp
                85                  90                  95

Pro Ala Val Asp Leu Arg Pro His Ala Leu Gly Ala Leu Val Ala Ala
            100                 105                 110

Met Thr Arg Arg Val Val Ile Asp Asp Ile Ala Pro Gly Pro Ile Asn
        115                 120                 125

Glu Trp Ala Glu Ala Phe Arg Thr Leu Leu Pro Thr Pro Ala Ala His
    130                 135                 140

Thr Asp
145

<210> SEQ ID NO 10
<211> LENGTH: 22
<212> TYPE: DNA
<213> ORGANISM: Artificial Sequence
<220> FEATURE:
<223> OTHER INFORMATION: PCR primer

<400> SEQUENCE: 10
cataatacga ctcactatag gg                                            22

<210> SEQ ID NO 11
<211> LENGTH: 18
<212> TYPE: DNA
<213> ORGANISM: Artificial Sequence
<220> FEATURE:
<223> OTHER INFORMATION: PCR primer

<400> SEQUENCE: 11
ttccccgaaa agtgccac                                                 18